(12) United States Patent
Hibi et al.

(10) Patent No.: US 7,078,405 B2
(45) Date of Patent: Jul. 18, 2006

(54) IMIDAZO[1,2-B]PYRIDAZINE COMPOUND

(75) Inventors: Shigeki Hibi, Ibaraki (JP); Yoshinori Takahashi, Ibaraki (JP); Yorihisa Hoshino, Ibaraki (JP); Koichi Kikuchi, Ibaraki (JP); Motohiro Soejima, Ibaraki (JP); Tatsuya Yoshiuchi, Ibaraki (JP); Kogyoku Shin, Ibaraki (JP); Mutsuko Ono, Ibaraki (JP); Hisashi Shibata, Ibaraki (JP); Mitsuhiro Ino, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/451,741

(22) PCT Filed: Feb. 8, 2002

(86) PCT No.: PCT/JP02/01098

§ 371 (c)(1),
(2), (4) Date: Jun. 25, 2003

(87) PCT Pub. No.: WO02/062800

PCT Pub. Date: Aug. 15, 2002

(65) Prior Publication Data
US 2004/0082781 A1 Apr. 29, 2004

(30) Foreign Application Priority Data

Feb. 8, 2001 (JP) ............................. 2001-032637
Apr. 27, 2001 (JP) ............................. 2001-133208

(51) Int. Cl.
A01N 43/58 (2006.01)
A01N 43/60 (2006.01)
A61K 31/50 (2006.01)
A61K 31/495 (2006.01)
C07D 487/00 (2006.01)

(52) U.S. Cl. ..................................... 514/248; 544/236
(58) Field of Classification Search ................ 544/236; 514/248
See application file for complete search history.

(56) References Cited

U.S. PATENT DOCUMENTS

| | | | |
|---|---|---|---|
| 4,596,872 A | 6/1986 | Davey | 546/121 |
| 4,910,199 A * | 3/1990 | Bourguignon et al. | 514/234.2 |
| 5,127,936 A * | 7/1992 | Selby | 71/92 |

FOREIGN PATENT DOCUMENTS

| | | |
|---|---|---|
| EP | 0068378 A1 | 1/1983 |
| EP | 0353902 A1 | 2/1990 |
| EP | 0611766 | 8/1994 |
| EP | 0611766 A1 | 8/1994 |
| JP | 3-506033 A | 12/1991 |
| JP | 10-72449 A | 3/1998 |
| JP | 2000-502723 A | 3/2000 |
| JP | 2000-109431 A | 4/2000 |
| WO | WO90/01030 A1 | 2/1990 |
| WO | WO94/13643 A1 | 6/1994 |
| WO | WO94/13644 A1 | 6/1994 |
| WO | WO94/13661 A1 | 6/1994 |
| WO | WO94/13676 A1 | 6/1994 |
| WO | WO95/10506 A1 | 4/1995 |
| WO | WO95/34563 A1 | 12/1995 |
| WO | WO97/29109 A1 | 8/1997 |
| WO | WO97/29110 A1 | 8/1997 |
| WO | WO98/08847 A1 | 3/1998 |
| WO | WO 98/35967 A2 | 8/1998 |
| WO | WO98/35967 A2 | 8/1998 |
| WO | WO99/40090 A1 | 8/1999 |

(Continued)

OTHER PUBLICATIONS

Kehne and De Lombert, "Non-Peptidic CRF1 Receptor Antagonists for the Treatment of Anxiety, Depression and Stress Disorders" Current Drug Targets, vol. 1(5), pp. 467-493 (2002).*

(Continued)

Primary Examiner—James O. Wilson
Assistant Examiner—Zachary C. Tucker
(74) Attorney, Agent, or Firm—Birch, Stewart, Kolasch & Birch, LLP

(57) ABSTRACT

The present invention provides a novel compound having an excellent corticotrophin-releasing-factor receptor antagonistic activity. That is, it provides a compound represented by the following formula or a salt thereof.

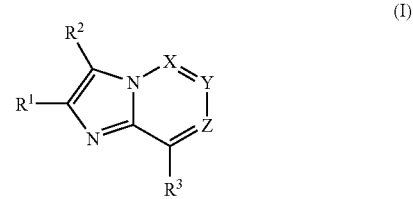

(I)

Wherein $R^1$ denotes a hydrogen atom, a $C_{1-6}$ alkyl group, a $C_{1-6}$ alkoxy group and the like; $R^2$ denotes a halogen atom, a cyano group, a nitro group, a $C_{1-10}$ alkyl group, a $C_{2-10}$ alkenyl group, $C_{2-10}$ alkynyl group and the like; $R^3$ denotes a $C_{6-14}$ aromatic hydrocarbon cyclic group or a 5- to 14-membered aromatic heterocyclic group, each of which may have a substituent; and X, Y and X are independent of each other and each denotes N or $CR^4$ (wherein $R^4$ denotes a hydrogen atom, a halogen atom, a cyano group, a nitro group, an optionally halogenated $C_{1-6}$ alkyl group and the like) and, in this case, at least two of X, Y and Z denote $CR^4$.

16 Claims, No Drawings

FOREIGN PATENT DOCUMENTS

| | | |
|---|---|---|
| WO | WO 99/40090 A1 | 8/1999 |
| WO | WO-02/06286 A2 | 1/2002 |

OTHER PUBLICATIONS

Dautzenberg and Hauger, "The CRF peptide family and their receptors: yet more partners discovered" Trends in Pharmacological Sciences, vol. 23(2), pp. 71-77 (Feb. 2002).*
Altemus et al., Arch Gen Psychiatry, vol. 51, pp. 794-803, (1994).
Bremner et al., Am. J. Psychiatry, vol. 154, No. 5, pp. 624-629, (1997).
Roy-Byrne et al., Am. J. Psychiatry, vol. 143, No. 7, pp. 896-899, (1986).
Monnikes et al., Brain Research, vol. 574, pp. 70-76, (1992).
Stenzel-Poore et al., J. of Neuroscience, vol. 14, No. 5, pp. 2579-2584, (1994).
Owens et al., J. of Pharma. and Exp. Therapeutics, vol. 258, No. 1, pp. 349-356, (1991).
Kalin et al., Brain Research, vol. 509, pp. 80-84, (1990).
Tazi et al., Regulatory Peptides, vol. 18, pp. 37-42, (1987).
Baldwin et al., Psychopharmacology, vol. 103, pp. 227-232, (1991).
Sirinathsinghji et al., Nature, vol. 305, pp. 232-235, (1983).
Sherman et al., Pharm. Bio. & Behavior, vol. 26, pp. 699-703, (1987).
Lyons et al., Brain Research, vol. 545, pp. 339-342, (1991).
Strijbos et al., Brain Research, vol. 656, pp. 405-408, (1994).
Ehlers et al., Brain Research, vol. 278, pp. 332-336, (1983).
Whitehouse et al., Neurology, vol. 37, pp. 905-909, (1987).
De Souza et al., Brain Research, vol. 437, pp. 355-359, (1987).
Diamant et al., Neuroendocrinology, vol. 57-pp. 1071-1081, (1993).
Stenzel-Poore et al., Endocrinology, vol. 130, No. 6, pp. 3378-3386, (1992).
Hotta et al., J. of Clinical Endocrinology and Metabolism, vol. 62, No. 2, pp. 319-324, (1986).
Levine et al., Neuropharmacology, vol. 22, No. 3A, pp. 337-339, (1983).
Krahn et al., Brain Research Bulletin, vol. 17, pp. 285-289, (1986).
Arase et al., Physiology & Behavior, vol. 45, pp. 565-570, (1989).
Plotsky et al., Endocrinology, vol. 130, No. 4, pp. 1931-1941, (1992).
Tache et al., American Journal of Phy., vol. 253, pp. G241-G245, (1987).
Barquist et al., American Journal of Phy., vol. 262, pp. G616-G620 (1992).
Gunion et al., American Journal of Phy., vol. 258, pp. G152-G157, (1990).
Bakke et al., Life Sciences, vol. 45, pp. 907-916, (1989).
Lenz et al., Gastroenterology, vol. 95, pp. 1510-1517, (1988).
Ford et al., Gastroenterology, vol. 109, pp. 1772-1780, (1995).
Lembo et al., Neurogastroenterol. Mot., vol. 8, pp. 9-18, (1996).
Fukudo et al., Gut, vol. 42, pp. 845-849, (1998).
Morimoto et al., J. of Physiology, vol. 460, pp. 221-229, (1993).
Karalis et al., Science, vol. 254, pp. 421-423, (1991).
Crofford et al., J. of Clinical Investigation, Inc., vol. 90, pp. 2555-2564, (1992).
Crofford et al., J. of Immunology, vol. 151, No. 3, pp. 1587-1596, (1993).
Theoharides et al., Endocrinology, vol. 139, No. 1, pp. 403-413, (1998).
Singh et al., J. of Pharmacology and Experimental Therapeutics, vol. 288, No. 3, pp. 1349-1356, (1999).
Scopa et al., Am. J. of Pathology, vol. 145, No. 5, pp. 1159-1167, (1994).
Poliak et al., J. of Immunology, vol. 158, pp. 5751-5756, (1997).
Murakami et al., Endocrine Journal, vol. 44, No. 4, pp. 627-629, (1997).
Singh et al., Neuroscience Letters, vol. 120, pp. 151-154, (1990).
Garrick et al., Regulatory Peptides, vol. 21, pp. 173-181, (1988).
Butler et al., J. of Neuroscience, vol. 10, No. 1, pp. 176-183, (1990).
Owens et al., Pharmacological Reviews, vol. 43, No. 4, pp. 425-473, (1991).
Banki et al., Am. J. Psychiatry, vol. 144, No. 7, pp. 873-877, (1987).
Raadsheer et al., Am. J. Psychiatry, vol. 152, No. 9, pp. 1372-1376, (1995).
Nemeroff et al., Arch. Gen. Psychiatry, vol. 45, pp. 577-579, (1988).
Gold et al., New England J. of Med., vol. 314, No. 21, pp. 1329-1335, (1986).
Chalmers et al., J. of Neuroscience, vol. 15, No. 10, pp. 6340-6350, (1995).
Liaw et al., Endocrinology, vol. 137, No. 1, pp. 72-77, (1996).
Valdenaire et al., Biochimica et Biophysica Acta, vol. 1352, pp. 129-132, (1997).
Vale et al., Recent Progress in Hormone Research, vol. 39, pp. 245-270, (1982).
Vale et al., Science, vol. 213, pp. 1394-1397, (1981).
Rivier et al., Proc. Natl. Acad. Sci., vol. 80, pp. 4851-4855, (1983).
Shibahara et al., EMBO Journal, vol. 2, No. 5, pp. 775-779, (1983).
Sasaki et al., J. of Clinical Endocrinology and Metabolism, vol. 65, No. 1, pp. 176-182, (1987).
Sasaki et al., J. of Clinical Endocrinology and Metabolism, vol. 67, No. 4, pp. 768-773, (1988).
Nicholson et al., Regulatory Peptides, vol. 18, pp. 173-188, (1987).
Petrusz et al., Peptides, vol. 5, Suppl. 1, pp. 71-78, (1984).
Jain et al., Endocrinology, vol. 128, No. 3, pp. 1329-1336, (1991).
Chappell et al., Biological Psychiatry, vol. 39, pp. 776-783, (1996).
Bohmer et al., E. J. of Pharmacology, vol. 182, pp. 405-411, (1990).
Nink et al., Acta Endocrinologica, vol. 127, pp. 200-204, (1992).
Rivier et al., Science, vol. 224, pp. 889-891, (1984).
Menzaghi et al., J. of Pharm. And Experimental Therapeutics, vol. 269, No. 2, pp. 564-572, (1994).
Dunn et al., Brain Research Reviews, vol. 15, pp. 71-100, (1990).
Whitten et al., J. Med. Chem., vol. 39, pp. 4354-4357, (1996).
Behan et al., Nature, vol. 378, p. 284-287, (1995).

* cited by examiner

IMIDAZO[1,2-B]PYRIDAZINE COMPOUND

This application is the national phase under 35 U.S.C. § 371 of PCT International Application No. PCT/JP02/01098 which has an International filing date of Feb. 8, 2002, which designated the United States of America.

FIELD OF THE INVENTION

The present invention relates to a novel compound having corticotropin-releasing-factor receptor antagonistic activity, a salt thereof and a hydrate of them, a process for preparing its and its medical use.

PRIOR ART

Corticotropin-releasing-factor (hereinafter, referred to as "CRF") is a neuropeptide comprising 41 amino acids, and isolated from sheep hypothalamus (Science, 213, 1394 (1981)) and, then, its presence was confirmed in a rat (Proc. Natl. Acad. Sci. USA, 80, 4851 (1983)) and a human being (EMBO J. 5, 775 (1983)). CRF is the most abundant in pituitary gland and hypothalamus and is widely distributed in a brain such as cerebral cortex, cerebellum and the like. In addition, in a peripheral tissue, CRF is confirmed to be present in placenta, adrenal gland, lung, lever, pancreas and digestive tract (J. Clin. Endocrinol. Metab., 65, 176 (1987), J. Clin. Endocrinol. Metab., 67, 768 (1988), Regul. Pept., 18, 173 (1987), peptides, 5 (Suppl. 1), 71 (1984)). Two subtypes CRF1 and CRF2 are present in a CRF receptor, and a CRF1 receptor is reported to be distributed at a large amount in cerebral cortex, cerebellum, olfactory bulb, pituitary gland, almond nucleus and the like. Recently, two subtypes CRF2α and CRF2β were confirmed to be present in a CRF2 receptor, and it was found that a CRF2α receptor is distributed in hypothalamus, septal area and choroid plexus at a large amount and a CRF2β is distributed in a peripheral tissue such as skeletal muscle and in a cerebrovascular part in central tissue (J. Neuroscience, 15 (10) 6340 (1995); Endocrinology, 137, 72 (1996); BBA, 1352, 129 (1997)). Since each receptor is distributed differently, it is suggested that its role is also different. CRF is produced in and secrete from hypothalamus and promotes the release of adrenocorticotropic hormone (ACTH) by stress (Recent Prog. Horm. Res., 39, 245(1983)). CRF serves as a neurotransmitter or a neuromodulator also in a brain and integrates electrophysiology to stress, autonomic nerve and action, in addition to a role to incretion (Brain Res. Rev., 15, 71, (1990); Pharmacol. Rev., 43, 425 (1991)).

Currently, CRF is thought to be involved in a variety of diseases and there are reports as follows:

CRF in a cerebrospinal liquid in a depression patient is at a higher value as compared with a healthy man (Am. J. Psychiatry, 144(7), 873 (1987)). A CRF-mRNA level in hypothalamus in a depression patient is a higher value as compared with a healthy man (Am. J. Psychiatry, 152, 1372 (1995)). A CRF receptor is decreased in a cerebral cortex of a person who commits suicide (Arch. Gen. Psychiatry, 45, 577 (1988)). A rise of ACTH in a plasma is small in a depression patient upon administration of CRF (N. Engl. J. Med., 314, 1329 (1986)). CRF in a cerebrospinal liquid of a certain anxiety patient such as compulsion disorder, post-traumatic stress disorder, teulett syndrome etc. is a higher value as compared with a healthy man (Arch. Gen. Psychiatry, 51, 794 (1994); Am. J. Psychiatry, 154, 624 (1997); Biol. Psychiatry, 39, 776 (1996)). A rise of ACTH in a plasma is small in a panic disorder patient upon administration of a CRF (Am. J. Psychiatry, 143, 896 (1986)). An anxiety behavior is recognized when CRF is administered in a brain of an experimental animal (Brain Res., 574, 70 (1992); J. Neurosci., 10 (1), 176 (1992)). In addition, many anxiety behavior are recognized in a CRF overexpressing mouse as compared with a normal animal (J. Neurosci., 14 (5), 2579 (1994)). CRF ceruleus is decreased by administration of an anti-anxiety agent (J. Pharmaco. Exp. Ther., 258, 349 (1991)). In addition, α-helical CRF (9–41) of a peptidic CRF antagonist exerts an anti-anxiety behavior in an animal model (Brain Res., 509, 80 (1990); Regulatory Peptize, 18, 37 (1987); J. Neurosci., 14 (5), 2579 (1994)). α-Helical CRF (9–41) of a peptidic CRF antagonist inhibits an abnormal behavior due to abstinence of dependency drug such as alcohol and cocaine (Psychopharmacology, 103, 227 (1991)). CRF suppresses a sexual behavior of a rat (Nature, 305, 232 (1983)). CRF is thought to be involved in sleep disorder because it reduces rat's sleep (Pharmacol. Biochem. Behav., 26, 699 (1987)). α-Helical CRF (9–41) of a peptidic CRF antagonist inhibits disorder of a brain and brain wave abnormality due to brain ischemia and activation of NMDA receptor (Brain Res., 545, 339 (1991), Brain Res. 656, 405 (1994)). CRF awakens abrainwave and induces convulsion (Brain Res., 278, 332 (1983)). CRF in a cerebrospinal liquid of a schizophrenia patient is a higher value as compared with a healthy man (Am. J. Psychiatry, 144(7), 873 (1987)). CRF in a cerebral cortex in an Alzheimer's disease, Parkinson's disease or progressive supranuclear palsy is reduced (Neurology, 37, 905 (1987)). CRF in a Huntington disease ganglion is reduced (Brain Res., 437, 355 (1987), Neurology, 37, 905 (1987)). In addition, it has been found that administration of CRF in a rat enhances learning and memory (Nature, 378, 384 (1995); Neuroendocrinology, 57, 1071 (1993)). CRF in a cerebrospinal liquid in an amyotrophic lateral sclerosis patient. In a CRF overexpressing mouse, oversecretion of ACTH and adrenal gland steroid hormone occurs and abnormality similar to Cushing syndrome such as muscular atrophy, alopecia and infertility (Endocrinology, 130(6), 3378 (1992)). CRF in a cerebrospinal liquid in an anorexia nervosa patient is a higher value as compared with a healthy man, and a rise of ACTH in a plasma is small in an anorexia nervosa upon administration of CRF (J. Clin. Endocrinol. Metab., 62, 319 (1986)). CRF suppresses eating in an experimental animal (Neuropharmacology, 22 (3A), 337 (1983)). In addition, α-helical CRF (9–41) of a peptidic CRF antagonist improved decrease in eating in an animal model due to stress load (Brain Res. Bull., 17 (3), 285 (1986)). CRF suppressed weight gain in a hereditary obesity animal (Physiol. Behav., 45, 565 (1989)). It is suggested that the lowness of a CRF value and obesity syndrome are related (Endocrinology, 130, 1931 (1992)). It is suggested that eating inhibition and weight loss action of a serotonine reuptake inhibiting agent is via release of CRF (Pharmacol. Rev., 43, 425 (1991)). CRF acts on centralness and peripheralness, weakens constriction of a stomach and reduces stomach excretion ability (Regulatory Peptides, 21, 173 (1983); Am. J. Physiol., 253, G241 (1987)) In addition, α-helical CRF (9–41) of a peptidic CRF antagonist has the recovery action on the functional decrease of stomach due to abdominal operation (Am. J. Physiol., 262, G616 (1992)). CRF promotes secretion of bicarbonate ions in stomach, decreases gastric acid secretion, and at the same time, inhibits coldconstraint stress ulcer (Am. J. Physiol., 258, G152 (1990)). In addition, ulcer is increased in a non-constraint animal by CRF administration (Life Sci., 45, 907 (1989)). CRF suppresses small intestine transport, promotes large intestine transport and induces defecation. In addition, α-helical CRF (9–41) of a peptidic CRF antagonist has the inhibitory action on decrease in gastric acid secretion, decrease in stomach excretion, decrease in small intestine transport and asthenia in large intestine (Gastroenterology, 95, 1510 (1988)).

26) In a healthy man, mental stress increases a gas and bellyache due to anxiety and gastrectasis and CRF reduces a threshold of uncomfort (Gastroenterol., 109, 1772 (1995); Neurogastroenterol. Mot., 8, 9 (1996)). In an irritable bowel syndrome patient, large intestine movement is excessively exasperated by administration of CRF as compared with a healthy man (Gut., 42, 845 (1998)). Administration of CRF increases blood pressure, heart rate and body temperature. In addition, α-helical CRF (9–41) of a peptidic CRF antagonist inhibits elevation of blood pressure, heart rate and body temperature (J. Physiol., 460, 221 (1993)). In an inflammatory part of an experimental animal and a joint liquid of a rheumatoid arthritis patient, production of CRF is locally increased (Science, 254, 421(1991); J. Clin. Invest., 90, 2555 (1992); J. Immunol., 151, 1587 (1993)). CRF induces degranulation of a mast cell and exasperates vessel permeability (Endocrinology, 139(1), 403 (1998); J. Parmacol. Exp. Ther., 288 3), 1349 (1999)). Also in an autoimmune thyroiditis patient, CRF is detected (Am. J. Pathol., 145, 1159 (1994)). When CRF is administered to an experimental autoimmune cerebrospinal meningitis rat, progression of symptom of palsy and the like was remarkably inhibited (J. Immunol., 158, 5751 (1997)). In a system for culturing pituitary gland adenocarcinoma of an acromegaly patient, urocortin (analogue of CRF) increased secretion of a growth hormone (Endocri, J., 44, 627 (1997)). In addition, CRF stimulates secretion of cytokin such as interleukin 1 and interleukin2 (J. Neuroimmunol., 23, 256(1989); Neurosci. Lett., 120, 151(1990)). Activity of natural killer cell and increase of T lymphocyte are decreased by administration of CRF and load of stress. α-Helical CRF(9–41) of a peptidic CRF antagonist improves decrease in the function of immune cells due to administration of CRF and stress load (Endocrinology, 128(3), 1329 (1991)). Breathing is remarkably increased by administration of CRF (Eur. J. Pharmacol., 182, 405 (1990)). In an advanced aged patient equipped with a long term artificial inhaler, animus of breathing and insomnia were recognized by administration of CRF (Acta Endcrinol. Copenh., 127, 200 (1992)).

From the above study reports, a CRF antagonist can be expected to exert the excellent effects in treating or preventing depression and depressive symptom including great depression, monostotic depression, recurrent depression, infant tyrannism by depression and postpartum depression, mania, anxiety, generalized anxiety disorder, panic disorder, phobia, compulsive disorder, posttraumatic stress disorder, Tourette syndrome, autism, emotional disorder, sentimental disorder, bipolar disorder, cyclothymia, schizophrenia, Alzheimer's disease, Alzheimer-type senile dementia, neurodegenerative disease such as Parkinson's disease and Huntington's disease, multi-infarct dementia, senile dementia, neurotic anorexia, appetite asthenia and other diet disorder, obesity, diabetes, alcohol dependence, pharmacophilia to cocaine, heroin, benzodiazepine etc., drug or alcohol withdrawal, sleep disorder, insomnia, migraine, stress headache, myotonic headache, ischemic neuropathy, excitation toxic neuropathy, cerebral apoplexy, progressive supranuclear palsy, amyotrophic lateral sclerosis, multiple sclerosis, muscular convulsion, chronic fatigue syndrome, mental social growth failure, epilepsy, head trauma, spinal trauma, graphospasm, spasmodic torticollis, muscular convulsion, neck-shoulder-arm syndrome, primary glaucoma, Meniere syndrome, autonomic imbalance, alopecia, neurosis including cardioneurosis, intestinal neurosis and bladder neurosis, peptic ulcer, irritable bowel syndrome, ulcerative colitis, Crohn's disease, diarrhea, coprostasis, postoperational ileus, gastrointestinal function abnormality associated with stress and neural vomiting, hypertension, cardiovascular disorder including neural angina, tachycardia, congestive cardioplegia, hyperpnea syndrome, bronchial asthma, apnea syndrome, infant sudden death syndrome, inflammatory disorder (for example, rheumatoid arthritis, bone arthritis, lumbago etc.), pain, allergic disease (for example, atopic dermatis, eczema, urticaria, psoriasis etc.), impotence, climacteric disorder, fertilization disorder, infertility, cancer, immune function abnormality upon infection with HIV, immune function abnormality by stress, hemorrhagic stress, Cushing syndrome, thyroid function disorder, encephalomyelitis, acromegaly, incontinence, osteoporosis etc. There is a report on a CRF antagonist, for example, a peptide-type CRF receptor antagonist in which a part of an amino acid sequence of a human being or other mammal is altered or deleted, and it is reported that the antagonist shows the ACTH release inhibitory action and anti-anxiety action of the antagonist (Science, 224, 889 (1984), J. Pharmacol. Exp. Ther., 269, 564 (1994), Brain Research Reviews, 15, 71 (1990)). However, it must be said that, from a viewpoint of pharmacokinetics such as the chemical stability in vivo, the bioavailability and the transferability to brain, the utility value thereof as a medicament is low.

On the other hand, regarding a non-peptide type CRF antagonist, there is the following report:

1) a compound represented by the formula:

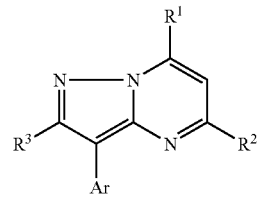

(wherein $R^1$ represents $NR^4R^5$ etc.; $R^2$ represents a $C_{1-6}$ alkyl group etc.; $R^3$ represents a $C_{1-6}$ alkyl group etc.; $R^4$ represents a $C_{1-16}$ alkyl group etc.; $R^5$ represents a $C_{1-6}$ alkyl group etc.; and Ar represents phenyl etc.), a stereoisomer thereof, or pharmaceutically acceptable acid addition salts thereof (WO97/29109);

2) a compound represented by the formula:

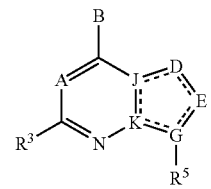

(wherein a broken line represents a single or double bond; A represents $CR^7$ etc.; B represents $NR^1R^2$ etc.; J and K are the same as or different from each other and each represents nitrogen atom etc.; D and E are the same as or different from each other and each represents nitrogen atom etc.; G denotes nitrogen atom etc.; R¹ represetns a $C_{1-6}$ alkyl group etc.; R² represents a $C_1$–$C_{12}$ alkyl group etc.; and R⁷ represents hydrogen atom etc.) or a pharmacologically acceptable salt thereof (WO98/08847);

3) an anilinopyrimidine compound described in WO95/10506, a pyrazolopyrimidine compound described in WO95/34563, a pyrazole compound described in WO94/13661, a pyrazole and pyrazolopyrimidine compound described in WO94/13643, aminopyrazole described in WO94/18644, a pyrazolopyrimidine compound described in WO94/13677, a pyrrolopyrimidine compound described in WO94/13676, a thiazole compound described in EP-659747, EP-611766, an anilinopyrimidine compound described in J. Med. Chem., 39, 4358 (1996), an anilinotriazine compound described in ibid. 39, 3454 (1996), a thienopyrimidine compound described in WO97/29110 and the like; and 4) as an imidazo[1,2-a]pyrazine compound, there is, for example, a compound described in EP0068378 and, as an imidazo[1,2-b]pyridazine compound, there is, for example, a compound described in EP0353902.

As described above, there is desired the provision of a CRF receptor antagonist which is useful as a medicament. However, a medicament which shows the excellent CRF receptor antagonism, and satisfies the pharmacological activity, the dose, the safety etc. as a medicament and effectively acts clinically has not been found. That is, an object of the present invention is to search and find such the excellent CRF receptor antagonist.

DISCLOSURE OF THE INVENTION

In view of the above-mentioned circumstances, the present inventors studied intensively and, as a result, they have succeeded in synthesizing a novel compound (hereinafter, referred to as "the compound (I)" in some cases) represented by the following formula:

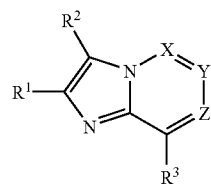

(I)

(wherein R¹ denotes a hydrogen atom, a halogen atom, a nitro group, a cyano group, a $C_{1-6}$ alkyl group, a $C_{2-8}$ alkenyl group, a $C_{2-8}$ alkynyl group, a $C_{3-8}$ cycloalkyl group, a $C_{3-8}$ cycloalkenyl group, a $C_{1-6}$ alkoxy group, a $C_{2-6}$ alkenyloxy group, or a group represented by —NR$^{1a}$R$^{1b}$ (R$^{1a}$ and R$^{1b}$ are the same as or different from each other and each denotes a hydrogen atom, a $C_{1-6}$ alkyl group, a $C_{2-6}$ alkenyl group, a $C_{2-6}$ alkynyl group, a $C_{1-6}$ alkylsulfinyl group, a $C_{1-6}$ alkylsulfonyl group or a $C_{1-7}$ aliphatic acyl group), —CO—NR$^{1a}$R$^{1b}$ (R$^{1a}$ and R$^{1b}$ have the same meanings as defined above, respectively), —CO-A¹ (A¹ denotes a $C_{1-6}$ alkyl group, a $C_{2-8}$ alkenyl group or a $C_{2-8}$ alkynyl group), -G¹-A² (G¹ denotes —O—CO—, S, SO or SO₂; and A² denotes a $C_{1-6}$ alkyl group or a $C_{2-6}$ alkenyl group) or —SO²—NR$^{1a}$R$^{1b}$ (R$^{1a}$ and R$^{1b}$ have the same meanings as defined above, respectively), and further, the R¹ may be substituted with at least one group selected from a halogen atom, a cyano group, a $C_{1-6}$ alkyl group, a $C_{2-8}$ alkenyl group, a $C_{2-8}$ alkynyl group, a $C_{1-6}$ alkoxy group, a $C_{1-6}$ alkenyloxy group, a $C_{1-6}$ alkylthio group and a $C_{2-6}$ alkenylthio group;

R² denotes:

(a) a halogen atom, a cyano group, a nitro group, a $C_{1-10}$ alkyl group, a $C_{2-10}$ alkenyl group, a $C_{2-10}$ alkynyl group, a $C_{3-8}$ cycloalkyl group, a $C_{3-8}$ cycloalkenyl group, a $C_{3-8}$ cycloalkyl $C_{1-6}$ alkyl group, a $C_{3-8}$ cycloalkyl $C_{2-6}$ alkenyl group, a $C_{1-10}$ alkoxy group, a $C_{2-6}$ alkenyloxy group, a $C_{1-10}$ alkoxy $C_{1-10}$ alkyl group, a $C_{1-6}$ alkoxy $C_{2-8}$ alkenyl group, a $C_{2-6}$ alkenyloxy $C_{1-6}$ alkyl group, a $C_{2-6}$ alkenyloxy $C_{2-6}$ alkenyl group, a group represented by —NR$^{2a}$R$^{2b}$ (R$^{2a}$ and R$^{2b}$ are independent of each other and each denotes a hydrogen atom, a $C_{1-8}$ alkyl group, a $C_{2-8}$ alkenyl group, a $C_{2-6}$ alkynyl group, a $C_{1-6}$ hydroxyalkyl group, a $C_{1-6}$alkyl group substituted with a 5- to 14-membered non-aromatic heterocyclic group, a $C_{1-6}$ alkylthio group, a $C_{1-6}$ alkylsulfinyl group, a $C_{1-6}$ alkylsulfonyl group, a $C_{1-6}$ alkoxy $C_{1-6}$ alkyl group, a $C_{1-6}$ alkylthio $C_{1-6}$ alkyl group, an aminocarbonyl $C_{1-6}$ alkyl group, a heteroarylcarbonyl group, a $C_{3-8}$ cycloalkyl group, a $C_{3-8}$ cycloalkyl $C_{1-6}$ alkyl group, a heteroaryl $C_{1-6}$ alkyl group, an aryl $C_{1-6}$ alkyl group, an aryl group, a 5- to 14-membered heterocyclic group, a $C_{1-6}$ alkoxycarbonyl group or a $C_{2-6}$ alkenyloxycarbonyl group), —CO—NR$^{2a}$R$^{2b}$ (R$^{2a}$ and R$^{2b}$ have the same meanings as defined above, respectively), —CO-A³ (A³ denotes a hydrogen atom, a hydroxyl group, a $C_{1-6}$ alkyl group, a $C_{2-8}$ alkenyl group, a $C_{2-8}$ alkynyl group, a $C_{1-6}$ alkoxy group, a $C_{2-8}$ alkenyloxy group, an aryl group or a heteroaryl group), —O—C(O)-A⁴ (A⁴ denotes a $C_{1-6}$ alkyl group, a $C_{2-8}$ alkenyl group or a $C_{2-8}$ alkynyl group) or -G²-A⁵ (G² denotes S, SO or SO₂; and A⁵ denotes a $C_{1-6}$ alkyl group or a $C_{2-6}$ alkenyl group), or a 5- to 14-membered non-aromatic heterocyclic group, or (b) may be bound together with R¹ to form a cycle, and further, in the case of (a) or (b), R² may be substituted with at least one group selected from a halogen atom, a hydroxyl group, a cyano group, a $C_{1-6}$ alkyl group, a $C_{2-6}$ alkenyl group, a $C_{2-6}$ alkynyl group, a $C_{3-8}$ cycloalkyl group, a $C_{3-8}$ cycloalkenyl group, a $C_{1-6}$ alkoxy group, a $C_{2-6}$ alkenyloxy group, a $C_{1-6}$ alkylthio group, a $C_{2-6}$ alkenylthio group, —NR$^{2a}$R$^{2b}$ (R$^{2a}$ and R$^{2b}$ have the same meanings as defined above, respectively), an aryl group and a heteroaryl group;

R³ denotes a $C_{6-14}$ aromatic hydrocarbon cyclic group or a 5- to 14-membered aromatic heterocyclic group, each of which may have a substituent; and X, Y and Z are independent of each other and each denotes (a) N or (b) CR⁴ (wherein R⁴ (aa) denotes a hydrogen atom, a halogen atom, a cyano group, a nitro group, an optionally halogenated $C_{1-6}$ alkyl group, a $C_{2-6}$ alkenyl group, a $C_{2-6}$ alkynyl group, a $C_{3-8}$ cycloalkyl group, a $C_{3-8}$ cycloalkenyl group, a $C_{1-6}$ alkoxy group, a $C_{2-6}$ alkenyloxy group, —NR$^{1a}$R$^{1b}$ (wherein R$^{4a}$ and R$^{4b}$ are independent of each other and each denotes a hydrogen atom, a $C_{1-8}$ alkyl group, a $C_{2-8}$ alkenyl group, a $C_{2-6}$ alkynyl group, a $C_{1-6}$ alkylthio group, a $C_{1-6}$ alkylsulfinyl group, a $C_{1-6}$ alkylsulfonyl group, a $C_{1-6}$ alkoxy $C_{1-6}$ alkyl group, a $C_{3-8}$ cycloalkyl group, a $C_{3-8}$ cycloalkyl $C_{1-6}$ alkyl group, a heteroaryl $C_{1-6}$ alkyl group, an aryl $C_{1-6}$ alkyl group, an aryl group, a 5 to 14-membered heterocyclic group, a $C_{1-6}$ alkoxycarbonyl group or a $C_{2-6}$ alkenyloxycarbonyl group) or -G³-A⁶ (wherein G³ denotes S, SO or SO₂; A⁶ denotes a $C_{1-6}$ alkyl group or a $C_{2-6}$ alkenyl group) or (bb) R⁴s, or R² and R⁴ may be bound together to form a ring); in this case, at least two of X, Y and Z denote CR⁴ (R⁴ has the same meaning as defined above), provided that, in the above definition, compounds in the following cases (1) to (4) are excluded:

(1) the case where $R^1$ and $R^2$ are a methyl group, X, Y and Z are CH, and $R^3$ is a 2,4-dichlorophenyl group, (2) the case where $R^2$ is a trifluoromethyl group, $R^2$ is a fluorine atom or a bromine atom, X is N, Y is =C(CH$_3$)—, Z is CH, and $R^3$ is a phenyl group, (3) the case where $R^1$ is a trifluoromethyl group, $R^2$ is an ethoxycarbonyl group or an amide group, X is N, Y is =C(CH$_3$)—, Z is CH, and $R^3$ is a 3-chlorophenyl group, and (4) the case where $R^1$ is a hydrogen atom, $R^2$ is a 4-morpholinylmethyl group, X is N, Y is =CR'— (R' denotes a phenyl group), Z is CH, and $R^3$ is a phenyl group), a salt thereof or a hydrate of them. Further, they have surprisingly found that the compound has an excellent CFR antagonism. Thus, they have completed the present invention.

That is, the present invention relates to:

(1) a compound represented by the above formula (I) or a salt thereof; (2) the compound described in the above (1) or a salt thereof, wherein $R^1$ is a $C_{1-6}$ alkyl group, a $C_{2-8}$ alkenyl group, a $C_{2-8}$ alkynyl group, a $C_{1-6}$ alkoxy group, a $C_{1-6}$ alkylthio group, a $C_{1-6}$ alkylsulfinyl group or a $C_{1-6}$ alkylsulfonyl group; (3) the compound described in the above (1) or a salt thereof, wherein $R^1$ is a methyl group, an ethyl group, a n-propyl group, an iso-propyl group, a methoxy group, an ethoxy group, a n-propyloxy group, an iso-propyloxy group, a methylthio group, an ethylthio group, a n-propylthio group, an iso-propylthio group, a methylsulfinyl group, an ethylsulfinyl group, a methylsulfonyl group or an ethylsulfonyl group; (4) the compound described in the above (1) or a salt thereof, wherein $R^1$ is -$G^4$-CH$_3$ (wherein $G^4$ denotes a single bond, CH$_2$, O or S); (5) the compound described in the above (1) or a salt thereof, wherein $R^2$ denotes a $C_{1-6}$alkyl group, $C_{1-6}$alkoxy $C_{1-6}$alkyl group, a $C_{1-6}$alkylsulfonyl group, a $C_{2-6}$alkenylsulfonyl group or —NR$^{2a}$R$^{2b}$ (R$^{2a}$ and R$^{2b}$ have the same meanings as defined above), each of which may be substituted; (6) the compound described in the above (1) or a salt thereof, wherein $R^2$ is —NR$^{2aa}$R$^{2bb}$ (wherein R$^{2aa}$ and R$^{2bb}$ are independent of each other and each denotes a hydrogen atom, a $C_{1-8}$ alkyl group, a $C_{2-8}$ alkenyl group, a $C_{2-6}$ alkynyl group, a $C_{1-6}$ alkyl group substituted with a 5- to 14-membered non-aromatic heterocyclic group, a $C_{1-8}$ alkoxy group, a $C_{1-8}$ alkoxy $C_{1-8}$ alkyl group, a $C_{1-6}$ alkylsulfinyl group, a $C_{1-6}$ alkylsulfonyl group, a $C_{3-8}$ cycloalkyl group, a $C_{3-8}$cycloalkyl $C_{1-6}$alkyl group or a 5- to 14-membered heterocyclic group, and further, the R$^{2aa}$ and R$^{2bb}$ are independent of each other and each may be substituted with a halogen atom); (7) the compound described in the above (1) or a salt thereof, wherein $R^2$ is a di($C_{1-6}$ alkyl)amino group; (8) the compound described in the above (1) or a salt thereof, wherein $R^3$ is a phenyl group or a pyridyl group, each of which may be substituted; (9) the compound described in the above (1) or a salt thereof, wherein $R^3$ is a phenyl group or a pyridyl group, each of which may be substituted with 1 to 4 group(s) selected from a halogen atom, a $C_{1-6}$ alkyl group, a halogeno-$C_{1-6}$ alkyl group, a $C_{1-6}$ alkoxy group, a halogeno-$C_{1-6}$ alkoxy group, a $C_{1-6}$ alkylthio group and a 5- to 8-membered aromatic heterocyclic group; (10) the compound described in the above (1) or a salt thereof, wherein $R^3$ is a phenyl group or a pyridyl group, each of which may be substituted with 1 to 3 group(s) selected from a fluorine atom, a chlorine atom, a bromine atom, a methyl group, an ethyl group, a trifluoromethyl group, a methoxy group, a trifluoromethoxy group, a methylthio group and a pyrrolyl group; (11) the compound described in the above (1) or a salt thereof, wherein any one of X, Y and Z is N, and remaining two are CR$^{4'}$ (wherein R$^{4'}$ denotes a hydrogen atom, a halogen atom, a cyano group, a $C_{1-6}$alkyl group or a $C_{1-6}$alkoxy group); (12) the compound described in the above (1) or a salt thereof, wherein X and Y are CR$^{4'}$ (wherein R$^4$ has the same meaning as defined above); and Z is N; (13) the compound described in the above (1) or a salt thereof, wherein X, Y and Z are a group represented by CR$^{4'}$ (wherein R$^{4'}$ has the same meaning as defined above); (14) the compound described in any one of the above (11) to (13) or a salt thereof, wherein $R^4$ is a hydrogen atom, a halogen atom, a methyl group, an ethyl group, a methoxy group or an ethoxy group; (15) the compound described in any one of the above (11) to (12) or a salt thereof, wherein R$^{4'}$ is a hydrogen atom; (16) the compound described in the above (1) which is represented by the following formula:

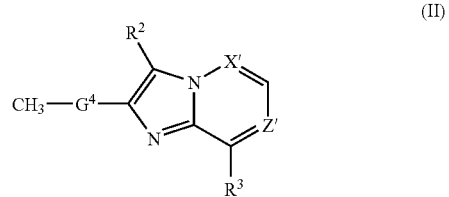

(II)

(wherein X' and Z' are independent of each other and each denotes N or CH (in this case, at least one of X' and Z' denotes CH); and $G^4$, $R^2$ and $R^3$ have the same meanings as defined above) or a salt thereof; (17) the compound described in the above (16) or a salt thereof, wherein $R^2$ is —NR$^{2aa}$R$^{2bb}$ (wherein R$^{2aa}$ and R$^{2bb}$ are independent of each other and each denotes a hydrogen atom, a $C_{1-8}$ alkyl group, a $C_{2-8}$ alkenyl group, a $C_{2-6}$ alkynyl group, a $C_{1-6}$ alkyl group which may be substituted with a 5- to 14-membered non-aromatic heterocyclic group, a $C_{1-8}$ alkoxy group, a $C_{1-8}$ alkoxy $C_{1-8}$ alkyl group, a $C_{1-6}$ alkylsulfinyl group, a $C_{1-6}$ alkylsulfonyl group, a $C_{3-8}$ cycloalkyl group, a $C_{3-8}$ cycloalkyl $C_{1-6}$ alkyl group or a 5- to 14-membered heterocyclic group, and further, the R$^{2aa}$ and R$^{2bb}$ are independent of each other and each may be substituted with a halogen atom) (18) the compound described in the above (16) or a salt thereof, wherein $R^2$ is a di($C_{1-6}$ alkyl)amino group; (19) the compound described in the above (16) or a salt thereof, wherein $R^3$ is a phenyl group or a pyridyl group, each of which may be substituted; (20) the compound described in the above (16) or a salt thereof, wherein $R^3$ is a phenyl group or a pyridyl group, each of which may be substituted with 1 to 4 group(s) selected from a halogen group, a $C_{1-6}$alkyl group, a halogeno-$C_{1-6}$alkyl group, a halogeno-$C_{1-6}$alkoxy group, a $C_{1-6}$alkoxy group, a $C_{1-6}$alkylthio group and a 5- to 8-membered aromatic heterocyclic group; (21) the compound described in the above (1) which is represented by the following formula:

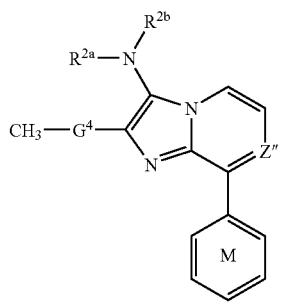

(wherein Z' denotes N or CH; the ring M denotes a benzene ring which may further have a substituent; and $G^4$, $R^{2a}$ and $R^{2b}$ have the same meanings as defined above) or a salt thereof; (22) the compound described in the above (21) or a salt thereof, wherein $R^{2a}$ and $R^{2b}$ are independent of each other and each represents a hydrogen atom, a $C_{1-8}$ alkyl group, a $C_{2-8}$ alkenyl group, a $C_{2-6}$ alkynyl group, a $C_{1-6}$ alkyl group which may be substituted with a 5- to 14-membered non-aromatic heterocyclic group, a $C_{1-8}$ alkoxy $C_{1-8}$ alkyl group, a $C_{3-8}$ cycloalkyl group or a $C_{3-8}$ cycloalkyl $C_{1-6}$ alkyl group, and further, each of which may be substituted with a halogen atom; (23) the compound described in the above (21) or a salt thereof, wherein $R^{2a}$ and $R^{2b}$ are a $C_{1-6}$ alkyl group; (24) the compound described in the above (21) or a salt thereof, wherein the ring M is a benzene ring which may be further substituted with 1 to 3 group(s) selected from a halogen atom, a $C_{1-6}$alkyl group, a $C_{1-6}$alkoxy group, a halogeno-$C_{1-6}$alkyl group and a halogeno-$C_{1-6}$alkoxy group; (25) the compound described in the above (1) or a salt thereof, wherein the compound is N-(2-ethyl-8-mesitylimidazo[1,2-a]pyrazin-3-yl)-N,N-dipropylamine hydrochloride, N-(2-ethyl-8-mesitylimidazo[1,2-a]pyrazin-3-yl)-N-(1-ethylpropyl)amine, N-[8-(2-chloro-4-methoxyphenyl)-2-ethylimdazo[1,2-a]pyrazin-3-yl]-N,N-dipropylamine hydrochloride, N-cyclopropylmethyl-N-[8-(2,4-dichloropheyl)-2-ethylimidazo[1,2-a]pyrazin-3-yl]-N-isobutylamine, N-[8-(2,4-dichlorophenyl)-2-ethylimidazo[1,2-a]pyrazin-3-yl]-N-propyl-N-tetrahydro-3-thiophenylamine, N3,N3-dipropyl-2-isopropyl-8-(2-methoxy-4,6-dimethylphenyl)imidazo[1,2-a]pyrazin-3-amine, N-[2-ethyl-8-(6-methyl-1,3-benzodioxol-5-yl)imidazo[1,2-a]pyrazin-3-yl]-N,N-dipropylamine, N-[2-ethyl-8-(4-methoxy-2,5-dimethylphenyl)imidazo[1,2-a]pyrazin-3-yl]-N,N-dipropylamine, N-cyclopropylmethyl-N-[8-(2,4-dichlorophenyl)-2-ethylimidazo[1,2-a]pyrazin-3-yl]-N-(2-methoxyethyl)amine hydrochloride, N-[8-(2-chloro-4-methoxyphenyl)-2-ethylimidazo[1,2-a]pyrazin-3-yl]-N,N-dicyclopropylmethylamine, N-8-[5-chloro-4-(2,5-dimethyl-1H-1-pyrroyl)-2methoxyphenyl]-2-ethylimidazo[1,2-a]pyrazin-3-yl-N,N-dicyclopropylmethylamine, N-[8-(2,4-dichlorophenyl)-2-ethyl-6-methylimidazo[1,2-a]pyrazin-3-yl]-N,N-dipropylamine hydrochloride, N3,N3-dipropyl-5-bromo-8-(2,4-dichlorophenyl)-2-ethylimidazo[1,2-a]pyrazin-3-amine, 8-(2,4-dichlorophenyl)-3-(dipropylamino)-2-ethylimidazo[1,2-a]pyrazin-6-yl cyanide, N-[8-(2,4-dichlorophenyl)-2-ethyl-6-methoxyimidazo[1,2-a]pyrazin-3-yl]-N,N-dipropylamine, N-[6-chloro-2-ethyl-8-(2-methoxy-4,6-dimethylphenyl)imidazo[1,2-a]pyrazin-3-yl]-N,N-dipropylamine, N3,N3-dipropyl-8-(2,4-dichlorophenyl)-2-(methylsulfanyl)imidazo[1,2-a]pyrazin-3-amine, N,N-dicyclopropylmethyl-N-[8-(2-methoxy-4,6-dimethylphenyl)-2-(methylsulfanyl)imidazo[1,2-a]pyrazin-3-yl]amine, N-[8-(2-chloro-4-methoxyphenyl)-2-(methylsulfanyl)imidazo[1,2-a]pyrazin-3-yl]-N-cyclopropylmethyl-N-propylamine, N-[8-(2-bromo-4-methoxyphenyl)-2-(methylsulfanyl)imidazo[1,2-a]pyrazin-3-yl]-N-cyclopropylmethyl-N-(3-fluoropropyl)amine, N-[8-(2-chloro-6-methoxy-4-methylphenyl)-2-(methylsulfanyl)imidazo[1,2-a]pyrazin-3-yl]-N,N-dicyclopropylmethylamine, N-[8-(2-chloro-4-methoxyphenyl)-2-(methylsulfanyl)imidazo[1,2-a]pyrazin-3-yl]-N-cyclopropylmethyl-N-isobutylamine, N-cyclopropylmethyl-N-[8-[2-methyl-4-(methylsulfinyl)phenyl]-2-(methylsulfinyl)imidazo[1,2-a]pyrazin-3-yl]-N-propylamine, N-[8-(2-chloro-4-methoxyphenyl)-2-(methylsulfonyl)imidazo[1,2-a]pyrazin-3-yl]-N-cyclopropylmethyl-N-propylamine, N-[8-[2-chloro-4-(trifluoromethoxy)phenyl]-2-(methylsulfanyl)imidazo[1,2-a]pyrazin-3-yl]-N,N-dicyclopropylmethylamine, 1-[[8-[2-chloro-4-(trifluoromethoxy)phenyl]-2-(methylsulfanyl)imidazo[1,2-a]pyrazin-3-yl](cyclopropylmethyl)amino]-2-propanol, 2-[[8-[2-chloro-4-(trifluoromethoxy)phenyl]-2-(methylsulfanyl)imidazo[1,2-a]pyrazin-3-yl](cyclopropylmethyl)amino]acetamide, 4-[3-[di(cyclopropylmethyl)amino]-2-(methylsulfanyl)imidazo[1,2-a]pyrazin-8-yl]-3-methoxybenzonitrile, N,N-dicyclopropylmethyl-N-[8-(2-methoxy-4-tetrahydro-1H-1-pyrrolylphenyl)-2-(methylsulfanyl)imidazo[1,2-a]pyrazin-3-yl]amine, N2-[8-[2-chloro-4-(trifluoromethoxy)phenyl]-2-(methylsulfanyl)imidazo[1,2-a]pyrazin-3-yl]-N2-cyclopropylmethyl-2-furamide, N-[8-[2-chloro-4-(trifluoromethoxy)phenyl]-2-(methylsulfanyl)imidazo[1,2-a]pyrazin-3-yl]-N-cyclopropylmethyl-N-(2-furylmethyl)amine, N-[8-[2-chloro-4-(trifluoromethoxy)phenyl]-2-(methylsulfanyl)imidazo[1,2-a]pyrazin-3-yl]-N-cyclopropylmethyl-N-(2-morpholinoethyl)amine, N-[8-[2-chloro-4-(trifluoromethoxy)phenyl]-2-(methylsulfanyl)imidazo[1,2-a]pyrazin-3-yl]-N-cyclopropylmethyl-N-[2-(1H-1-pyrazoyl)ethyl]amine, N-[8-[2-chloro-4-(trifluoromethoxy)phenyl]-2-(methylsulfanyl)imidazo[1,2-a]pyrazin-3-yl]-N-cyclopropylmethyl-N-[2-(1H-1-imidazoyl)ethyl]amine, 2-[2-ethyl-3-(1-ethylpropyl)imidazo[1,2-a]pyrazin-8-yl]-3,5-dimethylphenyl methyl ether, 3-(1-ethoxybutyl)-2-ethyl-8-(2-methoxy-4,6-dimethylphenyl)imidazo[1,2-a]pyrazine, 1-[8-(2-chloro-4-methoxyphenyl)-2-ethylimidazo[1,2-a]pyrazin-3-yl]-1-butanone O1-methyloxime, 3-(1-ethoxybutyl)-8-(2-methoxy-4,6-dimethylphenyl)-2-(methylsulfanyl)imidazo[1,2-a]pyrazine, N-[8-(2-chloro-4-methoxyphenyl)-2-methoxyimidazo[1,2-a]pyrazin-3-yl]-N-cyclopropylmethyl-N-propylamine, N-[2-ethyl-8-(4-methoxy-2-methylphenyl)imidazo[1,2-b]pyridazin-3-yl]-N,N-dipropylamine,
N-[2-ethyl-8-(2-methoxy-4,6-dimethylphenyl)imidazo[1,2-b]pridazin-3-yl]-N,N-dipropylamine,
N,N-dicyclopropylmethyl-N-[2-ethyl-8-(2-methoxy-4,6-dimethylphenyl)imidazo[1,2-b]pyridazin-3-yl]amine,
N-[8-(4-methoxy-2-methylphenyl)-2-(methylsulfanyl)imidazo[1,2-b]pyridazin-3-yl]-N,N-dipropylamine,
N-[8-(2,4-dichlorophenyl)-2-(methylsulfanyl)imidazo[1,2-a]pyridin-3-yl]-N,N-dipropylamine,
N-[8-(2-methoxy-4,6-dimethylphenyl)-2-(methylsulfanyl)imidazo[1,2-a]pyridin-3-yl]-N,N-dipropylamine,
N-[8-(2,6-dimethoxy-4-methylphenyl)-2-(methylsulfanyl)imidazo[1,2-a]pyridin-3-yl]-N,N-dipropylamine,
N-[8-(2,4-dimethoxy-6-methylphenyl)-2-(methylsulfanyl)imidazo[1,2-a]pyridin-3-yl]-N,N-dipropylamine,
N-[8-(2-chloro-6-methoxy-4-methylphenyl)-2-(methylsulfanyl)imidazo[1,2-a]pyridin-3-yl]-N,N-dipropylamine,
N-[8-(2,4-dichlorophenyl)-2-(methylsulfanyl)imidazo[1,2-a]pyridin-3-yl]-N-propyl-N-(2-propynyl)amine,
N-[8-(4-chloro-2-methoxyphenyl)-2-(methylsulfanyl)imidazo[1,2-a]pyridin-3-yl]-N,N-dipropylamine,
N-[8-(2,6-dimethoxy-4-methylphenyl)-2-(methylsulfanyl)imidazo[1,2-a]pyridin-3-yl]-N-propyl-N-(3-thienyl)amine,
N-[8-(4-methoxy-2-methylphenyl)-2-(methylsulfanyl)imidazo[1,2-a]pyridin-3-yl]-N,N-dipropylamine,
N-cyclobutylmethyl-N-[8-(2,6-dimethoxy-4-methylphenyl)-2-(methylsulfanyl)imidazo[1,2-a]pyridin-3-yl]-N-propylamine,
N-[8-(4-chloro-2,6-dimethoxyphenyl)-2-(methylsulfanyl)imidazo[1,2-a]pyridin-3-yl]-N,N-dipropylamine,
N-[8-(4-chloro-2,6-dimethoxyphenyl)-2-(methylsulfanyl)imidazo[1,2-a]pyridin-3-yl]-N-cyclobutylmethyl-N-propylamine,
N-butyl-N-cyclobutylmethyl-N-[8-(2,6-dimethoxy-4-methylphenyl)-2-(methylsulfanyl)imidazo[1,2-a]pyridin-3-yl]amine,
N-cyclobutylmethyl-N-cyclopropylmethyl-N-[8-(2,6-dimethoxy-4-methylphenyl)-2-(methylsulfanyl)imidazo[1,2-a]pyridin-3-yl]amine,
N3,N3-dipropyl-8-[6-(dimethylamino)-4-methyl-3pyridyl]-2-(methylsulfanyl)imidazo[1,2-a]pyridin-3-amine,
N-[8-(2,6-dimethoxy-4-methylphenyl)-2-(methylsulfanyl)imidazo[1,2-a]pyridin-3-yl]-N-propyl-N-tetrahydro-2H-4-pyranylamine,
N3-cyclobutylmethyl-N-3-propyl-8-[6-(dimethylamino)-4-methyl-3-pyridyl]-2-(methylsulfanyl)imidazo[1,2-a]pyridin-3-amine,
N3-cyclobutylmethyl-N-3-(3-fluoropropyl)-8-[6-(dimethylamino)-4-methyl-3-pyridyl]-2-(methylsulfanyl)imidazo[1,2-a]pyridin-3-amine,
N3,N3-dicyclopropylmethyl-8-[6-(dimethylamino)-4-methyl-3-pyridyl]-2-(methylsulfanyl)imidazo[1,2-a]pyridin-3-amine,
N3-propyl-N-3-tetrahydro-2H-4-pyranyl-8-[6-(dimethylamino)-4-methyl-3-pyridyl]-2-(methylsulfanyl)imidazo[1,2-a]pyridin-3-amine,
N-[8-(2,6-dimethoxy-4-methylphenyl)-2-(methylsulfanyl)imidazo[1,2-a]pyridin-3-yl]-N-cyclobutylmethyl-N-tetrahydro-2H-4-pyranylamine, or
N-cyclopropylmethyl-N-[8-(2,6-dimethoxy-4-methylphenyl)-2-(methylsulfanyl)imidazo[1,2-a]pyridin-3-yl]-N-tetrahydro-2H-4-pyranylamine;

(26) a pharmaceutical composition comprising the compound described in the above (1) or a salt thereof, and a pharmacologically acceptable carrier; (27) the composition described in the above (26), which is an agent for treating or preventing a disease to which corticotrophin-releasing factor (hereinafter, referred to as "CRF") and/or a CRF receptor relate; (28) the composition described in the above (26), which is a CRF receptor antagonist; (29) the composition described in the above (26), which is an antagonist for a CRF1 receptor or CRF2 receptor; (30) the composition described in the above (26), which is an agent for treating or preventing depression, depressive symptom, mania, anxiety, generalized anxiety disorder, panic disorder, phobia, compulsive disorder, posttraumatic stress disorder, Tourette syndrome, autism, emotional disorder, sentimental disorder, bipolar disorder, cyclothymia or schizophrenia; (31) the composition described in the above (30), which is an agent for treating or preventing depressive symptoms which is great depression, monostotic depression, recurrent depression, infant tyrannism by depression or postpartum depression; (32) the composition described in the above (26), which is an agent for treating or preventing peptic ulcer, irritable bowel syndrome, ulcerative colitis, Crohn's disease, diarrhea, coprostasis, postoperational ileus, gastrointestinal function abnormality associated with stress or neural vomiting; (33) the composition described in the above (26), which is an agent for treating or preventing Alzheimer's disease, Alzheimer-type senile dementia, neurodegenerative disease, multi-infarct dementia, senile dementia, neurotic anorexia, diet disorder, obesity, diabetes, alcohol dependence, pharmacophilia, drug abstinence symptoms, alcohol abstinence symptoms, sleep disorder, insomnia, migraine, stress headache, myotonic headache, ischemic neuropathy, excitation toxic neuropathy, cerebral apoplexy, progressive supranuclear palsy, amyotrophic lateral sclerosis, multiple sclerosis, muscular convulsion, chronic fatigue syndrome, mental social growth failure, epilepsy, head trauma, spinal trauma, graphospasm, spasmodic torticollis, muscular convulsion, neck-shoulder-arm syndrome, primary glaucoma, Meniere syndrome, autonomic imbalance, alopecia, neurosis, hypertension, cardiovascular disorder, tachycardia, congestive cardioplegia, hyperpnea syndrome, bronchial asthma, apnea syndrome, infant sudden death syndrome, inflammatory disorder, pain, allergic disease, impotence, climacteric disorder, fertilization disorder, infertility, cancer, immune function abnormality upon infection with HIV, immune function abnormality by stress, hemorrhagic stress, Cushing syndrome, thyroid function disorder, encephalomyelitis, acromegaly, incontinence or osteoporosis; (34) use of the compound described in the above (1) or a salt thereof for producing an antagonist for a CRF receptor; (35) use of the compound described in the above (1) or a salt thereof for producing an antagonist for a CRF1 receptor or a CRF2 receptor; (36) use of the compound described in the above (1) or a salt thereof for producing an agent for treating or preventing depression, depressive symptom, mania, anxiety, generalized anxiety disorder, panic disorder, phobia, compulsive disorder, posttraumatic stress disorder, Tourette syndrome, autism, emotional disorder, sentimental disorder, bipolar disorder, cyclothymia, schizophrenia, peptic ulcer, irritable bowel syndrome, ulcerative colitis, Crohn's disease, diarrhea, coprostasis, postoperational ileus, gastrointestinal function abnormality associated with stress or neural vomiting; (37) a method for treating or preventing a disease to which a CRF receptor relate, which comprises administering a therapeutically effective amount of the compound described in the above (1) or a salt thereof once or multiple times to a patient who is suffering from a disease to which a CRF receptor relate; (38) a medicine comprising the compound described in the above (1) or a salt thereof as the active ingredient; (39) the medicine described in the above (38), which is an agent for treating or preventing a disease to which a CRF and/or CRF receptor relate; (40) the medicine described in the above (38), which is a CRF receptor antagonist; (41) the medicine described in the above (38), which is an antagonist for a CRF1 receptor or a CRF2 receptor; (42) the medicine described in the above (38), which is an agent for treating or preventing depressive symptom, mania, anxiety, generalized anxiety disorder, panic disorder, phobia, compulsive disorder, posttraumatic stress disorder, Tourette syndrome, autism, emotional disorder, sentimental disorder, bipolar disorder, cyclothymia or schizophrenia; (43) the medicine described in the above (42), which is an agent for treating or preventing depressive symptoms which is great depression, monostotic depression, recurrent depression, infant tyrannism by depression or postpartum depression; (44) the medicine described in the above (38), which is an agent for treating or preventing peptic ulcer, irritable bowel syndrome, ulcerative colitis, Crohn's disease, diarrhea, coprostasis, postoperational ileus, gastrointestinal function abnormality associated with stress or neural vomiting; (45) the medicine described in the above (38), which is an agent for treating or preventing Alzheimer's disease, Alzheimer-type senile dementia, neurodegenerative disease, multi-infarct dementia, senile dementia, neurotic anorexia, diet disorder, obesity, diabetes, alcohol dependence, pharmacophilia, drug abstinence symptoms, alcohol abstinence symptoms, sleep disorder, insomnia, migraine, stress headache, myotonic headache, ischemic neuropathy, excitation toxic neuropathy, cerebral apoplexy, progressive supranuclear palsy, amyotrophic lateral sclerosis, multiple sclerosis, muscular convulsion, chronic fatigue syndrome, mental social growth failure, epilepsy, head trauma, spinal trauma, graphospasm, spasmodic torticollis, muscular convulsion, neck-shoulder-arm syndrome, primary glaucoma, Meniere syndrome, autonomic imbalance, alopecia, neurosis, hypertension, cardiovascular disorder, tachycardia, congestive cardioplegia, hyperpnea syndrome, bronchial asthma, apnea syndrome, infant sudden death syndrome, inflammatory disorder, pain, allergic disease, impotence, climacteric disorder, fertilization disorder, infertility, cancer, immune function abnormality upon infection with HIV, immune function abnormality by stress, hemorrhagic stress, Cushing syndrome, thyroid function disorder, encephalomyelitis, acromegaly, incontinence or osteoporosis; (46) use of the compound described in the above (1) or a salt thereof, for producing an agent for treating or preventing a disease to which a CRF and/or CRF receptor relate; (47) the use described in the above (36), wherein the depressive symptom is great depression, monostotic depression, recurrent depression, infant tyrannism by depression or postpartum depression; (48) use of the compound described in the above (1) or a salt thereof, for producing an agent for treating or preventing Alzheimer's disease, Alzheimer-type senile dementia, neurodegenerative disease, multi-infarct dementia, senile dementia, neurotic anorexia, diet disorder, obesity, diabetes, alcohol dependence, pharmacophilia, drug abstinence symptoms, alcohol abstinence symptoms, sleep disorder, insomnia, migraine, stress headache, myotonic headache, ischemic neuropathy, excitation toxic neuropathy, cerebral apoplexy, progressive supranuclear palsy, amyotrophic lateral sclerosis, multiple sclerosis, muscular convulsion, chronic fatigue syndrome, mental social growth failure, epilepsy, head trauma, spinal trauma, graphospasm, spasmodic torticollis, muscular convulsion, neck-shoulder-arm syndrome, primary glaucoma, Meniere syndrome, autonomic imbalance, alopecia, neurosis, hypertension, cardiovascular disorder, tachycardia, congestive cardioplegia, hyperpnea syndrome, bronchial asthma, apnea syndrome, infant sudden death syndrome, inflammatory disorder, pain, allergic disease, impotence, climacteric disorder, fertilization disorder, infertility, cancer, immune function abnormality upon infection with HIV, immune function abnormality by stress, hemorrhagic stress, Cushing syndrome, thyroid function disorder, encephalomyelitis, acromegaly, incontinence or osteoporosis; (49) a method for treating or preventing a disease to which a CRF and/or CRF receptor relate, by administering a pharmacologically effective amount of the compound described in the above (1) or a salt thereof to a patient; (50) a method for treating or preventing a disease against which the CRF receptor antagonistic activity is efficacious for treatment or prevention, by administering a pharmacologically effective amount of the compound described in the above (1) or a salt thereof to a patient; (51) a method for treating or preventing a disease against which a CRF1 receptor or CRF2 receptor antagonistic activity is efficacious for treatment or prevention, by administering a pharmacologically effective amount of the compound described in the above (1) or a salt thereof to a patient; (52) a method for treating or preventing depression, depressive symptom, mania, anxiety, generalized anxiety disorder, panic disorder, phobia, compulsive disorder, posttraumatic stress disorder, Tourette syndrome, autism, emotional disorder, sentimental disorder, bipolar disorder, cyclothymia, schizophrenia, peptic ulcer, irritable bowel syndrome, ulcerative colitis, Crohn's disease, diarrhea, coprostasis, postoperational ileus, gastrointestinal function abnormality associated with stress or neural vomiting, by administering a pharmacologically effective amount of the compound according to claim 1 or a salt thereof to a patient; (53) the method described in the above (52), wherein the depressive symptom is great depression, monostotic depression, recurrent depression, infant tyrannism by depression or postpartum depression; and (54) a method for treating or preventing Alzheimer's disease, Alzheimer-type senile dementia, neurodegenerative disease, multi-infarct dementia, senile dementia, neurotic anorexia, diet disorder, obesity, diabetes, alcohol dependence, pharmacophilia, drug abstinence symptoms, alcohol abstinence symptoms, sleep disorder, insomnia, migraine, stress headache, myotonic headache, ischemic neuropathy, excitation toxic neuropathy, cerebral apoplexy, progressive supranuclear palsy, amyotrophic lateral sclerosis, multiple sclerosis, muscular convulsion, chronic fatigue syndrome, mental social growth failure, epilepsy, head trauma, spinal trauma, graphospasm, spasmodic torticollis, muscular convulsion, neck-shoulder-arm syndrome, primary glaucoma, Meniere syndrome, autonomic imbalance, alopecia, neurosis, hypertension, cardiovascular disorder, tachycardia, congestive cardioplegia, hyperpnea syndrome, bronchial asthma, apnea syndrome, infant sudden death syndrome, inflammatory disorder, pain, allergic disease, impotence, climacteric disorder, fertilization disorder, infertility, cancer, immune function abnormality upon infection with HIV, immune function abnormality by stress, hemorrhagic stress, Cushing syndrome, thyroid function disorder, encephalomyelitis, acromegaly, incontinence or osteoporosis, by administering a pharmacologically effective amount of the compound described in the above (1) or a salt thereof to a patient.

The meanings of symbols, terms and the like described in the present specification will be explained below and the present invention will be explained in detail.

In the present specification, the structural formula of the compound represents a certain isomer for convenience in some cases, but the present invention includes all isomers such as geometrical isomer, optical isomer based on an asymmetrical carbon, stereoisomer, tautomer and the like which occur structurally and an isomer mixture and is not limited to the description of the formula for convenience, and may be any one of isomer or a mixture. Therefore, an asymmetrical carbon atom may be present in the molecule and an optically active compound and a racemic compound may be present in the present compound, but the present invention is not limited to them and includes any one. In addition, a crystal polymorphism may be present but is not limiting, but any crystal form may be single or a crystal form mixture, or an anhydride or hydrate. Further, so-called metabolite which is produced by degradation of the present compound in vivo is included in the scope of the present invention.

As used herein, 'neural degenerative disease' means acute degenerative disease or chronic degenerative disease, specifically, means neural disorder derived from subarachnoidal hemorrhage, cerebrovascular disorder acute phase and the like, Alzheimer's disease, Parkinson's disease, Huntington's chorea, amyotrophic lateral sclerosis, spinal cerebellar degenerative disease and the like. As used herein, 'diet disorder' means appetite sthenia, cibophobia and the like. As used herein, 'cardiovascular disorder' means neural angina and the like. As used herein, 'inflammatory disorder' menas, for example, rheumatoid arthritis, bone arthritis, lumbago and the like. 'Allergy disease' denotes, for example, atopic dermatis, eczema, urticaria, psoriasis and the like.

The "halogen atom" in the present specification denotes a fluorine atom, a chlorine atom, a bromine atom, an iodine atom, and the like, preferably a fluorine atom, a chlorine atom, and a bromine atom.

The "$C_{1-6}$ alkyl group" used in the present specification denotes an alkyl group having a carbon number of 1 to 6, and preferably, a methyl group, an ethyl group, an n-propyl group, an iso-propyl group, an n-butyl group, an iso-butyl group, a sec-butyl group, a tert-butyl group, an n-pentyl group, a 1,1-dimethylpropyl group, a 1,2-dimethylpropyl group, a 2,2-dimethylpropyl group, a 1-ethylpropyl group, a 2-ethylpropyl group, an n-hexyl group, a 1-methyl-2-ethylpropyl group, a 1-ethyl-2-methylpropyl group, a 1,1,2-trimethylpropyl group, a 1-propylpropyl group, a 1-methylbutyl group, a 2-methylbutyl group, a 1,1-dimethylbutyl group, a 1,2-dimethylbutyl group, a 2,2-dimethylbutyl group, a 1,3-dimethylbutyl group, a 2,3-dimethylbutyl group, a 2-ethylbutyl group, a 2-methylpentyl group, a 3-methylpentyl group, and the like may be proposed.

The "n-" in the present specification denotes normal, "sec-" denotes secondary, and "tert-" denotes tertiary, respectively.

The "$C_{2-6}$ alkenyl group" used in the present specification denotes an alkenyl group having a carbon number of 2 to 6, and examples of the preferable group include a vinyl group, an allyl group, a 1-propenyl group, a 2-propenyl group, an isopenyl group, a 2-methyl-1-propenyl group, a 3-methyl-1-propenyl group, a 2-methyl-2-propenyl group, a 3-methyl-2-propenyl group, a 1-butenyl group, a 2-butenyl group, a 3-butenyl group, a 1-pentenyl group, a 1-hexenyl group, a 1,3-hexanedienyl group, a 1,6-hexanedienyl group, and the like.

The "$C_{2-6}$ alkynyl group" used in the present specification denotes an alkynyl group having a carbon number of 2 to 6, and preferable examples of the group include an ethynyl group, a 1-propynyl group, a 2-propynyl group, a 1-butynyl group, a 2-butynyl group, a 3-butynyl group, a 3-methyl-1-propynyl group, a 1-ethynyl-2-propynyl group, a 2-methyl-3-propynyl group, a 1-pentynyl group, a 1-hexynyl group, a 1,3-hexanediynyl group, a 1,6-hexanediynyl group, and the like.

The "$C_{3-8}$ cycloalkyl group" in the present specification denotes a cycloalkyl group formed by 3 to 8 carbon atoms, and examples thereof include a cyclopropyl group, a cyclobutyl group, a cyclopentyl group, a cyclohexyl group, a cycloheptyl group, a cyclooctyl and the like. Examples of the $C_{3-8}$ cycloalkenyl group in the present specification include a 2-cyclopropen-1-yl group, a 3-cyclopropenyl group, a 1-cyclobutenyl group, a 4-cyclobutenyl group, a cyclopentenyl group, a cyclohexenyl group, a cycloheptenyl group, a cyclooctenyl group, and the like.

The "$C_{1-6}$ alkoxy group" used in the present specification denotes an alkoxy group having a carbon number of 1 to 6, such as a methoxy group, an ethoxy group, a n-propoxy group, an iso-propoxy group, a sec-propoxy group, an n-butoxy group, an iso-butoxy group, a sec-butoxy group, a tert-butoxy group, a n-pentyloxy group, an iso-pentyloxy group, a sec-pentyloxy group, a n-hexoxy group, an iso-hexoxy group, a 1,1-dimethylpropyloxy group, a 1,2-dimethylpropoxy group, a 2,2-dimethylpropyloxy group, a 2-ethylpropoxy group, a 1-methyl-2-ethylpropoxy group, a 1-ethyl-2-methylpropoxy group, a 1,1,2-trimethylpropoxy group, a 1,1,2-trimethylpropoxy group, a 1,1-dimethylbutoxy group, a 1,2-dimethylbutoxy group, a 2,2-dimethylbutoxy group, a 2,3-dimethylbutyloxy group, a 1,3-dimethylbutyloxy group, a 2-ethylbutoxy group, a 1,3-dimethylbutoxy group, a 2-methylpentoxy group, a 3-methylpentoxy group, a hexyloxy group, and the like.

The "$C_{2-6}$ alkenyloxy group" used in the present specification denotes an alkenyloxy group having a carbon number of 2 to 6, such as a vinyloxy group, an allyloxy group, a 1-propenyloxy group, a 2-propenyloxy group, an isopropenyloxy group, a 2-methyl-1-propenyloxy group, a 3-methyl-1-propenyloxy group, a 2-methyl-2-propenyloxy group, a 3-methyl-2-propenyloxy group, a 1-butenyloxy group, a 2-butenyloxy group, a 3-butenyloxy group, a 1-pentenyloxy group, a 1-hexenyloxy group, a 1,3-hexanedienyloxy group, a 1,6-hexanedienyl group, and the like.

The "$C_{1-6}$ alkylthio group" used in the present specification denotes an alkylthio group having a carbon number of 1 to 6. For example, a methylthio group, an ethylthio group, a n-propylthio group, an iso-propylthio group, a n-butylthio group, an iso-butylthio group, a sec-butylthio group, a tert-butylthio group, a n-pentylthio group, a 1,1-dimethylpropylthio group, a 1,2-dimethylpropylthio group, a 2,2-dimethylpropylthio group, a 1-ethylpropylthio group, a 2-ethylpropylthio group, a n-hexyl group, a 1-methyl-2-ethylpropylthio group, a 1-ethyl-2-methylpropylthio group, a 1,1,2-trimethylpropylthio group, a 1-propylpropylthio group, a 1-methylbutylthio group, a 2-methylbutylthio group, a 1,1-dimethylbutylthio group, a 1,2-dimethylbutylthio group, a 2,2-dimethylbutylthio group, a 1,3-dimethylbutylthio group, a 2,3-dimethylbutylthio group, a 2-ethylbutylthio group, a 2-methylpentylthio group, a 3-methylpentylthio group, and the like may be proposed.

The "a $C_{2-6}$ alkenylthio group" used in the present specification denotes an alkenylthio group having a carbon number of 2 to 6. For example, a vinylthio group, an allylthio group, a 1-propenylthio group, a 2-propenylthio group, an isopropenylthio group, a 2-methyl-1-propenylthio group, a 3-methyl-1-propenylthio group, a 2-methyl-2-propenylthio group, a 3-methyl-2-propenylthio group, a 1-butenylthio group, a 2-butenylthio group, a 3-butenylthio group, a 1-pentenylthio group, a 1-hexenylthio group, a 1,3-hexanedienylthio group, a 1,6-hexanedienylthio group, and the like may be proposed.

The $C_{6-14}$ aromatic hydrocarbon cyclic group in the "$C_{6-14}$ aromatic hydrocarbon cyclic group optionally having a substituent" used in the present specification refers to an aromatic hydrocarbon cyclic group having a carbon number of 6 to 14, and includes a fused ring such as a dicyclic group, a tricyclic group and the like in addition to a monocyclic group. Preferable examples of the group include a phenyl group, an indenyl group, a 1-naphthyl group, a 2-naphthyl group, an azulenyl group, a heptalenyl group, biphenyl group, an indacenyl group, an acenaphthyl group, a fluorenyl group, a phenalenyl group, a phenanthrenyl group, an anthracenyl group, a cyclopentacyclooctenyl group, a benzocyclooctenyl and the like.

The "allyl" and "aryl group" used in the present specification denote have the same meanings as the $C_{6-14}$ aromatic hydrocarbon cyclic group.

The 5- to 14-membered aromatic heterocyclic group in the "5- to 14-membered aromatic heterocyclic group optionally having a substituent" used in the present specification refers to a monocyclic, dicyclic or tricyclic 5- to 14-membered aromatic heterocyclic group containing at least one hetero atom selected from a nitrogen atom, a sulfur atom and an oxygen atom. Preferable examples of the group include, as the nitrogen-containing aromatic heterocyclic group, a pyrrolyl group, a pyridyl group, a pyridazinyl group, a pyrimidinyl group, a pyrazinyl group, a triazolyl group, a tetrazolyl group, a benzotriazolyl group, a pyrazolyl group, an imidazolyl group, a benzimidazolyl group, an indolyl group, an isoindolyl group, an indolizinyl group, a purinyl group, an indazolyl group, a quinolyl group, an isoquinolyl group, a quinolizyl group, a phthalazyl group, a naphthyridinyl group, a quinoxalyl group, a quinazolinyl group, a cinnolinyl group, a pteridinyl group, an imidazotriazinyl group, a pyrazinopyridazinyl group, an acridinyl group, a phenanthridinyl group, a carbazolyl group, a carbazolinyl group, a pyrimidinyl group, a phenanthrolinyl group, a phenacinyl group, an imidazopyridinyl group, an imidazopyrimidinyl group, a pyrazolopyridinyl group, a pyrazolopyridinyl group, and the like; as the sulfur-containing aromatic heterocyclic group, a thienyl group, a benzothienyl group, and the like; as the oxygen-containing aromatic heterocyclic group, a furyl group, a pyranyl group, a cyclopentapyranyl group, a benzofuryl group, an isobenzofuryl group, and the like; as the aromatic heterocyclic group containing two or more different hetero atoms, a thiazolyl group, an isothiazolyl group, a benzothiazolyl group, a benzthiadiazolyl group, a phenothiazinyl group, an isoxazolyl group, a furazanyl group, a phenoxazinyl group, an oxazolyl group, an isoxazolyl group, a benzoxazolyl group, oxadiazolyl group, a pyrazolooxazolyl group, an imidazothiazolyl group, a thienofuranyl group, a furopyrrolyl group, a pridoxazinyl group, and the like.

The "heteroaryl" and "heteroaryl group" used in the present specification have the same meanings as the 5- to 14-membered aromatic heterocyclic group.

The "5- to 14-membered non-aromatic heterocyclic group" used in the present specification refers to a a saturated or unsaturated, monocyclic, dicyclic or tricyclic 5- to 14-membered non-aromatic heterocyclic group having aromatic property and containing at least one hetero atom selected from a nitrogen atom, a sulfur atom and an oxygen atom. Preferable examples of the group include a pyrrolidinyl group, a pyrrolyl group, a piperidinyl group, a piperazinyl group, an imidazolyl group, a pyrazolidyl group, an imidazolidyl group, a morpholyl group, a pyranyl group, a tetrahydrofuryl group, a tetrahydropyranyl group, a pyrrolinyl group, a dihydrofuryl group, a dihydropyranyl group, an imidazolinyl group, an oxazolinyl group, and the like. In addition, the group includes groups derived from a pyridone ring, and groups derived from a non-aromatic fused ring (e.g. phthalimide ring, succinimide ring etc.).

The "5- to 14-membered heterocyclic group" used in the present specification denotes a 5- to 14-membered aromatic or non-aromatic heterocyclic group, and the meaning of each word is as defined above.

The "$C_{2-7}$ aliphatic acyl group" denotes an atomic entity obtained by removing a OH group from a carboxyl group of a $C_{2-7}$ aliphatic saturated carboxylic acid or $C_{2-7}$ aliphatic unsaturated carboxylic acid, and the preferable examples of the group include an acetyl group, a propionyl group, a butyroyl group, and the like.

The "$C_{1-6}$ alkylsulfinyl group" used in the present specification denotes a sulfinyl group to which the above-mentioned $C_{1-6}$ alkyl group is bound, and examples thereof include a methylmethylsulfinyl group, an ethylsulfinyl group, a n-propylsulfinyl group, an iso-propylsulfinyl group, and the like.

The "$C_{1-6}$ alkylsulfonyl group" used in the present specification denotes a sulfonyl group to which the above-mentioned $C_{1-6}$ alkyl group is bound, and examples thereof include a methylmethylsulfonyl group, an ethylsulfonyl group, a n-propylsulfonyl group, an iso-propylsulfonyl group, and the like.

The "$C_{3-8}$ cycloalkyl $C_{1-6}$ alkyl group" and "$C_{3-8}$ cycloalkyl $C_{2-6}$ alkenyl group" used in the present specification denote a $C_{1-6}$ alkyl group (examples of the alkyl group include a methyl group, an ethyl group, a n-propyl group, an iso-propyl group, etc.) and a $C_{2-6}$ alkenyl group (examples of the alkenyl group include a vinyl group, an allyl group, a 1-propenyl group, a 2-propenyl group, an isopropenyl group, etc.), each of which may be substituted with the above-mentioned $C_{3-8}$ cycloalkyl group (e.g. cyclopropyl group, cyclobutyl group, cyclopentyl group, cyclohexyl group, cyclheptyl group, cyclooctyl group, etc.). Preferable examples thereof are not particularly limited, but include a cyclopropylmethyl group, a cyclopropylethyl group, a cyclopropyl n-propyl group, a cyclobutylmethyl group, a cyclobutylethyl group and the like, and a cyclopropylvinyl group, a cyclopropylallyl group and the like, respectively.

The "$C_{1-10}$ alkoxy $C_{1-10}$ alkyl group" and "$C_{1-10}$ alkoxy $C_{2-8}$ alkenyl group" used in the present specification denote a $C_{1-1}$ alkyl group (examples of the alkyl group include a methyl group, an ethyl group, a n-propyl group, an iso-propyl group, a n-butyl group, an iso-butyl group, a sec-butyl group, a tert-butyl group, a n-pentyl group, a 1,1-dimethylpropyl group, etc.) and a $C_{2-8}$ alkenyl group (examples of the alkenyl group include a vinyl group, an allyl group, a 1-propenyl group, a 2-propenyl group, an isopropenyl group, etc.), each of which may be substituted with an alkoxy group having a carbon number of 1 to 10 (examples of the alkoxy group include a methoxy group, an ethoxy group, a n-propoxy group, an iso-propoxy group, etc.).

The "$C_{2-6}$ alkenyloxy $C_{1-6}$ alkyl group" and "$C_{2-6}$ alkenyloxy $C_{2-6}$ alkenyl group" used in the present specification denote a $C_{1-6}$ alkyl group (examples of the alkyl group include a methyl group, an ethyl group, a n-propyl group, an iso-propyl group, a n-butyl group, an iso-butyl group, a sec-butyl group, a tert-butyl group, a n-pentyl group, a 1,1-dimethylpropyl group, etc.) and a $C_{2-6}$ alkenyl group (examples of the alkenyl group include a vinyl group, an allyl group, a 1-propenyl group, a 2-propenyl group, an isopropenyl group, etc.), each of which may be substituted with the above-mentioned $C_{2-6}$ alkenyloxy group (examples of the alkenyloxy group include a vinyloxy group, an allyloxy group, a 1-propenyloxy group, a 2-propenyloxy group, an isopropenyloxy group, a 2-methyl-1-propenyloxy group, etc.).

The "a $C_{1-6}$ hydroxyalkyl group" used in the present specification denotes a $C_{1-6}$ alkyl group (examples of the alkyl group include a methyl group, an ethyl group, a n-propyl group, an iso-propyl group, a n-butyl group, an iso-butyl group, a sec-butyl group, a tert-butyl group, a n-pentyl group, a 1,1-dimethylpropyl group, etc.) optionally substituted with at least one hydroxyl group, and preferable examples thereof are not particularly limited, but include more preferably a $C_{1-6}$ alkyl group substituted with one hydroxyl group, such as a hydroxymethyl group, a 2-hydroxy-1-ethyl group, a 2-hydroxy-1-propyl group and the like.

The "$C_{1-6}$ alkyl group substituted with a 5- to 14-membered non-aromatic heterocyclic group" used in the present specification denotes a $C_{1-6}$ alkyl group substituted with the above-mentioned 5- to 14-membered non-aromatic heterocyclic group (e.g. pyrrolidinyl group, pyrrolyl group, piperidinyl group, piperazinyl group, imidazolyl group, pyrazolidyl group, imidazolidyl group, morpholyl group, tetrahydrofuryl group, pyranyl group, tetrahydropyranyl group, pyrrolinyl group, dihydrofuryl group, dihydropyranyl group, imidazolinyl group, oxazolinyl group, pyridone-yl group, phthalimide-yl group, succinimide-yl group etc.) at an arbitrary position. Preferable examples thereof are not particularly limited, but more preferable examples thereof include a methyl group, an ethyl group, a n-propyl group, an iso-butyl group, an n-butyl group and a tert-butyl group, each of which are substituted with a pyrrolidinyl group, a pyrrolyl group, a piperidinyl group, a piperazinyl group, an imidazolyl group, a pyrazolidyl group, an imidazolidyl group, a morpholyl group, a tetrahydrofuryl group, a pyranyl group or a tetrahydropyranyl group.

The "$C_{1-6}$ alkylthio $C_{1-6}$ alkyl group" used in the present specification denotes a $C_{1-6}$ alkyl group (examples of the alkyl group include a methyl group, an ethyl group, a n-propyl group, an iso-propyl group, a n-butyl group, an iso-butyl group, a sec-butyl group, a tert-butyl group, a n-pentyl group, a 1,1-dimethylpropyl group, etc.) substituted with the above-mentioned $C_{1-6}$ alkylthio group (e.g. methylthio group, ethylthio group, n-propylthio group, iso-propylthio group, etc.) at an arbitrary position.

The "aminocarbonyl $C_{1-6}$ alkyl group" used in the present specification denotes a $C_{1-6}$ alkyl group (examples of the alkyl group include a methyl group, an ethyl group, a n-propyl group, an iso-propyl group, a n-butyl group, an iso-butyl group, a sec-butyl group, a tert-butyl group, a n-pentyl group, a 1,1-dimethylpropyl group, etc.) substituted with a group represented by the formula —$CONH_2$ at an arbitral position.

The "heteroarylcarbonyl group" used in the present specification denotes a carbonyl group to which the above-mentioned heteroaryl group (e.g. pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizyl group, phthalazyl group, naphthyridinyl group, quinoxalyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenacinyl group, imidazopyridinyl group, imidazopyrimidinyl group, pyrazolopyridinyl group, pyrazolopyridinyl group, thienyl group, benzothienyl group, furyl group, pyranyl group, cyclopentapyranyl group, benzofuryl group, isobenzofuryl group, thiazolyl group, isothiazolyl group, benzothiazolyl group, benzthiadiazolyl group, phenothiazinyl group, isoxazolyl group, furazanyl group, phenoxazinyl group, oxazolyl group, isoxazolyl group, benzoxazolyl group, oxadiazolyl group, pyrazoloxazolyl group, imidazothiazolyl group, thienofuranyl group, furopyrrolylcarbonyl group or oxazinyl carbonyl group) is bound. Preferable examples thereof are not particularly limited, but more preferable examples thereof include a carbonyl group to which a monocyclic heteroaryl group (pyrrolyl group, thienyl group, furyl group, imidazolyl group, pyrazolyl group, thiazolyl group, pyridyl group, etc.) is bound.

The "heteroaryl $C_{1-6}$ alkyl group" used in the present specification denotes a $C_{1-6}$ alkyl group substituted with the above-mentioned heteroaryl group at an arbitrary position. Preferable examples thereof are not particularly limited, but more preferable examples thereof include a $C_{1-6}$ alkyl group (example of the alkyl group include a methyl group, an ethyl group, a n-propyl group, an iso-propyl group, a n-butyl group, an iso-butyl group, a sec-butyl group, a tert-butyl group, a n-pentyl group, a 1,1-dimethylpropyl group, etc.) to which a pyrrolyl group, a thienyl group, a furyl group, an imidazolyl group, a pyrazolyl group, a thiazolyl group or a pyridyl group is bound.

The "aryl $C_{1-6}$ alkyl group" used in the present specification denotes a $C_{1-6}$ alkyl group substituted with the above-mentioned aryl group (e.g. phenyl group, naphthyl group, etc,) at an arbitrary position, and is preferably a $C_{1-6}$ alkyl group substituted with a phenyl group, more preferably a benzyl group, a phenyl ethyl group, or the like.

The "$C_{1-6}$ alkoxycarbonyl group" used in the present specification denotes a carbonyl group to which a $C_{1-6}$ alkoxy group is bound. Preferable examples thereof include a methoxycarbonyl group, an ethoxycarbonyl group, a n-propoxycarbonyl group, an iso-propoxycarbonyl group, and the like. The "$C_{2-6}$alkenyloxycarbonyl group" denotes a carbonyl group to which a $C_{2-6}$ alkenyloxy group is bound. Preferable examples thereof include a vinyloxycarbonyl group, an allyloxycarbonyl group, a 1-propenyloxycarbonyl group, a 2-propenyloxycarbonyl group, an isopropenyloxycarbonyl group, a 2-methyl-1-propenyloxycarbonyl group and the like.

The "halogeno-$C_{1-6}$ alkyl group" used in the present specification denotes a $C_{1-6}$ alkyl group (examples of the alkyl group include a methyl group, an ethyl group, a n-propyl group, an iso-propyl group, a n-butyl group, an iso-butyl group, a sec-butyl group, a tert-butyl group, a n-pentyl group, etc.) substituted with at least one halogen atom (e.g. fluorine atom, chlorine atom, bromine atom, iodine atom, etc.) at an arbitrary position. Preferable examples thereof are not particularly limited, but more preferable examples thereof include a methyl group, an ethyl group, a n-propyl group, an iso-propyl group, a n-butyl group, an iso-butyl group, a sec-butyl group and tert-butyl group, each of which are substituted with 1 to 4 atom(s) selected from a fluorine atom, a chlorine atom and a bromine atom (e.g. trifluoromethyl group etc.).

The "halogeno-$C_{1-6}$ alkoxy group" used in the present specification denotes a $C_{1-6}$ alkoxy group (examples of the alkyl group include a methoxy group, an ethoxy group, a n-propoxy group, an iso-propoxy group, etc.) substituted with at least one halogen atom (e.g. fluorine atom, chlorine atom, bromine atom, iodine atom, etc.) at an arbitrary position. Preferable examples thereof are not particularly limited, but more preferable examples thereof include a methoxy group, an ethoxy group, a n-propoxy group, an iso-propoxy group, a n-butoxy group, an iso-butoxy group, a sec-butoxy group and a tert-butoxy group, each of which are substituted with 1 to 4 atom(s) selected from a fluorine atom and a chlorine atom (e.g. trifluoromethoxy group etc.).

In the present specification, $R^1$, $R^2$ and $R^3$ are the same as or different from each other and each may have a substituent. Preferable examples of the substituent include (1) a halogen atom, (2) a hydroxyl group, (3) a nitro group, (4) a cyano group, (5) a carboxyl group, (6) a $C_{1-6}$ alkyloxycarbonyl group, and (7) the formula—$S(O)_rR^{13}$ (wherein r denotes an integer of 0, 1 or 2; and $R^{13}$ denotes (a) a hydrogen atom, (b) a $C_{1-6}$ alkyl group, (c) the formula —$NR^{14}R^{15}$ (wherein $R^{14}$ and $R^{15}$ are the same as or different from each other and each denotes a hydrogen atom, a $C_{1-6}$ alkyl group optionally substituted with an optionally substituted aryl group, a $C_{1-4}$ alkylacyl group, an optionally substituted aryl $C_{1-4}$ alkyl group, an optionally substituted heteroaryl $C_{1-4}$ alkyl group, an optionally substituted aryl group or an optionally substituted heteroaryl group), (d) an optionally substituted aryl $C_{1-4}$ alkyl group, (e) an optionally substituted aryl group, (f) an optionally substituted heteroaryl $C_{1-4}$ alkyl group, or (g) an optionally substituted heteroaryl group, (h) —$NR^{16}R^{17}$ (wherein $R^{16}$ and $R^{17}$ are the same as or different from each other and each denotes a hydrogen atom, a $C_{1-6}$ alkyl group or a $C_{1-4}$ alkylacyl group), (i) a $C_{1-6}$ alkyl group, (j) a $C_{1-6}$ alkoxy group, (k) a $C_{3-8}$ cycloalkyl group optionally substituted with a $C_{1-4}$ alkyl group, (l) a $C_{1-4}$ alkoxy $C_{1-6}$ alkyl group, (m) a saturated 3- to 8-membered heterocyclic ring optionally substituted with a $C_{1-4}$ alkyl group, (n) an optionally substituted aryl group, (o) an optionally substituted heteroaryl group, (p) a $C_{2-6}$ alkenyl group, (q) a $C_{2-8}$ alkynyl group, (r) a $C_{2-6}$ alkenyloxy group, and the like).

The meanings of groups expressed as $R^1$, $R^2$, $R^3$, X, Y and X in the formula of Compound (I) of the present invention are as defined above.

Preferable examples of each group are not particularly limited, but more preferable examples in the case of $R^1$ include a $C_{1-6}$ alkyl group, a $C_{2-6}$ alkenyl group, a $C_{2-6}$ alkynyl group, a $C_{1-6}$ alkoxy group, -$G^1$-$A^2$ (wherein $G^1$ and $A^2$ have the same meanings as defined above) and the like, most preferably a $C_{1-6}$ alkyl group (e.g. methyl group, ethyl group, etc,), $C_{1-6}$ alkoxy group (e.g, methoxy group, ethoxy group, etc.), a $C_{1-6}$alkylthio group (e.g. methylthio group, ethylthio group, etc.) and the like.

More preferable examples in $R^2$ include a $C_{1-10}$ alkyl group, a $C_{2-10}$ alkenyl group, a $C_{2-10}$ alkynyl group, a $C_{3-8}$ cycloalkyl $C_{1-6}$ alkyl group, a $C_{3-8}$ cycloalkyl $C_{2-6}$ alkenyl group, a $C_{1-10}$ alkoxy $C_{1-10}$ alkyl group, a $C_{1-6}$ alkoxy $C_{2-8}$ alkenyl group, a $C_{2-6}$ alkenyloxy $C_{1-6}$ alkyl group, a $C_{2-6}$ alkenyloxy $C_{2-6}$ alkenyl group, —$NR^{2a}R^{2b}$ ($R^{2a}$ and $R^{2b}$ have the same meanings as defined above) and the like, most preferably —$NR^{2a}R^{2b}$ ($R^{2a}$ and $R^{2b}$ have the same meanings as those defined above).

More preferable examples in $R^3$ include a phenyl group optionally having a substituent, and a 5- or 6-membered aromatic heterocyclic group (e.g. pyrrolyl group, imidazolyl group, pyrazolyl group, thienyl group, furyl group, thiazolyl group, isothiazolyl group, pyridyl group, pyridazyl group, pyrimidyl and pyrazyl group) optionally having a substituent, and most preferable examples include a phenyl group and a pyridyl group, each of which may have a substituent. In addition, more preferable examples of the substituent include groups selected from a halogen atom (fluorine atom, chlorine atom, bromine atom or iodine atom), a hydroxyl group, a nitro group, a cyano group, a carboxyl group, a $C_{1-6}$ alkyloxycarbonyl group, —$S(O)_rR^{13}$ (wherein r denotes an integer of 0, 1 or 2; and $R^{13}$ denotes (a) a hydrogen atom, (b) a $C_{1-6}$ alkyl group, (c) the formula —$NR^{14}R^{15}$ (wherein $R^{14}$ and $R^{15}$ are the same as or different from each other and each denotes a hydrogen atom, a $C_{1-6}$ alkyl group optionally substituted with an optionally substituted aryl group, a $C_{1-4}$ alkylacyl group, an optionally substituted aryl $C_{1-4}$ alkyl group, an optionally substituted heteroaryl $C_{1-4}$ alkyl group, an optionally substituted aryl group or an optionally substituted heteroaryl group), (d) an optionally substituted aryl $C_{1-4}$ alkyl group, (e) an optionally substituted aryl group, (f) an optionally substituted heteroaryl $C_{1-4}$ alkyl group or (g) an optionally substituted heteroaryl group), —$NR^{16}R^{17}$ (wherein $R^{16}$ and $R^{17}$ are the same as or different from each other and each denotes a hydrogen atom, a $C_{1-6}$ alkyl group or a $C_{1-4}$ alkylacyl group), a $C_{1-6}$ alkyl group (e.g. methyl group, ethyl group, n-propyl group, iso-propyl group, etc.), a $C_{1-6}$ alkoxy group (e.g. methoxy group, ethoxy group, n-propoxy group, iso-propoxy group, etc.), a $C_{1-6}$ alkylthio group (e.g. methylthio group, ethylthio group, etc.), a $C_{1-4}$ alkoxy $C_{1-6}$ alkyl group (e.g. methoxymethyl group etc.) a halogeno-$C_{1-6}$ alkyl group (e.g. trifluoromethyl group etc.), a halogeno-$C_{1-6}$ alkoxy group (e.g. trifluoromethoxy group etc.), and the like, and more preferable examples include groups selected from a halogen atom, a cyano group, a $C_{1-6}$ alkyl group, a $C_{1-6}$ alkoxy group, a halogeno-$C_{1-6}$ alkyl group, a halogeno-$C_{1-6}$ alkoxy group, a monoalkylamino group, a dialkylamino group and the like. More specifically, most preferable examples in $R^3$ include a phenyl group and a pyridyl group, each of which may be substituted with 1, 2 or 3 group(s) selected from a halogen atom (fluorine atom, chlorine atom or bromine atom), a cyano group, a methyl group, an ethyl group, a methoxy group, an ethoxy group, a methylthio group, an ethylthio group, a trifluoromethyl group, a trifluoromethoxy group, a methylamino group and a dimethyl group.

In addition, a possible combination of X, Y and Z is not particularly limited as far as at least two denote $CR^4$ ($R^4$ has the same meaning as defined above) at the same time.

The preferable examples of the Compound (I) relating to the present invention are not particularly limited. More preferable examples thereof include a compound represented by formula:

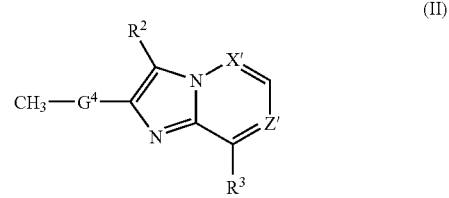

(II)

(wherein X' and Z' are independent of each other and each denotes N or CH (in this case, at least one of X' and Z' denote CH); and $G^4$, $R^2$ and $R^3$ have the same meanings as defined above each) or a salt thereof, further preferable examples thereof include a compound (hereinafter, referred to as "Compound (III)" in some cases) represented by the formula:

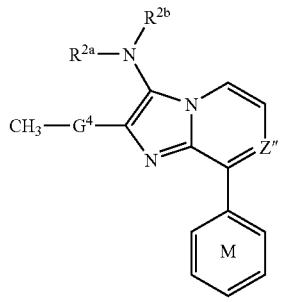

(wherein Z" denotes N or CH, the ring M denotes a benzene ring optionally further having a substituent; and $G^4$, $R^{2a}$ and $R^{2b}$ have the same meanings as defined above each) or a salt thereof, and most preferable examples include Compound (III) wherein $R^{2a}$ and $R^{2b}$ are independent of each other and each denotes a hydrogen atom, a $C_{1-8}$ alkyl group, a $C_{2-8}$ alkenyl group, a $C_{2-6}$ alkynyl group, a $C_{1-6}$ alkyl group substituted with a 5- to 14-membered non-aromatic heterocyclic group, a $C_{1-8}$ alkoxy $C_{1-8}$ alkyl group, a $C_{3-8}$ cycloalkyl group or a $C_{3-8}$ cycloalkyl $C_{1-6}$alkyl group, and respective groups may be further substituted, independently, with a halogen atom, and the ring M is a benzene ring optionally substituted with 1 to 3 group (s) selected from a halogen atom, a $C_{1-6}$ alkyl group, a halogeno-$C_{1-6}$ alkyl group, a halogeno-$C_{1-6}$ alkoxy group and a $C_{1-6}$ alkoxy group.

The "salt" used in the present specification is not particularly limited as far as it forms a salt with the compound of the present invention and is pharmacologically acceptable, and preferable examples of the salt include a hydrogen halide salt (e.g. hydrofluoride, hydrochloride, hydrobromide, hydroiodide, etc.), an inorganic acid salt (e.g. sulfate, nitrate, perchlorate, phosphate, carbonate, bicarbonate, etc.), an organic carboxylic acid salt (e.g. acetate, trifluoroacetate, oxalate, maleate, tartrate, fumarate, citrate, etc.), an organic sulfonic acid salt (e.g. methanesulfonate, trifluoromethanesulfonate, ethanesulfonate, benzenesulfonate, toluenesulfonate, camphorsulfonate, etc.), an amino acid salt (e.g. aspartate, glutamate, etc.), a quaternary amine salt, an alkali metal salt (e.g. sodium salt, potassium salt, etc.), an alkaline earth metal salt (magnesium salt, calcium salt, etc.) and the like, and more preferable examples of the "pharmacologically acceptable salt" include hydrochloride, oxalate, trifluoroacetate and the like.

A representative process for preparing the compound represented by the aforementioned formula (I) relating to the present invention will be shown below. In the following process schemes, $R^1$, $R^{2a}$, $R^{2b}$, X, Y and Z have the same meanings as defined above; $R^5$ and $R^6$ have the same meaning as $R^4$, and are independently defined; R denotes a hydrocarbon group; R' and R" are independent of each other and each denotes alkyl, alkenyl or alkynyl; $R^s$ denotes a $C_{1-6}$ alkyl group or the like; $R^g$ and $R^h$ denote a hydrocarbon group; Ar denotes an aryl or heteroaryl group; T denotes a halogen atom (particularly preferable are a chlorine atom, a bromine atom and an iodine atom); T' denotes a halogen atom (e.g. fluorine atom, chlorine atom, bromine atom, iodine atom, etc.); $T^s$ denotes a halogen atom or the like; a symbol represented by Pro denotes a protecting group; and a symbol represented by Lev represents a halogen atom or a leaving group (e.g. trifluoromethanesulfonyl group etc.). The "room temperature" described below refers to around 0 to 40° C.

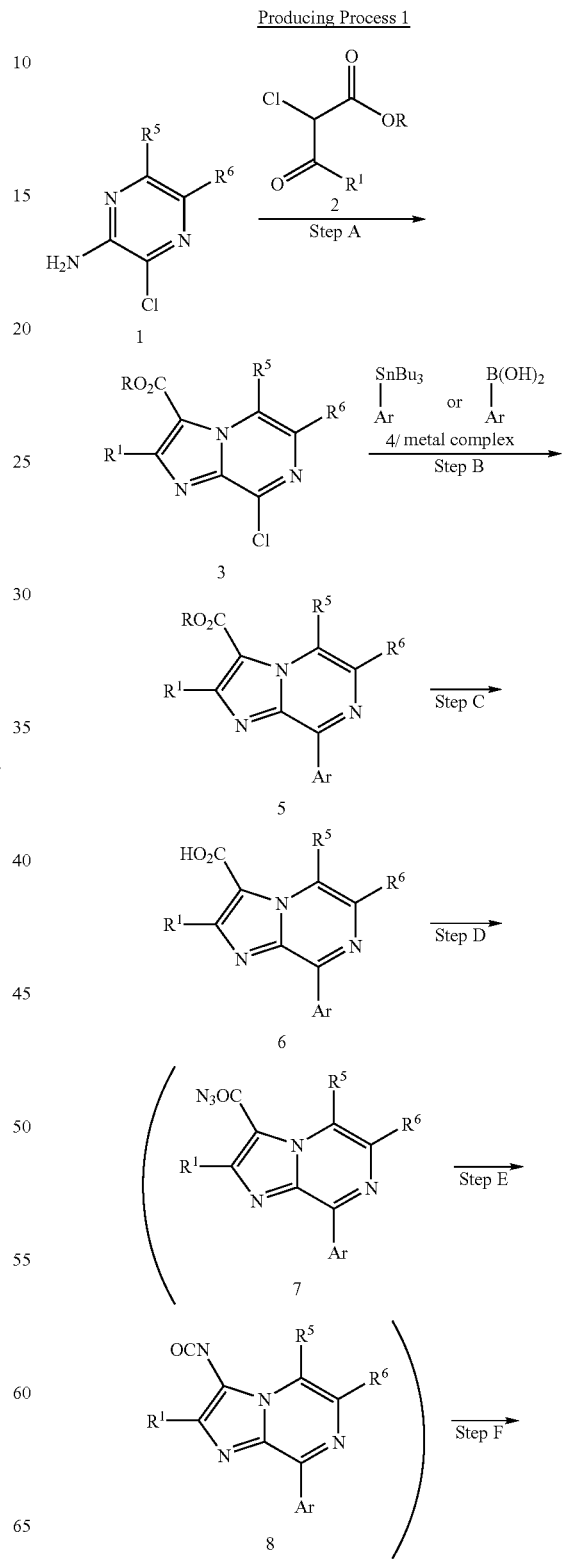

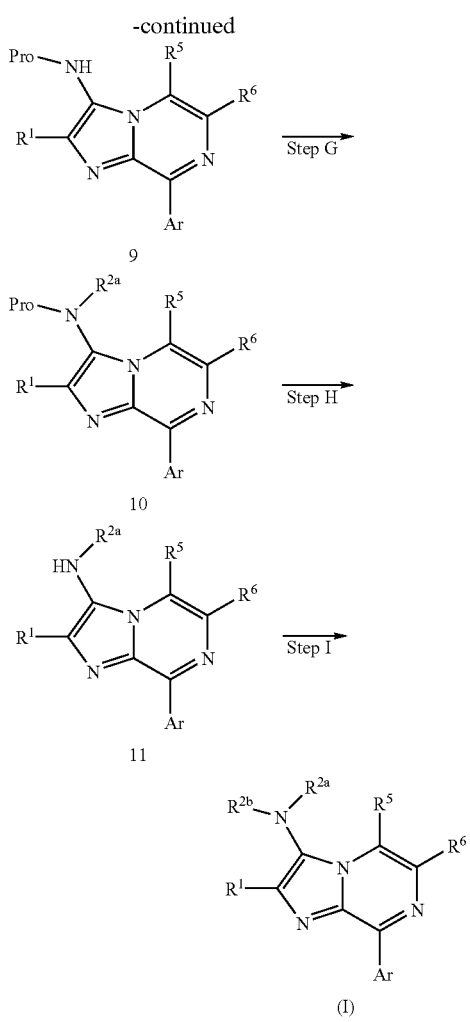

Step A: An imidazo[1,2-a]pyrazine derivative (3) can be obtained by reacting an aminopyrazine derivative (1) and an α-chloro-β-ketoester derivative (2) at 0 to 200° C. in a solvent or without a solvent. The solvent to be used is different depending on starting materials, regents and the like, and is not particularly limited as far as it does not inhibit a reaction and dissolves starting substances to some extent. Preferably, acetic acid, toluene, xylene, methanol, ethanol, ethylene glycol monomethyl ether, N,N-dimethylformamide and the like can be used alone or by mixing them.

Step B: An imidazo[1,2-a]pyrazine-3-carboxylic acid ester derivative (5) substituted with an aryl group at the 8-position can be obtained by reacting an imidazo[1,2-a]pyrazine-3-carboxylic acid ester derivative (3) with an aryl-metal compound (4 in the formula) such as an aryltin compound and an arylboronic acid compound at 0 to 250° C. using a palladium or nickel metal complex in the presence or absence of a base in a solvent or without a solvent. The solvent to be used is different depending on starting raw materials, regents and the like, and is not particularly limited as far as it does not inhibit a reaction and dissolves starting substances to some extent. Preferable examples of the solvent include benzene, toluene, xylene, anisole, N,N-dimeth ylformamide, 1,2-dimethoxyethane, tetrahydrofuran, dioxane, n-butanol, ethanol, methanol, N-methyl-2-pyridone, water and the like. In addition, the base to be used is different depending on starting raw materials, a solvent to be used, and the like, and is not particularly limited as far as it does not inhibit a reaction. Preferable examples of the base include potassium carbonate, sodium carbonate, cesium fluoride, potassium fluoride, sodium bicarbonate, barium hydroxide, triethylamine and the like. Examples of the palladium or nickel metal complex to be used include $Pd(PPh_3)_4$, $Pd(OAc)_2/PPh_3$, $PdCl_2$, $PdCl_2(dppf)$, $Ni(dpp)_2Cl_2$, $Cl_2$ and the like.

Step C: An imidazo[1,2-a]pyrazine-3-carboxylic acid derivative (6) can be obtained by hydrolyzing an imidazo[1,2-a]pyrazine-3-carboxylic acid ester derivative (5) at 0 to 200° C. in the presence of a base in a solvent or without a solvent. The solvent to be used is different depending on starting raw materials, regents and the like, and is not particularly limited as far as it does not inhibit a reaction and dissolves starting substances to some extent. Preferably, ethanol, methanol, n-butanol, t-butanol, tetrahydrofuran, dioxane, water and the like can be used alone or as a mixed solvent. The base to be used is different depending on starting raw materials, a solvent to be used, and the like, and is not particularly limited as far as it does not inhibit a reaction. Preferable examples of the base include sodium hydroxide, potassium hydroxide, potassium carbonate, sodium carbonate, cesium carbonate, and potassium t-butoxide.

Steps D, E, F: An imidazo[1,2-a]pyrazine-3-carboxylic acid derivative (6) is reacted with an aziding agent such as diphenylphosphorylazide (DPPA) at −70 to 250° C. in the presence or absence of a base in a solvent or without a solvent to obtain an acid azide derivative (7), this acid azide derivative is heated to a temperature of 0 to 250° C. to cause a rearrangement reaction such as Curtius rearrangement reaction, producing isocianate (8) in situ, which can be reacted with tert-butanol or the like to obtain 3-amino-imidazo[1,2-a]pyrazine derivative (9) protected with a carbamate group such as tert-butoxycarbonyl (Boc) and the like. The solvent to be used is different depending on starting raw materials, regents and the like, and is not particularly limited as far as it does not inhibit a reaction and dissolves starting substances to some extent. Preferably, benzene, toluene, xylene, diphenyl ether, t-butanol, tetrahydrofuran, dioxane, acetonitrile, N,N-dimethylformamide and the like can be used alone or as a mixed solvent. Examples of the base to be used include triethylamine, diisopropylethylamine, 4-(dimethylamino)pyridine, and pyridine.

On the other hand, acid azide derivative (7) can be also prepared by derivatizing an imidazo[1,2-a]pyrazine-3-carboxylic acid derivative (6) into acid chloride or mixed acid anhydride, and aziding the (6) with a aziding agent (e.g. sodium azide, trimethylsilylazide, etc.).

Alternatively, a 3-amino-imidazo[1,2-a]pyrazine derivative (9) may be prepared from Hofmman rearrangement reaction or Schmidt rearrangement reaction.

Step G: An imidazo[1,2-a]pyrazine derivative (10) can be obtained by reacting a 3-amino-imidazo[1,2-a]pyrazine derivative (9) with a carbonyl derivative such as diethyl ketone or an aldehyde derivative such as propionaldehyde at −10 to 150° C. in the presence of a reducing agent. When this step is performed in the presence or absence of an acid in a solvent or without a solvent, and in the presence or absence or an inorganic salt, the better results can be obtained. The solvent to be used is different depending on starting raw materials, regents and the like, and is not particularly limited as far as it does not inhibit a reaction and dissolves starting substance to some extent. Preferable examples include tetrahydrofuran, diethyl ether, 1,2-dichloroethane, dichloromethane, chloroform, acetonitrile, water and the like, and these can be used alone or as a mixed solvent. In addition, the acid to be used is different depending on starting raw materials, a solvent to be used, and the like, and is not particularly limited as far as it does not inhibit a reaction. Preferable examples include acetic acid, sulfuric acid and the like. In addition, an inorganic salt to be used is different depending on starting raw materials, a solvent to be used, and the like, and is not particularly limited as far as it does not inhibit a reaction. Preferable examples include sodium sulfate, magnesium sulfate and the like. In addition, examples of a reducing agent to be used include sodium triacetoxyborohydride, sodium borohydride, and sodium cyanotrihydridoborate.

Alternatively, an imidazo[1,2-a]pyrazine derivative (10) can be also obtained by reacting a 3-amino-imidazo[1,2-a]pyrazine derivative (9) with an alkylating agent (alkyl halide etc.) containing a leaving group such as halide, an acylating agent such as acid chloride and acid anhydride or sulfonic acid chloride such as p-toluenesulfonic acid chloride and the like at −70 to 200° C. in the presence or absence of a base in a solvent or without a solvent. The solvent to be used is different depending on the starting raw material, regents and the like, and is not particularly limited as far as it does not inhibit a reaction and dissolves starting substances to some extent. Preferable examples include tetrahydrofuran, diethyl ether, N,N-dimethylformamide, dimethyl sulfoxide and the like. In addition, examples of the base to be used include sodium hydride, potassium hydride, potassium carbonate, sodium carbonate, cesium carbonate, potassium hydroxide, sodium hydroxide, pyridine, triethylamine and the like.

Step H: An imidazo[1,2-a]pyrazine derivative (11) can be obtained by reacting an imidazo[1,2-a]pyrazine derivative (10) at −70 to 200° C. in the presence or absence of a deprotecting agent in a solvent or without a solvent, to deprotect a protecting group such as a tert-butoxycarbonyl group (Boc) and the like. The solvent to be used is different depending on starting raw materials, regents and the like, and is not particularly limited as far as it does not inhibit a reaction and dissolves starting substances to some extent. Preferable examples include ethyl acetate, tetrahydrofuran, diethyl ether, dioxane, acetonitrile, dichloromethane, chloroform, nitromethane, phenol, anisole, thiophenol and the like. Examples of the deprotecting agent to be used include hydrochloric acid, sulfuric acid, trifluoroacetic acid, methanesulfonic acid, iodotrimethylsilane, aluminum (III) chloride, trimethylsilyl triflate and the like. When a protecting group other than Boc (e.g. Fmoc, Troc etc.) is used, it is enough to use a deprotecting agent and a reaction suitable for the protecting group.

Step I: An imidazo[1,2-a]pyrazine derivative (I) of the present invention can be prepared as in the aforementioned step G.

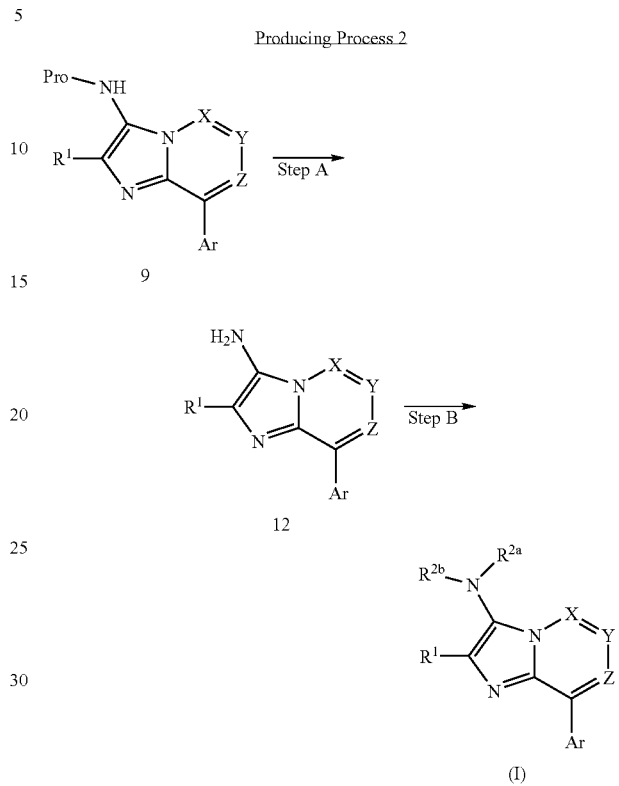

Step A: A deprotected derivative (12) can be obtained by subjecting a dicyclic nitrogen-containing heterocyclic derivative (9) having a protected amino group at the 3-position and having a fused imidazole ring, to the same reaction as that of step H in Producing Process 1.

Step B: A dicyclic nitrogen-containing heterocyclic derivative (I) having a fused imidazole ring, which is a compound of the present invention, can be prepared by subjecting an amine derivative (12) to the same reaction as that of the step G in Producing Process 1 to introduce a substituent therein.

Producing Process 3

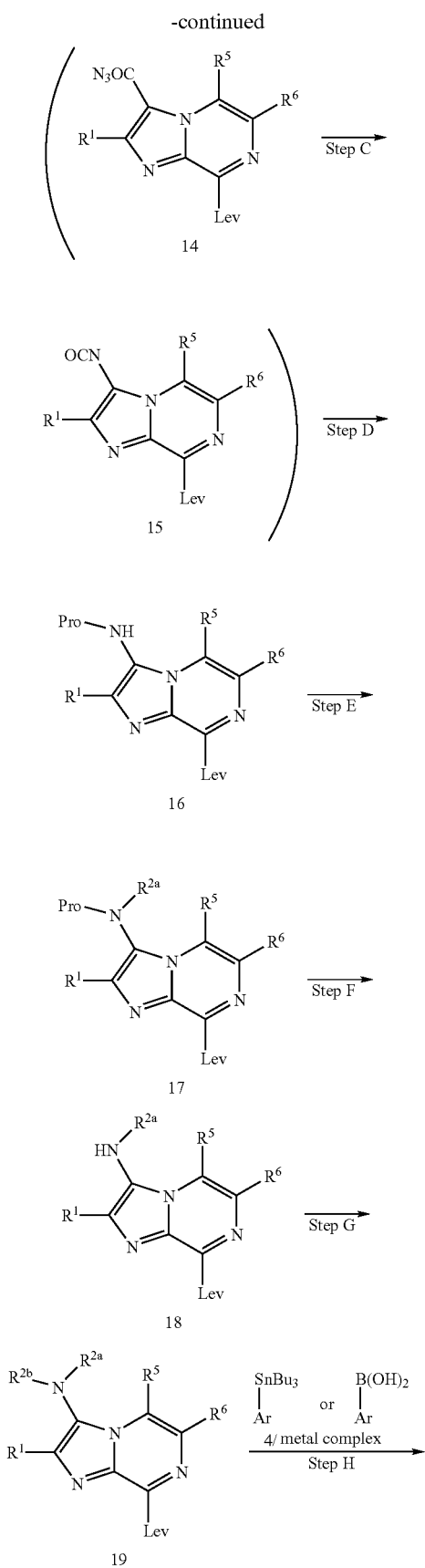

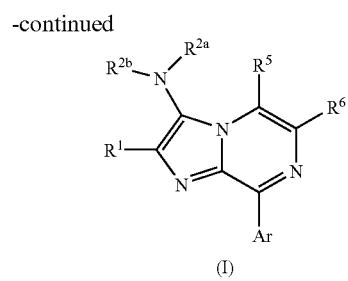
(I)

In the present process, first, Compound (13) can be prepared by subjecting Compound (3) to the same reaction as that of the step C in Producing Process 1 (step A). Compound (16) can be prepared by subjecting the Compound (13) obtained in step A to the same rearrangement reactions as those of steps D, E, F in Producing Process 1 (steps B, C and D). Compound (17) can be prepared by subjecting Compound (16) to the same reaction as that of the step G in Producing Process 1 (step E). Compound (18) can be prepared by subjecting Compound (17) to the same reaction as that of the step H in Producing Process 1 (step F). Compound (19) can be prepared by subjecting Compound (18) to the same reaction as that of the step I in Producing Process 1 (step G). Finally, Compound (19) can be subjected to the same reaction as that of the step B in Producing Process 1 to prepare the Compound (I) of the present invention (step H).

Producing Process 4

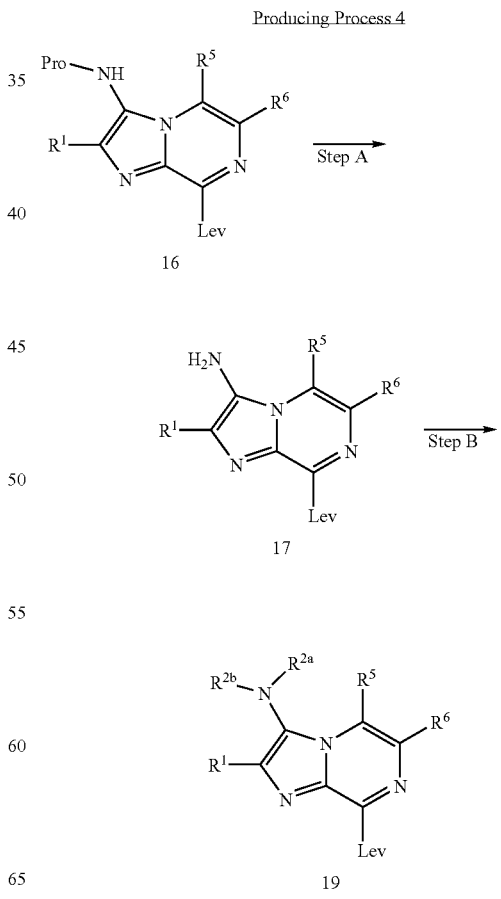

In the formula, Lev has the same meaning as defined above. In the present Producing Process, first, Compound (17) can be prepared by subjecting Compound (16) to the same deprotecting reaction as that of the step H in Producing Process 1 (step A). Finally, Compound (17) can be subjected to the same substituent introducing reaction as that of the step I in Producing Process 1 to prepare the Compound (I) relating to the present invention.

Producing Process 5

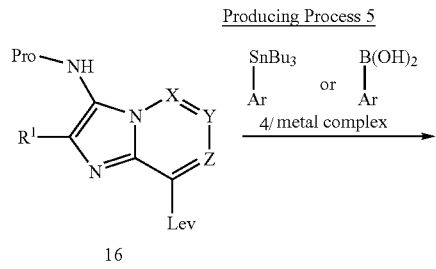

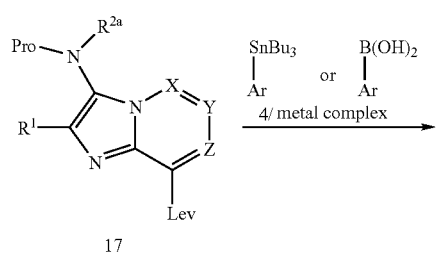

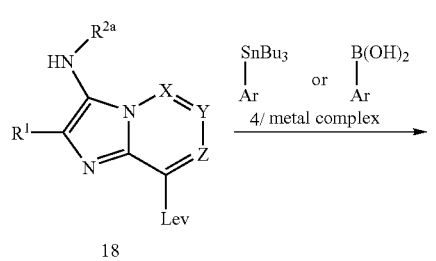

-continued

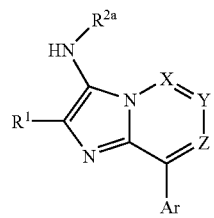

11

In the formula, Lev has the same meaning as defined above. In the present Producing Process, derivatives ((9), (10) or (11)) with an aryl group introduced at the 8-position can be prepared by subjecting Compound (16), (17) or (18) to the same coupling reaction as that of the step B in Producing Process 1, corresponding to respective starting raw materials.

Producing Process 6

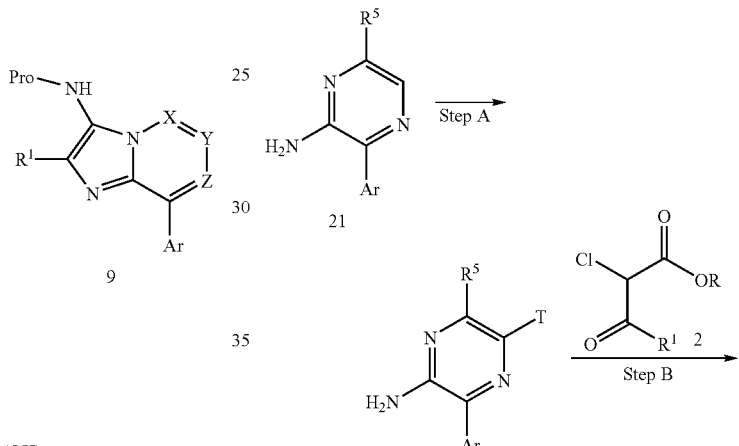

Step A: A halogenated 2-aminopyrazine derivative (22) can be obtained by reacting a 2-aminopyradine derivative (21) in the formula with a halogenating agent (e.g, N-chlorosuccinimide etc.) at 0 to 200° C. in a solvent or without a solvent. The solvent to be used is different depending on starting raw materials, reagents and the like, and is not particularly limited as far as it does not inhibit a reaction and dissolves starting substances to some extent. Preferable examples of the solvent include acetic acid, toluene, xylene, methanol, ethanol, diethyl ether, ethylene glycol monomethyl ether, N,N-dimethylformamide, dichloromethane, chloroform, carbon tetrachloride and the like, and these solvents can be used alone or by mixing them. As the halogenating agent, for example, chlorine, bromine, iodine, N-bromosuccinimide, N-chlorosuccinimide, N-iodosuccinimide and the like can be used. However, the carbon atom to which $R^4$ is bound is halogenated in some cases, depending on the halogenating conditions.

Step B: An imidazo[1,2-a]pyrazine derivative (5') can be obtained by subjecting a 2-aminopyrazine derivative (22) and an α-chloro-β-ketoester derivative (2) to the same reaction as that of the step A in Producing Process 1.

The derivative (5') in the present Producing Process 6 can be subjected to the same reaction as that using the derivative (5) in Producing Process 1 to prepare the Compound (I) of the present invention.

Step C: An imidazo[1,2-a]pyrazine derivative (3) can be prepared by subjecting an aminopyrazine derivative (25) and an α-chloro-β-ketoester derivative (2) to the same reaction as that of the step A in Producing Process 1.

The derivative (3) in the present Producing Process 7 can be subjected to the same reaction as the reaction using the derivative (3) in Producing Process 1 to prepare the Compound (I) of the present invention.

Producing Process 7

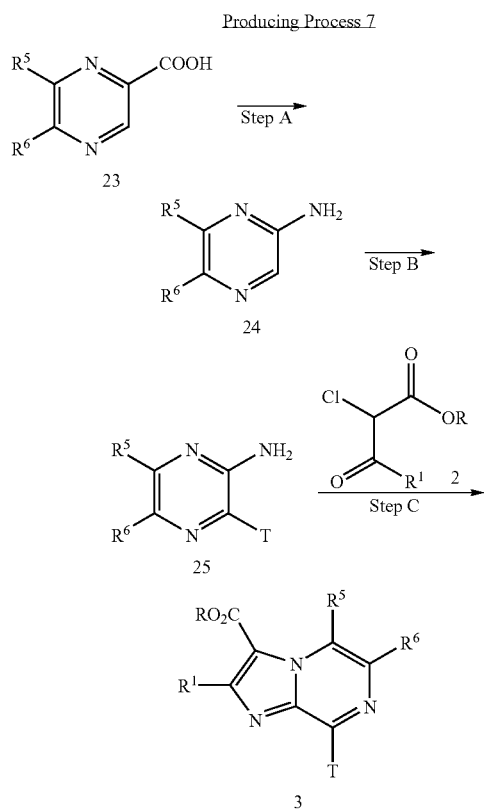

Producing Process 8

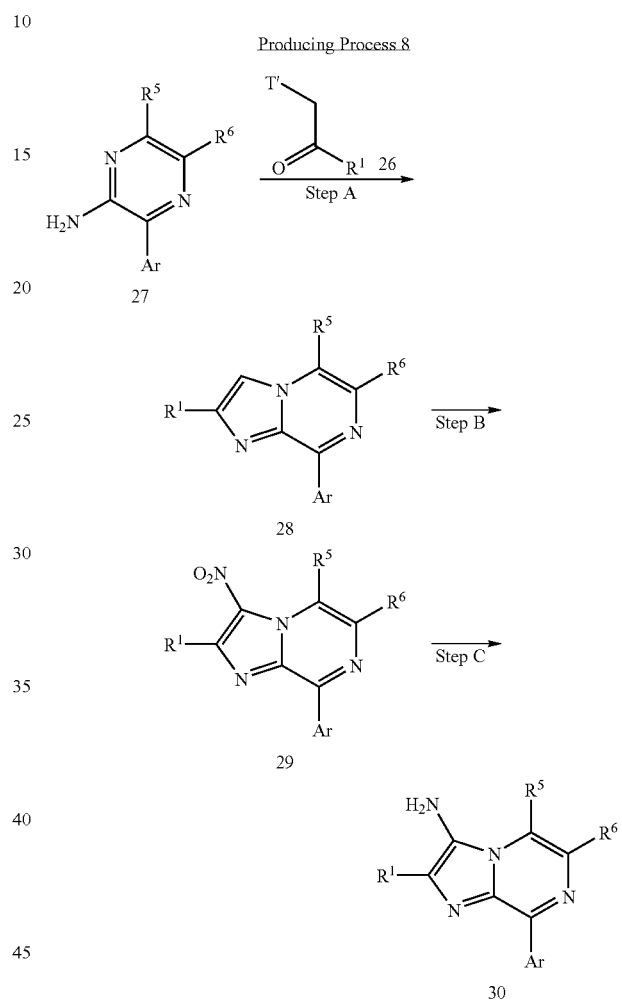

Step A: A 2-aminopyrazine acid derivative (24) can be prepared by subjecting a pyrazine-2-carboxylic acid derivative (23) to a rearrangement reaction such as Curtius rearrangement reaction and the like shown in steps D, E and F in a process 1.

Step B: A halogenated 2-aminopyrazine derivative (25) can be obtained by reacting a 2-aminopyrazine derivative (24) with a halogenating agent at a temperature between −70 and 200° C. in a solvent or without a solvent. The solvent to be used is different depending on starting raw materials, reagents and the like, and is not particularly limited as far as it is does not inhibit a reaction and dissolves starting substances to some extent. Preferable examples of the solvent include acetic acid, toluene, xylene, pyridine, pyrimidine, 4-(dimethylamino)pyridine, methanol, ethanol, diethyl ether, ethylene glycol monomethyl ether, N,N-dimethylformamide, dichloromethane, chloroform, carbon tetrachloride and the like, and these solvents can be used alone or by mixing them. As the halogenated agent, for examples, chlorine, bromine, iodine, N-bromosuccinimide, N-chlorosuccinimide, N-iodosuccinimide and the like can be used.

Step A: An imidazo[1,2-a]pyrazine derivative (28) can be prepared by reacting an aminopyrazine derivative (27) and an α-halogenoketone derivative (26) at between 0° C. and 200° C. in a solvent or without a solvent. The solvent to be used is different depending on starting raw materials, reagents, and the like, and is not particularly limited as far as it does not inhibit a reaction and dissolves starting substances to some extent. Preferable examples include acetic acid, toluene, xylene, methanol, ethanol, ethylene glycol monomethyl ether, N,N-dimethylformamide and the like, and these solvents can be used alone or by mixing them.

Step B: A 3-nitro-imidazo[1,2-a]pyrazine derivative (29) can be obtained by reacting a pyrazolo[1,5-a]pyrimidine derivative (28) with a nitrating agent at between −20° C. and 200° C. in a solvent or without a solvent. The solvent to be used is different depending on starting raw materials, reagents and the like, and is not particularly limited as far as it does not inhibit a reaction and dissolves starting substances to some extent. Preferable examples include acetic anhydride, acetic acid, sulfuric acid, trifluoroacetic anhydride, trifluoroacetic acid, acetonitrile acid and the like. Examples of the nitrating agent include copper nitrate trihydrate, nitric acid, fuming nitric acid, $NaNO_3$, $NH_4^+NO_3^-$, $NO_2BF_4$ and the like.

Step C: A 3-amino-imidazo[1,2-a]pyrazine derivative (30) can be obtained by reacting a 3-nitro-imidazo[1,2-a]pyrazine derivative (29) with a metal (powder) in the presence or absence of an acid in a solvent or without a solvent. The reaction temperature in the present step is usually between −10° C. and 150° C. Examples of the acid to be used include acetic acid, hydrochloric acid, sulfuric acid and the like. The solvent to be used is different depending on starting material, reagents and the like, and is not particularly limited as far as it does not inhibit a reaction and dissolves starting substances to some extent. Preferable examples of the solvent include methanol, ethanol, n-butanol, water and the like, and these can be used alone or as a mixed solvent. In addition, examples of the metal (powder) to be used include Zn, Fe, $SnCl_2$, $NiCl_2$ and the like.

Alternatively, a 3-amino-imidazo[1,2-a]pyrazine derivative (30) may be prepared alos by subjecting a 3-nitro-imidazo[1,2-a]pyrazine derivative (4) to a hydrogenating reaction at between 0° C. and 200° C. and at a pressure of hydrogen of 1 to 100 atm in hydrogen atmosphere using a metal catalyst in the presence or absence of an acid in a solvent or without a solvent. The solvent to be used is different depending on starting raw materials, reagents and the like, and is not particularly limited as far as it does not inhibit a reaction and dissolves starting substances to some extent. Preferable examples include methanol, ethanol, propanol, butanol, tetrahydrofuran, dioxane, ethyl acetate, acetone, N,N-dimethylformamide and the like. Examples of the acid to be used include acetic acid, hydrochloric acid and the like. Examples of the metal catalysis to be used include Pd—C, $PtO_2$, Pt—C, Raney-Ni and the like. Alternatively, the hydrogenating reaction in this alternative method may be also performed by generating hydrogen in situ by heating ammonium formate etc. in a solvent.

The derivative (30) in the present process 8 can be subjected to the same reaction as the reaction using the derivative (12) in the above-mentioned Producing Process 2 to prepare the Compound (I) of the present invention.

Producing Process 9

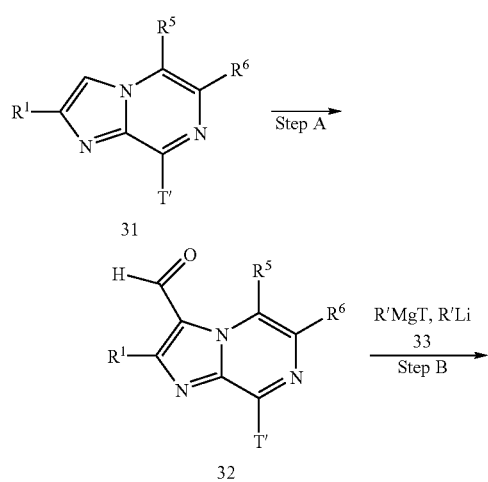

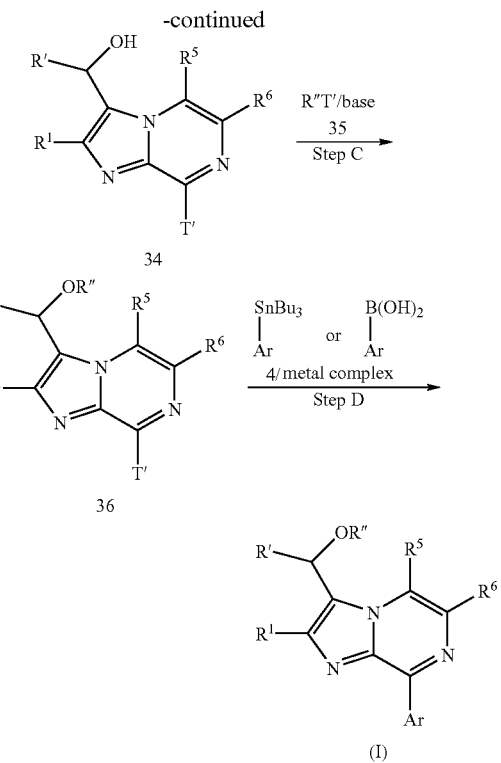

Step A: A 3-formyl compound (32) can be prepared by subjecting an imidazo[1,2-a]pyrazine derivative (31) to a reaction with phosphorus oxychloride under the conditions of Vilsmeier reaction. The present reaction is usually performed at a temperature of 0° C. to 200° C. in a solvent such as N,N-dimethylformamide and the like. Alternatively, a 3-formyl derivative (32) may be prepared by reacting an imidazo[1,2-a]pyrazine derivative (31) with dichloromethyl methyl ether in the presence of Lewis acid in a solvent or without a solvent. The solvent to be used is different depending on starting raw materials, reagents and the like, and is not particularly limited as far as it does not inhibit a reaction and dissolves starting substances to some extent. Preferable examples of the solvent include dichloromethane, chloroform, carbon tetrachloride, 1,2-dichloroethane and the like, and these can be used alone or by mixing them. Examples of Lewis acid to be used include titanium tetrachloride, aluminum chloride, tin chloride and the like.

Step B: A secondary alcohol derivative (34) can be prepared by reacting a 3-formyl-imidazo[1,2-a]pyrazine derivative (32) with Grignard regent or an organic metal reagent (33) such as an alkyllithium reagent and the like. The present reaction is usually performed at between −100° C. and 100° C. in a solvent or without a solvent. The solvent to be used is different depending on starting raw materials, reagents and the like, and is not particularly limited as far as it does not inhibit a reaction and dissolves starting substances to some extent. Preferable examples include diethyl ether, tetrahydrofuran, n-hexane, toluene and the like, and these can be used alone or by mixing them.

Step C: An ether derivative (36) can be prepared by reacting a secondary alcohol derivative (34) and an alkyl halide derivative (35) at between 0 and 200° C. in the presence of a base in a solvent or without a solvent. The solvent to be used is different depending on starting raw materials, reagents and the like, and is not particularly limited as far as it does not inhibit a reaction and dissolves starting substances to some extent. Preferable examples include diethyl ether, tetrahydrofuran, n-hexane, toluene, N,N-dimethylformamide, acetone and the like, and these can be used alone or by mixing them. The base to be used is different depending on starting raw materials, reagents and the like, and is not particularly limited as far as it does not inhibit a reaction and dissolves starting substances to some extent. Preferable examples include sodium hydride, potassium hydride, potassium carbonate, potassium tert-butoxide, sodium hydroxide, potassium hydroxide and the like, and these can be used alone or by mixing them.

Step D: Compound (36) can be subjected to the same reaction as that of the step B in the above Producing Process 1 to prepare Compound (I) of the present invention.

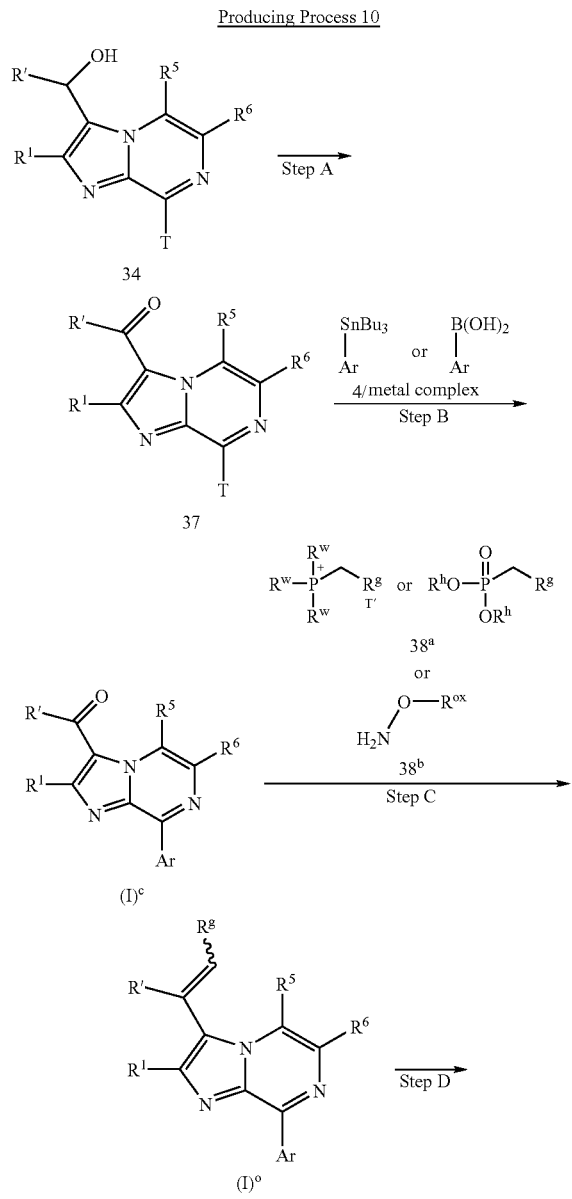

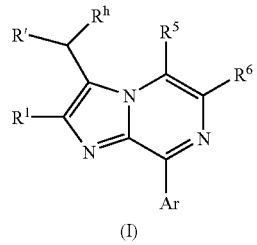

Step A: A carbonyl derivative (37) can be prepared by reacting a secondary alcohol derivative (34) with an oxidizing agent such as manganese(IV) oxide and the like in solvent or without a solvent. The present reaction is usually performed at between −100° C. and 150° C. The solvent to be used is different depending on starting raw materials, reagents and the like, and is not particularly limited as far as it does not inhibit a reaction and dissolves starting substances to some extent. Preferable examples include acetone, dichloromethane, n-hexane, toluene and the like, and these can be used alone or by mixing them. The oxidizing agent to be used is different depending on starting raw materials, reagents and the like, and is not particularly limited, but preferable examples thereof include manganese dichloride, Jones oxidizing regent, Kiliani regent, pyridinium dichromate, pyridinium chlorochromate, potassium dichromate and the like, and these maybe used alone or by mixing them. In addition, the oxidizing reaction in this step is not limited to a metal oxidizing agent, but may be performed under the oxidizing reaction conditions such as Swern oxidation and the like.

Step B: A derivative $(I)^C$ can be prepared by subjecting Compound (37) to the same reaction as that of the step B in Producing Process 1.

Step C: An olefin derivative $(I)^O$ can be prepared by treating a carbonyl derivative of the formula $(I)^C$ with Wittig regent or Horner-Emmons regent ($38^a$) (Wittig reaction or Horner-Emmons reaction). The present reaction is usually performed in a solvent or without a solvent. The solvent to be used is different depending on starting raw materials, reagents and the like, and is not particularly limited as far as it does not inhibit a reaction and dissolves starting substances to some extent. Preferable examples include tetrahydrofuran, diethyl ether, dichloromethane, n-hexane, toluene and the like, and these may be used alone or by mixing them. Alternatively, an olefin derivative $(I)^O$ can be prepared by Reformatsky reaction or the like. In addition, in the present step, a carbonyl derivative $(I)^C$ can be reacted with a hydroxylamine derivative or its salt derivative such as hydrochloride and the like ($38^b$) to prepare an oxime derivative. The reaction is usually performed at a temperature between 0° C. and 150° C. in a solvent or without a solvent. The solvent to be used is different depending on starting raw materials, reagents and the like, and is not particularly limited as far as it does not inhibit a reaction and dissolves starting substances to some extent. Preferable examples include tetrahydrofuran, diethyl ether, ethanol, methanol, n-propanol, water and the like, and these may be used alone or by mixing them.

Step D: An alkyl derivative (I) of the present invention can be prepared by subjecting an olefin derivative (I)$^O$ to a hydrogenating reaction in the presence or absence of an acid in the presence of a metal catalyst such as Pd—C and the like in a solvent or without a solvent. The present reaction is usually performed at a temperature of 0° C. to 200° C. in hydrogen atmosphere at a hydrogen pressure of 1 atm to 100 atm. The solvent to be used is different depending on starting raw materials, reagents and the like, and is not particularly limited as far as it does not inhibit a reaction and dissolves starting substances to some extent. Preferable examples include methanol, ethanol, propanol, butanol, ethyl acetate, dioxane, tetrahydrofuran, diethyl ether, N,N-dimethylformamide, n-hexane, toluene and the like, and these may be used alone or by mixing them. Examples of the acid to be used include acetic acid, hydrochloric acid and the like. Examples of the metal catalyst to be used include Pd—C, PtO$_2$, Pt—C, Raney-Ni and the like. Alternatively, an objective compound may be obtained by generating hydrogen in situ by heating ammonium formate etc. in a solvent such as methanol.

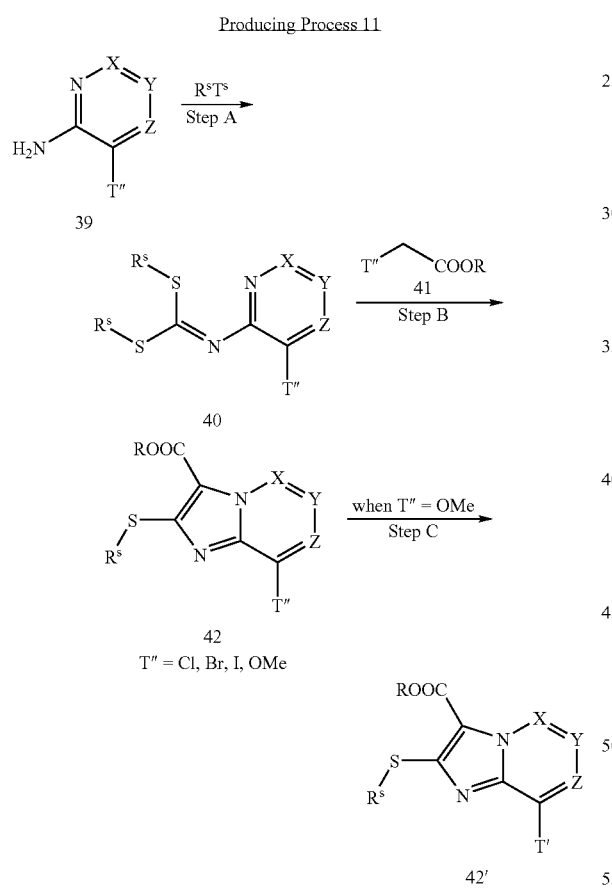

Step A: Alkyl(alkylsulfanyl)methaneimido thioate (40) can be prepared by first reacting a 6-membered nitrogen-containing heterocyclic ring having an amino group (39) with a base at a temperature of 0° C. to 100° C. in a solvent or without a solvent, allowing to stand for a little while, reacting with carbon disulfide at a temperature of 0° C. to 100° C., further, adding a base at a temperature of 0° C. to 100° C., and subjecting to a reaction with alkyl halide (compound represented by R$^S$T$^S$ in the formula) at a temperature of 0° C. to 100° C. The solvent to be used is different depending on starting raw materials, reagents and the like, and is not particularly limited as far as it does not inhibit a reaction and dissolves starting substances to some extent. Preferable examples include N,N-dimethylformamide, methanol, ethanol, ethylene glycol monomethyl ether, toluene, water and the like, and these may be used alone or by mixing them. Examples of the base to be used include preferably sodium hydroxide, potassium hydroxide, barium hydroxide, lithium hydroxide and the like.

Step B: A dicyclic nitrogen-containing heterocyclic ring (42) which has an ester group at the 3-position and is fused with an imidazole ring, can be prepared by reacting alkyl(alkylsulfanyl)methaneimido thioate (40) with halogenoacetic acid ester (41) at a temperature of 0° C. to 200° C. in a solvent or without a solvent, then, cooling the reaction mixture to a room temperature, and treating the mixture with a base such as triethylamine and the like. The solvent to be used is different depending on starting raw materials, reagents and the like, and is not particularly limited as far as it does not inhibit a reaction and dissolves starting materials to some extent. Preferable examples include N,N-dimethylformamide, methanol, ethanol, ethylene glycol monomethyl ether, toluene and the like, and these can be used alone or by mixing them. Examples of the base to be used include triethylamine, pyridine, sodium hydroxide, potassium hydroxide, barium hydroxide, lithium hydroxide and the like.

When T" in the formula is a halogen atom in Compounds 39 and 42 in the present Producing Process 11, the compounds can be derived into a derivative with an aryl group or the like introduced therein by performing the same coupling reaction as that of the step B in the above Producing Process 1. Alternatively, a derivative (42) can be prepared by subjecting to the same reaction as the reaction treating the derivative (5) in the above Producing Process 1.

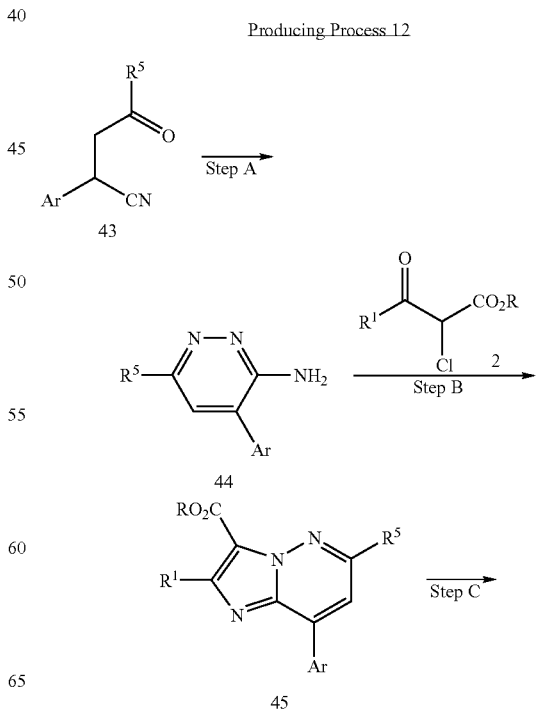

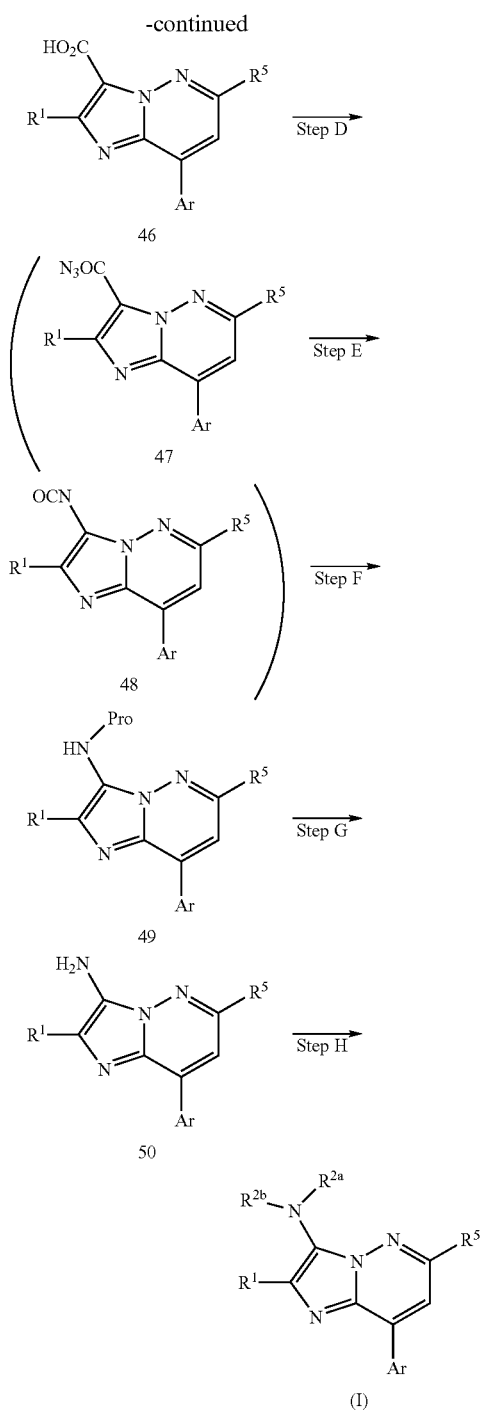

Step A: A 3-aminopyridazine derivative (44) can be prepared by reacting a 3-oxo-alkyl cyanide derivative (43) with hydrazine at a temperature of 0° C. to 200° C. in a solvent or without a solvent. The solvent to be used is different depending on starting raw materials, reagents and the like, and is not particularly limited as far as it does not inhibit a reaction and dissolves starting substances to some extent. Preferable examples include acetic acid, toluene, xylene, methanol, ethanol, ethylene glycol monomethyl ether, N,N-dimethylformamide, water and the like, and these can be used alone or by mixing them. Hydrazine may be also used as a corresponding salt such as hydrazine monohydrochloride and the like in the reaction.

Step B: An imidazo[1,2-b]pyridazine derivative (45) can be prepared by reacting a 3-aminopyridazine derivative (44) and an α-chloro-β-ketoester derivative (2) at a temperature of 0° C. to 200° C. in a solvent or without a solvent. The solvent to be used is different depending on starting raw materials, reagents and the like, and is not particularly limited as far as it does not inhibit a reaction and dissolves starting substances to some extent. Preferable examples include toluene, xylene, methanol, ethanol, ethylene glycol monomethyl ether, N,N-dimethylformamide, dimethyl sulfoxide and the like, and these can be used alone or by mixing them.

Step C: An imidazo[1,2-b]pyridazine-3-carboxylic acid derivative (46) can be prepared by subjecting an imidazo[1,2-b]pyridazine-3-carboxylic acid ester derivative (45) or the like to a hydrolyzing reaction at a temperature of 0° C. to 200° C. in the presence of a base in a solvent or without a solvent. The solvent to be used is different depending on starting raw materials, reagents and the like, and is not particularly limited as far as it does not inhibit a reaction and dissolves starting substances to some extent. Preferable examples include ethanol, methanol, n-butanol, tert-butanol, tetrahydrofuran, dioxane, water and the like, and these can be used alone or as a mixed solvent. Examples of the base to be used include sodium hydroxide, potassium hydroxide, potassium carbonate, sodium carbonate, cesium carbonate, potassium t-butoxide and the like.

Steps D, E, F: A 3-aminoimidazo[1,2-b]pyridazine derivative (49) protected with a carbamate group (e.g. tert-butoxycarbonyl (Boc) etc.) can be prepared by reacting an imidazo[1,2-b]pyridazine-3-carboxylic acid derivative (46) with a aziding agent (e.g. diphenylphosphorylazide etc.) at a temperature of −70° C. to 250° C. in the presence or absence of a base in a solvent or without a solvent to prepare an acid azide derivative (47), then, subjecting the acid azide derivative to a rearrangement reaction such as Curtius rearrangement reaction and the like by heating to 0 to 250° C., to generate isocyanate (48) in situ and, further, reacting this with tert-butanol or the like. The solvent to be used is different depending on starting materials, reagents and the like, and is not particularly limited as far as it does not inhibit a reaction and dissolves starting substances to some extent. Preferable examples include benzene, toluene, xylene, diphenyl ether, tert-butanol, tetrahydrofuran, dioxane, acetonitrile, N,N-dimethylformamide and the like, and these may be used alone or as a mixed solvent. Examples of the base to be used include triethylamine, diisopropylethylamine, 4-(dimethylamino)pyridine, and pyridine.

Besides, as another method of a process for preparing an acid azide derivative (47), the derivative may be prepared by deriving an imidazo[1,2-b]pyridazine3-carboxylic acid derivative (46) into acid chloride or mixed acid anhydride and, then, subjecting the derivative to a reaction with an aziding agent (e.g. sodium azide, trimethylsilylazide etc.). In addition, as another method for preparing a 3-amino-imidazo [1,2-b]pyridazine derivative (49), there are processes using Hofmann rearrangement reaction and Schmidt rearrangement reaction.

Step G: A 3-amino-imidazo[1,2-b]pyridazine derivative (50) can be prepared by subjecting a protected imidazo[1,2-b] pyridazine derivative (49) to a deprotecting reaction at a temperature of −70 to 200° C. in the presence or absence of a deprotecting agent in a solvent or without a solvent. The solvent to be used is different depending on starting raw materials, reagents and the like, and is not particularly limited as far as it does not inhibit a reaction and dissolves starting substances to some extent. Preferable examples include ethyl acetate, tetrahydrofuran, diethyl ether, dioxane, acetonitrile, dichloromethane, chloroform, nitoromethane, phenol, anisole, thiophenol and the like. In addition, examples of the deprotecting agent to be used include hydrochloric acid, sulfuric acid, trifluoroacetic acid, methanesulfonic acid, iodotrimethylsilane, aluminum (III) chloride, trimethylsilyl triflate and the like. In addition, when a protecting group other than Boc (e.g. Fmoc, Troc, etc.) is used as a protecting group for Compound (49), the compound is deprotected by a deprotecting agent and a reaction which are suitable for each protecting group.

Step H: An imidazo[1,2-b]pyridazine derivative (I) of the present invention can be obtained by reacting a 3-aminoimidazo[1,2-b]pyridazine derivative (50) with a carbonyl derivative (e.g. diethyl ketone) or an aldehyde derivative (e.g. propionaldehyde) in the presence or absence of an acid and in the presence or absence of an inorganic salt in a solvent or without a solvent, to form an imine derivative in the reaction system and, then, adding a reducing agent at a temperature of −10 to 150° C. to react them. The solvent to be used is different depending on starting raw materials, reagents and the like, and is not particularly limited as far as it does not inhibit a reaction and dissolves starting substances to some extent. Preferable examples include tetrahydrofuran, diethyl ether, 1,2-dichloroethane, dichloromethane, chloroform, acetonitrile, water and the like, and these can be used alone or as a mixed solvent. Examples of the acid to be used include acetic acid, sulfuric acid and the like. Examples of the inorganic salt to be used include sodium sulfate, magnesium sulfate and the like. Examples of the reducing agent to be used include sodium triacetoxyborohydride, sodium borohydride, sodium cyanotrihydroborohydride and the like.

As another method regarding the present step, an imidazo[1,2-b]pyridazine derivative (I) can be prepared by reacting a 3-amino-imidazo[1,2-b]pyridazine derivative (50) with an alkylating agent containing a leaving group such as halide (e.g. alkyl halide etc.), an acylating agent (e.g. acid chloride, acid anhydride, etc.) or sulfonic acid chloride (e.g. tosylate chloride etc.) at a temperature of −70° C. to 200° C. in the presence or absence of a base in a solvent or without a solvent. The solvent to be used is different depending on starting raw materials, reagents and the like, and is not particularly limited as far as it does not inhibit a reaction and dissolves starting substances to some extent. Preferable examples include tetrahydrofuran, diethyl ether, N,N-dimethylformamide, dimethyl sulfoxide and the like. Examples of the base to be used include sodium hydride, potassium hydride, potassium carbonate, sodium carbonate, cesium carbonate, potassium hydroxide, sodium hydroxide, pyridine, triethylamine and the like.

Producing Process 13

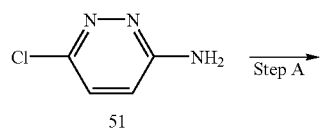

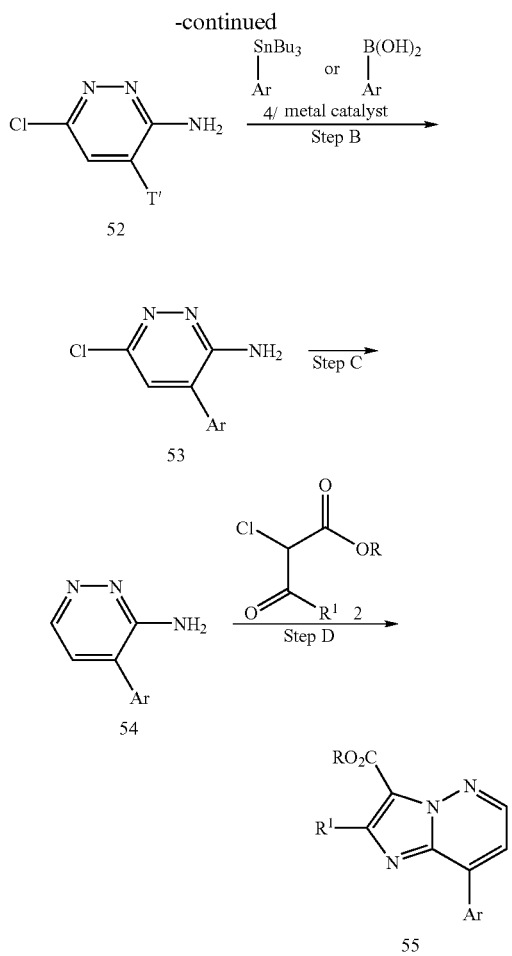

Step A: An aminopyridazine derivative (52) can be prepared by treating a 3-amino-6-chloropyridazine (51) with a halogenating agent, which is subjected to a halogenating reaction. The present reaction is usually performed in the presence or absence of a base in a solvent or without a solvent, and a reaction temperature is usually 0 to 200° C. The halogenating agent to be used is different depending on starting raw materials, a solvent to be used, and the like, and is not particularly limited as far as it does not inhibit a reaction. Preferable examples include bromine, iodine, N-chlorosuccinimide, N-bromosuccinimide, N-iodosuccinimide, tetrabutylammonium tribromide and the like. The solvent to be used is different depending on starting raw materials, reagents and the like, and is not particularly limited as far as it does not inhibit a reaction and dissolves starting substances to some extent. Preferable examples include tetrahydrofuran, N,N-dimethylformamide, 1,4-dioxane, methanol, ethanol, dichloromethane, acetic acid, carbon tetrachloride, water and the like. Examples of the base to be used include potassium carbonate, sodium carbonate, calcium carbonate, sodium bicarbonate and the like.

Step B: An aminopyridazine derivative (53) substituted with an aryl group at the 4-position can be prepared by subjecting an aminopyridazine derivative (52) to the same reaction as that of the step B in the above Producing Process 1.

Step C: A 3-aminopyridazine derivative (54) can be prepared by subjecting a 3-amino-4-aryl-6-chloropyridazine derivative (53) to a catalytic hydrogenating reaction. Such the catalytic hydrogenating reaction is usually performed in the presence or absence of a base and in the presence of a metal regent such as Pd—C and the like in a solvent or without a solvent, a hydrogen pressure is usually 1 to 100 atm, and a reaction temperature is usually 0 to 200° C. The solvent to be used is different depending on starting raw materials, reagents and the like, and is not particularly limited as far as it does not inhibit a reaction and dissolves starting substances to some extent. Preferable examples include methanol, ethanol, propanol, butanol, ethyl acetate, dioxane, tetrahydrofuran, diethyl ether, N,N-dimethylformamide, n-hexane, toluene, acetic acid and the like, and these can be used alone or by mixing them. Examples of the base to be used include sodium hydroxide, potassium hydroxide, barium hydroxide, lithium hydroxide and the like. Examples of the metal regent to be used include Pd—C, $PtO_2$, Pt—C, Raney-Ni and the like.

As another process regarding this step, a 3-aminopyridazine derivative (54) may be prepared by generating hydrogen in situ by heating a hydrogen source such as ammonium formate and the like in a solvent. The solvent to be used is different depending on starting raw materials, reagents and the like, and is not particularly limited as far as it does not inhibit a reaction and dissolves starting substances to some extent. Preferable examples include acetic acid, methanol, ethanol, n-propanol and the like. Examples of the hydrogen source to be used include $NaH_2PO_2$, $HCO_2NH_4$, $HCO_2NH(CH_2)_3$ and the like.

Step D: An imidazo[1,2-b]pyridazine derivative (55) can be prepared by reacting an aminopyridazine derivative (54) and an α-chloro-β-ketoester derivative (2) at a temperature of 0 to 200° C. in a solvent or without a solvent. The solvent to be used is different depending on starting raw materials, reagents and the like, and is not particularly limited as far as it does not inhibit a reaction and dissolves starting substances to some extent. Preferable examples include acetic acid, toluene, xylene, methanol, ethanol, ethylene glycol monomethyl ether, N,N-dimethylformamide and the like, and these can be used alone or by mixing them.

Finally, the imidazo[1,2-b]pyridazine derivative (55) prepared by the present process can be subjected to the same reaction treating the imidazo[1,2-b]pyridazine derivative (45) in the above Producing Process 12, to prepare the compound of the present invention.

Producing Process 14

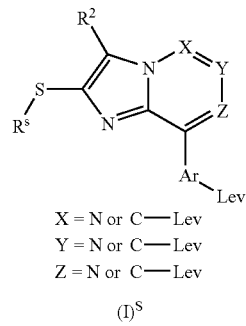

Step A: A nitrogen-containing heterocyclic derivative $(I)^L$ can be prepared by subjecting a dicyclic nitrogen-containing heterocyclic derivative $(I)^S$ to an oxidizing reaction, and converting a substituted sulfide group which binds to the 2-position of $(I)^S$, into a leaving group (e.g. substituted sulfonyl group etc.). The oxidizing reaction is usually performed in a solvent or without a solvent, and a reaction temperature is −70 to 150° C. The solvent to be used is different depending on starting raw materials, reagents and the like, and is not particularly limited as far as it does not inhibit a reaction and dissolves starting substances to some extent. Preferable examples include toluene, xylene, methanol, ethanol, tetrahydrofuran, ethylene glycol monomethyl ether, dichloromethane, chloroform and the like, and these can be used alone or by mixing them. Examples of the oxidizing agent to be used include meta-chloroperbenzoic acid, oxone and the like.

Step B: This step is for converting a dicyclic nitrogen-containing heterocyclic derivative $(I)^L$ having a leaving group (e.g. halogen atom, trifluoromethanesulfonyl group, etc.) into a dicyclic nitrogen-containing heterocyclic derivative $(I)^n$ to which a desired substituent $R^n$ binds. As the reaction, a nucleophilic reaction using alkoxide, a metal cyan compound and the like, a coupling reaction using a Pd catalyst can be used. The number of a substituent to be introduced is not limited to one, and a derivative in which two or more substituents are introduced can be easily prepared.

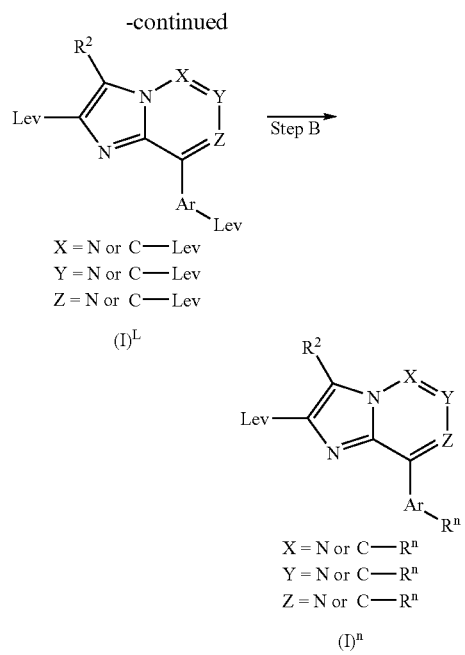

Producing Process 15

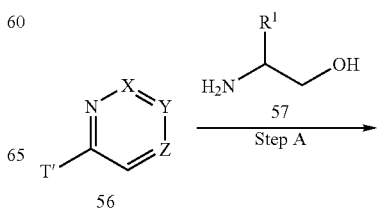

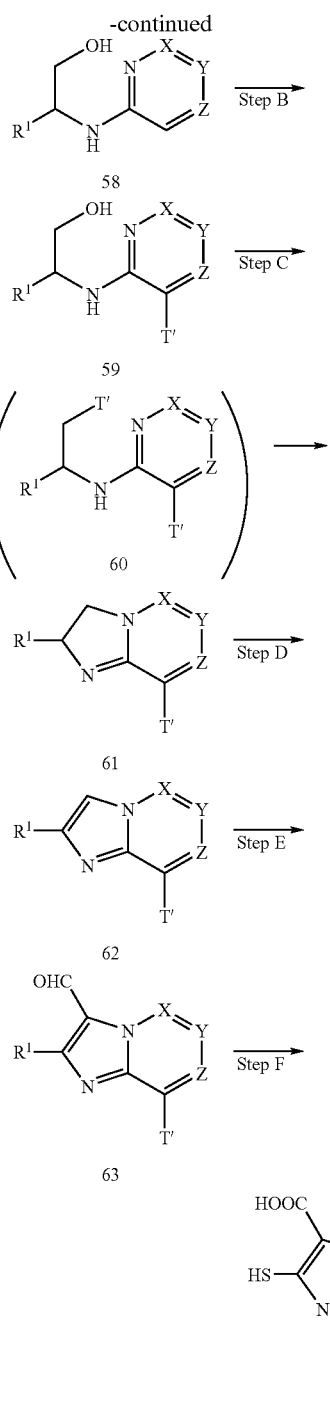

reaction and dissolves starting substances to some extent. Preferable examples include toluene, xylene, tetrahydrofuran, ethylene glycol dimethyl ether, N,N-dimethylformamide, 1,4-dioxane and the like, and these can be used alone or by mixing them. Examples of the base to be used include triethylamine, pyridine, 4-(dimethylamino)pyridine and the like.

Step B: A monocyclic nitrogen-containing heterocyclic derivative (59) substituted with halogen at the 3-position can be prepared by subjecting a monocyclic nitrogen-containing heterocyclic derivative (58) substituted with an amino group at the 2-position to a halogenating reaction. The halogenating reaction is usually performed by treating with a halogenating agent in a solvent or without a solvent, and a reaction temperature is usually 0 to 200° C. The solvent to be used is different depending on starting raw materials, reagents and the like, and is not particularly limited as far as it does not inhibit a reaction and dissolves starting substances to some extent. Preferable examples include acetic acid, toluene, xylene, methanol, ethanol, diethyl ether, ethylene glycol monomethyl ether, N,N-dimethylformamide, dichloromethane, chloroform, carbon tetrachloride and the like, and these can be used alone or by mixing them. As the halogenating agent, for example, chlorine, bromine, iodine, N-bromosuccinimide, N-chlorosuccinimide, N-iodosuccinimide and the like can be used.

Step C: A derivative (61) in which a dihydroimidazole ring is formed can be prepared by subjecting a monocyclic nitrogen-containing heterocyclic derivative (59) to a halogenating reaction, followed by cyclizing reaction. The reaction is usually performed in a solvent or without a solvent, and a reaction temperature is usually 0 to 200° C. The solvent to be used is different depending on starting raw materials, reagents and the like, and is not particularly limited as far as it does not inhibit a reaction and dissolves starting substances to some extent. Preferable examples include acetic acid, toluene, xylene, tetrahydrofuran, ethylene glycol momomethyl ether, N,N-dimethylformamide, dichloromethane, chloroform, carbon tetrachloride and the like, and these can be used alone or by mixing them. As the halogenating agent, for example, chlorine, bromine, iodine, thionyl chloride, thionyl bromide and the like can be used.

Step D: A nitrogen-containing heterocyclic derivative (62) having an imidazole ring can be prepared by reacting a dicyclic nitrogen-containing heterocyclic derivative (61) having a dihydroimidazole ring with an oxidizing agent or an aromatizing agent. The reaction is usually performed in a solvent, and a reaction temperature is usually 0 to 250° C. The solvent to be used is different depending on starting raw materials, reagents and the like, and is not particularly limited as far as it does not inhibit a reaction and dissolves starting substances to some extent. Preferable examples include acetone, dichloromethane, n-hexane, toluene, xylene, 1-methyl-2-pyrrolidinone and the like, and these can be used alone by mixing them. The oxidizing agent to be used is different depending on starting raw materials, reagents and the like, and is not particularly limited, but preferable examples include manganese (IV) oxide, pyridinium dichromate, pyridinium chlorochromate, potassium dichromate and the like, and these can be used alone or by mixing them. Examples of the aromatizing agent include 2,3-dichloro-5,6-dicyano-1,4-benzoquinone, air oxidizing and the like.

Step A: A monocyclic nitrogen-containing heterocyclic derivative (58) substituted with an amino group of the above ethanolamine derivative at the 2-position can be prepared by reacting a monocyclic nitrogen-containing heterocyclic derivative (56) substituted with a halogen atom at the 2-position with the ethanolamine derivative (57). The reaction is performed in the presence or absence of a base and in a solvent or without a solvent, and a reaction temperature is usually 0 to 250° C. The solvent to be used is different depending on starting raw materials, reagents and the like, and is not particularly limited as far as it does not inhibit a Step E: An aldehyde compound (63) can be prepared by subjecting the nitrogen-containing heterocyclic derivative (62) having an imidazole ring to the same reaction as that of the step A in Producing Process 9.

Step F: The carboxylic acid compound (64) can be prepared by reacting an aldehyde compound (63) and an oxidizing agent. The reaction is usually performed in a solvent or without a solvent, and a reaction temperature is usually −10 to 200° C. The solvent to be used is different depending on starting raw materials, reagents and the like, and is not particularly limited as far as it does not inhibit a reaction and dissolves starting substances to some extent. Preferable examples include acetone, dichloromethane, n-hexane, toluene, xylene, acetonitrile, water and the like, and these can be used alone or by mixing them. The oxidizing agent to be used is different depending on starting raw materials, reagents and the like, and is not particularly limited, but preferable examples include potassium permanganate, silver oxide, activated manganese (IV) oxide, pyridinium dichromate, sodium chlorate and the like, and these can be used alone or by mixing them. The above derivative (64) can be subjected to the same reaction as that treating the derivative (13) in the above Producing Process 2 to prepare Compound (I) of the present invention.

The foregoing are representative examples of a process for preparing the Compound (I) of the present invention, but raw material compounds and various reagents in preparing the present compound may form a salt or a hydrate, and any of a salt and a hydrate is different depending on starting raw materials, a solvent to be used, and the like, and is not particularly limited as far as it does not inhibit a reaction. The solvent to be used is also different depending on starting raw materials, reagents and the like, and it goes without saying that the solvent is not particularly limited as far as it does not inhibit a reaction and dissolves starting substances to some extent. When Compound (I) of the present invention is obtained as a free compound, it can be converted into a salt which may be formed by the Compound (I), according to the conventional method. In addition, various isomers (e.g. geometrical isomer, optical isomer based on asymmetric carbon, rotamer, stereo isomer, tautomer, etc.) obtained for Compound (I) of the present invention can be purified and isolated by using the conventional separating means, for example, recrystallization, diastereomer salt method, enzyme dissolution method, a variety of chromatographies (e.g. thin layer chromatography, column chromatography, gas chromatography, etc.) and the like.

A compound represented by the aforementioned formula (I) of the present invention, a salt thereof or a hydrate of them can be used as it is, or can be formulated into preparations by mixing with a known per se pharmaceutically acceptable carrier, according to the conventional method. Examples of a preferable dosage form include tablets, powders, fine granules, granules, coated tablets, capsules, syrups, troches, inhalants, suppositories, injections, ointments, eye ointments, eye drops, nasal drops, ear drops, cataplasms, lotions and the like. For formulation into preparations, fillers, binders, disintegrating agents, lubricants, coloring agents, flavoring agents and, if necessary, stabilizer, emulsifying agents, absorption promoting agents, surfactants, pH adjusting agents, preservatives and antioxidants which are normally used can be employed, and can be formulated into preparations by incorporating components which are used as a raw material for general pharmaceutical preparations, according to the conventional method.

Examples of these components include animal and vegetable oils such as soybean oil, beef tallow, synthetic glyceride and the like; hydrocarbons such as liquid paraffin, squalane, solid paraffin and the like; ester oils such as octyldodecyl myristate, isopropyl myristate and the like; higher alcohols such as cetostearyl alcohol, behenyl alcohol and the like; silicone resins; silicone oils; surfactants such as polyoxyethylene fatty acid esters, sorbitan fatty acid ester, glycerin fatty acid ester, polyoxyethylene sorbitan fatty acid ester, polyoxyethylene hydrogenated castor oil, polyoxyethylene-polyoxypropylene block copolymer and the like; water-soluble polymers such as hydroxyethyl cellulose, polyacrylic acid, carboxyvinyl polymer, polyethylene glycol, polyvinylpyrrolidone, and methyl cellulose; lower alcohols such as ethanol and isopropanol; polyhydric alcohols such as glycerin, propylene glycol, dipropylene glycol and sorbitol; sugars such as glucose and sucrose; inorganic powders such as silisic anhydride, aluminum magnesium silicate, and aluminum silicate; purified water. As an filler, for example, lactose, corn starch, sucrose, glucose, mannitol, sorbitol, crystalline cellulose, silicon dioxide and the like are used; as a binder, for example, polyvinyl alcohol, polyvinyl ether, methyl cellulose, ethyl cellulose, gum arabic, tragacanth, gelatin, shellac, hydroxypropyl cellulose, hydroxypropylmethyl celulose, polyvinylpyrrolidone, polypropylene glycol-polyoxyethylene block polymer, meglumine, calcium citrate, dextrin, pectin and the like are used; as a disintegrating agent, for example, starch, agar, gelatin powder, crystalline cellulose, calcium carbonate, sodium bicarbonate, calcium citrate, dextrin, pectin, calcium carboxymethyl celluose and the like are used; as a lubricant, for example, magnesium stearate, talc, polyethylene glycol, silica, hydrogenated vegetable oil and the like are used; as a coloring agent, any colorants may be used as far as they are permitted to add to medicaments; as a flavoring agent, cocoa powder, 1-menthol, aromatic powder, mentha oil, Borneo camphor, powdered cinnamon bark and the like are used; as an antioxidant, those which are permitted to add to medicaments, such as ascorbic acid, α-tocopherol and the like are used.

An oral preparation is formulated into powders, fine granules, granules, tablets, coated tablets, capsules or the like according to the conventional method after a filler and, if necessary, a binder, a disintegrating agent, a lubricant, a colorant and a flavoring agent are added to the compound of the present invention or a salt thereof.

In the case of tablets and granules, of course, they may be subjected to sugar coating, gelatin coating and, if necessary, other suitable coating.

In the case of solutions such as syrups, injections, eye drops and the like, a pH adjusting agent, a dissolving agent, an isotonic and the like and, if necessary, a solublizer, a stabilizer, a buffer, a suspending agent, an antioxidant and the like are added, which is formulated into a preparation according to the conventional method. In the case of the solutions, they can be formulated into freeze-dried materials, and injections can be administered intravenously, subcutaneously or intramuscularly. Preferable examples of the suspending agent include methylcellulose, Polysorbate 80, hydroxyethyl cellulose, gum arabic, tragacanth powder, sodium carboxymethyl cellulose, polyoxyethylene sorbitan monolaurate and the like; preferable examples of the solubilizer include polyoxyethylene hydrogenated castor oil, Polysorbate 80, nicotinamide, polyoxyethylene sorbitan monolaurate and the like; preferable examples of the stabilizer include sodium sulfite, sodium metasulfite, ether and the like; and preferable examples of the preservative include methyl paraoxybenzoate, ethyl paraoxybenzoate, sorbic acid, phenol, cresol, chlorocresol and the like.

In the case of an external preparation, a process for preparing it is not particularly limited, but it can be prepared by the conventional method. As the base raw material to be used, various raw materials which are normally used for medicaments, quasi-drugs, cosmetics and the like can be used, and examples thereof include raw materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water and, if necessary, a pH adjusting agent, an antioxidant, a chelating agent, a preservative, an antifungal agent, a colorant and a perfume can be added. Further, if necessary, ingredients such as an ingredient having the differentiation inducing activity, a blood flow promoter, a sterilizer, an anti-inflammatory, a cell activating agent, vitamins, an amino acid, a humectant, a keratin dissolving agent and the like may be also incorporated.

A pharmaceutical preparation containing Compound (I) of the present invention, a salt or a hydrate of them as an active ingredient is useful for treating or preventing a mammal (e.g. human, mouse, rat, guinea pig, rabbit, dog, horse, monkey, etc.), in particular, treating or preventing human. A dose of a pharmaceutical of the present invention is different depending on an extent of symptom, age, sex, weight, dosage form, a kind of a salt, a difference in sensitivity to a drug, a specific kind of diseases, and the like and, in the case of human, usually, in the case of an adult, about 30 μg to 10 g, preferably 100 μg to 500 mg, more preferably 100 μg to 100 mg is orally administered, or about 1 to 3000 μg/kg, preferably 3 to 1000 μg/kg is administered by injection, per day once or a few times.

According to the present invention, novel compounds having the CRF receptor antagonism, a pharmacologically acceptable salt thereof and hydrates thereof can be provided. The compound of the present invention, a pharmacologically acceptable salt thereof or hydrates thereof have an excellent antagonism to a CRF receptor, are low toxic, highly safe and highly useful as a drug. The compounds of the present invention are useful as an agent for treating or preventing diseases to which CRF and/or its receptor relate. In particular, they are useful as an agent for treating or preventing depression, depressive symptom (great depression, monostotic depression, recurrent depression, infant tyrannism by depression, postpartum depression etc.), mania, anxiety, generalized anxiety disorder, panic disorder, phobia, compulsive disorder, posttraumatic stress disorder, Tourette syndrome, autism, emotional disorder, sentimental disorder, bipolar disorder, cyclothymia, schizophrenia, peptic ulcer, irritable bowel syndrome, ulcerative colitis, Crohn's disease, diarrhea, coprostasis, postoperational ileus, gastrointestinal function abnormality associated with stress, neural vomiting etc.

EXAMPLES

The following Reference Examples, Examples and Experimental Examples are merely illustrative, and compounds of the present invention are not limited by the following embodiments in any case. A person skilled in the art can implement the present invention at maximum by variously altering not only the following Examples but also claims of the present specification, and such the alterations are included in claims of the present specification.

Reference Example 1

8-Chloro-2-ethylimidazo[1,2-a]pyrazine-3-carboxylic acid methyl ester

3-Chloro-2-aminopyrazine (2.1 g, 16.2 mmol) and methyl 2-chloro-3-oxopentanoate (6.7 mL, 48.6 mmol) were mixed, and heated under stirring at 170° C. for 2 hours. After being allowed to cool, the unnecessary materials were filtered off and washed with ethyl acetate, and then filtrates were combined and evaporated. The resulting residue was purified by silica gel column chromatography (n-hexane:ethyl acetate=4:1) to give the title compound (0.99 g) as white crystals.

$^1$H NMR (400 MHz, CDCl$_3$) δ 1.37 (t, J=7.6 Hz, 3H), 3.18 (q, J=7.6 Hz, 2H), 4.03 (s, 3H), 7.87 (d, J=4.6 Hz, 1H), 9.14 (d, J=4.6 Hz, 1H).

Reference Example 2

5-Chloro-3-(2,4-dichlorophenyl)-2-pyrazinamine 3-(2,4-Dichlorophenyl)-2-pyrazinamine (1.43 g, 6.0 mmol) was dissolved in chloroform (9 mL), N-chlorosuccinimide (0.96 g, 7.2 mmol) was added thereto, and the mixture was stirred by heating under reflux for 4 hours. After being allowed to cool, water was added to the reaction mixture, which was extracted with ethyl acetate. The organic layer was dried over anhydrous magnesium sulfate and evaporated. The resulting residue was purified by silica gel column chromatography (ethyl acetate:n-hexane=1:2) to give the title compound (1.54 g) as yellow crystals.

$^1$H NMR (400 MHz, CDCl$_3$) δ 4.55 (br s, 2H), 7.38 (d, J=8.2 Hz, 1H), 7.41 (dd, J=1.8, 8.2 Hz, 1H), 7.55 (d, J=1.8 Hz, 1H), 8.10 (s, 1H).

Reference Example 3

8-Bromo-2-ethyl-6-methylimidazo[1,2-a]pyrazine-3-carboxylic acid methyl ester

3-Bromo-5-methyl-2-pyrazineamine (3.5 g, 18.6 mmol) and methyl 2-chloro-3-oxopentanoate (6.7 mL, 48.6 mmol) were mixed, and the mixture was heated under stirring at 130° C. for 1 hour. After being allowed to cool, the unnecessary materials were filtered off and washed with ethyl acetate, and then the filtrates were combined and evaporated. The resulting residue was purified by silica gel column chromatography (n-hexane:ethyl acetate=3:1) to give the title compound (0.32 g) as pale yellow crystals.

$^1$H NMR (400 MHz, CDCl$_3$) δ 1.35 (t, J=7.5 Hz, 3H), 2.56 (s, 3H), 3.15 (q, J=7.5 Hz, 2H), 4.01 (s, 3H), 8.98 (s, 1H).

Reference Example 4

8-Chloro-2-ethylimidazo[1,2-a]pyrazine-3-carbaldehyde

8-Chloro-2-ethylimidazo[1,2-a]pyrazine (600 mg, 3.3 mmol) was dissolved in N,N-dimethylformamide (3.3 mL), phosphorus oxychloride (1.2 mL, 13.2 mmol) was added dropwise at room temperature, and the mixture was heated under stirring at 90° C. for 2 hours. After being allowed to cool, the reaction mixture was poured into ice and extracted with ethyl acetate. The organic layer was dried over anhydrous magnesium sulfate and evaporated to give the title compound (472 mg) as white crystals.

$^1$H NMR (400 MHZ, CDCl$_3$) δ 1.49 (t, J=7.5 Hz, 3H), 3.18 (q, J=7.5 Hz, 2H), 7.97 (d, J=4.4 Hz, 1H), 9.31 (d, J=4.4 Hz, 1H), 10.18 (s, 1H).

Reference Example 5

1-(8-Chloro-2-ethylimidazo[1,2-a]pyrazin-3-yl)butyl ethyl ether

8-Chloro-2-ethylimidazo[1,2-a]pyrazine-3-carbaldehyde (146 mg, 0.70 mmol) was dissolved in tetrahydrofuran (1.4 mL), then a 0.90M propylmagnesium bromide solution in tetrahydrofuran (1.6 mL, 1.4 mmol) was added thereto under ice-cooling, and the mixture was stirred for 30 minutes. An aqueous saturated ammonium chloride solution was added to the reaction mixture, which was extracted with ethyl acetate. The organic layer was dried over anhydrous magnesium sulfate and evaporated. The resulting alcohol compound was used in the next reaction without purification.

The resulting 1-(8-chloro-2-ethylimidazo[1,2-a]pyrazin-3-yl)-1-butanol was dissolved in N,N-dimethylformamide (2.2 mL), then iodoethane (0.079 mL, 0.99 mmol) and sodium hydride (65% in oil; 49 mg, 1.32 mmol) were added thereto under ice-cooling, and the mixture was stirred for 3 hours. Water was added to the reaction mixture, which was extracted with ethyl acetate and evaporated. The resulting residue was purified by silica gel column chromatography (ethyl acetate:n-hexane=1:3) to give the title compound (55 mg) as a colorless oil.

$^1$H NMR (400 MHz, CDCl$_3$) δ 0.88–0.96 (m, 3H), 1.12–1.17 (m, 3H), 1.18–1.37 (m, 4H), 1.39–1.52 (m, 1H), 1.69–1.81 (m, 1H), 1.97–2.07 (m, 1H), 2.75–2.89 (m, 2H), 3.18–3.27 (m, 1H), 3.33–3.42 (m, 1H), 4.70–4.76 (m, 1H), 7.60 (d, J=4.6 Hz, 1H). 8.35 (d, J=4.6 Hz, 1H).

Reference Example 6

1-(8-Chloro-2-ethylimidazo[1,2-a]pyrazin-3-yl)-1-butanone

8-Chloro-2-ethylimidazo[1,2-a]pyrazine-3-carbaldehyde (328 mg, 1.6 mmol) was dissolved in tetrahydrofuran (3.2 mL), then a 0.90M propylmagnesium bromide solution in tetrahydrofuran (4.4 mL, 4.0 mmol) was added thereto under ice-cooling, and the mixture was stirred for 30 minutes. An aqueous saturated ammonium chloride solution was added to the reaction mixture, which was extracted with ethyl acetate. The organic layer was dried over anhydrous magnesium sulfate and evaporated. The resulting 1-(8-chloro-2-ethylimidazo[1,2-a]pyrazin-3-yl)-1-butanol was used in the next reaction without purification.

The resulting 1-(8-chloro-2-ethylimidazo[1,2-a]pyrazin-3-yl)-1-butanol was dissolved in ethyl acetate (4 mL) and methylene chloride (1 mL), then activated manganese (IV) oxide (3 g) was added thereto, and the mixture was heated under stirring at 60° C. for 5 hours. After being allowed to cool, the reaction mixture was filtered and washed with ethyl acetate, and then the filtrates were combined and evaporated. The resulting residue was purified by silica gel column chromatography (ethyl acetate:n-hexane=1:3) to give the title compound (226 mg) as white crystals.

$^1$H NMR (400 MHz, CDCl$_3$) δ 1.06 (t, J=7.3 Hz, 3H), 1.49 (t, J=7.5 Hz, 3H), 1.84 (tq, J=7.3, 7.3 Hz, 2H), 2.97 (t, J=7.3 Hz, 2H), 3.23 (q, J=7.5 Hz, 2H), 7.88 (d, J=4.6 Hz, 1H), 9.53 (d, J=4.6 Hz, 1H).

Reference Example 7

(E)-4-(2,4-Dimethylphenyl)-3-butene-2-one

1-Triphenylphosphoranilidene-2-propanone (49.08 g, 0.225 mol) was added to a solution of 2,4-dimethylbenzaldehyde (15.08 g, 0.112 mol) in dichloromethane (100 mL), and the mixture was heated at 60° C. for 20 hours. The reaction mixture was evaporated as it was. The residue was purified by silica gel column chromatography (ethyl acetate:n-hexane=1:5) to give the title compound (18.32 g, 94%).

$^1$H NMR (400 MHz, CDCl$_3$) δ 2.33 (s, 3H), 2.37 (s, 3H), 2.42 (s, 3H), 6.62 (d, J=16.1 Hz, 1H), 7.00–7.08 (m, 2H), 7.48 (d, J=8.4 Hz, 1H), 7.79 (d, J=16.1 Hz, 1H).

Reference Example 8

1-(2,4-Dimethylphenyl)-3-oxobutyl cyanide

Ammonium chloride (6.84 g, 0.126 mol) and potassium cyanide (13.68 g, 0.210 mol) were added to a mixed solution (100 mL) of a 15% aqueous solution of (E)-4-(2,4-dimethylphenyl)-3-butene-2-one (18.32 g, 0.105 mol) and N,N-dimethylformamide, and the mixture was heated under reflux for 6 hours. Water was added to the reaction mixture, which was extracted with ethyl acetate. The organic layer was washed with an aqueous saturated sodium bicarbonate solution and brine, dried over anhydrous magnesium sulfate and evaporated. The residue was purified by silica gel column chromatography (ethyl acetate:n-hexane=1:5) to give the title compound (10.13 g, 48%).

$^1$H NMR (400 MHz, CDCl$_3$) δ 2.20 (s, 3H), 2.30 (s, 3H), 2.33 (s, 3H), 2.87 (dd, J=5.2, 18.0 Hz, 1H), 3.16 (dd, J=8.9, 18.0 Hz, 1H), 4.44 (dd, J=5.2, 8.9 Hz, 1H), 7.01 (s, 1H), 7.04 (d, J=7.9 Hz, 1H), 7.27 (d, J=10.3 Hz, 1H).

Reference Example 9

4-Bromo-6-chloro-3-pyridazineamine

Sodium bicarbonate (13.0 g, 155 mmol) and bromine (4.0 mL, 78 mmol) were added to a solution of 3-amino-6-chloropyridazine (10.0 g, 78 mmol) in methanol (150 mL) at room temperature, and the mixture was stirred for 15 hours. The reaction mixture was filtered, and the solvent was evaporated. Water was added thereto, which was extracted with ethyl acetate. The organic layer was washed with a 10% aqueous sodium thiosulfate solution, an aqueous saturated sodium bicarbonate solution and a brine, dried over anhydrous magnesium sulfate and evaporated. The residue was purified by silica gel column chromatography (ethyl acetate:n-hexane=1:1) to give the title compound (8.6 g, 53%) as tan crystals.

$^1$H NMR (400 MHz, CDCl$_3$) δ 5.35 (br s, 2H), 7.54 (s, 1H).

Reference Example 10

6-Chloro-4-(2,4-dimethylphenyl)-3-pyridazineamine

Ethanol (8 mL), a 2M aqueous sodium carbonate solution (4 mL), 2,4-dimethylbenzeneboric acid (650 mg, 4.3 mmol) and tetrakistriphenylphosphine palladium complex (456 mg, 0.39 mmol) were added to a solution of 3-amino-4-bromo-6-chloropyridazine (822 mg, 3.9 mmol) in toluene (40 mL), and the mixture was heated at 100° C. for 2 hours. Water was added thereto, which was extracted with ethyl acetate. The organic layer was washed with an aqueous saturated sodium bicarbonate solution and brine, dried over anhydrous magnesium sulfate and evaporated. The residue was purified by silica gel column chromatography (ethyl acetate:n-hexane=1:3) to give the title compound (759 mg, 82%) as a pale brown powder.

$^1$H NMR (400 MHz, CDCl$_3$) δ 2.15 (s, 3H), 2.37 (s, 3H), 5.03 (br s, 2H), 7.03 (d, J=7.7 Hz, 1H), 7.07 (s, 1H), 7.12 (d, J=7.7 Hz, 1H), 7.15 (s, 1H).

Reference Example 11

4-(2,4-Dimethylphenyl)-3-pyridazineamine

10% Pd—C (759 mg, 50 wt %) and ammonium formate (1.23 g, 19 mmol) were added to a solution of 6-chloro-4-(2,4-dimethylphenyl)-3-pyridazineamine (759 mg, 3.2 mmol) in methanol (40 mL), and the mixture was heated under reflux for 1 hour. The reaction solution was filtered through Celite, and the solvent was evaporated. The residue was purified by silica gel column chromatography (ethyl acetate) to give the title compound (640 mg, 99%) as a pale yellow oil.

$^1$H NMR (400 MHz, CDCl$_3$) δ 2.13 (s, 3H), 2.37 (s, 3H), 4.89 (br s, 2H), 7.03 (d, J=4.6 Hz, 1H), 7.04 (d, J=7.1 Hz, 1H), 7.11 (d, J=7.7 Hz, 1H), 7.14 (s, 1H), 8.63 (d, J=4.6 Hz, 1H).

Reference Example 12

8-(2,4-Dimethylphenyl)-2-ethylimidazo[1,2-b]pyridazine-3-carboxylic acid methyl ester Methyl 2-chloro-3-oxopentanoate (5 mL) was added to 4-(2,4-dimethylphenyl)-3-pyridazineamine (640 mg, 3.2 mmol), and the mixture was heated at 155° C. for 30 minutes. Water was added to the resulting reaction mixture, and the mixture was extracted with ethyl acetate. The organic layer was washed with a 5N aqueous sodium hydroxide solution and brine, dried over anhydrous magnesium sulfate, and the solvent was evaporated. The residue was purified by silica gel column chromatography (ethyl acetate: N-hexane=1:3) to give the title compound (373 mg, 37%) as a brown oil.

$^1$H NMR (400 MHz, CDCl$_3$) δ 1.29 (t, J=7.5 Hz, 3H), 2.21 (s, 3H), 2.38 (s, 3H), 3.11 (q, J=7.5 Hz, 2H), 4.01 (s, 3H), 7.06 (d, J=4.6 Hz, 1H), 7.12 (d, J=7.7 Hz, 1H), 7.16 (s, 1H), 7.28 (d, J=7.7 Hz, 1H), 8.55 (d, J=4.6 Hz, 1H).

Reference Example 13

8-Bromo-6-methyl-2-(methylsulfanyl)imidazo[1,2-a]pyridin-3-carboxylic acid ethyl ester 3-Bromo-5-methyl-2-pyridineamine (5.0 g) was dissolved in N,N-dimethylformamide (30 mL), and a 20M aqueous sodium hydroxide solution (1.35 mL) was added thereto slowly at room temperature. After stirred at room temperature for 30 minutes, carbon disulfide (2.4 mL) was added thereto, and the mixture was further stirred for 30 minutes. Thereafter, a 20M aqueous sodium hydroxide solution (1.35 mL) was added thereto slowly at room temperature, which was stirred for 2 hours. Then, methyl iodide (7.7 g) was added thereto, followed by stirring overnight. Ice was added to the resulting mixture, which was extracted with ethyl acetate, dried over anhydrous magnesium sulfate, and evaporated. The resulting methyl N-(3-bromo-5-methyl-2-pyridyl)-(methylsulfanyl)methaneimidothioate was subjected to the next reaction without purification.

Ethyl bromoacetate (5.4 g) was added to methyl N-(3-bromo-5-methyl-2-pyridyl)(methylsulfanyl)methaneimidothioate, and the mixture was stirred at 60° C. for 4 hours. After cooled to room temperature, triethylamine was added to treat the material, and water was further added thereto. The reaction mixture was extracted with ethyl acetate, dried over anhydrous magnesium sulfate and evaporated. The resulting residue was purified by column chromatography (ethyl acetate:n-hexane=1:9) to give 8-bromo-6-methyl-2-(methylsulfanyl)imidazo[1,2-a]pyridin-3-carboxylic acid ethyl ester (2.4 g) as a white powder.

$^1$H NMR (400 MHz, CDCl$_3$) δ 1.46 (t, J=7.2 Hz, 3H), 2.37 (s, 3H), 2.73 (s, 3H), 4.44 (q, J=7.2 Hz, 2H), 7.49 (d, J=1.6 Hz, 1H), 9.07 (d, J=2.4 Hz, 1H).

Reference Example 14

8-Bromo-6-methyl-2-(methylsulfanyl)imidazo[1,2-a]pyridin-3-carboxylic acid

8-Bromo-6-methyl-2-(methylsulfanyl)imidazo[1,2-a]pyridin-3-carboxylic acid ethyl ester (1.33 g) was dissolved in ethanol (50 mL), then a 5N aqueous sodium hydroxide solution (3 mL) was added thereto, and the mixture was stirred under reflux for 1 hour. Ice was added to the reaction mixture, then 2N hydrochloric acid (8 mL) was further added thereto, and as a result, the precipitates were obtained. The resulting precipitates were collected by filtration, washed with water, and dried under reduced pressure to give 8-bromo-6-methyl-2-(methylsulfanyl)imidazo[1,2-a]pyridine-3-carboxylic acid (1.1 g) as a white powder.

$^1$H NMR (400 MHz, DMSO-d$_6$) δ 2.34 (s, 3H), 2.48 (s, 3H), 7.77 (s, 1H), 9.02 (s, 1H), 13.4 (br s, 1H).

Reference Example 15 tert-Butyl N-[8-bromo-6-methyl-2-(methylsulfanyl)imidazo[1,2-a]pyridin-3-yl]carbamate 8-Bromo-6-methyl-2-(methylsulfanyl)imidazo[1,2-a]pyridine-3-carboxylic acid (500 mg) was dissolved in a mixture of tert-butyl alcohol (15 mL) and toluene (50 mL), then diphenylphospholylazide (500 mg) and triethylamine (206 mg) were added thereto. After the mixture was heated at 70° C. for 2 hours, it was stirred for 2 hours by heating under reflux. After cooled to room temperature, the reaction mixture was evaporated. The resulting residue was purified by silica gel column chromatography (ethyl acetate:n-hexane=1:9) to give tert-butyl N-[8-bromo-6-methyl-2-(methylsulfanyl)imidazo[1,2-a]pyridin-3-yl]carbamate (0.85 g) as a white powder.

$^1$H NMR (400 MHz, CDCl$_3$) δ 1.50 (br s, 9H), 2.33 (s, 3H), 2.60 (s, 3H), 6.18 (br s, 1H), 7.32 (s, 1H), 7.61 (s, 1H).

Reference Example 16 tert-Butyl N-[8-bromo-6-methyl-2-(methylsulfanyl)imidazo[1,2-a]pyridin-3-yl]-N-propylcarbamate tert-Butyl N-[8-bromo-6-methyl-2-(methylsulfanyl)imidazo[1,2-a]pyridin-3-yl]carbamate (123 mg) was dissolved in N,N-dimethylformamide (10 mL), then sodium hydride (65% in oil; 15 mg) was added thereto under ice-cooling, and the mixture was stirred for 10 minutes. Iodopropane (67 mg) was added thereto under ice-cooling, and the mixture was stirred at room temperature for 1 hour. The reaction mixture was poured into water, which was extracted with ethyl acetate. The extracted organic layers were combined, dried over anhydrous magnesium sulfate and evaporated, to give the title compound (133 mg) as a brown oil.

$^1$H NMR (400 MHz, CDCl$_3$) δ 0.87 (t, J=7.2 Hz, 3H), 1.31 (br s, 9H), 1.45–1.60 (m, 2H), 2.33 (s, 3H), 2.60 (s, 3H), 3.50–3.63 (m, 2H), 7.31 (s, 1H), 7.44 (s, 1H).

Reference Example 17

N-[8-Bromo-6-methyl-2-(methylsulfanyl)imidazo[1,2-a]pyridin-3-yl]-N-propylamine tert-Butyl N-[8-bromo-6-methyl-2-(methysulfanyl)imidazo[1,2-a]pyridin-3-yl]-N-propylcarbamate was dissolved in ethyl acetate (5 mL), then a 4N hydrochloric acid-ethyl acetate solution (10 mL) was added thereto at room temperature, and the mixture was stirred at room temperature for 20 hours. Under ice-cooling, a 5N aqueous sodium hydroxide solution was added to neutralize the solution, which was extracted with ethyl acetate. The organic layers were combined, which was dried over anhydrous magnesium sulfate, and evaporated, to give the title compound (103 mg) as a yellow amorphous.

$^1$H NMR (400 MHz, CDCl$_3$) δ 1.01 (t, J=7.6 Hz, 3H), 1.57–1.63 (m, 2H), 2.32 (s, 3H), 2.54 (s, 3H), 2.95–3.00 (m, 2H), 7.24 (s, 1H), 7.71 (s, 1H).

Reference Example 18

N-[8-Bromo-6-methyl-2-(methylsulfanyl)imidazo[1,2-a]pyridin-3-yl]-N,N-dipropylamine N-[8-Bromo-6-methyl-2-(methylsulfanyl)imidazo[1,2-a]pyridin-3-yl]-N-propylamine (103 mg) and propionaldehyde (57 mg) were dissolved in tetrahydrofuran (1.2 mL), then 3M sulfuric acid (0.24 mL) was added thereto, follwed by adding sodium borohydride (24 mg) under ice-cooling, and then the mixture was stirred for 3 hours. Water was added to the reaction mixture, which was neutralized with a 2N aqueous sodium hydroxide solution and extracted with ethyl acetate. The organic layer was dried over anhydrous magnesium sulfate and evaporated. The resulting residue was purified by silica gel column chromatography (ethyl acetate:n-hexane=1:9) to give the title compound (79 mg) as a white powder.

$^1$H NMR (400 MHz, CDCl$_3$) δ 0.85 (t, J=7.2 Hz, 6H), 1.33–1.40 (m, 4H), 2.31 (s, 3H), 2.62 (s, 3H), 3.00–3.10 (m, 4H), 7.23 (s, 1H), 7.81 (s, 1H).

Reference Example 19

Methyl N-(3-Methoxy-2-pyrazinyl)(methylsulfanyl)methaneimidothioate

A 20N aqueous sodium hydroxide solution (11.3 mL) was added to a solution of 3-methoxy-2-pyrazineamine (28.3 g) in N,N-dimethylformamide (230 mL) at room temperature. After stirred for 1 hour, carbon disulfide (20.4 mL) was added thereto, followed by further stirring for 1 hour. A 20N aqueous sodium hydroxide solution (11.3 mL) was added thereto at room temperature, and the mixture was stirred for 1 hour. Thereafter, methyl iodide (28.2 mL) was added thereto, and the mixture was stirred for 1 hour. Water was added to the reaction mixture, which was extracted with ethyl acetate, dried over anhydrous magnesium sulfate, and evaporated. The resulting residue was purified by silica gel column chromatography (ethyl acetate:n-hexane=1:5) to give the title compound (19.1 g) as yellow crystals.

$^1$H NMR (400 MHz, DMSO-d$_6$) δ 2.58 (s, 6H), 3.99 (s, 3H), 7.83 (d, J=2.9 Hz, 1H), 7.91 (d, J=2.9 Hz, 1H).

Reference Example 20

Ethyl 8-methoxy-2-(methylsulfanyl)imidazo[1,2-a]pyrazine-3-carboxylate

Ethyl bromoacetate (18.5 mL) and iso-dipropylethylamine (29 mL) were added to a solution of methyl N-(3-methoxy-2-pyrazinyl)-(methylsulfanyl)methaneimidothioate (19.1 g) in acetonitrile (42 mL), and the mixture was heated under stirring at 100° C. for 14 hours. After the reaction mixture was cooled to room temperature, water was added thereto, which was extracted with ethyl acetate, washed with water, dried over anhydrous magnesium sulfate, and evaporated. The resulting residue was washed with n-hexane to give the title compound (10.7 g) as pale yellow crystals.

$^1$H NMR (400 MHz, CDCl$_3$) δ 1.47 (t, J=7.1 Hz, 3H), 2.74 (s, 3H), –4.19 (s, 3H), 4.46 (q, J=7.1 Hz, 2H), 7.55 (d, J=4.6 Hz, 1H), 8.72 (d, J=4.6 Hz, 1H).

Reference Example 21

Ethyl 8-chloro-2-(methylsulfanyl)imidazo[1,2-a]pyridine-3-carboxylate

Phosphorus oxychloride (75 mL) was added to ethyl 8-methoxy-2-(methylsulfanyl)imidazo[1,2-a]pyrazine-3-carboxylate (10.7 g), and the mixture was heated under stirring at 130° C. for 8 hours. The resulting reaction mixture was cooled to room temperature, and poured on ice. Then, the residue was collected by filtration and washed with ethanol and water, and dried under reduced pressure to give the title compound (7.6 g) as pale yellow crystals.

$^1$H NMR (400 MHz, CDCl$_3$) δ 1.48 (t, J=7.1 Hz, 3H), 2.76 (s, 3H), 4.48 (q, J=7.1 Hz, 2H), 7.85 (d, J=4.7 Hz, 1H), 9.07 (d, J=4.7 Hz, 1H).

Reference Example 22 tert-Butyl N-[8-chloro-2-(methylsulfanyl)imidazo[1,2-a]pyrazin-3-yl]carbamate

Ethyl 8-chloro-2-(methylsulfanyl)imidazo[1,2-a]pyrazine-3-carboxylate (2.0 g) was dissolved in tetrahydrofuran (36 mL) and ethanol (9 mL), then a 2N aqueous sodium hydroxide solution (9 mL) was added thereto, and the mixture was stirred at room temperature. Under ice-cooling, 1N hydrochloric acid (19 mL) was added thereto, then the solvent was ebaporated. The resulting crude 8-chloro-2-(methylsulfanyl)imidazo[1,2-a]pyrazine-3-carboxylic acid was used in the next reaction without purification.

The resulting crude 8-chloro-2-(methylsulfanyl)imidazo[1,2-a]pyrazine-3-carboxylic acid was dissolved in toluene (71 mL), then tert-butyl alcohol (14 mL), triethylamine (1.1 mL) and diphenylphospholylazide (1.7 mL) were added thereto, and the mixture was heated at 100° C. for 4 hours. After completion of the reaction, it was evaporated, which was added with water, extracted with ethyl acetate, and washed with water. After that, it was dried over anhydrous magnesium sulfate and evaporated. The resulting residue was purified by silica gel column chromatography (ethyl acetate:n-hexane=1:2) to give the title compound (880 mg) as pale red crystals.
$^1$H NMR (400 MHz, CDCl$_3$) δ 1.51 (br s, 9H), 2.69 (s, 3H), 6.25 (br s, 1H), 7.70 (d, J=4.6 Hz, 1H), 7.77 (d, J=4.6 Hz, 1H).

Reference Example 23

N-[8-Chloro-2-(methylsulfanyl)imidazo[1,2-a]pyrazin-3-yl]-N-propylamine

According to the same manner as that of Reference Examples 16 and 17, tert-butyl N-[8-chloro-2-(methylsulfanyl)imidazo[1,2-a]pyrazin-3-yl]carbamate was used to give the title compound as a yellow oil.
$^1$H NMR (400 MHz, CDCl$_3$) δ 1.01 (t, J=7.3 Hz, 3H), 1.59 (ddq, J=7.1, 7.1, 7.3 Hz, 2H), 2.64 (s, 3H), 3.05 (ddd, J=7.1, 7.1, 7.1 Hz, 2H), 3.30 (t, J=7.1 Hz, 1H), 7.62 (d, J=4.6 Hz, 1H), 7.82 (d, J=4.6 Hz, 1H).

Reference Example 24

N-[8-Chloro-2-(methylsulfanyl)imidazo[1,2-a]pyrazin-3-yl]-N,N-dipropylamine

According to the same manner as that of Reference Example 18, N-[8-chloro-2-(methylsulfanyl)imidazo[1,2-a]pyrazin-3-yl]-N,N-dipropylamine was used to give the title compound as pale yellow crystals.
$^1$H NMR (400 MHz, CDCl$_3$) δ 0.86 (t, J=7.5 Hz, 6H), 1.36 (ddq, J=7.5, 7.5, 7.5 Hz, 4H), 2.71 (s, 3H), 3.08 (dd, J=7.5, 7.5 Hz, 4H), 7.62 (d, J=4.6 Hz, 1H), 7.92 (d, J=4.6 Hz, 1H).

Reference Example 25

6-Chloro-4-(4-methoxy-2-methylphenyl)-3-pyridazineamine

4-Bromo-6-chloro-3-pyridazineamine (12 g) and 4-methoxy-2-methylphenylboronic acid (10.5 g) were dissolved in a mixed solvent of toluene (240 mL) and ethanol (45 mL), then tetrakistriphenylphosphine palladium complex (6.7 g) and a 2M aqueous sodium carbonate solution (24 mL) were added thereto, and the mixture was heated under stirring at 100° C. for 12 hours. After completion of the reaction, the solvent was evaporated. The residue was extracted with ethyl acetate, washed with water, and dried over anhydrous magnesium sulfate, and then the solvent was evaporated. The residue was purified by silica gel column chromatography (ethyl acetate:n-hexane=1:4) to give the title compound (7.89 g) as brown crystals.
$^1$H NMR (400 MHz, CDCl$_3$) δ 2.18 (s, 3H), 3.85 (s, 3H), 5.43 (br s, 2H), 6.82–6.90 (m, 2H), 7.08 (d, J=8.2 Hz, 1H), 7.14 (s, 1H).

Reference Example 26

4-(4-Methoxy-2-methylphenyl)-3-pyridazineamine

10% Pd—C (hydrous product; 7.89 g) and ammonium formate (11.96 g) were added to a solution of 6-chloro-4-(4-methoxy-2-methylphenyl)-3-pyridazineamine (7.89 g) in methanol (100 mL), and the mixture was heated under reflux for 1.5 hours. The reaction mixture was filtered through Celite, and the solvent was evaporated. The resulting residue was purified by silica gel column chromatography (ethyl acetate:ethanol=10:1) to give the title compound (6.16 g) as white crystals.
$^1$H NMR (400 MHz, CDCl$_3$) δ 2.15 (s, 3H), 3.83 (s, 3H), 4.89 (br s, 2H), 6.80–6.90 (m, 2H), 7.02 (d, J=4.6 Hz, 1H), 7.08 (d, J=8.2 Hz, 1H), 8.62 (d, J=4.8 Hz, 1H).

Reference Example 27

Methyl N-[4-(4-methoxy-2-methylphenyl)-3-pyridazinyl]-(methylsulfanyl)methaneimidothioate A 20N aqueous sodium hydroxide solution (1.43 mL) was added to a solution of 4-(4-methoxy-2-methylphenyl)-3-pyridazineamine (6.16 g) in N,N-dimethylformamide (60 mL) at room temperature. After stirred for 1 hour, carbon disulfide (3.45 mL) was added thereto, and the mixture was further stirred for 1 hour. In addition, a 20N aqueous sodium hydroxide solution (1.43 mL) was added thereto at room temperature. Methyl iodide (3.57 mL) was added thereto, followed by stirring for 1 hour. Water was added to the reaction mixture, which was extracted with ethyl acetate, dried over anhydrous magnesium sulfate, and evaporated. The resulting residue was purified by silica gel column chromatography (ethyl acetate:nhexane=2:1) to give the title compound (1.25 g) as a brown oil.
$^1$H NMR (400 MHz, CDCl$_3$) δ 2.15 (s, 3H), 2.35 (s, 6H), 3.83 (s, 3H), 6.72–6.84 (m, 2H), 7.07 (d, J=8.2 Hz, 1H), 7.32 (d, J=4.6 Hz, 1H), 8.97 (d, J=4.6 Hz, 1H).

Reference Example 28

Ethyl 8-(4-methoxy-2-methylphenyl)-2-(methylsulfanyl)imidazo[1,2-b]pyridazine-3-carboxylate Ethyl bromoacetate (0.87 mL) and i-Pr$_2$EtN (1.36 mL) were added to a solution of methyl N-[4-(4-methoxy-2-methylphenyl)-3-pyridazinyl]-(methylsulfanyl)methaneimidothioate (1.25 g) in acetonitrile (10 mL), and the mixture was heated under stirring at 100° C. for 14 hours. The reaction mixture was cooled to room temperature, which was added with water, extracted with ethyl acetate, and washed with water. After that, it was dried over anhydrous magnesium sulfate and evaporated. The resulting residue was purified by silica gel column chromatography (ethyl acetate:n-hexane=1:3) to give the title compound (628 mg) as a red brown oil.
$^1$H NMR (400 MHz, CDCl$_3$) δ 1.38 (t, J=7.1 Hz, 3H), 2.10 (s, 3H), 2.72 (s, 3H), 3.85 (s, 3H), 4.33 (q, J=7.1 Hz, 2H), 6.79–6.95 (m, 2H), 7.13 (d, J=8.8 Hz, 1H), 7.39 (d, J=4.7 Hz, 1H), 8.53 (br s, 1H).

Reference Example 29

2-[(6-Chloro-4-pyrimidinyl)amino]-1-butanol 4,6-Dichloropyrimidine (5.0 g) and 2-amino-1-butanol (6.5 mL) were heated under reflux in 1,4-dioxane (26 mL) for 1 hour. The reaction mixture was evaporated, and the resulting residue was purified by silica gel column chromatography (ethyl acetate:n-hexane=1:10) to give the title compound (5.6 g) as a pale orange oil.
$^1$H NMR (400 MHz, CDCl$_3$) δ0.98 (t, J=7.2 Hz, 3H), 1.52–1.64 (m, 2H), 2.58 (br s, 1H), 3.66 (dd, J=10.8, 5.2 Hz, 1H), 3.77 (dd, J=10.8, 3.6 Hz, 1H), 3.85 (br s, 1H), 5.42 (br s, 1H), 6.40 (s, 1H), 8.30 (s, 1H).

Reference Example 30

2-(4-Pyrimidinylamino)-1-butanol

2-[(6-Chloro-4-pyrimidinyl)amino]-1-butanol was dissolved in ethanol (110 mL), which was sequentially added with a 5N aqueous sodium hydroxide solution (5.5 mL) and Pd—C (hydrous product; 0.55 g), and hydrogenation was performed under hydrogen atmosphere at a normal temperature and a normal pressure. After completion of the reaction, Pd—C was filtered off, and the solvent was evaporated. The resulting residue was extracted with dichloromethane-methanol, and the solvent was removed to give the title compound (4.3 g) as white crystals.

$^1$H NMR (400 MHz, CDCl$_3$) δ 0.99 (t, J=7.6 Hz, 3H), 1.52–1.64 (m, 2H), 2.46 (br s, 1H), 3.66 (dd, J=11.2, 6.0 Hz, 1H), 3.77 (dd, J=11.2, 3.6 Hz, 1H), 3.88 (br s, 1H), 5.16 (br s, 1H), 6.38 (d, J=6.0 Hz, 1H), 8.11 (d, J=6.0 Hz, 1H), 8.51 (s, 1H).

Reference Example 31

2-[(5-Bromo-4-pyrimidinyl)amino]-1-butanol 2-(4-Prymidinylamino)-1-butanol (4.2 g) was dissolved in acetic acid (42 mL), and bromine (1.5 mL) was added dropwise at a normal temperature. After stirred for 1 day at the same temperature, the solution was neutralized with a 5N aqueous sodium hydroxide solution and extracted with ethyl acetate, and the solvent was evaporated. The resulting residue was purified by silica gel column chromatography (ethyl acetate:n-hexane=1.1) to give the title compound (4.4 g) as white crystals.

$^1$H NMR (400 MHz, CDCl$_3$) δ 1.01 (t, J=7.6 Hz, 3H), 1.58–1.81 (m, 2H), 3.72 (dd, J=10.8, 5.6 Hz, 1H), 3.82 (dd, J=10.8, 3.6 Hz, 1H), 4.12–4.20 (m, 1H), 5.56 (br s, 1H), 8.30 (s, 1H), 8.45 (s, 1H).

Reference Example 32

8-Bromo-2-ethyl-2,3-dihydroimidazo[1,2-c]pyrimidine

2-[(5-Bromo-4-pyrimidinyl)amino]-1-butanol (3.3 g) was dissolved in xylene (27 mL), then thionyl chloride (4.9 mL) was added thereto, and the mixture was heated under stirring at 100° C. for 1 day. The precipitated crystals were collected by filtration and suspended in a 1M aqueous sodium carbonate solution. This mixture was extracted with dichloromethane to give the crude title compound (3.0 g) as an orange oil. This title compound was used in the next reaction without purification.

$^1$H NMR (400 MHz, CDCl$_3$) δ 0.98 (t, J=7.6 Hz, 3H), 1.55–1.67 (m, 1H), 1.79–1.91 (m, 1H), 3.82 (dd, J=11.2, 8.0 Hz, 1H), 4.21–4.30 (m, 2H), 7.62 (s, 1H), 7.77 (s, 1H).

Reference Example 33

8-Bromo-2-ethylimidazo[1,2-c]pyrimidine

8-Bromo-2-ethyl-2,3-dihydroimidazo[1,2-c]pyrimidine (3.0 g) was dissolved in toluene (60 mL), then activated manganese(IV) dioxide (3.5 g) was added thereto, and the mixture was heated under stirring at 90° C. for 1 day. Manganese(IV) oxide was filtered off through Celite, and the solvent was evaporated. The resulting residue was purified by silica gel column chromatography (ethyl acetate:n-hexane=1:10) to give the title compound (1.3 g) as white crystals.

$^1$H NMR (400 MHz, CDCl$_3$) δ 1.36 (t, J=7.6 Hz, 3H), 2.84–2.99 (m, 2H), 7.49 (s, 1H), 8.08 (s, 1H), 8.89 (s, 1H).

Reference Example 34

8-Bromo-2-ethylimidazo[1,2-c]pyrimidine-3-carbaldehyde

8-Bromo-2-ethylimidazo[1,2-c]pyrimidine (1.0 g) was added to a mixture of phosphorus oxychloride (1.2 mL) and N,N-dimethylformamide (4.4 mL) at room temperature. The mixture was heated under stirring as it was at 80° C. for 1 day. After cooled to room temperature, it was poured slowly on ice. The material was extracted with ethyl acetate and washed with water, and the solvent was evaporated. The resulting residue was purified by silica gel column chromatography (ethyl acetate:n-hexane=1:5) to give the title compound (0.5 g) as white crystals.

$^1$H NMR (400 MHz, CDCl$_3$) δ 1.47 (t, J=7.6 Hz, 3H), 3.15 (q, J=7.6 Hz, 2H), 8.41 (s, 1H), 10.11 (s, 1H), 10.16 (s, 1H).

Reference Example 35

1-(8-Bromo-2-ethylimidazo[1,2-c]pyrimidin-3-yl)-1-butanol

8-Bromo-2-ethylimidazo[1,2-c)pyrimidine-3-carbaldehyde was reacted in the same manner as that of Reference Example 5 to give the title compound as white crystals.

$^1$H NMR (400 MHz, CDCl$_3$) δ 0.95 (t, J=7.2 Hz, 3H), 1.22–1.36 (m, 1H), 1.31 (t, J=7.6 Hz, 3H), 1.41–1.54 (m, 1H), 1.771.87 (m, 1H), 2.01–2.11 (m, 1H), 2.70–2.82 (m, 2H), 5.22 (t, J=7.2 Hz, 1H), 8.10 (s, 1H), 9.38 (s, 1H).

Reference Example 36

1-(8-Bromo-2-ethylimidazo[1,2-c]pyrimidin-3-yl) butyl ethyl ether 1-(8-Bromo-2-ethylimidazo[1,2-c]pyrimidin-3-yl)-1-butanol was reacted in the same manner as that of Reference Example 5 to give the title compound as a colorless oil.

$^1$H NMR (400 MHz, CDCl$_3$) δ 0.92 (t, J=7.2 Hz, 3H), 1.15 (t, J=7.2 Hz, 3H), 1.18–1.30 (m, 1H), 1.33 (t, J=7.6 Hz, 3H), 1.38–1.50 (m, 1H), 1.71–1.81 (m, 1H), 1.99–2.09 (m, 1H), 2.73–2.88 (m, 2H), 3.22–3.43 (m, 2H), 4.73 (t, J=7.2 Hz, 1H), 8.08 (s, 1H), 9.28 (s, 1H).

Example 1

8-(2,4-Dichlorophenyl)-2-ethylimidazo[1,2-a]pyrazine-3-carboxylic acid methyl ester 8-Chloro-2-ethylimidazo[1,2-a]pyrazine-3-carboxyilic methyl ester (0.92 g, 3.8 mmol) synthesized in Reference Example 1 was dissolved in a mixed solvent of toluene (32 mL) and methanol (8 mL), then 2,4-dichlorobenzeneboronic acid (1.49 g, 7.8 mmol) and tetrakistriphenylphosphine palladium complex (230 mg, 0.2 mmol) were added thereto, and the mixture was heated under reflux for 2 hours under nitrogen atmosphere. The reaction mixture was allowed to cool, and purified by silica gel column chromatography (n-hexane:ethyl acetate=3:1) to give the title compound (1.03 g) as a pale yellow crystals.
$^1$H NMR (400 MHz, CDCl$_3$) δ 1.31 (t, J=7.5 Hz, 3H), 3.14 (q, J=7.5 Hz, 2H), 4.03 (s, 3H), 7.41 (dd, J=2.0, 8.2 Hz, 1H), 7.57 (d, J=2.0 Hz, 1H), 7.61 (d, J=8.2 Hz, 1H), 8.20 (d, J=4.6 Hz, 1H), 9.23 (d, J=4.6 Hz, 1H).

Example 2 tert-Butyl N-[8-(2,4-dichlorophenyl)-2-ethylimidazo [1,2-a]pyrazin-3-yl]carbamate 8-(2,4-Dichlorophenyl)-2-ethylimidazo[1,2-a]pyrazine-3-carboxylic acid methyl ester (1.03 g, 2.9 mmol) was dissolved in ethanol (11 mL), then a 2N aqueous sodium hydroxide solution (3.7 mL, 7.3 mmol) was added thereto, and the mixture was stirred for 1 hour by heating under reflux. After completion of the reaction, the material was cooled to an ice temperature, which was added with 2N hydrochloric acid (7.3 mL) to adjust pH to 5. The resulting reaction mixture was extracted with ethyl acetate and then washed with water. The organic layer was dried over anhydrous magnesium sulfate and evaporated. The resulting 8-(2,4-dichlorophenyl)-2-ethylimidazo[1,2-a]pyrazine-3-carboxylic acid was used in the next reaction without purification.

The resulting 8-(2,4-dichlorophenyl)-2-ethylimidazo[1,2-a]pyrazine-3-carboxylic acid was dissolved in tert-butyl alcohol (15 mL), then diphenylphosphorylazide (0.69 mL, 3.2 mmol) and triethylamine (0.49 mL, 3.5 mmol) were added thereto, and the mixture was stirred for 2 hours by heating under reflux. After being cooled to room temperature, the reaction mixture was evaporated. The resulting residue was purified by silica gel column chromatography (ethyl acetate:n-hexane=1:2) to give the title compound (0.85 g) as a white amorphous.
$^1$H NMR (400 MHz, CDCl$_3$) δ 1.29 (t, J=7.5 Hz, 3H), 1.54 (br s, 9H), 2.81 (q, J=7.5 Hz, 2H), 6.20 (br s, 1H), 7.39 (dd, J=2.0, 8.2 Hz, 1H), 7.55 (d, J=2.0 Hz, 1H), 7.62 (d, J=8.2 Hz, 1H), 7.86 (d, J=4.5 Hz, 1H), 8.02 (d, J=4.5 Hz, 1H).

Example 3

N-[8-(2,4-Dichlorophenyl)-2-ethylimidazo[1,2-a] pyrazin-3-yl]-N-propylamine tert-Butyl N-[8-(2,4-dichlorophenyl)-2-ethylimidazo[1,2-a]pyrazin-3-yl]carbamate (200 mg, 0.49 mmol) was dissolved in N,N-dimethylformamide (1.6 mL), then sodium hydride (65% in oil; 27 mg, 0.74 mmol) was added thereto under ice-cooling, and the mixture was stirred at room temperature for 10 minutes. Iodopropane (0.062 mL, 0.64 mmol) was added thereto under ice-cooling, and the mixture was stirred at room temperature for 1 hour. The reaction mixture was poured into water, which was extracted with ethyl acetate. The extracted organic layers were combined, which was dried over anhydrous magnesium sulfate and evaporated. The resulting tert-butyl N-[8-(2,4-dichlorophenyl)-2-ethylimidazo[1,2-a]pyrazin-3-yl]-N-propylcarbamate was subjected to the next reaction without purification.

tert-Butyl N-[8-(2,4-dichlorophenyl)-2-ethylimidazo[1,2-a]pyrazin-3-yl]-N-propylcarbamate was dissolved in ethyl acetate (1 mL), then a 4N hydrochloric acid-ethyl acetate solution (1.9 mL, 7.4 mmol) was added thereto at room temperature, and the mixture was stirred at room temperature for 20 hours. Under ice-cooling, a 5N aqueous sodium hydroxide solution was added thereto, which was extracted with ethyl acetate. The organic layers were combined, which was dried over anhydrous magnesium sulfate and evaporated. The resulting residue was purified by silica gel column chromatography (n-hexane:ethyl acetate=3:4) to give the title compound (151 mg) as a yellow oil.
$^1$H NMR (400 MHz, CDCl$_3$) δ 1.00–1.07 (m, 3H), 1.30 (t, J=7.5 Hz, 3H), 1.56–1.69 (m, 2H), 2.81 (q, J=7.5 Hz, 2H), 2.99–3.08 (m, 2H), 7.38 (dd, J=2.0, 8.2 Hz, 1H), 7.55 (d, J=2.0 Hz, 1H), 7.63 (d, J=8.2 Hz, 1H), 7.94 (d, J=4.5 Hz, 1H), 7.97 (d, J=4.5 Hz, 1H).

Example 4

N-[8-(2,4-Dichlorophenyl)-2-ethylimidazo[1,2-a] pyrazin-3-yl]-N,N-dipropylamine hydrochloride N-[8-(2,4-Dichlorophenyl)-2-ethylimidazo[1,2-a]pyrazin-3-yl]-N-propylamine (296 mg, 0.85 mmol) and propionaldehyde (0.19 mL, 2.6 mmol) were dissolved in tetrahydrofuran (1.1 mL), and 3M sulfuric acid (0.87 mL, 2.6 mmol) was added thereto. Sodium borohydride (70 mg) was added thereto under ice-cooling, and the mixture was stirred for 3 hours. Water was added to the reaction mixture, which was neutralized with a 2N aqueous sodium hydroxide solution and extracted with ethyl acetate. The organic layer was dried over anhydrous magnesium sulfate, and evaporated. The resulting residue was purified by silica gel column chromatography (ethyl acetate:n-hexane=1:2) to give N-[8-(2,4-dichlorophenyl)-2-ethylimidazo[1,2-a]pyrazin-3-yl]-N,N-dipropylamine (272 mg) as pale yellow crystals. The resulting free compound was converted into hydrochloride with hydrochloric acid-ether using the conventional method, to give the title compound (250 mg) as white crystals.
$^1$H NMR (400 MHz, DMSO-d$_6$) δ 0.79–0.87 (m, 6H), 1.21 (t, J=7.5 Hz, 3H), 1.32–1.44 (m, 4H), 2.78 (q, J=7.5 Hz, 2H), 3.05–3.13 (m, 4H), 7.66 (dd, J=2.0, 8.2 Hz, 1H), 7.69 (d, J=8.2 Hz, 1H), 7.88 (d, J=2.0 Hz, 1H), 8.29 (d, J=4.2 Hz, 1H), 8.59 (d, J=4.2 Hz, 1H).

Example 5

6-Chloro-8-(2,4-dichlorophenyl)-2-ethylimidazo[1, 2-a]pyrazine-3-carboxylic acid methyl ester 5-Chloro-3-(2,4-dichlorophenyl)-2-pyrazineamine (1.1 g, 4.0 mmol) and methyl 2-chloro-3-oxopentanoate (5.7 mL) were mixed, and the mixture was heated under stirring at 170° C. 3 hours. After being allowed to cool, the reaction mixture was purified by silica gel column chromatography (n-hexane:ethyl acetate=20:1), and the resulting residue was washed with hexane to give the title compound (0.56 g) as pale yellow crystals.
$^1$H NMR (400 MHz, CDCl$_3$) δ 1.30 (t, J=7.5 Hz, 3H), 3.12 (q, J=7.5 Hz, 2H), 4.04 (s, 3H), 7.42 (dd, J=2.0, 8.2 Hz, 1H), 7.57 (d, J=2.0 Hz, 1H), 7.61 (d, J=8.2 Hz, 1H), 9.34 (s, 1H).

Example 6 tert-Butyl N-[6-chloro-8-(2,4-dichlorophenyl)-2-ethylimidazo[1,2-a]pyrazin-3-yl]carbamate By using 6-chloro-8-(2,4-dichlorophenyl)-2-ethylimidazo [1,2-a]pyrazine-3-caboxylic acid methyl ester, the title compound was obtained as a yellow oil according to the same manner as that of Example 2.

$^1$H NMR (400 MHz, CDCl$_3$) δ 1.29 (t, J=7.5 Hz, 3H), 1.54 (br s, 9H), 2.80 (q, J=7.5 Hz, 2H), 6.17 (br s, 1H), 7.40 (dd, J=2.0, 8.2 Hz, 1H), 7.55 (d, J=2.0 Hz, 1H), 7.62 (d, J=8.2 Hz, 1H), 7.93 (s, 1H).

Example 7

N-[6-Chloro-8-(2,4-dichlorophenyl)-2-ethylimidazo[1,2-a]pyrazin-3-yl]-N-propylamine By using tert-butyl N-[6-chloro-8-(2,4-dichlorophenyl)-2-ethylimidazo[1,2-a]pyrazin-3-yl]carbamate, the title compound was obtained as a red brawn oil according to the same manner as that of Example 3.

$^1$H NMR (400 MHz, CDCl$_3$) δ 1.00–1.07 (m, 3H), 1.30 (t, J=7.5 Hz, 3H), 1.56–1.70 (m, 2H), 2.80 (q, J=7.5 Hz, 2H), 2.98–3.08 (m, 2H), 7.38 (dd, J=2.0, 8.2 Hz, 1H), 7.54 (d, J=2.0 Hz, 1H), 7.62 (d, J=8.2 Hz, 1H), 8.02 (s, 1H).

Example 8

N-[6-Chloro-8-(2,4-dichlorophenyl)-2-ethylimidazo[1,2-a]pyrazin-3-yl]-N,N-dipropylamine By using N-[6-chloro-8-(2,4-dichlorophenyl)-2-ethylimidazo[1,2-a]pyrazin-3-yl]-N-propylamine, the title compound was obtained as pale yellow crystals according to the same manner as that of Example 3.

$^1$H NMR (400 MHz, CDCl$_3$) δ 0.87–0.94 (m, 6H), 1.29 (t, J=7.5 Hz, 3H), 1.37–1.49 (m, 4H), 2.78 (q, J=7.5 Hz, 2H), 3.03–3.11 (m, 4H), 7.38 (dd, J=2.0, 8.2 Hz, 1H), 7.54 (d, J=2.0 Hz, 1H), 7.65 (d, J=8.2 Hz, 1H), 8.08 (s, 1H).

Example 9

8-(2,4-Dichlorophenyl)-2-ethyl-6-methylimidazo[1,2-a]pyrazine-3-carboxylic acid methyl ester 8-Bromo-2-ethyl-6-methylimidazo[1,2-a]pyrazine-3-carboxylic acid methyl ester (0.30 g, 1.0 mmol) was dissolved in a mixed solvent of toluene (5.6 mL) and methanol (1.4 mL). Then 2,4-dichlorobenzeneboronic acid (0.382 g, 2.0 mmol) and tetrakistriphenylphosphine palladium complex (116 mg, 0.1 mmol) were added thereto, and the mixture was heated under reflux for 4 hours under nitrogen atmosphere. After the reaction mixture was allowed to cool, the solvent was removed. Then the residue was purified by silica-gel column chromatography (n-hexane:ethyl acetate=5:1) to give the title compound (391 mg) as white crystals.

$^1$H NMR (400 MHz, CDCl$_3$) δ 1.29 (t, J=7.5 Hz, 3H), 2.65 (s, 3H), 3.11 (q, J=7.5 Hz, 2H), 4.02 (s, 3H), 7.41 (dd, J=2.0, 8.2 Hz, 1H), 7.56 (d, J=2.0 Hz, 1H), 7.58 (d, J=8.2 Hz, 1H), 9.08 (s, 1H).

According to the processes of Examples 1 to 4, the following compounds of Examples 10 to 12 were synthesized.

Example 10 tert-Butyl N-[8-(2,4-dichlorophenyl)-2-ethyl-6-methylimidazo[1,2-a]pyrazin-3-yl]carbamate White Amorphous
$^1$H NMR (400 MHz, CDCl$_3$) δ 1.28 (t, J=7.5 Hz, 3H), 1.55 (br s, 9H), 2.58 (s, 3H), 2.78 (q, J=7.5 Hz, 2H), 6.14 (br s, 1H), 7.38 (dd, J=2.0, 8.2 Hz, 1H), 7.54 (d, J=2.0 Hz, 1H), 7.58 (d, J=8.2 Hz, 1H), 7.67 (s, 1H).

Example 11

N-[8-(2,4-dichlorphenyl)-2-ethyl-6-methylimidazo[1,2-a]pyrazin-3-yl]-N-propylamine Yellow Oil
$^1$H NMR (400 MHz, CDCl$_3$) δ 1.00–1.07 (m, 3H), 1.29 (t, J=7.5 Hz, 3H), 1.56–1.69 (m, 2H), 2.57 (s, 3H), 2.78 (q, J=7.5 Hz, 2H), 2.98–3.06 (m, 2H), 7.37 (dd, J=2.0, 8.2 Hz, 1H), 7.53 (d, J=2.0 Hz, 1H), 7.59 (d, J=8.2 Hz, 1H), 7.78 (s, 1H).

Example 12

N-[8-(2,4-dichlorophenyl)-2-ethyl-6-methylimidazo[1,2-a]pyrazin-3-yl]-N,N-dipropylamine hydrochloride White Crystals
$^1$H NMR (400 MHz, CDCl$_3$) δ 0.89–0.96 (m, 6H), 1.40–1.55 (m, 7H), 2.74 (s, 3H), 3.03–3.15 (m, 6H), 7.52 (dd, J=2.0, 8.2 Hz, 1H), 7.60 (d, J=8.2 Hz, 1H), 7.64 (d, J=2.0 Hz, 1H), 8.04 (s, 1H).

Example 13

8-(2,4-Dichlorphenyl)-2-methyl-3-nitroimidazo[1,2-a]pyrazine 8-(2,4-Dichlorophenyl)-2-methylimidazo[1,2-a]pyrazine (0.10 g, 0.36 mmol) was dissolved in acetonitrile (0.36 mL), then nitronium tetrafluoroborate (72 mg, 0.54 mmol) was added thereto, and the mixture was stirred at room temperature for 1 hour under nitrogen atmosphere. Water was added to the reaction mixture, and it was extracted with ethyl acetate. The organic layer was dried over anhydrous magnesium sulfate and evaporated. The resulting residue was purified by silica gel column chromatography (ethyl acetate: n-hexane=1:3) to give 8-(2,4-dichlorphenyl)-2-methyl-3-nitroimidazo[1,2-a]pyrazine (1.54 g) as a yellow oil.

$^1$H NMR (400 MHz, CDCl$_3$) δ 2.92 (s, 3H), 7.47 (dd, J=2.0, 8.2 Hz, 1H), 7.55 (d, J=8.2 Hz, 1H), 7.63 (d, J=2.0 Hz, 1H), 8.48 (d, J=4.6 Hz, 1H), 9.36 (d, J=4.6 Hz, 1H).

Example 14

8-(2,4-Dichlorophenyl)-2-methylimidazo[1,2-a]pyrazin-3-amine 8-(2,4-Dichlorophenyl)-2-methyl-3-nitroimidazo[1,2-a]pyrazine (25 mg, 0.077 mmol) was dissolved in ethanol (0.36 mL), then acetic acid (0.5 mL) and iron powders (22 mg) were added thereto, and the mixture was stirred for 1 hour by heating under reflux. After the reaction mixture was allowed to cool, the solvent was evaporated and it was extracted with ethyl acetate. The organic layer was dried over anhydrous magnesium sulfate and evaporated. The resulting residue was purified by silica gel column chromatography (ethyl acetate:n-hexane=4:1) to give 8-(2,4-dichlorophenyl)-2-methylimidazo[1,2-a]pyrazin-3-amine (8 mg) as yellow crystals.

$^1$H NMR (400 MHz, CDCl$_3$) δ 2.47 (s, 3H), 3.23 (br s, 2H), 7.39 (dd, J=2.0, 8.2 Hz, 1H), 7.55 (d, J=2.0 Hz, 1H), 7.58 (d, J=8.2 Hz, 1H), 7.39 (d, J=4.4 Hz, 1H), 7.96 (d, J=4.4 Hz, 1H).

According to the processes of Examples 1 to 4, the following compounds of Examples 15 to 109 were synthesized.

Example 15

N-[8-(2,4-Dichlorophenyl)-2-methylimidazo[1,2-a]pyrazin-3-yl]-N,N-dipropylamine hydrochloride Yellow Crystals $^1$H NMR (400 MHz, CDCl$_3$) δ 0.88–0.95 (m, 6H), 1.40–1.53 (m, 4H), 2.73 (s, 3H), 3.10–3.17 (m, 4H), 7.51 (d, J=8.2 Hz, 1H), 7.62 (d, J=8.2 Hz, 1H), 7.65 (s, 1H), 8.24 (br s, 1H), 8.34 (br s, 1H).

Example 16

N-[8-(2,4-Dichlorophenyl)-2-methylimidazo[1,2-a]pyrazin-3 μl]-N-(1-ethylpropyl)amine Orange Crystals $^1$H NMR (400 MHz, CDCl$_3$) δ 1.02 (t, J=7.2 Hz, 6H), 1.44–1.60 (m, 4H), 2.45 (s, 3H), 2.85 (br s, 1H), 2.92–3.00 (m, 1H), 7.39 (dd, J=2.0, 8.4 Hz, 1H), 7.56 (d, J=2.0 Hz, 1H), 7.61 (d, J=8.4 Hz, 1H), 7.94 (d, J=4.8 Hz, 1H), 7.97 (d, J=4.8 Hz, 1H).

Example 17

N-(2-Ethyl-8-mesitylimidazo[1,2-a]pyrazin-3-yl)-N,N-dipropylamine hydrochloride

Yellow Crystals $^1$H NMR (400 MHz, DMSO-d$_6$) δ 0.80–0.88 (m, 6H), 1.19 (t, J=7.5 Hz, 3H), 1.34–1.47 (m, 4H), 1.94 (s, 6H), 2.33 (s, 3H), 2.76 (q, J=7.5 Hz, 2H), 3.07–3.15 (m, 4H), 7.04 (s, 2H), 8.24 (br s, 1H), 8.57 (br s, 1H).

Example 18

N-[8-(2,4-Dichlorophenyl)-2-ethylimidazo[1,2-a]pyrazin-3-yl]-N-(1-ethylpropyl)amine hydrochloride Orange Crystals $^1$H NMR (400 MHz, DMSO-d$_6$) δ 0.87–0.97 (m, 6H), 1.20 (t, J=7.5 Hz, 3H), 1.44–1.60 (m, 4H), 2.82 (q, J=7.5 Hz, 2H), 3.16–3.28 (m, 1H), 7.67 (dd, J=2.0, 8.2 Hz, 1H), 7.72 (d, J=8.2 Hz, 1H), 7.90 (d, J=2.0 Hz, 1H), 8.07 (d, J=4.9 Hz, 1H), 8.57 (d, J=4.9 Hz, 1H).

Example 19

N-Butyl-N-[8-(2,4-dichlorophenyl)-2-ethylimidazo[1,2-a]pyrazin-3-yl]-N-ethylamine hydrochloride Pale Yellow Crystals $^1$H NMR (400 MHz, CDCl$_3$) δ 0.87–0.95 (m, 3H), 1.09 (t, J=7.1 Hz, 3H), 1.29–1.50 (m, 4H), 1.47 (t, J=7.7 Hz, 3H), 3.09 (q, J=7.7 Hz, 2H), 3.15–3.22 (m, 2H), 3.24 (q, J=7.1 Hz, 2H), 7.53 (dd, J=2.0, 8.2 Hz, 1H), 7.66 (d, J=2.0 Hz, 1H), 8.29 (d, J=4.6 Hz, 1H), 8.38 (d, J=4.6 Hz, 1H).

Example 20

N-(2-Ethyl-8-mesitylimidazo[1,2-a]pyrazin-3-yl)-N-(1-ethylpropyl)amine

White Crystals $^1$H NMR (400 MHz, CDCl$_3$) δ 0.98–1.05 (m, 6H), 1.25 (t, J=7.5 Hz, 3H), 1.44–1.61 (m, 4H), 2.02 (s, 6H), 2.32 (s, 3H), 2.75 (q, J=7.5 Hz, 2H), 3.07–3.15 (m, 4H), 6.94 (s, 2H), 7.90 (d, J=4.4 Hz, 1H), 7.94 (d, J=4.4 Hz, 1H).

Example 21

N-[8-(2,4-Dimethoxyphenyl)-2-ethylimidazo[1,2-a]pyrazin-3-yl]-N,N-dipropylamine hydrochloride Yellow Crystals $^1$H NMR (400 MHz, DMSO-d$_6$) δ 0.78–0.88 (m, 6H), 1.26 (t, J=7.5 Hz, 3H), 1.33–1.47 (m, 4H), 2.82 (q, J=7.5 Hz, 2H), 3.06–3.15 (m, 4H), 3.82 (s, 3H), 3.89 (s, 3H), 6.78 (dd, J=2.3, 8.6 Hz, 1H), 6.81 (d, J=2.3 Hz, 1H), 7.70 (d, J=8.6 Hz, 1H), 8.24 (br s, 1H), 8.54 (br s, 1H).

Example 22

N-[8-(2,4-Dimethoxy-6-methylphenyl)-2-ethylimidazo[1,2-a]pyrazin-3-yl]-N,N-dipropylamine hydrochloride White Crystals $^1$H NMR (400 MHz, CDCl$_3$) δ 0.85–0.93 (m, 6H), 1.25 (t, J=7.5 Hz, 3H), 1.38–1.49 (m, 4H), 2.06 (s, 3H), 2.76 (q, J=7.5 Hz, 2H), 3.02–3.11 (m, 4H), 3.69 (s, 3H), 3.84 (s, 3H), 6.44 (d, J=1.8 Hz, 1H), 6.45 (d, J=1.8 Hz, 1H), 7.90 (d, J=4.6 Hz, 1H), 7.98 (d, J=4.6 Hz, 1H).

Example 23

N-[2-Ethyl-8-(2,4,6-trimethoxyphenyl)imidazo[1,2-a]pyrazin-3-yl]-N,N-dipropylamine hydrochloride White Crystals $^1$H NMR (400 MHz, DMSO-d$_6$) δ 0.80–0.88 (m, 6H), 1.22 (t, J=7.5 Hz, 3H), 1.35–1.47 (m, 4H), 2.80 (q, J=7.5 Hz, 2H), 3.07–3.16 (m, 4H), 3.68 (s, 6H), 3.89 (s, 3H), 6.44 (s, 2H), 8.30 (br s, 1H), 8.60 (br s, 1H).

Example 24

N-[2-Ethyl-8-(4-methoxy-2,6-dimethylphenyl)imidazo[1,2-a]pyrazin-3-yl]-N,N-dipropylamine hydrochloride White Amorphous $^1$H NMR (400 MHz, DMSO-d$_6$) δ 0.77–0.89 (m, 6H), 1.20 (t, J=7.3 Hz, 3H), 1.32–1.47 (m, 4H), 1.97 (s, 6H), 2.77 (q, J=7.3 Hz, 2H), 3.05–3.17 (m, 4H), 3.80 (s, 3H), 6.80 (s, 2H), 8.19 (br s, 1H), 8.56 (br s, 1H).

Example 25

N-[2-Ethyl-8-(4-methoxy-2-methylphenyl)imidazo[1,2-a]pyrazin-3-yl]-N,N-dipropylamine hydrochloride Pale Yellow Crystals
$^1$H NMR (400 MHz, DMSO-$d_6$) δ 0.80–0.88 (m, 6H), 1.23 (t, J=7.5 Hz, 3H), 1.34–1.47 (m, 4H), 2.29 (s, 3H), 2.80 (q, J=7.5 Hz, 2H), 3.06–3.14 (m, 4H), 3.84 (s, 3H), 6.98 (dd, J=2.6, 8.4 Hz, 1H), 7.01 (d, J=2.6 Hz, 1H), 7.55 (d, J=8.4 Hz, 1H), 8.20 (d, J=4.8 Hz, 1H), 8.54 (d, J=4.8 Hz, 1H).

Example 26

N-[8-(2-Chloro-4-methoxypheny)-2-ethylimidazo[1,2-a]pyrazin-3-yl]-N,N-dipropylamine hydrochloride Pale Yellow Oil
$^1$H NMR (400 MHz, CDCl$_3$) δ 0.86–0.94 (m, 6H), 1.34 (t, J=7.5 Hz, 3H), 1.38–1.52 (m, 4H), 2.87 (q, J=7.5 Hz, 2H), 3.05–3.13 (m, 4H), 3.88 (s, 3H), 6.98 (dd, J=2.6, 8.6 Hz, 1H), 7.10 (d, J=2.6 Hz, 1H), 7.67 (d, J=8.6 Hz, 1H), 8.02 (d, J=4.0 Hz, 1H), 8.08 (d, J=4.0 Hz, 1H).

Example 27

N-[6-Chloro-8-(2-chloro-4-methoxyphenyl)-2-ethylimidazo[1,2-a]pyrazin-3-yl]-N,N-dipropylamine $^1$H NMR (400 MHz, CDCl$_3$) δ 0.86–0.93 (m, 6H), 1.29 (t, J=7.5 Hz, 3H), 1.37–1.48 (m, 4H), 2.76 (q, J=7.5 Hz, 2H), 3.02–3.09 (m, 4H), 3.82 (s, 3H), 7.04 (d, J=2.0 Hz, 1H), 7.07 (dd, J=2.0, 8.1 Hz, 1H), 7.55 (d, J=8.1 Hz, 1H), 8.02 (s, 1H).

Example 28

3-Chloro-4-[6-chloro-3-(dipropylamino)-2ethylimidazo[1,2-a]pyrazin-8-yl]benzonitrile Pale Yellow Crystals
Hereinafter, compounds were synthesized in the same process as that of Example 1 or a similar process.

Example 29

N-[8-(2,6-Dimethoxy-4-methylphenyl)-2-ethylimidazo[1,2-a]pyrazin-3-yl]-N,N-dipropylamine Yellow Crystals
$^1$H NMR (400 MHZ, DMSO-$d_6$) δ 0.79–0.88 (m, 6H), 1.22 (t, J=7.5 Hz, 3H), 1.34–1.47 (m, 4H), 2.42 (s, 3H), 2.79 (q, J=7.5 Hz, 2H), 3.06–3.15 (m, 4H), 3.66 (s, 6H), 6.72 (s, 2H), 8.31 (br s, 1H), 8.60 (br s, 1H).

Example 30

N-[8-(4-Chlorophenyl)-2-ethylimidazo[1,2-a]pyrazin-3-yl]N,N-dipropylamine

Orange Crystals
$^1$H NMR (400 MHz, CDCl$_3$) δ 0.84–0.92 (m, 6H), 1.35–1.46 (m, 4H), 1.40 (t, J=7.5 Hz, 3H), 2.84 (q, J=7.5 Hz, 2H), 3.03–3.11 (m, 4H), 7.50 (d, J=8.5 Hz, 2H), 7.89 (d, J=4.4 Hz, 1H), 7.99 (d, J=4.4 Hz, 1H), 8.71 (d, J=8.5 Hz, 2H).

Example 31

N-[2-Ethyl-8-(4-methoxyphenyl)imidazo[1,2-a]pyrazin-3-yl]-N,N-dipropylamine

Orange Crystals
$^1$H NMR (400 MHZ, CDCl$_3$) δ 0.86–0.94 (m, 6H), 1.38–1.52 (m, 4H), 1.45 (t, J=7.5 Hz, 3H), 2.94 (q, J=7.5 Hz, 2H), 3.09–3.17 (m, 4H), 3.94 (s, 3H), 7.18 (d, J=9.2 Hz, 2H), 8.09 (s, 2H), 8.96 (d, J=9.2 Hz, 2H).

Example 32

N-[2-Ethyl-8-(2-methoxy-4,6-dimethylphenyl)imidazo[1,2-a]pyrazin-3-yl]-N,N-dipropylamine Pale Yellow Crystals
$^1$H NMR (400 MHz, CDCl$_3$) δ 0.88–0.97 (m, 6H), 1.39 (t, J=7.5 Hz, 3H), 1.43–1.55 (m, 4H), 2.16 (s, 3H), 2.41 (s, 3H), 2.99 (q, J=7.5 Hz, 2H), 3.08–3.17 (m, 4H), 3.84 (s, 3H), 6.78 (s,1H), 6.80 (s, 1H), 8.20 (d, J=4.9 Hz, 1H), 8.24 (d, J=4.9 Hz, 1H).

Example 33

N-Cyclopropylmethyl-N-[2-ethyl-8-(2-methoxy-4,6-dimethylphenyl)imidazo[1,2-a]pyrazin-3-yl]-N-isobutylamine Pale Yellow Crystals
$^1$H NMR (400 MHz, CDCl$_3$) δ −0.10–0.00 (m, 2H), 0.27–0.38 (m, 2H), 0.75–0.85 (m, 1H), 0.92–0.99 (m, 6H), 1.25 (t, J=7.5 Hz, 3H), 1.59–1.72 (m, 1H), 2.01 (s, 3H), 2.36 (s, 3H), 2.77 (q, J=7.5 Hz, 2H), 2.79–3.05 (m, 4H), 3.69 (s, 3H), 6.68 (s, 1H), 6.73 (s, 1H), 7.90 (d, J=4.6 Hz, 1H), 8.08 (d, J=4.6 Hz, 1H).

Example 34

N-[2-Ethyl-6-methoxy-8-(2-methoxy-4,6-dimethylphenyl)imidazo[1,2-a]pyrazin-3-yl]-N,N-dipropylamine Pale Yellow Crystals
$^1$H NMR (400 MHz, CDCl$_3$) δ 0.86–0.93 (m, 6H), 1.23 (t, J=7.5 Hz, 3H), 1.36–1.50 (m, 4H), 2.07 (s, 3H), 2.36 (s, 3H), 2.73 (q, J=7.5 Hz, 2H), 3.01–3.08 (m, 4H), 3.70 (s, 3H), 3.94 (s, 3H), 6.69 (s, 1H), 6.74 (s, 1H), 7.55 (s, 1H).

Example 35

N-[8-(2,6-Dimethoxy-3-pyridyl)-2-ethylimidazo[1,2-a]pyrazin-3-yl]-N,N-dipropylamine Colorless Oil
$^1$H NMR (400 MHz, CDCl$_3$) δ 0.89 (t, J=7.4 Hz, 6H), 1.31 (t, J=7.6 Hz, 3H), 1.37–1.47 (m, 4H), 2.78 (q, J=7.6 Hz, 2H), 3.03–3.09 (m, 4H), 3.99 (s, 3H), 3.99 (s, 3H), 6.47 (d, J=8.2 Hz, 1H), 7.90 (d, J=4.4 Hz, 1H), 7.96 (d, J=4.4 Hz, 1H), 8.09 (d, J=8.2 Hz, 1H).

Example 36

N-[2-Ethyl-8-(6-methoxy-2-methyl-3-pyridyl)imidazo[1,2-a]pyrazin-3-yl]-N,N-dipropylamine Colorless Oil $^1$H NMR (400 MHz, CDCl$_3$) δ 0.90 (t, J=7.4 Hz, 6H), 1.32 (t, J=7.5 Hz, 3H), 1.48–1.58 (m, 4H), 2.53 (s, 3H), 2.79 (q, J=7.5 Hz, 2H), 3.05–3.11 (m, 4H), 3.99 (s, 3H), 6.69 (d, J=8.5 Hz, 1H), 7.89 (d, J=4.6 Hz, 1H), 7.97 (d, J=8.5 Hz, 1H), 7.99 (d, J=4.6 Hz, 1H).

Example 37

N3,N3-Dipropyl-8-[6-(dimethylamino)-4-methyl-3-pyridyl]-2-ethylimidazo[1,2-a]pyrazin-3-amine Colorless Oil $^1$H NMR (400 MHz, CDCl$_3$) δ0.89 (t, J=7.4 Hz, 6H), 1.31 (t, J=7.5 Hz, 3H), 1.38–1.48 (m, 4H), 2.40 (s, 3H), 2.77 (q, J=7.5 Hz, 2H), 3.04–3.09 (m, 4H), 3.14 (s, 6H), 6.44 (s, 1H), 7.85 (d, J=4.6 Hz, 1H), 7.93 (d, J=4.6 Hz, 1H), 8.65 (s, 1H).

Example 38

N-[2-Ethyl-8-(2,4,6-trimethyl-3-pyridyl)imidazo[1,2-a]pyrazin-3-yl]-N,N-dipropylamine Colorless Oil $^1$H NMR (400 MHz, CDCl$_3$) δ 0.91 (t, J=7.4 Hz, 6H), 1.26 (t, J=7.6 Hz, 3H), 1.38–1.48 (m, 4H), 2.07 (s, 3H), 2.28 (s, 3H), 2.55 (s, 3H), 2.77 (q, J=7.6 Hz, 2H), 3.06–3.11 (m, 4H), 6.96 (s, 1H), 7.91 (d, J=4.4 Hz, 1H), 8.04 (d, J=4.4 Hz, 1H).

Example 39

N-[2-Ethyl-8-(3-methyl-2-pyridyl)imidazo[1,2-a]pyrazin-3-yl]-N,N-dipropylamine

Colorless Oil $^1$H NMR (400 MHz, CDCl$_3$) δ 0.89 (t, J=7.4 Hz, 6H), 1.29 (t, J=7.6 Hz, 3H), 1.37–1.47 (m, 4H), 2.35 (s, 3H), 2.80 (q, J=7.6 Hz, 2H), 3.06–3.10 (m, 4H), 7.30 (dd, J=7.8, 4.6 Hz, 1H), 7.64–7.68 (m, 1H), 7.93 (d, J=4.4 Hz, 1H), 8.06 (d, J=4.4 Hz, 1H), 8.58–8.62 (m, 1H).

Example 40

N-[2-Ethyl-8-(6-methoxy-2,4-dimethyl-3-pyridyl)imidazo[1,2-a]pyrazin-3-yl]-N,N-dipropylamine Colorless Oil $^1$H NMR (400 MHz, CDCl$_3$) δ 0.91 (t, J=7.4 Hz, 6H), 1.26 (t, J=7.5 Hz, 3H), 1.38–1.48 (m, 4H), 2.05 (s, 3H), 2.22 (s, 3H), 2.78 (q, J=7.5 Hz, 2H), 3.06–3.11 (m, 4H), 3.95 (s, 3H), 6.52 (s, 1H), 7.90 (d, J=4.6 Hz, 1H), 8.03 (d, J=4.6 Hz, 1H).

Example 41

N-(2-Ethyl-8-(6-methyl-1,3-benzodioxol-5-yl)imidazo[1,2-a]pyrazin-3-yl]-N,N-dipropylamine Colorless Oil $^1$H NMR (400 MHz, CDCl$_3$) δ 0.90 (t, J=7.3 Hz, 6H), 1.31 (t, J=7.5 Hz, 3H), 1.38–1.48 (m, 4H), 2.27 (s, 3H), 2.79 (q, J=7.5 Hz, 2H), 3.04–3.10 (m, 4H), 5.97 (s, 2H), 6.79 (s, 1H), 7.16 (s, 1H), 7.86 (d, J=4.4 Hz, 1H), 7.98 (d, J=4.4 Hz, 1H).

Example 42

N-[2-Ethyl-8-(4-methoxy-2,5-dimethylphenyl)imidazo[1,2-a]pyrazin-3-yl]-N,N-dipropylamine Colorless Oil $^1$H NMR (400 MHz, CDCl$_3$) δ 0.89 (t, J=7.4 Hz, 6H), 1.31 (t, J=7.5 Hz, 3H), 1.37–1.48 (m, 4H), 2.21 (s, 3H), 2.33 (s, 3H), 2.78 (q, J=7.5 Hz, 2H), 3.04–3.10 (m, 4H), 3.87 (s, 3H), 6.76 (s, 1H), 7.41 (s, 1H), 7.86 (d, J=4.6 Hz, 1H), 7.97 (d, J=4.6 Hz, 1H).

Example 43

N-[8-(2,4-Dichlorophenyl)-2-ethylimidazo[1,2-a]pyrazin-3-yl]-N-isobutyl-N-propylamine Yellow Oil $^1$H NMR (400 MHz, CDCl$_3$) δ 0.89 (t, J=7.2 Hz, 3H), 0.94 (d, J=6.8 Hz, 6H), 1.30 (t, J=7.6 Hz, 3H), 1.38–1.48 (m, 2H), 1.55–1.68 (m, 1H), 2.80 (q, J=7.2 Hz, 2H), 2.94 (d, J=6.8 Hz, 2H), 3.04 (t, J=7.6 Hz, 2H), 7.40 (d, J=8.0 Hz, 1H), 7.56 (s, 1H), 7.66 (d, J=8.0 Hz, 1H), 7.94 (d, J=4.4 Hz, 1H), 8.07 (d, J=4.4 Hz, 1H).

MS (ESI) m/z 405 MH$^+$

Example 44

N-Cyclopropylmethyl-N-[8-(2,4-dichlorophenyl)-2-ethylimidazo[1,2-a]pyrazin-3-yl]-N-propylamine Yellow Oil $^1$H NMR (400 MHz, CDCl$_3$) δ 0.00 (br s, 2H), 0.36 (d, J=8.4 Hz, 2H), 0.76–0.92 (m, 1H), 0.91 (t, J=7.6 Hz, 3H), 1.30 (t, J=7.6 Hz, 3H), 1.43–1.48 (m, 2H), 2.80 (q, J=8.0 Hz, 2H), 2.96 (d, J=6.8 Hz, 2H), 3.16 (t, J=7.2 Hz, 2H), 7.39 (d, J=8.4 Hz, 1H), 7.55 (s, 1H), 7.67 (d, J=8.4 Hz, 1H), 7.93 (d, J=4.8 Hz, 1H), 8.13 (d, J=4.4 Hz, 1H).

MS (ESI) m/z 403 MH$^+$

Example 45

N-[8-(2,4-Dichlorophenyl)-2-ethylimidazo[1,2-a]pyrazin-3-yl]-N-(3-fluoropropyl)-N-propylamine Yellow Oil $^1$H NMR (400 MHz, CDCl$_3$) δ 0.91 (t, J=7.6 Hz, 3H), 1.30 (t, J=7.6 Hz, 3H), 1.40–1.50 (m, 2H), 1.72–1.78 (m, 1H), 1.80–1.86 (m, 1H), 2.81 (q, J=7.6 Hz, 2H), 3.09 (dd, J=7.6, 7.6 Hz, 2H), 3.30 (t, J=7.2 Hz, 2H), 4.45 (t, J=6.0 Hz, 1H) 4.57 (t, J=5.6 Hz, 1H), 7.39 (d, J=8.0 Hz, 1H), 7.56 (s, 1H), 7.66 (d, J=8.0 Hz, 1H), 7.95 (d, J=4.8 Hz, 1H), 8.05 (d, J=4.4 Hz, 1H).

MS (ESI) m/z 409 MH$^+$

Example 46

N-Cyclopropylmethyl-N-[8-(2,4-dichlorophenyl)-2-ethylimidazo[1,2-a]pyrazin-3-yl]-N-isobutylamine Yellow Oil $^1$H NMR (400 MHz, CDCl$_3$) δ 0.00 (br s, 2H), 0.37 (br d, J=6.8 Hz, 2H), 0.74–0.88 (m, 1H), 0.97 (d, J=6.4 Hz, 6H), 1.32 (t, J=7.6 Hz, 3H), 1.60–1.72 (m, 1H), 2.83 (q, J=7.6 Hz, 2H), 2.95 (d, J=7.2 Hz, 2H), 3.02 (d, J=6.8 Hz, 2H), 7.41 (d, J=8.4 Hz, 1H), 7.57 (s, 1H), 7.68 (d, J=8.0 Hz, 1H), 7.95 (d, J=4.4 Hz, 1H), 8.17 (d, J=4.4 Hz, 1H).
MS (ESI) m/z 417 MH$^+$

Example 47

N-[8-(2,4-Dichlorophenyl)-2-ethylimidazo[1,2-a]pyrazin-3-yl]-N,N-diisobutylaminehydrochloride White Crystals
$^1$H NMR (400 MHz, CDCl$_3$) δ 0.95 (d, J=6.8 Hz, 12H), 1.29 (t, J=7.2 Hz, 3H), 1.56–1.64 (m, 2H), 2.80 (q, J=7.6 Hz, 2H), 2.89 (d, J=6.4 Hz, 4H), 7.38 (dd, J=8.0, 2.0 Hz, 1H), 7.54 (d, J=2.0 Hz, 1H), 7.65 (d, J=8.4 Hz, 1H), 7.93 (d, J=4.8 Hz, 1H), 8.07 (d, J=4.4 Hz, 1H).
MS (ESI) m/z 419 MH$^+$

Example 48

N-[8-(2,4-Dichlorophenyl)-2-ethylimidazo[1,2-a]pyrazin-3yl]-N-isobutylamine

MS (FAB) m/z 363 MH$^+$

Example 49

N-[8-(2,4-Dichlorophenyl)-2-ethylimidazo[1,2-a]pyrazin-3-yl]-N-ethyl-N-isobutylamine MS (FAB) m/z 391 MH$^+$

Example 50

N-Butyl-N-[8-(2,4-dichlorophenyl)-2-ethylimidazo[1,2-a]pyrazin-3-yl]-N-isobutylamine MS (FAB) m/z 419 MH$^+$

Example 51

N-Benzyl-N-[8-(2,4-dichlorophenyl)-2-ethylimidazo[1,2-a]pyrazin-3-yl]-N-isobutylamine MS (FAB) m/z 453 MH$^+$

Example 52

N-[8-(2,4-Dichlorophenyl)-2-ethylimidazo[1,2-a]pyrazin-3-yl]-N-isobutyl-N-(2-thienylmethyl)amine MS (FAB) m/z 459 MH$^+$

Example 53

N-[8-(2,4-Dichlorophenyl)-2-ethylimidazo[1,2-a]pyrazin-3-yl]-N-(2-furylmethyl)-N-isobutylamine MS (FAB) m/z 443 MH$^+$

Example 54

N-[8-(2,4-Dichlorophenyl)-2-ethylimidazo[1,2-a]pyrazin-3-yl]-N-isobutyl-N-isopentylamine MS (FAB) m/z 433 MH$^{30}$

Example 55

N-[8-(2,4-Dichlorophenyl)-2-ethylimidazo[1,2-a]pyrazin-3-yl]-N-isobutyl-N-[3-(methylsulfanyl)propyl]amine MS (FAB) m/z 451 MH$^+$

Example 56

N-[8-(2,4-Dichlorophenyl)-2-ethylimidazo[1,2-a]pyrazin-3-yl]-N-isobutyl-N-pentylamine MS (FAB) m/z 433 MH$^{30}$

Example 57

N-Cyclohexylmethyl-N-[8-(2,4-dichlorophenyl)-2-ethylimidazo[1,2-a]pyrazin-3-yl]-N-isobutylamine MS (FAB) m/z 459 MH$^+$

Example 58

N-[8-(2,4-Dichlorophenyl)-2-ethylimidazo[1,2-a]pyrazin-3-yl]-N-(3-fluoropropyl)amine MS (FAB) m/z 367 MH$^+$

Example 59

N-[8-(2,4-Dichlorophenyl)-2-ethylimidazo[1,2-a]pyrazin-3-yl]-N-ethyl-N-(3-fluoropropyl)amine MS (FAB) m/z 395 MH$^+$

Example 60

N-Butyl-N-[8-(2,4-dichlorophenyl)-2-ethylimidazo[1,2-a]pyrazin-3-yl]-N-(3-fluoropropyl)amine MS (FAB) m/z 423 MH$^+$

Example 61

N-Benzyl-N-[8-(2,4-dichlorophenyl)-2-ethylimidazo[1,2-a]pyrazin-3-yl]-N-(3-fluoropropyl)amine MS (FAB) m/z 457 MH$^+$

Example 62

N-[8-(2,4-Dichlorophenyl)-2-ethylimidazo[1,2-a]pyrazin-3-yl]-N-(3-fluoropropyl)-N-(2-thienylmethyl)amine MS (FAB) m/z 463 MH$^+$

Example 63

N-[8-(2,4-Dichlorophenyl)-2-ethylimidazo[1,2-a]pyrazin-3-yl]-N-(3-fluoropropyl)-N-(2-furylmethyl)amine MS (FAB) m/z 447 MH$^+$

Example 64

N-[8-(2,4-Dichlorophenyl)-2-ethylimidazo[1,2-a]pyrazin-3-yl]-N-(3-fluoropropyl)-N-isopentylamine MS (FAB) m/z 437 MH$^+$

Example 65

N-[8-(2,4-Dichlorophenyl)-2-ethylimidazo[1,2-a]pyrazin-3-yl]-N-(3-fluoropropyl)-N-[3-(methylsulfanyl)propyl]amine MS (FAB) m/z 455 MH$^+$

Example 66

N-[8-(2,4-Dichlorophenyl)-2-ethylimidazo[1,2-a]pyrazin-3-yl]-N-(3-fluoropropyl)-N-pentylamine MS (FAB) m/z 437 MH$^+$

Example 67

N-Cyclohexylmethyl-N-[8-(2,4-dichlorophenyl)-2-ethylimidazo[1,2-a]pyrazin-3-yl]-N-(3-fluoropropyl)amine MS (FAB) m/z 463 MH$^+$

Example 68

N-[8-(2,4-Dichlorophenyl)-2-ethylimidazo[1,2-a]pyrazin-3-yl]-N-(3-fluoropropyl)-N-(4,4,4-trifluorobutyl)amine MS (FAB) m/z 477 MH$^+$

Example 69

N-Cyclopropylmethyl-N-[8-(2,4-dichlorophenyl)-2-ethylimidazo[1,2-a]pyrazin-3-yl]-N-(3-fluoropropyl)amine MS (FAB) m/z 421 MH$^+$

Example 70

N-[8-(2,4-Dichlorophenyl)-2-ethylimidazo[1,2-a]pyrazin-3-yl]-N-(3-fluoropropyl)-N-isobutylamine MS (FAB) m/z 423 MH$^+$

Example 71

N-[8-(2,4-Dichlorophenyl)-2-ethylimidazo[1,2-a]pyrazin-3-yl]-N-isobutyl-N-(4,4,4-trifluorobutyl)amine MS (FAB) m/z 473 MH$^+$

Example 72

N-[8-(2,4-Dichlorophenyl)-2-ethylimidazo[1,2-a]pyrazin-3-yl]-N-isopentylanine

MS (FAB) m/z 377 MH$^+$

Example 73

N-[8-(2,4-Dichlorophenyl)-2-ethylimidazo[1,2-a]pyrazin-3-yl]-N-ethyl-N-isopentylamine MS (FAB) m/z 405 MH$^+$

Example 74

N-Butyl-N-[8-(2,4-dichlorophenyl)-2-ethylimidazo[1,2-a]pyrazin-3-yl]-N-isopentylamine MS (FAB) m/z 433 MH$^+$

Example 75

N-[8-(2,4-Dichlorophenyl)-2-ethylimidazo[1,2-a]pyrazin-3-yl]-N-isopentyl-N-(2-thienylmethyl)amine MS (FAB) m/z 473 MH$^+$

Example 76

N-[8-(2,4-Dichlorophenyl)-2-ethylimidazo[1,2-a]pyrazin-3-yl]-N,N-diisopentylamine MS (FAB) m/z 447 MH$^+$

Example 77

N-[8-(2,4-Dichlorophenyl)-2-ethylimidazo[1,2-a]pyrazin-3-yl]-N-isopentyl-N-[3-(methylsulfanyl)propyl]amine MS (FAB) m/z 465 MH$^+$

Example 78

N-[8-(2,4-Dichlorophenyl)-2-ethylimidazo[1,2-a]pyrazin-3-yl]-N-isopentyl-N-pentylamine MS (FAB) m/z 447 MH$^+$

Example 79

N-[8-(2,4-Dichlorophenyl)-2-ethylimidazo[1,2-a]pyrazin-3-yl]-N-isopentyl-N-(4,4,4-triflurobutyl)amine MS (FAB) m/z 487 MH$^+$

Example 80

N-Cyclopropylmethyl-N-[8-(2,4-dichlorophenyl)-2-ethylimidazo[1,2-a]pyrazin-3-yl]-N-isopentylamine MS (FAB) m/z 432 MH$^+$

Example 81

N-[8-(2,4-Dichlorophenyl)-2-ethylimidazo[1,2-a]pyrazin-3-yl]-N-isopentyl-N-propylamine MS (FAB) m/z 419 MH$^+$

Example 82

N-[8-(4-Chloro-2-methoxyphenyl)-2-ethylimidazo[1,2-a]pyrazin-3-yl]-N,N-dipropylamine Yellow Oil $^1$H NMR (400 MHz, CDCl$_3$) δ 0.89 (t, J=7.2 Hz, 6H), 1.29 (t, J=7.6 Hz, 3H), 1.47–1.38 (m, 4H), 2.78 (q, J=7.6 Hz, 2H), 3.06 (dd, J=7.2, 8.8 Hz, 4H), 3.02 (s, 3H), 7.05 (d, J=2.0 Hz, 1H), 7.08 (dd, J=2.0, 8.4 Hz, 1H), 7.59 (d, J=8.0 Hz, 1H), 7.90 (d, J=4.4 Hz, 1H), 7.99 (d, J=4.8 Hz, 1H).

Example 83

N-[8-(4-Bromo-2-chlorophenyl)-2-ethylimidazo[1,2-a]pyrazin-3-yl]-N,N-dipropylamine Orange Oil $^1$H NMR (400 MHz, CDCl$_3$) δ 0.90 (t, J=7.2 Hz, 6H), 1.29 (t, J=7.6 Hz, 3H), 1.47–1.38 (m, 4H), 2.80 (q, J=8.0 Hz, 2H), 3.06 (dd, J=7.6, 7.6 Hz, 4H), 7.53 (ddd, J=0.4, 2.0, 8.4 Hz, 1H), 7.59 (d, J=8.0 Hz, 1H), 7.71 (d, J=1.6 Hz, 1H), 7.93 (dd, J=0.4, 4.8 Hz, 1H), 8.05 (dd, J=0.4, 4.8 Hz, 1H).

Example 84

N-[8-(2,4-Dibromophenyl)-2-ethylimidazo[1,2-a]pyrazin-3-yl]-N,N-dipropylamine

Orange Oil $^1$H NMR (400 MHz, CDCl$_3$) δ 0.90 (t, J=7.6 Hz, 6H), 1.29 (t, J=7.2 Hz, 3H), 1.46–1.38 (m, 2H), 2.79 (q, J=7.2 Hz, 2H), 3.08 (dd, J=7.2, 7.2 Hz, 4H), 7.57 (s, 1H), 7.57 (dd, J=0.8, 2.0 Hz, 1H), 7.89 (d, J=1.6 Hz, 1H), 7.92 (d, J=4.4 Hz, 1H) 8.05 (dd, J=0.4, 4.4 Hz, 1H).

Example 85

N-[8-(4-Bromo-2-fluorophenyl)-2-ethylimidazo[1,2-a]pyrazin-3-yl]-N,N-dipropylamine Yellow Crystals $^1$H NMR (400 MHz, CDCl$_3$) δ 0.89 (t, J=7.6 Hz, 6H), 1.32 (t, J=7.2 Hz, 3H), 1.45–1.38 (m, 4H), 2.81 (q, J=7.6 Hz, 2H), 3.07 (dd, J=7.6, 7.6 Hz, 4H), 7.43 (dd, J=2.0, 10.0 Hz, 1H), 7.45 (ddd, J=0.4, 1.6, 7.6 Hz, 1H), 7.86 (dd, J=7.2, 8.0 Hz, 1H), 7.93 (d, J=4.4 Hz, 1H), 8.04 (d, J=4.8 Hz, 1H).

Example 86

N-[8-(2-Bromo-4-methoxyphenyl)-2-ethylimidazo[1,2-a]pyrazin-3-yl]-N,N-dipropylamine Yellow Oil $^1$H NMR (400 MHz, CDCl$_3$) δ 0.90 (t, J=7.2 Hz, 6H), 1.30 (t, J=7.6 Hz, 3H), 1.46–1.40 (m, 2H), 2.80 (q, J=7.6 Hz, 2H) 3.07 (t, J=7.6 Hz, 4H), 6.98 (dd, J=2.8, 8.8 Hz, 1H), 7.27 (d, J=2.8 Hz, 1H), 7.63 (d, J=8.4 Hz, 1H), 7.91 (d, J=4.4 Hz, 1H), 8.01 (d, J=4.4 Hz, 1H).

Example 87

N-(sec-Butyl)-N-[8-(2,4-dichlorophenyl)-2-ethylimidazo[1,2-a]pyrazin-3-yl]-N-propylamine Yellow Oil $^1$H NMR (400 MHz, CDCl$_3$) δ 0.84 (t, J=7.6 Hz, 3H), 0.95 (t, J=7.6 Hz, 3H), 1.08 (d, J=6.0 Hz, 3H), 1.30 (t, J=7.6 Hz, 3H), 1.30–1.44 (m, 2H), 1.74–1.62 (m, 2H), 2.79 (q, J=7.2 Hz, 2H), 3.18–3.04 (m, 3H), 7.38 (dd, J=2.0, 8.4 Hz, 1H), 7.55 (d, J=2.0 Hz, 1H), 7.67 (d, J=8.4 Hz, 1H), 7.91 (d, J=4.4 Hz, 1H), 8.04 (d, J=4.4 Hz, 1H).

Example 88

N-(sec-Butyl)-N-cyclopropylmethyl-N-[8-(2,4-dichlorophenyl)-2-ethylimidazo[1,2-a]pyrazin-3-yl]amine Yellow Oil $^1$H NMR (400 MHz, CDCl$_3$) δ −0.02–0.0 (m, 2H), 0.25–0.29 (m, 2H), 0.70–0.60 (m, 1H), 0.95 (t, J=7.2 Hz, 3H), 1.06 (m, 3H), 1.31 (t, J=7.6 Hz, 3H), 1.67 (m, 2H), 2.79 (q, J=7.6 Hz, 2H), 3.04–2.94 (m, 2H), 3.20 (br s, 1H), 7.39 (dd, J=2.0, 8.4 Hz, 1H), 7.55 (d, J=2.0 Hz, 1H), 7.68 (d, J=8.4 Hz, 1H), 7.92 (d, J=4.4 Hz, 1H), 8.14 (d, J=4.8 Hz, 1H).

Example 89

N-Butyl-N-(sec-butyl)-N-[8-(2,4-dichlorophenyl)-2-ethylimidazo[1,2-a]pyrazin-3-yl]amine Yellow Oil $^1$H NMR (400 MHz, CDCl$_3$) δ 0.84 (t, J=6.8 Hz, 3H), 0.95 (t, J=7.2 Hz, 3H), 1.02–1.12 (m, 3H), 1.31 (t, J=7.6 Hz, 3H), 1.20–1.46 (m, 4H), 1.64–1.78 (m, 2H), 2.80 (q, J=7.6 Hz, 2H), 3.02–3.20 (m, 3H), 7.39 (dd, J=2.0, 8.4 Hz, 1H), 7.55 (d, J=2.0 Hz, 1H), 7.69 (d, J=8.0 Hz, 1H), 7.92 (d, J=4.4 Hz, 1H), 8.04 (d, J=4.4 Hz, 1H).

Example 90

N-(sec-Butyl)-N-[8-(2,4-dichlorophenyl)-2-ethylimidazo[1,2-a]pyrazin-3-yl]-N-isobutylamine Yellow Oil $^1$H NMR (400 MHz, CDCl$_3$) δ 0.92–0.80 (m, 6H), 1.01 (t, J=7.2 Hz, 3H), 1.09 (dd, J=6.8, 9.8 Hz, 3H), 1.31 (t, J=7.6 Hz, 3H), 1.30–1.46 (m, 2H), 1.62–1.82 (m, 2H), 2.78–2.90 (m, 3H), 2.92–3.12 (m, 2H), 7.39 (dd, J=2.0, 8.4 Hz, 1H), 7.55 (d, J=2.0 Hz, 1H), 7.69 (d, J=8.0 Hz, 1H), 7.92 (d, J=4.4 Hz, 1H), 8.06 (d, J=4.8 Hz, 1H).

Example 91

N-Cyclopropylmethyl-N-[8-(2,4-dichlorophenyl)-2-ethylimidazo[1,2-a]pyrazin-3-yl]-N-tetrahydro-3-thiophenylamine Yellow Oil $^1$H NMR (400 MHz, CDCl$_3$) δ −0.23–0.10 (m, 1H), 0.00–0.12 (m, 1H), 0.18–0.32 (m, 1H), 0.28–0.40 (m, 1H), 0.67–0.73 (m, 1H), 1.34 (t, J=7.6 Hz, 3H), 1.90–2.02 (m, 1H), 2.00–2.24 (m, 1H), 2.46–2.55 (m, 1H), 2.56–2.72 (m, 1H), 2.81 (q, J=7.6 Hz, 2H), 2.86–3.12 (m, 4H), 4.00–4.10

(m, 1H), 7.41 (dd, J=2.0, 8.4 Hz, 1H), 7.56 (d, J=2.0 Hz, 1H), 7.68 (d, J=8.0 Hz, 1H), 7.98 (d, J=4.4 Hz, 1H), 8.22–8.14 (m, 1H).

Example 92

N-[8-(2,4-Dichlorophenyl)-2-ethylimidazo[1,2-a]pyrazin-3-yl]-N-propyl-N-tetrahydro-3-thiophenylamine Yellow Oil
$^1$H NMR (400 MHz, CDCl$_3$) δ 0.88 (t, J=7.2 Hz, 3H), 1.28–1.40 (m, 2H), 1.36 (t, J=7.6 Hz, 3H), 1.90–2.20 (m, 2H), 2.50–3.02 (m, 6H), 3.01–3.21 (m, 2H), 3.96–4.03 (m, 1H), 7.42 (dd, J=2.0, 8.4 Hz, 1H), 7.58 (d, J=2.0 Hz, 1H), 7.67 (d, J=8.4 Hz, 1H), 8.01–8.06 (m, 1H), 8.15 (d, J=4.4 Hz, 1H).

Example 93

N-[8-(2,6-Dimethoxy-4-methylphenyl)-2-ethylimidazo[1,2-a]pyrazin-3-yl]-N,N-diisobutylamine Yellow Crystals
$^1$H NMR (400 MHz, CDCl$_3$) δ 0.94 (d, J=6.8 Hz, 12H), 1.25 (t, J=7.6 Hz, 3H), 1.58–1.65 (m, 2H), 2.40 (s, 3H), 2.79 (q, J=7.6 Hz, 2H), 2.87 (d, J=6.8 Hz, 4H), 3.70 (s, 6H), 6.50 (s, 2H), 7.92 (d, J=4.8 Hz, 1H), 8.03 (d, J=4.4 Hz, 1H).

Example 94

N-[8-(2-Chloro-4-methoxyphenyl)-2-ethylimidazo[1,2-a]pyrazin-3-yl]-N,N-diisobutylamine Yellow Oil

Example 95

N-[2-Ethyl-8-(2-methoxy-4,6-dimethylphenyl)imidazo[1,2-a]pyrazin-3-yl]-N,N-diisobutylamine Yellow Oil
$^1$H NMR (400 MHz, CDCl$_3$) δ 0.95 (d, J=6.4 Hz, 12H), 1.26 (t, J=7.6 Hz, 3H), 1.56–1.68 (m, 2H), 2.03 (s, 3H), 2.36 (s, 3H), 2.79 (q, J=7.6 Hz, 2H), 2.89 (d, J=6.8 Hz, 4H), 3.70 (s, 3H), 6.68 (s, 1H), 6.74 (s, 1H), 7.92 (d, J=4.4 Hz, 1H), 8.06 (d, J=4.4 Hz, 1H).

Example 96

N-(2-Ethyl-8-mesitylimidazo[1,2-a]pyrazin-3-yl)-N,N-diisobutylamine

Yellow Oil
$^1$H NMR (400 MHz, CDCl$_3$) δ 0.95 (d, J=7.6 Hz, 12H), 1.25 (t, J=7.6 Hz, 3H), 1.58–1.65 (m, 2H), 2.03 (s, 6H), 2.32 (s, 3H), 2.79 (q, J=7.2 Hz, 2H), 2.90 (d, J=6.8 Hz, 4H), 6.94 (s, 2H), 7.91 (d, J=4.8 Hz, 1H), 8.07 (d, J=4.4 Hz, 1H).

Example 97

N-Butyl-N-[8-(2-chloro-4-methoxyphenyl)-2-ethylimidazo[1,2-a]pyrazin-3-yl]-N-isobutylamine Yellow Oil
$^1$H NMR (400 MHz, CDCl$_3$) δ 0.88 (t, J=7.2 Hz, 3H), 0.94 (d, J=6.8 Hz, 6H), 1.31 (t, J=7.2 Hz, 3H), 1.25–1.42 (m, 4H), 1.58–1.65 (m, 1H), 2.81 (q, J=7.2 Hz, 2H), 2.93 (d, J=7.2 Hz, 2H), 3.06 (d, J=6.8 Hz, 2H), 3.86 (s, 3H), 6.94 (dd, J=2.8, 8.8 Hz, 1H), 7.08 (d, J=2.8 Hz, 1H), 7.68 (d, J=8.8 Hz, 1H), 7.93 (d, J=4.4 Hz, 1H), 8.03 (d, J=4.4 Hz, 1H).

Example 98

N-Butyl-N-(2-ethyl-8-mesitylimidazo[1,2-a]pyrazin-3-yl)-N-isobutylamine

Yellow Oil
$^1$H NMR (400 MHz, CDCl$_3$) δ 0.87 (t, J=7.2 Hz, 3H), 0.95 (d, J=6.8 Hz, 6H), 1.25 (t, J=7.6 Hz, 3H), 1.24–1.46 (m, 4H), 1.48–1.67 (m, 1H), 2.03 (s, 6H), 2.32 (s, 3H), 2.78 (q, J=7.8 Hz, 2H), 2.94 (d, J=7.2 Hz, 2H), 3.07 (t, J=6.8 Hz, 2H), 6.94 (s, 2H), 7.92 (d, J=4.4 Hz, 1H), 8.04 (d, J=4.4 Hz, 1H).

Example 99

N-Butyl-N-[8-(2,6-dimethoxy-4-methylphenyl)-2-ethylimidazo[1,2-a]pyrazin-3-yl]-N-isobutylamine Yellow Crystals
$^1$H NMR (400 MHz, CDCl$_3$) δ 0.88 (t, J=7.2 Hz, 3H), 0.94 (d, J=6.8 Hz, 6H), 1.26 (t, J=7.6 Hz, 3H), 1.25–1.42 (m, 4H), 1.58–1.68 (m, 1H), 2.40 (s, 3H), 2.79 (q, J=7.6 Hz, 2H), 2.91 (d, J=7.2 Hz, 2H), 3.05 (t, J=7.2 Hz, 2H), 3.70 (s, 6H), 6.50 (d, J=0.8 Hz, 2H), 7.93 (d, J=4.0 Hz, 1H), 7.99 (d, J=4.4 Hz, 1H).

Example 100

N-Butyl-N-[2-ethyl-8-(2-methoxy-4,6-dimethylphenyl)imidazo[1,2-a]pyrazin-3-yl]-N-isobutylamine Yellow Oil
$^1$H NMR (400 MHz, CDCl$_3$) δ 0.88 (t, J=6.8 Hz, 3H), 0.94 (d, J=6.8 Hz, 6H), 1.26 (t, J=7.6 Hz, 3H), 1.20–1.41 (m, 4H), 1.59–1.68 (m, 1H), 2.03 (s, 3H), 2.37 (s, 3H), 2.79 (q, J=7.6 Hz, 2H), 2.92 (d, J=6.8 Hz, 2H), 3.06 (t, J=7.6 Hz, 2H), 3.71 (s, 3H), 6.69 (s, 1H), 6.74 (d, J=0.8 Hz, 1H), 7.93 (d, J=4.8 Hz, 1H), 8.02 (d, J=4.4 Hz, 1H).

Example 101

N-[8-(2-Chloro-4-methoxyphenyl)-2-ethylimidazo[1,2-a]pyrazin-3-yl]-N-cyclopropylethyl-N-isobutylamine Yellow Oil
$^1$H NMR (400 MHz, CDCl$_3$) δ −0.05–0.04 (m, 2H), 0.36–0.42 (m, 2H), 0.76–0.96 (m, 1H), 0.94 (d, J=6.8 Hz, 6H), 1.33 (t, J=7.2 Hz, 3H), 1.60–1.70 (m, 1H), 2.83 (q, J=7.6 Hz, 2H), 2.94 (d, J=7.2 Hz, 2H), 3.01 (t, J=7.2 Hz, 2H), 3.88 (s, 3H), 6.96 (dd, J=2.4, 8.4 Hz, 1H), 7.09 (d, J=2.8 Hz, 1H), 7.69 (d, J=8.4 Hz, 1H), 7.94 (d, J=4.4 Hz, 1H), 8.13 (d, J=4.4 Hz, 1H).

Example 102

N-Cyclopropylmethyl-N-[8-(2,6-dimethoxy-4-methylphenyl)-2-ethylimidazo[1,2-a]pyrazin-3-yl]-N-isobutylamine Yellow Crystals
$^1$H NMR (400 MHz, CDCl$_3$) δ −0.12–0.02 (m, 2H), 0.29–0.40 (m, 2H), 0.73–0.85 (m, 1H), 0.95 (d, J=6.8 Hz, 6H), 1.29 (t, J=7.2 Hz, 3H), 1.63–1.70 (m, 1H), 2.41 (s, 3H), 2.90–2.75 (m, 1H), 2.92 (d, J=6.8 Hz, 2H), 3.00 (d, J=7.2 Hz, 2H), 3.72 (s, 6H), 6.51 (s, 2H), 7.94–8.04 (m, 1H), 8.08–8.13 (m, 1H).

Example 103

N3,N3-Dipropyl-6-bromo-8-(4-chlorophenyl)-2-ethylimidazo[1,2-a]pyrazin-3-amine

Colorless Oil
$^1$H NMR (400 MHz, CDCl$_3$) δ0.88 (t, J=7.2 Hz, 6H), 1.361–146 (m, 7H), 2.85 (q, J=7.6 Hz, 2H), 3.05–3.09 (m, 4H), 7.51 (d, J=8.8 Hz, 2H), 8.44 (s, 1H), 8.78 (d, J=8.8 Hz, 2H).

Example 104

N3,N3-Dipropyl-5-bromo-8-(2,4-dichlorophenyl)-2-ethylimidazo[1,2-a]pyrazin-3-amine Orange Oil
$^1$H NMR (400 MHz, CDCl$_3$) δ 0.90 (t, J=7.6 Hz, 6H), 1.29 (t, J=7.6 Hz, 3H), 1.38–1.48 (m, 4H), 2.78 (q, J=7.6 Hz, 2H), 3.04–3.09 (m, 4H), 7.38 (dd, J=8.4, 2.0 Hz, 1H), 7.54 (d, J=2.0 Hz, 1H), 7.65 (d, J=8.4 Hz, 1H), 8.08 (s, 1H).

Example 105

8-(2,4-Dichlorophenyl)-3-(dipropylamino)-2-ethylimidazo[1,2-a]pyrazin-6-yl cyanide Orange Oil
$^1$H NMR (400 MHz, CDCl$_3$) δ0.90 (t, J=7.6 Hz, 6H), 1.30 (t, J=7.6 Hz, 3H), 1.38–1.48 (m, 4H), 2.81 (q, J=7.6 Hz, 2H), 3.05–3.11 (m, 4H), 7.40 (dd, J=8.4, 2.0 Hz, 1H), 7.57 (d, J=2.0 Hz, 1H), 7.62 (d, J=8.4 Hz, 1H), 8.50 (s, 1H).

Example 106

N3-Isobutyl-N-3-propyl-6-bromo-8-(2,4-dichlorophenyl)-2-ethylimidazo[1,2-a]pyrazin-3-amine Colorless Crystals
$^1$H NMR (400 MHz, CDCl$_3$) δ0.89 (t, J=7.6 Hz, 3H), 0.94 (d, J=6.8 Hz, 6H), 1.29 (t, J=7.6 Hz, 3H), 1.38–1.48 (m, 2H), 1.54–1.68 (m, 1H), 2.79 (q, J=7.6 Hz, 2H), 2.92 (d, J=7.2 Hz, 2H), 2.99–3.04 (m, 2H), 7.38 (dd, J=8.4, 2.0 Hz, 1H), 7.54 (d, J=2.0 Hz, 1H), 7.64 (d, J=8.4 Hz, 1H), 8.18 (s, 1H).

Example 107

N3,N3-Dipropyl-6-bromo-8-(2,4-dichlorophenyl)-2-ethylimidazo[1,2-a]pyrazin-3-amine Orange Oil
$^1$H NMR (400 MHz, CDCl$_3$) δ0.90 (t, J=7.6 Hz, 6H), 1.29 (t, J=7.6 Hz, 3H), 1.38–1.48 (m, 4H), 2.79 (q, J=7.6 Hz, 2H), 3.03–3.09 (m, 4H), 7.38 (dd, J=8.4, 2.0 Hz, 1H), 7.54 (d, J=2.0 Hz, 1H), 7.64 (d, J=8.4 Hz, 1H), 8.17 (s, 1H).

Example 108

N3,N3-Dipropyl-8-(2,4-dichlorophenyl)-2 isopropylimidazo[1,2-a]pyrazin-3-amine

Colorless Crystals
$^1$H NMR (400 MHz, CDCl$_3$) δ 0.89 (t, J=7.6 Hz, 6H), 1.31 (d, J=6.8 Hz, 6H), 1.38–1.48 (m, 4H), 3.05–3.10 (m, 4H), 3.14–3.22 (m, 1H), 7.39 (dd, J=8.4, 2.0 Hz, 1H), 7.56 (d, J=2.0 Hz, 1H), 7.73 (d, J=8.4 Hz, 1H), 7.92 (d, J=4.4 Hz, 1H), 8.04 (d, J=4.4 Hz, 1H).

Example 109

N3,N3-Dipropyl-2-isopropyl-8-(2-methoxy-4,6-dimethylphenyl)imidazo[1,2-a]pyrazin-3-amine Colorless Oil
$^1$H NMR (400 MHz, CDCl$_3$) δ 0.90 (t, J=7.6 Hz, 6H), 1.28 (dd, J=6.8 Hz, 3.2 Hz, 6H), 1.38–1.48 (m, 4H), 2.05 (s, 3H), 2.38 (s, 3H), 3.05–3.10 (m, 4H), 3.12–3.20 (m, 1H), 3.72 (s, 3H), 6.71 (s, 1H), 6.75 (s, 1H), 7.91 (d, J=4.4 Hz, 1H), 8.00 (d, J=4.4 Hz, 1H).

Example 110

1-[8-(2,4-Dichlorophenyl)-2-ethylimidazo[1,2-a]pyrazin-3-yl]butyl ethyl ether

By performing a coupling reaction in the same manner as that of Example 1 using 1-(8-chloro-2-ethylimidazo[1,2-a]pyrazin-3-yl)butyl ethyl ether obtained in Reference Example 5, the title compound could be obtained as a pale yellow oil.

$^1$H NMR (400 MHz, CDCl$_3$) δ 0.92–0.98 (m, 3H), 1.15–1.37 (m, 7H), 1.42–1.56 (m, 1H), 1.76–1.88 (m, 1H), 2.03–2.15 (m, 1H), 2.72–2.88 (m, 2H), 3.24–3.33 (m, 1H), 3.35–3.46 (m, 1H), 4.75–4.81 (m, 1H), 7.40 (dd, J=2.0, 8.4 Hz, 1H), 7.56 (d, J=2.0 Hz, 1H), 7.66 (d, J=8.4 Hz, 1H), 7.92 (d, J=4.6 Hz, 1H), 8.42 (d, J=4.6 Hz, 1H).

According to the process of Example 110, the following compounds of Examples 111 to 114 were synthesized.

Example 111

3-(1-Ethoxybutyl)-2-ethyl-8-(2-methoxy-4,6-dimethylphenyl)imidazo[1,2-a]pyrazine White Crystals
$^1$H NMR (400 MHz, CDCl$_3$) δ 0.91–0.98 (m, 3H), 1.15–1.34 (m, 7H), 1.41–1.55 (m, 1H), 1.76–1.88 (m, 1H), 2.02 (s, 3H), 2.04–2.15 (m, 1H), 2.37 (s, 3H), 2.70–2.82 (m, 2H), 3.21–3.44 (m, 2H), 3.69 (s, 3H), 4.72–4.78 (m, 1H), 6.68 (s, 1H), 6.74 (s, 1H), 7.89 (d, J=4.6 Hz, 1H), 8.34 (d, J=4.6 Hz, 1H).

Example 113

8-(2,6-Dimethoxy-4-methylphenyl)-3-(1-ethoxybutyl)-2-ethylimidazo[1,2-a]pyrazine White Crystals
$^1$H NMR (400 MHz, CDCl$_3$) δ 0.89–0.98 (m, 3H), 1.13–1.35 (m, 7H), 1.40–1.55 (m, 1H), 1.74–1.86 (m, 1H), 2.02–2.14 (m, 1H), 2.40 (s, 3H), 2.68–2.83 (m, 2H), 3.24–3.43 (m, 2H), 3.69 (s, 3H), 3.70 (s, 3H), 4.70–4.77 (m, 1H), 6.50 (s, 2H), 7.89 (d, J=4.8 Hz, 1H), 8.31 (d, J=4.8 Hz, 1H).

Example 114

8-(2-Chloro-4-methoxyphenyl)-3-(1-ethoxybutyl)-2-ethylimidazo[1,2-a]pyrazine

Pale Yellow Oil
$^1$H NMR (400 MHz, CDCl$_3$) δ 0.90–0.98 (m, 3H), 1.19 (t, J=7.0 Hz, 3H), 1.22–1.36 (m, 4H), 1.40–1.55 (m, 1H), 1.77–1.88 (m, 1H), 2.03–2.15 (m, 1H), 2.72–2.87 (m, 2H), 3.29 (dq, J=9.3, 7.0 Hz, 1H), 3.39 (dq, J=9.3, 7.0 Hz, 1H), 3.87 (s, 3H), 4.73–4.80 (m, 1H), 6.95 (dd, J=2.6, 8.6 Hz, 1H), 7.08 (d, J=2.6 Hz, 1H), 7.66 (d, J=8.6 Hz, 1H), 7.90 (d, J=4.6 Hz, 1H), 8.37 (d, J=4.6 Hz, 1H).

Example 115

4-[2-Ethyl-8-(2-methoxy-4,6-dimethylphenyl)imidazo[1,2-a]pyrazin-3-yl]-4-heptanol 1-(8-Chloro-2-ethylimidazo[1,2-a]pyrazin-3-yl)-1-butanone (226 mg, 0.90 mmol) and 4,6-dimethyl-2-methoxybenzeneboronic acid (198 mg, 1.1 mmol) were dissolved in a mixed solvent of 1,2-dimethoxyethane (4.5 mL) and water (0.75 mL). Barium hydroxide octahydrate (347 mg, 1.1 mmol) and tetrakis(triphenylphosphine)palladium complex (79 mg, 0.068 mmol) were added thereto, and the mixture was heated under reflux for 4 hours under nitrogen atmosphere. After being allowed to cool, the reaction mixture was filtered and washed with ethyl acetate. Then, the filtrates were combined and washed with a 1N aqueous sodium hydroxide solution. It was extracted with ethyl acetate and evaporated. The resulting residue was purified by silica gel column chromatography (ethyl acetate:n-hexane=1:3) to give 1-[2-ethyl-8-(2-methoxy-4,6-dimethylphenyl)imidazo[1,2-a]pyrazin-3-yl]-1-butanone (245 mg) as a white amorphous.

The resulting 1-[2-ethyl-8-(2-methoxy-4,6-dimethylphenyl)imidazo[1,2-a]pyrazin-3-yl]-1-butanone (220 mg, 0.63 mmol) was dissolved in tetrahydrofuran (2 mL), then a 0.90M propylmagnesium bromide solution in tetrahydrofuran (3.6 mL, 3.2 mmol) was added thereto under ice-cooling, and the mixture was stirred at room temperature for 2 hours. An aqueous saturated ammonium chloride solution was added to the reaction mixture, which was extracted with ethyl acetate and evaporated. The resulting residue was purified by silica gel column chromatography (ethyl acetate: n-hexane=6:5) to give the title compound (150 mg) as white crystals.

$^1$H NMR (400 MHz, CDCl$_3$) δ 0.87–0.96 (m, 6H), 1.18–1.45 (m, 4H), 1.25 (t, J=7.5 Hz, 3H), 1.90–2.12 (m, 4H), 2.02 (s, 3H) 2.37 (s, 3H), 2.82 (q, J=7.5 Hz, 2H), 3.68 (s, 3H), 6.68 (s, 1H), 6.74 (s, 1H), 7.81 (d, J=4.9 Hz, 1H), 8.75 (d, J=4.9 Hz, 1H).

Example 116

2-[2-Ethyl-3-[(Z)-1-propyl-1-butenyl]imidazo[1,2-a]pyrazin-8-yl]-3,5-dimethylphenyl methyl ether 4-[2-Ethyl-8-(2-methoxy-4,6-dimethylphenyl)imidazo[1,2-a]pyrazin-3-yl]-4-heptanol (115 mg, 0.29 mmol) and triethylamine (0.48 mL, 3.5 mmol) were dissolved in methylene chloride (3 mL), then methanesulfonyl chloride (0.13 mL, 1.7 mmol) was added thereto under ice-cooling, and the mixture was stirred at room temperature for 1 hour. An aqueous saturated sodium bicarbonate solution was added to the reaction mixture, which was extracted with ethyl acetate and evaporated. The resulting residue was purified by silica gel column chromatography (ethyl acetate:n-hexane=1:1) to give the title compound (111 mg) as a colorless oil.

$^1$H NMR (400 MHz, CDCl$_3$) δ 0.87–0.93 (m, 3H), 1.12 (t, J=7.4 Hz, 3H), 1.22 (t, J=7.5 Hz, 3H), 1.24–1.36 (m, 2H), 2.04 (s, 3H), 2.33 (dq, J=7.5, 7.4 Hz, 2H), 2.37 (s, 3H), 2.38–2.44 (m, 2H), 2.74 (q, J=7.5 Hz, 2H), 3.70 (s, 3H), 5.71 (t, J=7.5 Hz, 1H), 6.68 (s, 1H), 6.74 (s, 1H), 7.81 (d, J=4.6 Hz, 1H), 7.88 (d, J=4.6 Hz, 1H).

Example 117

2-[2-Ethyl-3-(1-propylbutyl)imidazo[1,2-a]pyrazin-8-yl]-3,5-dimethylphenyl methyl ether 2-[2-Ethyl-3-[(Z)-1-propyl-1-butenyl]imidazo[1,2-a]pyrazin-8-yl]-3,5-dimethylphenyl methyl ether (41 mg, 0.12 mmol) was dissolved in ethanol (1.5 mL), then 10% palladium-carbon (50% hydrous product; 120 mg) was added thereto, and the mixture was heated under stirring at 45° C. for 4 hours at a normal pressure under hydrogen atmosphere. The mixture was further stirred at room temperature for 15 hours. The reaction mixture was filtered and washed with ethyl acetate, and then the filtrates were combined and evaporated. The resulting residue was purified by silica gel column chromatography (ethyl acetate:n-hexane=1:1) to give the title compound (25 mg) as white crystals.

$^1$H NMR (400 MHz, CDCl$_3$) δ 0.84–0.92 (m, 6H), 1.04–1.33 (m, 4H), 1.23 (t, J=7.5 Hz, 3H), 1.71–1.91 (m, 4H), 2.01 (s, 3H), 2.36 (s, 3H), 2.76 (q, J=7.5 Hz, 2H), 3.05–3.15 (m, 1H), 3.69 (s, 3H), 6.68 (s, 1H), 6.74 (s, 1H), 7.87 (d, J=4.8 Hz, 1H), 7.92 (d, J=4.8 Hz, 1H).

According to the processes of Examples 116 and 117, compounds of Examples 118 to 120 were synthesized.

Example 118

2-[2-Ethyl-3-[(Z)-1-ethyl-1-propenyl]imidazo[1,2-a]pyrazin-8-yl]-3,5-dimethylphenyl methyl ether Orange Oil
$^1$H NMR (400 MHz, CDCl$_3$) δ 0.93 (t, J=7.5 Hz, 3H), 1.22 (t, J=7.5 Hz, 3H), 1.92 (d, J=7.0 Hz, 3H), 2.04 (s, 3H), 2.37 (s, 3H), 2.47 (q, J=7.5 Hz, 2H), 2.73 (q, J=7.5 Hz, 2H), 3.70 (s, 3H), 5.76 (q, J=7.0 Hz, 1H), 6.68 (s, 1H), 6.74 (s, 1H), 7.79 (d, J=4.6 Hz, 1H), 7.88 (d, J=4.6 Hz, 1H).

Example 119

2-[2-Ethyl-3-(1-ethylpropyl)imidazo[1,2-a]pyrazin-8-yl]3,5-dimethylphenyl methyl ether White Crystals
$^1$H NMR (400 MHz, CDCl$_3$) δ 0.79–0.87 (m, 6H), 1.23 (t, J=7.5 Hz, 3H), 1.82–1.94 (m, 4H), 2.01 (s, 3H), 2.37 (s, 3H), 2.77 (q, J=7.5 Hz, 2H), 2.87–2.97 (m, 1H), 3.69 (s, 3H), 6.68 (s, 1H), 6.74 (s, 1H), 7.87 (d, J=4.8 Hz, 1H), 7.92 (d, J=4.8 Hz, 1H).

Example 120

8-(2,4-Dimethoxyphenyl)-2-ethyl-3-(1-ethylpropyl) imidazo[1,2-a]pyrazine

Colorless Oil $^1$H NMR (400 MHz, CDCl$_3$) δ0.78–0.86 (m, 6H), 1.29 (t, J=7.5 Hz, 3H), 1.82–1.92 (m, 4H), 2.79 (q, J=7.5 Hz, 2H), 2.872–197 (m, 1H), 3.81 (s, 3H), 3.87 (s, 3H), 6.60–6.67 (m, 2H), 7.64–7.68 (m, 1H), 7.85 (d, J=4.6 Hz, 1H), 7.88 (d, J=4.6 Hz, 1H).

Example 121

N-[8-(2,4-Dimethylphenyl)-2-ethyl-6-methylimidazo[1,2-b]pyridazin-3-yl]-N,N-dipropylamine

Acetic acid (5 mL) and hydrazine monohydrate (2.52 g, 0.05 mol) were added to a solution of 1-(2,4-dimethylphenyl)-3-oxobutyl cyanide (10.13 g, 0.05 mol) in ethanol (100 mL), and the mixture was heated under reflux for 8 hours. The reaction mixture was evaporated as it was. Water was added thereto, and the mixture was extracted with ethyl acetate. The organic layer was washed with an aqueous saturated sodium bicarbonate solution and brine, dried over anhydrous magnesium sulfate and evaporated, to give 4-(2,4-dimethylphenyl)-6-methyl-3-pyridazinamine as a crude product.

Methyl 2-chloro-3-oxopentanoate (7 mL) was added to a solution of the resulting 4-(2,4-dimethylphenyl)-6-methyl-3-pyridazinamine in N,N-dimethylformamide (60 mL), and the mixture was heated at 140° C. for 6 hours. Water was added thereto, which was extracted with ethyl acetate. The organic layer was washed with an aqueous saturated sodium bicarbonate solution and brine, dried over anhydrous magnesium sulfate and evaporated, to give 8-(2,4-dimethylphenyl)-2-ethyl-6-methylimidazo[1,2-b]pyridazine-3-carboxylic acid methyl ester as a crude product.

A 5N aqueous sodium hydroxide solution (20 mL) was added to a solution of the resulting 8-(2,4-dimethylphenyl)-2-ethyl-6-methylimidazo[1,2-b]pyridazin-3-carboxylic acid methyl ester in ethanol (100 mL), and the mixture was heated under reflux for 3 hours. The reaction mixture was evaporated as it was. Water was added thereto, which was extracted with ethyl acetate. 5N Hydrochloric acid (pH=1) was added to the aqueous layer, and the solution was extracted with ethyl acetate, dried over anhydrous magnesium sulfate and evaporated, to give 8-(2,4-dimethylphenyl)-2-ethyl-6-methylimidazo[1,2-b]pyridazine-3-carboxylic acid as a crude compound (2.8 g).

Triethylamine (20 mL), tert-butyl alcohol (30 mL) and diphenylphospholylazide (1.95 mL, 9.05 mmol) were added to a solution of the resulting 8-(2,4-dimethylphenyl)-2-ethyl-6-methylimidazo[1,2-b]pyridazine-3-carboxylic acid (2.8 g, 9.05 mmol) in toluene (40 mL), and the mixture was heated at 140° C. for 6 hours. Water was added thereto, which was extracted with ethyl acetate. The organic layer was washed with an aqueous saturated sodium bicarbonate solution and brine, dried over anhydrous magnesium sulfate and evaporated, to give tert-butyl N-[8-(2,4-dimethylphenyl)-2-ethyl-6-methylimidazo[1,2-b]pyridazin-3-yl]carbamate as a crude compound.

4N hydrochloric acid/ethyl acetate (30 mL) was added to a solution of the resulting tert-butyl N-[8-(2,4-dimethylphenyl)-2-ethyl-6-methylimidazo[1,2-b]pyridazin-3-yl]carbamate in ethyl acetate (10 mL), and the mixture was stirred at room temperature for 14 hours. The mixture was neutralized by adding 5N aqueous sodium hydroxide solution under ice-cooling, which was extracted with ethyl acetate. The organic layer was washed with brine, dried over anhydrous magnesium sulfate and evaporated, to give 8-(2,4-dimethylphenyl)-2-ethyl-6-methylimidazo[1,2-b]pyridazin-3-amine as a crude product.

Propionaldehyde (3.26 mL, 45.25 mmol) was added to a solution of the resulting 8-(2,4-dimethylphenyl)-2-ethyl-6-methylimidazo[1,2-b]pyridazin-3-amine (9.05 mmol) in dichloromethane (60 mL), and the mixture was stirred at room temperature for 10 minutes. Sodium triacetoxyborohydride (5.75 g, 27.15 mmol) was gradually added thereto, then acetic acid (1 mL) was further added dropwise, and the mixture was stirred for 5 hours. Water was added thereto, which was extracted with ethyl acetate. The organic layer was washed with an aqueous saturated sodium bicarbonate solution and brine, dried over anhydrous magnesium sulfate and evaporated. The resulting residue was purified by silica gel column chromatography (ethyl acetate:n-hexane=1:9) to give the title compound (8.8 mg) as a pale green oil.

$^1$H NMR (400 MHz, CDCl$_3$) δ 0.88 (t, J=7.3 Hz, 6H), 1.25 (t, J=7.6 Hz, 3H), 1.31–1.44 (m, 4H), 2.24 (s, 3H), 2.37 (s, 3H), 2.57 (s, 3H), 2.75 (q, J=7.6 Hz, 2H), 3.20 (t, J=7.4 Hz, 4H), 6.65 (s, 1H), 7.09 (d, J=7.7 Hz, 1H), 7.13 (s, 1H), 7.28 (d, J=7.7 Hz, 1H).

MS (ESI) m/z 365 MH$^+$

Example 122

N-[8-(2,4-Dimethylphenyl)-2-ethylimidazo[1,2-b]pyridazin-3-yl]-N,N-dipropylamine

A 5N aqueous sodium hydroxide solution (0.603 mL, 3.0 mmol) was added to a solution of methyl 8-(2,4-dimethylphenyl)-2-ethylimidazo[1,2-b]pyridazine-3-carboxylate (373 mg, 1.20 mmol) in ethanol (15 mL), and the mixture was heated under reflux for 1 hour. 5N hydrochloric acid (0.603 mL) was added thereto under ice-cooling and the solvent was evaporated, to give 8-(2,4-dimethylphenyl)-2-ethylimidazo[1,2-b]pyridazine-3-carboxylic acid as a crude compound.

Triethylamine (0.202 mL, 1.4 mmol), t-butyl alcohol (5 mL) and diphenylphospholylazide (0.26 mL, 1.2 mmol) were added to a solution of the crude 8-(2,4-dimethylphenyl)-2-ethylimidazo[1,2-b]pyridazine-3-carboxylic acid (1.206 mmol) in toluene (10 mL), and the mixture was heated at 90° C. for 1 hour and 110° C. for 4 hours. Water was added thereto, which was extracted with ethyl acetate. The organic layer was washed with an aqueous saturated sodium bicarbonate solution and brine, dried over anhydrous magnesium sulfate and evaporated, to give crude tert-butyl N-[8-(2,4-dimethylphenyl)-2-ethylimidazo[1,2-b]pyridazin-3-yl]carbamate.

4N hydrochloric acid/ethyl acetate (15 mL) was added to a solution of the crude tert-butyl N-[8-(2,4-dimethylphenyl)-2-ethylimidazo[1,2-b]pyridazin-3-yl]carbamate in ethyl acetate (5 mL), and the mixture was stirred at room temperature for 15 hours. The mixture was neutralized by adding a 5N aqueous sodium hydroxide solution under ice-cooling, and extracted with ethyl acetate. It was washed with brine, dried over anhydrous magnesium sulfate and evaporated, to give crude 8-(2,4-dimethylphenyl)-2-ethylimidazo[1,2-b]pyridazin-3-amine.

Propionaldehyde (0.435 mL, 6.0 mmol) and 3M sulfuric acid (2.01 mL, 6.0 mmol) were added to a solution of the crude 8-(2,4-dimethylphenyl)-2-ethylimidazo[1,2-b]pyridazin-3-amine (1.2 mmol) in tetrahydrofuran (10 mL)

under ice-cooling, and sodium borohydride (182 mg, 4.8 mmol) was gradually added at the same temperature. After heating under stirring for 30 minutes, it was stirred at room temperature for 20 minutes, and neutralized by adding a 5N aqueous sodium hydroxide solution under ice-cooling. Water was added thereto, which was extracted with ethyl acetate, washed with brine, dried over anhydrous magnesium sulfate and evaporated. The residue was purified by silica gel column chromatography (ethyl acetate:n-hexane=1:15) to give the title compound (42 mg, 10% (4 steps)) as yellow crystals.

$^1$H NMR (400 MHz, CDCl$_3$) δ 0.88 (t, J=7.4 Hz, 6H), 1.28 (t, J=7.5 Hz, 3H), 1.32–1.46 (m, 4H), 2.25 (s, 3H), 2.38 (s, 3H), 2.79 (q, J=7.5 Hz, 2H), 3.20 (t, J=7.5 Hz, 4H), 6.79 (br s, 1H), 7.10 (d, J=7.9 Hz, 1H), 7.15 (s, 1H), 7.32 (d, J=7.9 Hz, 1H), 8.26 (d, J=4.4 Hz, 1H).

Hereinafter, compounds of Examples 123 to 126 were synthesized in the same manner as that of Example 122.

Example 123

N-[8-(2,4-Dimethoxyphenyl)-2-ethylimidazo[1,2-b]pyridazin-3-yl]-N,N-dipropylamine Yellow Crystals $^1$H NMR (400 MHz, CDCl$_3$) δ 0.87 (t, J=7.3 Hz, 6H), 1.31 (t, J=7.6 Hz, 3H), 1.32–1.44 (m, 4H), 2.80 (q, J=7.5 Hz, 2H), 3.19 (t, J=7.5 Hz, 4H), 3.83 (s, 3H), 3.87 (s, 3H), 6.59 (d, J=2.4 Hz, 1H), 6.66 (dd, J=2.4, 8.6 Hz, 1H), 7.16 (d, J=4.8 Hz, 1H), 8.01 (d, J=7.3 Hz, 1H), 8.23 (d, J=5.1 Hz, 1H).

MS (ESI) m/z 383 MH$^+$

Example 124

N-[8-(2,4-Dimethoxyphenyl)-2-ethylimidazo[1,2-b]pyridazin-3-yl]-N-isobutylamine

Orange Crystals $^1$H NMR (400 MHz, CDCl$_3$) δ 1.01 (d, J=6.8 Hz, 6H), 1.34 (t, J=7.6 Hz, 3H), 1.75–1.88 (m, 1H), 2.84–2.95 (m, 2H), 3.07 (d, J=6.8 Hz, 2H), 3.83 (s, 3H), 3.87 (s, 3H), 6.59 (d, J=2.2 Hz, 1H), 6.65 (dd, J=2.4, 8.6 Hz, 1H), 7.07 (d, J=4.6 Hz, 1H), 7.94 (br s, 1H), 8.24 (d, J=3.7 Hz, 1H).

Example 125

N-Cyclopropylmethyl-N-[8-(2,4-dimethoxyphenyl)-2-ethylimidazo[1,2-b]pyridazin-3-yl)-N-isobutylamine Yellow Crystals $^1$H NMR (400 MHz, CDCl$_3$) δ 0.02–0.06 (m, 2H), 0.34–0.44 (m, 2H), 0.84–1.00 (m, 1H), 1.02 (d, J=6.6 Hz, 6H), 1.43 (t, J=7.6 Hz, 3H), 1.63–1.76 (m, 1H), 2.95 (q, J=7.5 Hz, 2H), 3.17 (t, J=7.7 Hz, 4H), 3.93 (s, 3H), 3.97 (s, 3H), 6.69 (d, J=2.4 Hz, 1H), 6.76 (dd, J=2.4, 8.6 Hz, 1H), 7.26 (d, J=4.8 Hz, 1H), 8.12 (d, J=8.2 Hz, 1H), 8.32 (d, J=4.8 Hz, 1H).

MS (ESI) m/z 409 MH$^+$

Example 126

N-[2-Ethyl-8-(4-methoxy-2-methylphenyl)imidazo[1,2-b]pyridazin-3-yl]-N, N-dipropylamine Yellow Crystals $^1$H NMR (400 MHz, CDCl$_3$) δ 0.88 (t, J=7.4 Hz, 6H), 1.28 (t, J=7.6 Hz, 3H), 1.33–1.45 (m, 4H), 2.29 (s, 3H), 2.79 (q, J=7.5 Hz, 2H), 3.20 (t, J=7.5 Hz, 4H), 3.85 (s, 3H), 6.79 (br s, 1H), 6.82–6.90 (m, 2H), 7.39 (d, J=8.2 Hz, 1H), 8.26 (d, J=4.2 Hz, 1H).

MS (ESI) m/z 367 MH$^+$

Example 127

N-[8-(2,4-Dichlorophenyl)-6-methyl-2-(methylsulfanyl)imidazo[1,2-a]pyridin-3-yl]-N,N-dipropylamine N-[8-Bromo-6-methyl-2-(methylsulfanyl)imidazo[1,2-a]pyridin-3-yl]-N,N-dipropylamine (50 mg) was dissolved in a mixed solvent of 1,2-dimethoxyethane (6 mL) and water (1 mL). 2,4-Dichlorobenzeneboronic acid (53 mg), barium hydroxide octahydrate (88 mg) and tetrakistriphenylphosphine palladium complex (16 mg) were added thereto, and the mixture was heated under reflux for 2 hours under nitrogen atmosphere. After being allowed to cool, the reaction mixture was purified by silica gel column chromatography (ethyl acetate:n-hexane=1:9) to give N-[8-(2,4-dichlorophenyl)-6-methyl-2-(methylsulfanyl)imidazo[1,2-a]pyridin-3-yl]-N,N-dipropylamine (43 mg) as a pale yellow oil.

$^1$H NMR (400 MHz, CDCl$_3$) δ 0.88 (t, J=7.2 Hz, 6H), 1.38–1.44 (m, 4H), 2.36 (s, 3H), 2.50 (s, 3H), 3.02–3.18 (m, 4H), 6.99 (d, J=2.0 Hz, 1H), 7.32 (dd, J=2.4, 8.8 Hz, 1H), 7.51 (d, J=2.0 Hz, 1H), 7.59 (d, J=8.4 Hz, 1H), 7.87 (d, J=1.6 Hz, 1H).

Hereinafter, according to the process of Example 127, compounds of Examples of 128 and 129 were synthesized.

Example 128

N3,N3-Dipropyl-8-(2,4-dichlorophenyl)-2-(methylsulfanyl)imidazo[1,2-a]pyrazin-3-amine Colorless Oil $^1$HNMR (400 MHz, CDCl$_3$) δ0.89 (t, J=7.6 Hz, 6H), 1.35–1.46 (m, 4H), 2.59 (s, 3H), 3.08–3.12 (m, 4H), 7.38 (ddd, J=8.4, 2.0, 0.4 Hz, 1H), 7.56 (d, J=2.0 Hz, 1H), 7.73 (dd, J=8.4, 0.4 Hz, 1H), 7.94 (d, J=4.4 Hz, 1H), 8.01 (d, J=4.4 Hz, 1H).

Example 129

N3-Isobutyl-N-3-propyl-8-(2,4-dichlorophenyl)-2-(methylsulfanyl)imidazo[1,2-a]pyrazin-3-amine Colorless Oil $^1$H NMR (400 MHz, CDCl$_3$) δ 0.88 (t, J=7.6 Hz, 6H), 0.93 (d, J=6.4 Hz, 6H), 1.37–1.47 (m, 2H), 1.54–1.62 (m, 1H), 2.59 (s, 3H), 2.98 (d, J=7.2 Hz, 2H), 3.02–3.08 (m, 2H), 7.39 (dd, J=8.4, 2.0 Hz, 1H), 7.56 (d, J=2.0 Hz, 1H), 7.69 (d, J=8.4 Hz, 1H), 7.95 (d, J=4.4 Hz, 1H), 8.02 (d, J=4.4 Hz, 1H).

Hereinafter, according to the process of Example 4, compounds of Examples of 130 to 187 were synthesized.

Example 130

N-[8-(2,4-Dichloro-6-methylphenyl)-2-ethylimidazo[1,2-a]pyrazin-3-yl]-N,N-dipropylamine Pale Yellow Oil $^1$H NMR (400 MHz, CDCl$_3$) δ 0.90 (t, J=7.6 Hz, 6H), 1.25 (t, J=7.6 Hz, 3H), 1.38–1.48 (m, 4H), 2.09 (s, 3H), 2.78 (q, J=7.6 Hz, 2H), 3.07 (dd, J=6.4, 8.0 Hz, 4H), 7.64–7.67 (m, 1H), 7.80 (br s, 1H), 7.83 (d, J=8.0 Hz, 1H), 7.94–7.97 (m, 1H), 8.08 (d, J=4.4 Hz, 1H).

Example 131

N-8-[2-Chloro-4-(trifluoromethyl)phenyl]-2-ethylimidazo[1,2-a]pyrazin-3-yl-N,N-dipropylamine Pale Yellow Oil $^1$H NMR (400 MHz, CDCl$_3$) δ 0.90 (t, J=7.2 Hz, 6H), 1.29 (t, J=7.6 Hz, 3H), 1.38–1.48 (m, 4H), 2.80 (q, J=7.6 Hz, 2H), 3.08 (dd, J=6.4, 8.0 Hz, 4H), 7.64–7.67 (m, 1H), 7.79–7.80 (m, 1H), 7.81–7.84 (m, 1H), 7.94 (d, J=4.4 Hz, 1H), 8.08 (d, J=4.4 Hz, 1H).

Example 132

N-[8-(2-Bromo-4-isopropylphenyl)-2-ethylimidazo[1,2-a]pyrazin-3-yl]-N,N-dipropylamine Yellow Oil $^1$H NMR (400 MHz, CDCl$_3$) δ 0.90 (t, J=7.6 Hz, 6H), 1.28 (d, J=6.8 Hz, 6H), 1.29 (t, J=7.6 Hz, 3H), 1.38–1.48 (m, 4H), 2.80 (q, J=7.6 Hz, 2H), 2.94 (hept., J=6.8 Hz, 1H), 3.07 (dd, J=6.4, 8.0 Hz, 4H), 7.28 (d, J=1.6, 8.4 Hz, 1H), 7.58 (d, J=8.4 Hz, 1H), 7.91 (d, J=4.4 Hz, 1H), 8.02 (d, J=4.4 Hz, 1H).

Example 133

N-[8-(2-Bromo-6-methoxy-4-methylphenyl)-2-ethylimidazo[1,2-a]pyrazin-3-yl]-N,N-dipropylamine Pale Yellow Oil $^1$H NMR (400 MHz, CDCl$_3$) δ 0.89 (t, J=7.6 Hz, 6H), 1.24 (t, J=7.6 Hz, 3H), 1.38–1.48 (m, 4H), 2.38 (s, 3H), 2.77 (q, J=7.6 Hz, 2H), 3.07 (dd, J=6.4, 8.0 Hz, 4H), 3.70 (s, 3H), 6.78 (s, 1H), 7.12 (s, 1H), 7.90 (d, J=4.8 Hz, 1H), 8.02 (d, J=4.8 Hz, 1H).

Example 134

N-[8-(2-Bromo-4,6-dimethylphenyl)-2-ethylimidazo[1,2-a]pyrazin-3-yl]-N,N-dipropylamine Pale Yellow Oil $^1$H NMR (400 MHz, CDCl$_3$) δ 0.90 (t, J=7.2 Hz, 6H), 1.24 (t, J=7.6 Hz, 3H), 1.37–1.47 (m, 4H), 2.08 (s, 3H), 2.34 (s, 3H), 2.77 (q, J=7.6 Hz, 2H), 3.07 (dd, J=6.4, 8.0 Hz, 4H), 7.05 (s, 1H), 7.34 (s, 1H), 7.91 (d, J=4.4 Hz, 1H), 8.04 (d, J=4.4 Hz, 1H).

Example 135

N-[8-(2,4-Dimethylphenyl)-2-ethylimidazo[1,2-a]pyrazin-3-yl]-N,N-dipropylamine

Pale Yellow Oil $^1$H NMR (400 MHz, CDCl$_3$) δ 0.89 (t, J=7.2 Hz, 6H), 1.29 (t, J=7.6 Hz, 3H), 1.37–1.47 (m, 4H), 2.35 (s, 3H), 2.37 (s, 3H), 2.77 (q, J=7.6 Hz, 2H), 3.07 (dd, J=6.4, 8.0 Hz, 4H), 7.09–7.14 (m, 2H), 7.53 (d, J=7.6 Hz, 1H), 7.87 (d, J=4.4 Hz, 1H), 7.98 (d, J=4.4 Hz, 1H).

Example 136

N-[8-(2-Chloro-4-methylphenyl)-2-ethylimidazo[1,2-a]pyrazin-3-yl]-N,N-dipropylamine Yellow Oil $^1$H NMR (400 MHz, CDCl$_3$) δ 0.90 (t, J=7.6 Hz, 6H), 1.30 (t, J=7.6 Hz, 3H), 1.37–1.47 (m, 4H), 2.34 (s, 3H), 2.79 (q, J=7.6 Hz, 2H), 3.07 (dd, J=6.0, 7.2 Hz, 4H), 7.29 (dd, J=2.0, 8.0 Hz, 1H), 7.30–7.32 (m, 1H), 7.60 (d, J=8.0 Hz, 1H), 7.90 (d, J=4.8 Hz, 1H), 8.02 (d, J=4.8 Hz, 1H).

Example 137

N-[8-(2-Chloro-6-methoxy-4-methylphenyl)-2-ethylimidazo[1,2-a]pyrazin-3-yl]-N,N-dipropylamine Pale Yellow Oil $^1$H NMR (400 MHz, CDCl$_3$) δ 0.89 (t, J=7.6 Hz, 6H), 1.24 (t, J=7.2 Hz, 3H), 1.38–1.48 (m, 4H), 2.38 (s, 3H), 2.77 (q, J=7.6 Hz, 2H), 3.06 (t, J=7.6 Hz, 4H), 3.71 (s, 3H), 6.74 (s, 1H), 6.94 (s, 1H), 7.91 (d, J=4.4 Hz, 1H), 8.01 (d, J=4.4 Hz, 1H).

Example 138

N-[8-(2-Bromo-4-methylphenyl)-2-ethylimidazo[1,2-a]pyrazin-3-yl]-N,N-dipropylamine Pale Yellow Oil $^1$H NMR (400 MHz, CDCl$_3$) δ 0.90 (t, J=7.2 Hz, 6H), 1.29 (t, J=7.2 Hz, 3H), 1.38–1.48 (m, 4H), 2.40 (s, 3H), 2.79 (q, J=7.2 Hz, 2H), 3.07 (t, J=7.6 Hz, 4H), 7.22–7.25 (m, 1H), 7.54–7.56 (m, 2H)), 7.92 (d, J=4.4 Hz, 1H), 8.03 (d, J=4.4 Hz, 1H).

Example 139

N-[8-(2-Chloro-4,6-dimethylphenyl)-2-ethylimidazo[1,2-a]pyrazin-3-yl]-N,N-dipropylamine Colorless Oil $^1$H NMR (400 MHz, CDCl$_3$) δ 0.90 (t, J=7.6 Hz, 6H), 1.25 (t, J=7.6 Hz, 3H), 1.37–1.47 (m, 4H), 2.07 (s, 3H), 2.34 (s, 3H), 2.78 (q, J=7.6 Hz, 2H), 3.08 (t, J=7.6 Hz, 4H), 7.02 (s, 1H), 7.16 (s, 1H), 7.92 (d, J=4.8 Hz, 1H), 8.04 (d, J=4.8 Hz, 1H).

Example 140

N-Cyclopropylmethyl-N-[8-(2,4-dichlorophenyl)-2-ethylimidazo[1,2-a]pyrazin-3-yl]-N-(2-methoxyethyl)amine hydrochloride Yellow Oil $^1$H NMR (400 MHz, CDCl$_3$) δ 0.00 (br s, 2H), 0.35 (d, J=8.0 Hz, 2H), 0.76–0.90 (m, 1H), 1.30 (t, J=7.6 Hz, 3H), 2.79 (q, J=7.6 Hz, 2H), 3.04 (d, J=7.2 Hz, 2H), 3.26 (s, 3H), 3.30–3.42 (m, 4H), 7.39 (d, J=8.4 Hz, 1H), 7.55 (s, 1H), 7.66 (d, J=8.4 Hz, 1H), 7.93 (d, J=4.4 Hz, 1H), 8.19 (d, J=4.4 Hz, 1H).

Example 141

N-[8-(2,4-Dichlorophenyl)-2-ethylimidazo[1,2-a]pyrazin-3-yl]-N-(2-methoxyethyl)amine MS (FAB) m/z 365 MH$^+$

Example 142

N-[8-(2,4-Dichlorophenyl)-2-ethylimidazo[1,2-a]pyrazin-3-yl]-N-(2-methoxyethyl)-N-propylamine MS (FAB) m/z 407 MH$^+$

Example 143

N-Butyl-N-[8-(2,4-dichlorophenyl)-2-ethylimidazo[1,2-a]pyrazin-3-yl]-N-(2-methoxyethyl)amine MS (FAB) m/z 421 MH$^+$

Example 144

N-[8-(2,4-Dichlorophenyl)-2-ethylimidazo[1,2-a]pyrazin-3-yl]-N-(2-methoxyethyl)-N-pentylamine MS (FAB) m/z 434 MH$^+$

Example 145

N-[8-(2,4-Dichlorophenyl)-2-ethylimidazo[1,2-a]pyrazin-3-yl]-N-isobutyl-N-(2-methoxyethyl)amine MS (FAB) m/z 421 MH$^+$

Example 146

N-Cyclopropylmethyl-N-[8-(2,4-dichlorophenyl)-2-ethylimidazo[1,2-a]pyrazin-3-yl]-N-(2-methylbutyl)amine Yellow Oil $^1$H NMR (400 MHz, CDCl$_3$) δ 0.00 (br s, 2H), 0.36 (br s, 2H) 0.78–0.85 (m, 1H), 0.90 (t, J=7.6 Hz, 3H), 0.97 (d, J=7.8 Hz, 3H), 1.10–1.21 (m, 1H), 1.33 (t, J=7.6 Hz, 3H), 1.401–151 (m, 1H), 1.51–1.60 (m, 1H), 2.84 (q, J=7.6 Hz, 2H), 2.88–2.89 (m, 3H), 3.17 (dd, J=6.4, 6.8 Hz, 1H), 7.40 (d, J=8.0 Hz, 1H), 7.55 (s, 1H), 7.67 (d, J=8.4 Hz, 1H), 7.96 (d, J=4.4 Hz, 1H), 8.18 (d, J=4.4 Hz, 1H).

Example 147

N-[8-(2,4-Dichlorophenyl)-2-ethylimidazo[1,2-a]pyrazin-3-yl]-N-isobutyl-N-(2-methylbutyl)amine Yellow Oil $^1$H NMR (400 MHz, CDCl$_3$) δ 0.86 (t, J=7.2 Hz, 3H), 0.94 (d, J=6.8 Hz, 6H), 0.96 (d, J=6.8 Hz, 3H), 1.04–1.16 (m, 1H), 1.30–1.44 (m, 1H), 1.46–1.64 (m, 2H), 2.81 (q, J=7.6 Hz, 2H), 2.84–2.96 (m, 3H), 3.04 (dd, J=6.0, 6.0 Hz, 1H), 7.39 (d, J=8.4 Hz, 1H), 7.56 (s, 1H), 7.67 (d, J=8.0 Hz, 1H), 7.93 (d, J=4.4 Hz, 1H), 8.10 (d, J=4.4 Hz, 1H).

Example 148

N-Cyclobutylmethyl-N-cyclopropylmethyl-N-[8-(2,4-dichlorophenyl)-2-ethylimidazo[1,2-a]pyrazin-3-yl]amine Yellow Oil $^1$H NMR (400 MHz, CDCl$_3$) δ 0.00 (br s, 2H), 0.36 (br s, 2H), 0.72–0.82 (m, 1H), 1.30 (t, J=7.6 Hz, 3H), 1.56–1.72 (m, 2H), 1.74–1.96 (m, 4H), 2.24–2.34 (m, 1H), 2.79 (q, J=7.6 Hz, 2H), 2.94 (d, J=7.2 Hz, 2H), 3.20 (d, J=7.6 Hz, 2H), 7.39 (d, J=8.0 Hz, 1H), 7.55 (s, 1H), 7.66 (d, J=8.0 Hz, 1H), 7.92 (d, J=4.4 Hz, 1H), 8.09 (d, J=4.4 Hz, 1H).

Example 149

N-Cyclobutylmethyl-N-[8-(2,4-dichlorophenyl)-2-ethylimidazo[1,2-a]pyrazin-3-yl]-N-propylamine Yellow Oil $^1$H NMR (400 MHz, CDCl$_3$) δ 0.90 (t, J=7.6 Hz, 3H), 1.30 (t, J=7.2 Hz, 3H), 1.42 (q, J=7.2 Hz, 2H), 1.54–1.66 (m, 2H), 1.72–1.94 (m, 4H), 2.22–2.34 (m, 1H), 2.79 (q, J=7.6 Hz, 2H), 3.06 (t, J=7.4 Hz, 2H), 3.14 (d, J=7.2 Hz, 2H), 7.39 (d, J=8.4 Hz, 1H), 7.55 (s, 1H), 7.66 (d, J=8.4 Hz, 1H), 7.92 (d, J=4.4 Hz, 1H), 8.02 (d, J=4.4 Hz, 1H).

Example 150

N-Cyclobutylmethyl-N-[8-(2,4-dichlorophenyl)-2-ethylimidazo[1,2-a]pyrazin-3-yl]-N-isobutylamine Yellow Oil $^1$H NMR (400 MHz, CDCl$_3$) δ 0.90 (t, J=7.6 Hz, 3H), 1.30 (t, J=7.6 Hz, 3H), 1.38–1.48 (m, 2H), 1.50–1.78 (m, 4H), 2.80 (q, J=7.6 Hz, 2H), 3.09 (dd, J=7.6, 7.6 Hz, 2H), 3.17 (t, J=7.6 Hz, 2H), 4.37 (t, J=6.0 Hz, 1H), 4.48 (t, J=6.0 Hz, 1H), 7.39 (d, J=8.4 Hz, 1H), 7.55 (s, 1H), 7.66 (d, J=8.4 Hz, 1H), 7.93 (d, J=4.4 Hz, 1H), 8.02 (d, J=4.4 Hz, 1H).

Example 151

N-[8-(2,4-Dichlorophenyl)-2-ethylimidazo[1,2-a]pyrazin-3-yl]-N-(4-fluorobutyl)-N-propylamine Yellow Oil $^1$H NMR (400 MHz, CDCl$_3$) δ 0.90 (t, J=7.6 Hz, 3H), 1.30 (t, J=7.6 Hz, 3H), 1.38–1.48 (m, 2H), 1.50–1.78 (m, 4H), 2.80 (q, J=7.6 Hz, 2H), 3.09 (dd, J=7.6, 7.6 Hz, 2H), 3.17 (t, J=7.6 Hz, 2H), 4.37 (t, J=6.0 Hz, 1H), 4.48 (t, J=6.0 Hz, 1H), 7.39 (d, J=8.4 Hz, 1H), 7.55 (s, 1H), 7.66 (d, J=8.4 Hz, 1H), 7.93 (d, J=4.4 Hz, 1H), 8.02 (d, J=4.4 Hz, 1H).

Example 152

N-Cyclopropylmethyl-N-[8-(2,4-dichlorophenyl)-2-ethylimidazo[1,2-a]pyrazin-3-yl]-N-(4-fluorobutyl)amine Yellow Oil $^1$H NMR (400 MHz, CDCl$_3$) δ 0.00 (br s, 2H), 0.38 (d, J=8.0 Hz, 2H), 0.74–0.84 (m, 1H), 1.31 (t, J=7.6 Hz, 3H), 1.50–1.60 (m, 2H), 1.64–1.82 (m, 2H), 2.81 (q, J=7.6 Hz, 2H), 2.97 (d, J=6.8 Hz, 2H), 3.26 (t, J=7.6 Hz, 2H), 4.38 (t, J=5.6 Hz, 1H), 4.50 (t, J=5.6 Hz, 1H), 7.40 (d, J=8.4 Hz, 1H), 7.57 (s, 1H), 7.67 (d, J=8.4 Hz, 1H), 7.94 (d, J=4.4 Hz, 1H), 8.11 (d, J=4.4 Hz, 1H).

Example 153

N-[8-(2,4-Dichlorophenyl)-2-ethylimidazo[1,2-a]pyrazin-3-yl]-N-(4-fluorobutyl)-N-isobutylamine Yellow Oil $^1$H NMR (400 MHz, CDCl$_3$) δ 0.95 (t, J=6.8 Hz, 6H), 1.30 (t, J=7.6 Hz, 3H), 1.50–1.76 (m, 5H), 2.80 (q, J=7.6 Hz, 2H), 2.94 (d, J=7.2 Hz, 2H), 3.13 (dd, J=8.0, 8.0 Hz, 2H), 4.367 (t, J=6.0 Hz, 1H), 4.48 (t, J=6.0 Hz, 1H), 7.38 (d, J=8.4 Hz, 1H), 7.55 (s, 1H), 7.66 (d, J=8.4 Hz, 1H), 7.94 (d, J=4.4 Hz, 1H), 8.05 (d, J=4.4 Hz, 1H).

Example 154

N,N-Dicyclopropylmethyl-N-[8-(2,4-dichlorophenyl)-2-ethylimidazo[1,2-a]pyrazin-3-yl]amine Yellow Oil $^1$H NMR (400 MHz, CDCl$_3$) δ 0.03 (br s, 4H), 0.36 (d, J=7.6 Hz, 4H), 0.74–0.86 (m, 2H), 1.30 (t, J=7.6 Hz, 3H), 2.80 (q, J=7.6 Hz, 2H), 3.03 (d, J=6.4 Hz, 4H), 7.38 (t, J=8.4 Hz, 1H), 7.53 (s, 1H), 7.66 (d, J=8.4 Hz, 1H), 7.93 (d, J=4.4 Hz, 1H), 8.20 (d, J=4.4 Hz, 1H).

Example 155

N1-[8-(2,4-Dichlorophenyl)-2-ethylimidazo[1,2-a]pyrazin-3-yl]-N1-(3-fluoropropyl)butaneamide Yellow Oil $^1$H NMR (400 MHz, CDCl$_3$) δ 0.83 (t, J=7.2 Hz, 3H), 1.33 (t, J=7.6 Hz, 3H), 1.50–2.08 (m, 6H), 2.74 (q, J=7.6 Hz, 2H), 3.68–3.98 (m, 2H), 4.48 (t, J=5.7 Hz, 1H), 4.60 (t, J=5.7 Hz, 1H), 7.44 (d, J=8.4 Hz, 1H), 7.59 (s, 1H), 7.71 (d, J=8.4 Hz, 1H), 7.79 (d, J=4.4 Hz, 1H), 8.09 (d, J=4.8 Hz, 1H).

MS (ESI) m/z 437 MH$^+$

Example 156

3-[[8-(2,4-Dichlorophenyl)-2-ethylimidazo[1,2-a]pyrazin-3-yl](propyl)amino]propanenitrile Yellow Oil $^1$H NMR (400 MHz, CDCl$_3$) δ 0.94 (t, J=7.6 Hz, 3H), 1.31 (t, J=7.6 Hz, 3H), 1.48 (q, J=7.2 Hz, 2H), 2.46 (br s, 2H), 2.79 (q, J=7.6 Hz, 2H), 3.14 (t, J=7.6 Hz, 2H), 3.47 (t, J=6.4 Hz, 2H), 7.40 (d, J=8.4 Hz, 1H), 7.56 (s, 1H), 7.65 (d, J=8.4 Hz, 1H), 8.01 (d, J=4.4 Hz, 1H), 8.22 (d, J=4.8 Hz, 1H).

Example 157

3-(Cyclopropylmethyl)[8-(2,4-dichlorophenyl)-2-ethylimidazo[1,2-a]pyrazin-3-yl]aminopropanenitrile Yellow Oil $^1$H NMR (400 MHz, CDCl$_3$) δ 0.00 (br s, 2H), 0.40 (br s, 2H) 0.78–0.88 (m, 1H), 1.31 (t, J=7.6 Hz, 3H), 2.40–2.56 (m, 1H) 2.80 (q, J=7.6 Hz, 2H), 2.96–3.04 (m, 2H), 3.46–3.58 (m, 2H) 7.39 (d, J=8.0 Hz, 1H), 7.56 (s, 1H), 7.65 (d, J=8.4 Hz, 1H), 8.00 (d, J=4.4 Hz, 1H), 8.28 (d, J=4.4 Hz, 1H).

Example 158

N-Butyl-N-cyclobutylmethyl-N-[8-(2,4-dichlorophenyl)-2-ethylimidazo[1,2-a]pyrazin-3-yl]amine Yellow Oil $^1$H NMR (400 MHz, CDCl$_3$) δ 0.88 (t, J=7.2 Hz, 3H), 1.30 (t, J=7.6 Hz, 3H), 1.32–1.20 (m, 4H), 1.54–1.66 (m, 2H), 1.74–1.92 (m, 4H), 2.22–2.32 (m, 1H), 2.79 (q, J=7.6 Hz, 2H), 3.09 (t, J=7.6 Hz, 2H), 3.13 (d, J=7.2 Hz, 2H), 7.39 (d, J=8.4 Hz, 1H), 7.55 (s, 1H), 7.66 (d, J=8.4 Hz, 1H), 7.92 (d, J=4.4 Hz, 1H), 8.01 (d, J=4.4 Hz, 1H).

Example 159

N-Butyl-N-cyclopropylmethyl-N-[8-(2,4-dichlorophenyl)-2-ethylimidazo[1,2-a]pyrazin-3-yl]amine Yellow Oil $^1$H NMR (400 MHz, CDCl$_3$) δ 0.01 (br s, 2H), 0.36 (d, J=8.0 Hz, 2H), 0.76–0.88 (m, 1H), 0.89 (t, J=7.2 Hz, 3H), 1.31 (t, J=7.6 Hz, 3H), 1.32–1.44 (m, 4H), 2.81 (q, J=7.6 Hz, 2H), 2.96 (d, J=7.2 Hz, 2H), 3.20 (t, J=7.2 Hz, 2H), 7.40 (d, J=8.0 Hz, 1H), 7.56 (s, 1H), 7.68 (d, J=8.4 Hz, 1H), 7.94 (d, J=4.8 Hz, 1H), 8.12 (d, J=4.4 Hz, 1H).

Example 160

N-Butyl-N-[8-(2-chloro-6-methoxy-4-methylphenyl)-2-ethylimidazo[1,2-a]pyrazin-3-yl]-N-isobutylamine Yellow Oil $^1$H NMR (400 MHz, CDCl$_3$) δ 0.87 (t, J=7.2 Hz, 3H), 0.94 (d, J=6.8 Hz, 6H), 1.25 (t, J=7.6 Hz, 3H), 1.24–1.46 (m, 4H), 1.56–1.70 (m, 1H), 2.39 (s, 3H), 2.78 (q, J=7.6 Hz, 2H), 2.92 (d, J=7.2 Hz, 2H), 3.06 (t, J=7.2 Hz, 2H), 3.71 (s, 3H), 6.75 (s, 1H), 6.95 (s, 1H), 7.92 (d, J=4.8 Hz, 1H), 8.04 (d, J=4.4 Hz, 1H).

MS (ESI) m/z 429 MH$^+$

Example 161

N-[8-(2-Chloro-6-methoxy-4-methylphenyl)-2-ethylimidazo[1,2-a]pyrazin-3-yl]-N,N-dicyclopropylmethylamine Yellow Oil $^1$H NMR (400 MHz, CDCl$_3$) δ 0.00 (br s, 4H), 0.36 (br s, 4H) 0.74–0.88 (m, 2H), 1.26 (t, J=7.6 Hz, 3H), 2.39 (s, 3H), 2.77 (q, J=7.6 Hz, 2H), 2.94–3.10 (m, 4H), 3.71 (s, 3H), 6.74 (s, 1H), 6.95 (s, 1H), 7.92 (d, J=4.4 Hz, 1H), 8.15 (d, J=4.4 Hz, 1H).

MS (ESI) m/z 425 MH$^+$

Example 162

N,N-Dicyclopropylmethyl-N-[8-(2,6-dimethoxy-4-methylphenyl)-2-ethylimidazo[1,2-a]pyrazin-3-yl]amine Yellow Oil
MS (ESI) m/z 421 MH$^+$

Example 163

N-[8-(2-Chloro-4-methoxyphenyl)-8-ethylimidazo[1,2-a]pyrazin-3-yl]-N,N-dichloropropylmethylamine Yellow Oil
$^1$H NMR (400 MHz, CDCl$_3$) δ 0.03 (br s, 4H), 0.37 (d, J=7.6 Hz, 4H), 0.76–0.88 (m, 2H), 1.31 (m, J=7.6 Hz, 3H), 2.81 (q, J=8.0 Hz, 2H), 3.03 (d, J=6.8 Hz, 4H), 3.86 (s, 3H), 6.95 (d, J=8.4 Hz, 1H), 7.07 (s, 1H), 7.67 (d, J=8.8 Hz, 1H), 7.91 (d, J=4.4 Hz, 1H), 8.16 (d, J=4.4 Hz, 1H).
MS (ESI) m/z 411 MH$^+$

Example 164

N,N-Dicyclopropylmethyl-N-[2-ethyl-3-(2-methoxy-4,6-dimethylphenyl)imidazo[1,2-a]pyrazin-3-yl]amine Yellow Oil
MS (ESI) m/z 405 MH$^+$

Example 165

N-[8-(2-Chloro-6-methoxy-4-methylphenyl)-2-ethylimidazo[1,2-a]pyrazin-3-yl]-N-cyclopropylmethyl-N-(2-methylbutyl)amine
Yellow Oil
MS (ESI) m/z 441 MH$^+$

Example 166

N-Cyclopropylmethyl-N-[8-(2,6-dimethoxy-4-methylphenyl)-2-ethylimidazo[1,2-a]pyrazin-3-yl]-N-(2-methylbutyl)amine Yellow Oil
$^1$H NMR (400 MHZ, CDCl$_3$) δ 0.00 (br s, 2H), 0.33 (br s, 2H), 0.74–0.86 (m, 1H), 0.87 (t, J=7.6 Hz, 3H), 0.93 (d, J=6.8 Hz, 3H), 1.06–1.18 (m, 1H), 1.25 (t, J=7.6 Hz, 3H), 1.381–1.60 (m, 2H), 2.41 (s, 3H), 2.77 (q, J=7.6 Hz, 2H), 2.82–3.18 (m, 4H), 3.69 (s, 6H), 6.50 (s, 2H), 7.90 (d, J=4.8 Hz, 1H), 7.55 (s, 1H), 7.66 (d, J=8.0 Hz, 1H), 7.92 (d, J=4.4 Hz, 1H), 8.05 (d, J=4.4 Hz, 1H).
MS (ESI) m/z 437 MH$^+$

Example 167

N-[8-(2-Chloro-4-methoxyphenyl)-2-ethylimidazo[1,2-a]pyrazin-3-yl]-N-cyclopropylmethyl-N-(2-methylbutyl)amine Yellow Oil
$^1$H NMR (400 MHz, CDCl$_3$) δ 0.00 (br s, 2H), 0.35 (br s, 2H), 0.74–0.84 (m, 1H), 0.87 (t, J=7.6 Hz, 3H), 0.93 (d, J=7.4 Hz, 3H), 1.08–1.18 (m, 1H), 1.31 (t, J=7.6 Hz, 3H), 1.36–1.60 (m, 2H), 2.81 (q, J=7.6 Hz, 2H), 2.84–3.18 (m, 4H), 3.86 (s, 3H), 6.94 (d, J=8.8 Hz, 1H), 7.07 (s, 1H), 7.67 (d, J=8.8 Hz, 1H), 7.91 (d, J=4.4 Hz, 1H), 8.10 (d, J=4.8 Hz, 1H).
MS (ESI) m/z 427 MH$^+$

Example 168

N-Cyclopropylmethyl-N-[2-ethyl-8-(2-methoxy-4,6-dimethylphenyl)imidazo[1,2-a]pyrazin-3-yl]-N-(2-methylbutyl)amine Yellow Oil
$^1$H NMR (400 MHz, CDCl$_3$) δ −0.01 (br s, 2H), 0.33 (br s, 2H), 0.74–0.84 (m, 1H), 0.87 (t, J=7.2 Hz, 3H), 0.94 (d, J=6.4 Hz, 3H), 1.06–1.16 (m, 1H), 1.25 (t, J=7.6 Hz, 3H), 1.40–1.60 (m, 2H), 2.01 (s, 1H), 2.37 (s, 3H), 2.77 (q, J=7.2 Hz, 2H), 2.80–3.18 (m, 4H), 3.69 (s, 3H), 6.68 (s, 1H), 6.74 (s, 1H), 7.90 (d, J=4.4 Hz, 1H), 8.07 (d, J=4.8 Hz, 1H).
MS (ESI) m/z 421 MH$^+$

Example 169

N-[8-(2-Chloro-6-methoxy-4-methylphenyl)-2-ethylimidazo[1,2-a]pyrazin-3-yl]-N-cyclopropylmethyl-N-propylamine Yellow Oil
$^1$H NMR (400 MHz, CDCl$_3$) δ −0.01 (br s, 2H), 0.34 (d, J=7.8 Hz, 2H), 0.74–0.84 (m, 1H), 0.92 (t, J=7.2 Hz, 3H), 1.25 (t, J=7.6 Hz, 3H), 1.40–1.50 (m, 2H), 3.39 (s, 3H), 2.77 (q, J=7.2 Hz, 2H), 2.86–3.02 (m, 2H), 3.15 (dd, J=7.6, 7.6 Hz, 2H), 3.71 (s, 3H), 6.74 (s, 1H), 6.94 (s, 1H), 7.91 (d, J=4.4 Hz, 1H), 8.09 (d, J=4.4 Hz, 1H).
MS (ESI) m/z 413 MH$^+$

Example 170

N-Cyclopropylmethyl-N-[8-(2,6-dimethoxy-4-methylphenyl)-2-ethylimidazo[1,2-a]pyrazin-3-yl]-N-propylamine Yellow Oil
$^1$H NMR (400 MHz, CDCl$_3$) δ 0.00 (br s, 2H), 0.36 (br s, 2H), 0.78–0.88 (m, 1H), 0.92 (t, J=7.2 Hz, 3H), 1.25 (t, J=7.6 Hz, 3H), 1.40–1.50 (m, 2H), 2.41 (s, 3H), 2.77 (q, J=7.2 Hz, 2H), 2.94 (d, J=6.8 Hz, 2H), 3.15 (t, J=7.2 Hz, 2H), 3.70 (s, 6H), 6.51 (s, 2H), 7.91 (d, J=4.8 Hz, 1H), 8.04 (d, J=4.4 Hz, 1H).
MS (FAB) m/z 409 MH$^+$

Example 171

N-[8-(2-Chloro-4-methoxyphenyl)-2-ethylimidazo[1,2-a]pyrazin-3-yl]-N-cyclopropylmethyl-N-propylamine Yellow Oil
$^1$H NMR (400 MHz, CDCl$_3$) δ 0.00 (br s, 2H), 0.36 (d, J=8.1 Hz, 2H), 0.76–0.86 (m, 1H), 0.91 (t, J=7.6 Hz, 3H), 1.31 (t, J=7.6 Hz, 3H), 1.38–1.48 (m, 2H), 2.81 (q, J=7.6 Hz, 2H), 2.96 (d, J=6.8 Hz, 2H), 3.16 (t, J=7.2 Hz, 2H), 3.87 (s, 3H), 6.95 (dd, J=2.4, 8.8 Hz, 1H), 7.08 (d, J=2.4 Hz, 1H), 7.67 (d, J=8.4 Hz, 1H), 7.91 (d, J=4.4 Hz, 1H), 8.09 (d, J=4.4 Hz, 1H).
MS (FAB) m/z 399 MH$^+$

Example 172

N-Cyclopropylmethyl-N-[2-ethyl-8-(2-methoxy-4,6-dimethylphenyl)imidazo[1,2-a]pyrazin-3-yl]-N-propylamine Yellow Oil
$^1$H NMR (400 MHz, CDCl$_3$) δ 0.00 (br s, 2H), 0.36 (d, J=8.4 Hz, 2H), 0.80–0.90 (m, 1H), 0.95 (t, J=7.2 Hz, 3H), 1.27 (t, J=7.6 Hz, 3H), 1.42–1.52 (m, 2H), 2.04 (s, 3H), 2.39 (s, 3H), 2.79 (q, J=7.2 Hz, 2H), 2.88–3.06 (m, 2H), 3.18 (t, J=7.2 Hz, 2H), 3.71 (s, 3H), 6.71 (s, 1H), 6.76 (s, 1H), 7.93 (d, J=4.8 Hz, 1H), 8.08 (d, J=4.8 Hz, 1H).
MS (FAB) m/z 393 MH$^+$

Example 173

N-[8-(2-Chloro-6-methoxy-4-methylphenyl)-2-ethylimidazo[1,2-a]pyrazin-3-yl]-N,N-diisobutylamine Yellow Oil
$^1$H NMR (400 MHz, CDCl$_3$) δ 0.95 (d, J=6.4 Hz, 6H), 1.27 (t, J=7.6 Hz, 3H), 1.52–1.66 (m, 2H), 2.40 (s, 3H), 2.82 (q, J=7.6 Hz, 2H), 2.89 (d, J=6.8 Hz, 4H), 3.73 (s, 3H), 6.76 (s, 1H), 6.95 (s, 1H), 7.96 (d, J=4.4 Hz, 1H), 8.10 (d, J=4.8 Hz, 1H).

Example 174

N-[8-(2-Chloro-6-methoxy-4-methylphenyl)-2-ethylimidazo[1,2-a]pyrazin-3-yl]-N-cyclopropylmethyl-N-isobutylamine Yellow Oil
$^1$H NMR (400 MHz, CDCl$_3$) δ −0.10–0.05 (m, 2H), 0.32–0.24 (m, 2H), 0.78–0.92 (m, 1H), 1.01 (d, J=6.4 Hz, 6H), 1.34 (t, J=7.2 Hz, 3H), 1.64–1.76 (m, 1H), 2.45 (s, 3H), 2.45 (s, 3H), 2.89 (q, J=7.2 Hz, 2H), 2.89–3.04 (m, 2H), 3.06 (d, J=8.8 Hz, 2H), 3.79 (s, 3H), 6.82 (s, 1H), 7.01 (s, 1H), 8.05 (br s, 1H), 8.22 (d, J=4.4 Hz, 1H).

Example 175

N-[8-(2-Chloro-4-methoxyphenyl)-2-ethylimidazo[1,2-a]pyrazin-3-yl]-N-(3-fluoropropyl)-N-propylamine Yellow Oil
$^1$H NMR (400 MHz, CDCl$_3$) δ 0.90 (t, J=7.6 Hz, 3H), 1.30 (t, J=7.6 Hz, 3H), 1.45 (q, J=7.6 Hz, 2H), 1.72–1.86 (m, 2H), 2.80 (q, J=7.6 Hz, 2H), 3.09 (t, J=7.6 Hz, 2H), 3.30 (t, J=7.2 Hz, 2H), 3.86 (s, 3H), 4.45 (t, J=5.6 Hz, 1H), 4.56 (t, J=5.6 Hz, 1H), 6.98 (dd, J=2.4, 8.0 Hz, 1H), 7.27 (s, 1H), 7.63 (d, J=8.4 Hz, 1H), 7.92 (d, J=4.8 Hz, 1H), 7.99 (d, J=4.4 Hz, 1H).

Example 176

N-[8-(2-Chloro-6-methoxy-4-methylphenyl)-2-ethylimidazo[1,2-a]pyrazin-3-yl]-N-(3-fluoropropyl)-N-propylamine White Crystals
$^1$H NMR (400 MHz, CDCl$_3$) δ 0.90 (t, J=7.2 Hz, 3H), 1.25 (t, J=7.6 Hz, 3H), 1.40–1.50 (m, 2H), 1.72–1.86 (m, 2H), 2.38 (s, 3H), 2.78 (q, J=7.2 Hz, 2H), 3.08 (t, J=7.6 Hz, 2H), 3.29 (t, J=7.6 Hz, 2H), 3.71 (s, 3H), 4.45 (t, J=5.6 Hz, 1H), 4.56 (t, J=5.6 Hz, 1H), 6.74 (s, 1H), 6.94 (s, 1H), 7.93 (d, J=4.4 Hz, 1H), 7.99 (d, J=4.4 Hz, 1H).

Example 177

N,N-Dicyclopropylmethyl-N-[8-(2,4-dibromophenyl)-2-ethylimidazo[1,2-a]pyrazin-3-yl]amine Yellow Oil
$^1$H NMR (400 MHz, CDCl$_3$) δ 0.00 (br s, 4H), 0.33 (d, J=7.6 Hz, 4H), 0.72–0.82 (m, 2H), 1.28 (t, J=7.2 Hz, 3H), 2.77 (q, J=7.6 Hz, 2H), 3.01 (d, J=7.2 Hz, 4H), 7.53 (d, J=8.0 Hz, 1H), 7.57 (d, J=8.0 Hz, 1H), 7.86 (s, 1H), 7.90 (d, J=4.8 Hz, 1H), 8.16 (d, J=4.4 Hz, 1H).

Example 178

N-[8-(2-Bromo-6-methoxy-4-methylphenyl)-2-ethylimidazo[1,2-a]pyrazin-3-yl]-N,N-dicyclopropylmethylamine Yellow Oil
$^1$H NMR (400 MHz, CDCl$_3$) δ 0.00 (br s, 4H), 0.33 (d, J=8.4 Hz, 4H), 0.76–0.86 (m, 2H), 1.25 (t, J=7.6 Hz, 3H), 2.37 (s, 3H), 2.76 (t, J=7.6 Hz, 2H), 2.92–3.12 (m, 4H), 3.69 (s, 3H) 6.77 (s, 1H), 7.11 (s, 1H), 7.91 (d, J=4.4 Hz, 1H), 8.14 (d, J=4.8 Hz, 1H).

Example 179

N-[8-(2-Bromo-4-methoxyphenyl)-2-ethylimidazo[1,2-a]pyrazin-3-yl]-N,N-dicyclopropylmethylamine Yellow Oil
$^1$H NMR (400 MHz, CDCl$_3$) δ 0.00 (br s, 4H), 0.33 (d, J=7.6 Hz, 4H), 0.72–0.84 (m, 2H), 1.28 (t, J=7.6 Hz, 3H), 2.76 (q, J=7.6 Hz, 2H), 3.01 (d, J=7.2 Hz, 4H), 3.83 (s, 3H), 6.96 (dd, J=2.4, 8.4 Hz, 1H), 7.23 (s, 1H), 7.61 (d, J=8.4 Hz, 1H), 7.88 (d, J=4.8 Hz, 1H), 8.13 (d, J=4.4 Hz, 1H).
MS (ESI) m/z 455 MH$^+$

Example 180

N,N-Dicyclopropylmethyl-N-[8-(2,4-dichloro-6-methoxyphenyl)-2-ethylimidazo[1,2-a]pyrazin-3-yl]amine Yellow Oil
$^1$H NMR (400 MHz, CDCl$_3$) δ 0.00 (br s, 4H), 0.34 (d, J=7.4 Hz, 4H), 0.76–0.86 (m, 2H), 1.25 (t, J=7.6 Hz, 3H), 2.76 (q, J=7.6 Hz, 2H), 2.96–3.08 (m, 4H), 3.71 (s, 3H), 6.92 (d, J=1.6 Hz, 1H), 7.13 (d, J=2.0 Hz, 1H), 7.91 (d, J=4.8 Hz, 1H), 8.16 (d, J=4.8 Hz, 1H).

Example 181

N-[8-(2-Bromo-4,6-dimethylphenyl)-2-ethylimidazo[1,2-a]pyrazin-3-yl]-N,N-dicyclopropylmethylamine Yellow Oil
$^1$H NMR (400 MHz, CDCl$_3$) δ −0.40–0.40 (m, 4H), 0.38 (d, J=8.0 Hz, 4H), 0.78–0.88 (m, 2H), 1.30 (t, J=7.6 Hz, 3H), 2.07 (s, 3H), 2.35 (s, 3H), 2.89 (q, J=7.6 Hz, 2H), 2.98–3.16 (m, 4H), 7.10 (s, 1H), 7.35 (s, 1H), 8.35 (d, J=4.8 Hz, 1H), 8.40 (d, J=4.8 Hz, 1H).

Example 182

N-[8-(2-Bromo-4,6-dimethylphenyl)-2-ethylimidazo[1,2-a]pyrazin-3-yl]-N-cyclopropylmethyl-N-propylamine Yellow Oil $^1$H NMR (400 MHz, CDCl$_3$) δ −0.30–0.40 (m, 2H), 0.36–0.46 (m, 2H), 0.82–0.92 (m, 1H), 1.01 (t, J=7.2 Hz, 3H), 1.38 (t, J=7.6 Hz, 3H), 1.54–1.62 (m, 2H), 2.16 (s, 3H), 2.43 (s, 3H), 2.98 (q, J=7.6 Hz, 2H), 3.00–3.16 (m, 2H), 3.25 (t, J=7.2 Hz, 2H), 7.18 (s, 1H), 7.44 (s, 1H), 8.40 (d, J=4.4 Hz, 1H), 8.42 (d, J=4.8 Hz, 1H).

Example 183

N-[8-(2,4-Dibromophenyl)-2-ethylimidazo[1,2-a]pyrazin-3-yl ]-N,N-diisobutylamine Yellow Oil $^1$H NMR (400 MHz, CDCl$_3$) δ 0.95 (d, J=6.8 Hz, 12H), 1.29 (t, J=7.6 Hz, 3H), 1.56–1.64 (m, 2H), 2.80 (q, J=8.0 Hz, 2H), 2.99 (d, J=6.4 Hz, 4H), 7.55 (d, J=8.0 Hz, 1H), 7.57 (d, J=8.0 Hz, 1H), 7.89 (s, 1H), 7.93 (d, J=4.4 Hz, 1H), 8.11 (d, J=4.4 Hz, 1H).

Example 184

N-8-[5-Chloro-4-(2,5-dimethyl-1H-1-pyrroyl)-2-methoxyphenyl]-2-ethylimidazo[1,2-a]pyrazin-3-yl-N,N-dicyclopropylmethylamine Yellow Oil $^1$H NMR (400 MHz, CDCl$_3$) δ 0.00 (br s, 4H), 0.32 (d, J=7.6 Hz, 4H), 0.70–0.82 (m, 2H), 1.30 (t, J=7.6 Hz, 3H), 2.02 (s, 6H), 2.77 (q, J=7.6 Hz, 2H), 2.99 (d, J=7.2 Hz, 4H), 3.74 (s, 3H), 5.91 (s, 2H), 6.94 (s, 1H), 8.82 (s, 1H), 7.89 (d, J=4.4 Hz, 1H), 8.13 (d, J=4.4 Hz, 1H).

Example 185

N3, N3-Dicyclopropylmethyl-8-(4-amino-5-chloro-2-methoxyphenyl)-2-ethylimidazo[1,2-a]pyrazin-3-amine Yellow Oil $^1$H NMR (400 MHz, CDCl$_3$) δ 0.00 (br s, 4H), 0.32 (d, J=7.2 Hz, 4H), 1.72–1.80 (m, 2H), 1.29 (t, J=7.6 Hz, 3H), 2.75 (q, J=7.2 Hz, 2H), 2.97 (d, J=6.8 Hz, 4H), 3.73 (s, 3H), 4.20 (br s, 2H), 6.41 (s, 1H), 7.62 (s, 1H), 7.83 (d, J=4.4 Hz, 1H), 8.03 (d, J=4.4 Hz, 1H).
MS (ESI) m/z 426 MH$^+$

Example 186

N-8-[2-Chloro-4-(trifluoromethoxy)phenyl]-2-ethylimidazo[1,2-a]pyrazin-3-yl-N,N-dicyclopropylmethylamine Yellow Oil $^1$H NMR (400 MHz, CDCl$_3$) δ −0.04–0.04 (m, 4H), 0.30–0.36 (m, 4H), 0.72–0.82 (m, 2H), 1.27 (t, J=7.6 Hz, 3H), 2.76 (q, J=7.6 Hz, 2H), 3.01 (d, J=6.8 Hz, 4H), 7.24 (dd, J=2.0, 7.6 Hz, 1H), 7.38 (d, J=2.0 Hz, 1H), 7.73 (d, J=8.4 Hz, 1H), 7.90 (d, J=4.4 Hz, 1H), 8.17 (d, J=4.4 Hz, 1H).

Example 187

N-8-[2-Chloro-4-(trifluoromethyl)phenyl]-2-ethylimidazo[1,2-a]pyrazin-3-yl-N,N-dicyclopropylmethylamine Yellow Oil $^1$H NMR (400 MHz, CDCl$_3$) δ −0.04–0.04 (m, 4H), 0.28–0.38 (m, 4H), 0.70–0.82 (m, 2H), 1.26 (t, J=7.6 Hz, 3H), 2.76 (q, J=7.6 Hz, 2H), 3.00 (d, J=7.2 Hz, 4H), 7.62 (d, J=8.0 Hz, 1H), 7.77 (s, 1H), 7.80 (d, J=8.4 Hz, 1H), 7.91 (d, J=4.4 Hz, 1H), 8.19 (d, J=4.4 Hz, 1H).

Hereinafter, compounds of Example 188 to Example 195 were synthesized in the same manner as that of Example 8.

Example 188

N-[8-(2,4-Dichlorophenyl)-2-ethyl-6-methoxyimidazo[1,2-a]pyrazin-3-yl]-N,N-dipropylamine Yellow Oil $^1$H NMR (400 MHz, CDCl$_3$) δ 0.89 (t, J=7.3 Hz, 6H), 1.29 (t, J=7.5 Hz, 3H), 1.43 (ddq, J=7.3, 7.3, 7.3 Hz, 4H), 2.76 (q, J=7.5 Hz, 2H), 3.05 (dd, J=7.3, 7.3 Hz, 4H), 3.98 (s, 3H), 7.38 (dd, J=2.0, 8.2 Hz, 1H), 7.55 (d, J=2.0 Hz, 1H), 7.61 (s, 1H), 7.78 (d, J=8.2 Hz, 1H).

Example 189

N-[6-Chloro-2-ethyl-8-(2-methoxy-4,6-dimethylphenyl)imidazo[1,2-a]pyrazin-3-yl]-N,N-dipropylamine White Crystals $^1$H NMR (400 MHz, CDCl$_3$) δ 0.90 (t, J=7.3 Hz, 6H), 1.24 (t, J=7.5 Hz, 3H), 1.44 (ddq, J=7.3, 7.3, 7.3 Hz, 4H), 2.05 (s, 3H), 2.35 (s, 3H), 2.75 (q, J=7.5 Hz, 2H), 3.06 (dd, J=7.3, 7.3 Hz, 4H), 3.69 (s, 3H), 6.66 (s, 1H), 6.72 (s, 1H), 8.01 (s, 1H).

Example 190

N-[6-Chloro-2-ethyl-8-(2-methoxy-4,6-dimethylphenyl)imidazo[1,2-a]pyrazin-3-yl]-N,N-dicyclopropylmethylamine White Crystals $^1$H NMR (400 MHz, CDCl$_3$) δ −0.06–0.08 (m, 4H), 0.31–0.43 (m, 4H), 0.78–0.90 (m, 2H), 1.25 (t, J=7.5 Hz, 3H), 2.03 (s, 3H), 2.35 (s, 3H), 2.74 (q, J=7.5 Hz, 2H), 2.92–3.11 (m, 4H), 3.68 (s, 3H), 6.66 (s, 1H), 6.73 (s, 1H), 8.16 (s, 1H).

Example 191

N-[6-Chloro-2-ethyl-8-(2-methoxy-4,6-dimethylphenyl)imidazo[1,2-a]pyrazin-3-yl]-N-cyclopropylmethyl-N-propylamine Pale Yellow Crystals $^1$H NMR (400 MHz, CDCl$_3$) δ −0.11–0.03 (m, 2H), 0.28–0.42 (m, 2H), 0.77–0.86 (m, 1H), 0.92 (t, J=7.3 Hz, 3H), 1.24 (t, J=7.5 Hz, 3H), 1.45 (ddq, J=7.3, 7.3, 7.3 Hz, 2H), 2.04 (s, 3H), 2.35 (s, 3H), 2.75 (q, J=7.5 Hz, 2H), 2.86–3.03 (m, 2H), 3.14 (dd, J=7.3, 7.3 Hz, 2H), 3.68 (s, 3H), 6.66 (s, 1H), 6.72 (s, 1H), 8.09 (s, 1H).

Example 192

N-[6-Chloro-2-ethyl-8-(2-methoxy-4,6-dimethylphenyl)imidazo[1,2-a]pyrazin-3-yl]-N-cyclopropylmethyl-N-(3-fluoropropyl)amine White Crystals $^1$H NMR (400 MHz, CDCl$_3$) δ −0.09–0.05 (m, 2H), 0.31–0.44 (m, 2H), 0.77–0.88 (m, 1H), 1.25 (t, J=7.5 Hz, 3H), 1.74–1.90 (m, 2H), 2.04 (s, 3H), 2.36 (s, 3H), 2.76 (q, J=7.5 Hz, 2H), 2.88–3.05 (m, 2H), 3.32–3.40 (m, 2H), 3.68 (s, 3H), 4.44–4.50 (m, 1H), 4.56–4.62 (m, 1H), 6.67 (s, 1H), 6.73 (s, 1H), 8.07 (s, 1H).

Example 193

N-[6-Chloro-8-(2-chloro-4-methoxyphenyl)-2-ethylimidazo[1,2-a]pyrazin-3-yl]-N-cyclopropylmethyl-N-(3-fluoropropyl)amine Yellow Oil $^1$H NMR (400 MHz, CDCl$_3$) δ −0.03–0.08 (m, 2H), 0.35–0.45 (m, 2H), 0.76–0.87 (m, 1H), 1.31 (t, J=7.5 Hz, 3H), 1.72–1.88 (m, 2H), 2.80 (q, J=7.5 Hz, 2H), 2.93–3.00 (m, 2H), 3.33–3.41 (m, 2H), 3.86 (s, 3H), 4.43–4.49 (m, 1H), 4.55–4.62 (m, 1H), 6.94 (dd, J=2.6, 8.6 Hz, 1H), 7.07 (d, J=2.6 Hz, 1H), 7.67 (d, J=8.6 Hz, 1H), 8.10 (s, 1H).

Example 194

N-[6-Chloro-8-(2-chloro-4-methoxyphenyl)-2-ethylimidazo[1,2-a]pyrazin-3-yl]-N-(3-fluoropropyl)-N-propylamine Yellow Oil $^1$H NMR (400 MHz, CDCl$_3$) δ 0.91 (t, J=7.3 Hz, 3H), 1.30 (t, J=7.5 Hz, 3H), 1.45 (ddq, J=7.3, 7.3, 7.3 Hz, 2H), 1.72–1.88 (m, 2H), 2.79 (q, J=7.5 Hz, 2H), 3.08 (dd, J=7.3, 7.3 Hz, 2H), 3.25–3.33 (m, 2H), 3.86 (s, 3H), 4.42–4.48 (m, 1H), 4.53–4.60 (m, 1H), 6.94 (dd, J=2.6, 8.6 Hz, 1H), 7.07 (d, J=2.6 Hz, 1H), 7.67 (d, J=8.6 Hz, 1H), 8.02 (s, 1H).

Example 195

N-[6-Chloro-8-(2-chloro-4-methoxyphenyl)-2-ethylimidazo[1,2-a]pyrazin-3-yl]-N-(1-ethylpropyl)amine Yellow Crystals $^1$H NMR (400 MHz, CDCl$_3$) δ 0.98–1.05 (m, 6H), 1.30 (t, J=7.5 Hz, 3H), 1.42–1.54 (m, 4H), 2.78 (q, J=7.5 Hz, 2H), 2.86 (br s, 1H), 2.91–3.00 (m, 1H), 3.86 (s, 3H), 6.93 (dd, J=2.6, 8.6 Hz, 1H), 7.06 (d, J=2.6 Hz, 1H), 7.65 (d, J=8.6 Hz, 1H), 7.97 (s, 1H).

Example 196

N-[8-(2-Chloro-4-methoxyphenyl)-2-(methylsulfanyl)imidazo[1,2-a]pyrazin-3-yl]-N,N-dipropylamine Yellow Oil $^1$H NMR (400 MHz, CDCl$_3$) δ 0.89 (t, J=7.3 Hz, 6H), 1.41 (ddq, J=7.3, 7.3, 7.3 Hz, 4H), 2.60 (s, 3H), 3.10 (dd, J=7.3, 7.3 Hz, 4H), 3.88 (s, 3H), 6.94 (dd, J=2.6, 8.6 Hz, 1H), 7.08 (d, J=2.6 Hz, 1H), 7.71 (d, J=8.6 Hz, 1H), 7.93 (d, J=4.4 Hz, 1H), 7.98 (d, J=4.4 Hz, 1H).

Hereinafter, compounds of Examples 197 to 260 were synthesized in the same manners as in Example 196.

Example 197

N-[8-(2-Methoxy-4,6-dimethylphenyl)-2-(methylsulfanyl)imidazo[1,2-a]pyrazin-3-yl]-N,N-dipropylamine White Crystals $^1$H NMR (400 MHz, CDCl$_3$) δ 0.89 (t, J=7.3 Hz, 6H), 1.41 (ddq, J=7.3, 7.3, 7.3 Hz, 4H), 2.04 (s, 3H), 2.38 (s, 3H), 2.53 (s, 3H), 3.10 (dd, J=7.3, 7.3 Hz, 4H), 3.70 (s, 3H), 6.68 (s, 1H), 6.74 (s, 1H), 7.91 (d, J=4.6 Hz, 1H), 7.96 (d, J=4.6 Hz, 1H).

Example 198

N-Isobutyl-N-[8-(2-methoxy-4,6-dimethylphenyl)-2-(methylsulfanyl)imidazo[1,2-a]pyrazin-3-yl]-N-propylamine Pale Yellow Crystals $^1$H NMR (400 MHz, CDCl$_3$) δ 0.84–0.97 (m, 9H), 1.37–1.48 (m, 2H), 1.52–1.68 (m, 1H), 2.04 (s, 3H), 2.38 (s, 3H), 2.53 (s, 3H), 2.91–3.10 (m, 4H), 3.70 (s, 3H), 6.68 (s, 1H), 6.74 (s, 1H), 7.92 (d, J=4.6 Hz, 1H), 7.98 (d, J=4.6 Hz, 1H).

Example 199

N-[8-(2-Chloro-4-methoxyphenyl)-2-(methylsulfanyl)imidazo[1,2-a]pyrazin-3-yl]-N-isobutyl-N-propylamine Pale Yellow Crystals $^1$H NMR (400 MHz, CDCl$_3$) δ 0.88 (t, J=7.5 Hz, 3H), 0.93 (d, J=6.8 Hz, 6H), 1.43 (ddq, J=7.5, 7.5, 7.5 Hz, 2H), 1.58 (tqq, J=7.1, 6.8, 6.8 Hz, 1H), 2.60 (s, 3H), 2.98 (d, J=7.1 Hz, 2H), 3.05 (dd, J=7.5, 7.5 Hz, 2H), 3.88 (s, 3H), 6.94 (dd, J=2.6, 8.6 Hz, 1H), 7.08 (d, J=2.6 Hz, 1H), 7.71 (d, J=8.6 Hz, 1H), 7.93 (d, J=4.6 Hz, 1H), 7.99 (d, J=4.6 Hz, 1H).

Example 200

N-[8-(2,6-Dimethoxy-4-methylphenyl)-2-(methylsulfanyl)imidazo[1,2-a]pyrazin-3-yl]-N,N-dipropylamine Yellow Green Oil $^1$H NMR (400 MHz, CDCl$_3$) δ 0.89 (t, J=7.3 Hz, 6H), 1.41 (ddq, J=7.3, 7.3, 7.3 Hz, 4H), 2.42 (s, 3H), 2.53 (s, 3H), 3.09 (dd, J=7.3, 7.3 Hz, 4H), 3.71 (s, 6H), 6.50 (s, 2H), 7.92 (d, J=4.6 Hz, 1H), 7.93 (d, J=4.6 Hz, 1H).

Example 201

N-[8-(2,4-Dimethoxyphenyl)-2-(methylsulfanyl)imidazo[1,2-a]pyrazin-3-yl]-N,N-dipropylamine Yellow Oil $^1$H NMR (400 MHz, CDCl$_3$) δ 0.88 (t, J=7.3 Hz, 6H), 1.40 (ddq, J=7.3, 7.3, 7.3 Hz, 4H), 2.60 (s, 3H), 3.09 (dd, J=7.3, 7.3 Hz, 4H), 3.83 (s, 3H), 3.88 (s, 3H), 6.62 (dd, J=2.2, 9.0 Hz, 1H), 6.63 (d, J=2.2 Hz, 1H), 7.70 (d, J=9.0 Hz, 1H), 7.90 (d, J=4.6 Hz, 1H), 7.92 (d, J=4.6 Hz, 1H).

Example 202

N-[8-(2,4-Dimethoxy-6-methylphenyl)-2-(methylsulfanyl)imidazo[1,2-a]pyrazin-3-yl]-N,N-dipropylamine Pale Yellow Crystals
$^1$H NMR (400 MHz, CDCl$_3$) δ 0.90 (t, J=7.5 Hz, 6H), 1.42 (ddq, J=7.5, 7.5, 7.5 Hz, 4H), 2.08 (s, 3H), 2.54 (s, 3H), 3.11 (dd, J=7.5, 7.5 Hz, 4H), 3.69 (s, 3H), 3.86 (s, 3H), 6.44 (s, 1H), 6.46 (s, 1H), 7.91 (d, J=4.6 Hz, 1H), 7.96 (d, J=4.6 Hz, 1H).

Example 203

N,N-Dicyclopropylmethyl-N-[8-(2-methoxy-4,6-dimethylphenyl)-2-(methylsulfanyl)imidazo[1,2-a]pyrazin-3-yl]amine White Crystals
$^1$H NMR (400 MHz, CDCl$_3$) δ −0.06–0.06 (m, 4H), 0.22–0.36 (m, 4H), 0.75–0.85 (m, 2H), 2.03 (s, 3H), 2.38 (s, 3H), 2.53 (s, 3H), 2.97–3.12 (m, 4H), 3.69 (s, 3H), 6.68 (s, 1H), 6.75 (s, 1H), 7.92 (d, J=4.6 Hz, 1H), 8.12 (d, J=4.6 Hz, 1H).

Example 204

N-[8-(2-Chloro-4-methoxyphenyl)-2-(methylsulfanyl)imidazo[1,2-a]pyrazin-3-yl]-N,N-dicyclopropylmethylamine Yellow Oil
$^1$H NMR (400 MHz, CDCl$_3$) δ −0.02–0.06 (m, 4H), 0.26–0.35 (m, 4H), 0.72–0.83 (m, 2H), 2.61 (s, 3H), 3.00–3.07 (m, 4H), 3.88 (s, 3H), 6.94 (dd, J=2.6, 8.6 Hz, 1H), 7.08 (d, J=2.6 Hz, 1H), 7.71 (d, J=8.6 Hz, 1H), 7.93 (d, J=4.6 Hz, 1H), 8.15 (d, J=4.6 Hz, 1H).

Example 205

N-Cyclopropylmethyl-N-[8-(2-methoxy-4,6-dimethylphenyl)-2-(methylsulfanyl)imidazo[1,2-a]pyrazin-3-yl]-N-propylamine Pale Yellow Crystals
$^1$H NMR (400 MHz, CDCl$_3$) δ −0.15–0.00 (m, 2H), 0.20–0.34 (m, 2H), 0.72–0.84 (m, 1H), 0.91 (t, J=7.3 Hz, 3H), 1.42 (ddq, J=7.3, 7.3, 7.3 Hz, 2H), 2.03 (s, 3H), 2.38 (s, 3H), 2.53 (s, 3H), 2.90–3.04 (m, 2H), 3.18 (dd, J=7.3, 7.3 Hz, 2H), 3.69 (s, 3H), 6.69 (s, 1H), 6.74 (s, 1H), 7.92 (d, J=4.6 Hz, 1H), 8.05 (d, J=4.6 Hz, 1H).

Example 206

N-[8-(2-Chloro-4-methoxyphenyl)-2-(methylsulfanyl)imidazo[1,2-a]pyrazin-3-yl]-N-cyclopropylmethyl-N-propylamine Yellow Oil
$^1$H NMR (400 MHz, CDCl$_3$) δ −0.05–0.03 (m, 2H), 0.28–0.35 (m, 2H), 0.71–0.82 (m, 1H), 0.90 (t, J=7.3 Hz, 3H), 1.40 (ddq, J=7.3, 7.3, 7.3 Hz, 2H), 2.60 (s, 3H), 2.94–3.01 (m, 2H), 3.18 (dd, J=7.3, 7.3 Hz, 2H), 3.88 (s, 3H), 6.94 (dd, J=2.6, 8.6 Hz, 1H), 7.08 (d, J=2.6 Hz, 1H), 7.70 (d, J=8.6 Hz, 1H), 7.93 (d, J=4.6 Hz, 1H), 8.07 (d, J=4.6 Hz, 1H).

Example 207

N-Cyclopropylmethyl-N-(3-fluoropropyl)-N-[8-(2-methoxy-4,6-dimethylphenyl)-2-(methylsulfanyl)imidazo[1,2-a]pyrazin-3-yl]amine White Crystals
$^1$H NMR (400 MHz, CDCl$_3$) δ −0.13–0.02 (m, 2H), 0.32–0.48 (m, 2H), 0.74–0.85 (m, 1H), 1.71–1.87 (m, 2H), 2.03 (s, 3H), 2.39 (s, 3H), 2.54 (s, 3H), 2.91–3.07 (m, 2H), 3.35–3.45 (m, 2H), 3.69 (s, 3H), 4.46–4.50 (m, 1H), 4.56–4.62 (m, 1H), 6.69 (s, 1H), 6.75 (s, 1H), 7.93 (d, J=4.6 Hz, 1H), 8.01 (d, J=4.6 Hz, 1H).

Example 208

N-[8-(2-Chloro-4-methoxyphenyl)-2-(methylsulfanyl)imidazo[1,2-a]pyrazin-3-yl]-N-cyclopropylmethyl-N-(3-fluoropropyl)amine Yellow Oil
$^1$H NMR (400 MHz, CDCl$_3$) δ −0.05–0.05 (m, 2H), 0.28–0.38 (m, 2H), 0.72–0.85 (m, 1H), 1.68–1.85 (m, 2H), 2.61 (s, 3H), 2.96–3.02 (m, 2H), 3.35–3.46 (m, 2H), 3.88 (s, 3H), 4.43–4.48 (m, 1H), 4.54–4.60 (m, 1H), 6.94 (dd, J=2.6, 8.6 Hz, 1H), 7.08 (d, J=2.6 Hz, 1H), 7.70 (d, J=8.6 Hz, 1H), 7.94 (d, J=4.6 Hz, 1H), 8.04 (d, J=4.6 Hz, 1H).

Example 209

N,N-Dicyclopropylmethyl-N-[8-(2,6-dimethoxy-4-methylphenyl)-2-(methylsulfanyl)imidazo[1,2-a]pyrazin-3-yl]amine White Crystals
$^1$H NMR (400 MHz, CDCl$_3$) δ −0.06–0.08 (m, 4H), 0.24–0.38 (m, 4H), 0.73–0.86 (m, 2H), 2.42 (s, 3H), 2.53 (s, 3H), 3.00–3.08 (m, 4H), 3.70 (s, 6H), 6.50 (s, 2H), 7.93 (d, J=4.5 Hz, 1H), 8.10 (d, J=4.5 Hz, 1H).

Example 210

N-Cyclopropylmethyl-N-[8-(2,6-dimethoxy-4-methylphenyl)-2-(methylsulfanyl)imidazo[1,2-a]pyrazin-3-yl]-N-propylamine White Crystals
$^1$H NMR (400 MHz, CDCl$_3$) δ −0.07–0.00 (m, 2H), 0.27–0.34 (m, 2H), 0.73–0.84 (m, 1H), 0.91 (t, J=7.5 Hz, 3H), 1.41 (ddq, J=7.5, 7.5, 7.5 Hz, 2H), 2.42 (s, 3H), 2.53 (s, 3H), 2.93–3.00 (m, 2H), 3.18 (dd, J=7.5, 7.5 Hz, 2H), 3.70 (s, 3H), 6.50 (s, 2H), 7.92 (d, J=4.6 Hz, 1H), 8.02 (d, J=4.6 Hz, 1H).

Example 211

N-Cyclopropylmethyl-N-[8-(2,6-dimethoxy-4-methylphenyl)-2-(methylsulfanyl)imidazo[1,2-a]pyrazin-3-yl]-N-(3-fluoropropyl)amine White Crystals
$^1$H NMR (400 MHz, CDCl$_3$) δ −0.06–0.03 (m, 2H), 0.28–0.37 (m, 2H), 0.74–0.85 (m, 1H), 1.70–1.86 (m, 2H), 2.42 (s, 3H), 2.54 (s, 3H), 2.95–3.01 (m, 2H), 3.36–3.45 (m, 2H), 3.70 (s, 3H), 4.43–4.49 (m, 1H), 4.55–4.61 (m, 1H), 6.51 (s, 2H), 7.94 (d, J=4.6 Hz, 1H), 7.99 (d, J=4.6 Hz, 1H).

Example 212

N-[8-(2-Chloro-6-methoxy-4-methylphenyl)-2-(methylsulfanyl)imidazo[1,2-a]pyrazin-3-yl]-N-cyclopropylmethyl-N-(3-fluoropropyl)amine Pale Yellow Crystals $^1$H NMR (400 MHz, CDCl$_3$) δ −0.13–0.02 (m, 2H), 0.22–0.37 (m, 2H), 0.73–0.84 (m, 1H), 1.71–1.87 (m, 2H), 2.41 (s, 3H), 2.54 (s, 3H), 2.92–3.06 (m, 2H), 3.37–3.46 (m, 2H), 3.72 (s, 3H), 4.43–4.50 (m, 1H), 4.56–4.62 (m, 1H), 6.75 (s, 1H), 6.95 (s, 2H), 7.95 (d, J=4.6 Hz, 1H), 8.04 (d, J=4.6 Hz, 1H).

Example 213

N-[8-(2-Bromo-4-methoxyphenyl)-2-(methylsulfanyl)imidazo[1,2-a]pyrazin-3-yl]-N-cyclopropylmethyl-N-(3-fluoropropyl)amine Pale Yellow Oil $^1$H NMR (400 MHz, CDCl$_3$) δ −0.06–0.03 (m, 2H), 0.28–0.37 (m, 2H), 0.73–0.85 (m, 1H), 1.69–1.85 (m, 2H), 2.61 (s, 3H), 2.97–3.02 (m, 2H), 3.37–3.45 (m, 2H), 3.87 (s, 3H), 4.42–4.48 (m, 1H), 4.54–4.61 (m, 1H), 6.99 (dd, J=2.6, 8.6 Hz, 1H), 7.27 (d, J=2.6 Hz, 1H), 7.66 (d, J=8.6 Hz, 1H), 7.94 (d, J=4.6 Hz, 1H), 8.04 (d, J=4.6 Hz, 1H).

Example 214

N,N-Dicyclopropylmethyl-N-[2-(methylsulfanyl)-8-(2,4,6-trimethoxyphenyl)imidazo[1,2-a]pyrazin-3-yl]amine White Crystals $^1$H NMR (400 MHz, CDCl$_3$) δ −0.03–0.06 (m, 4H), 0.26–0.36 (m, 4H), 0.73–0.86 (m, 2H), 2.54 (s, 3H), 3.00–3.08 (m, 4H), 3.70 (s, 6H), 3.88 (s, 3H), 6.25 (s, 2H), 7.92 (d, J=4.6 Hz, 1H), 8.09 (d, J=4.6 Hz, 1H).

Example 215

N-[8-(2-Chloro-6-methoxy-4-methylphenyl)-2-(methylsulfanyl)imidazo[1,2-a]pyrazin-3-yl]-N,N-dicyclopropylmethylamine Pale Yellow Crystals $^1$H NMR (400 MHz, CDCl$_3$) δ −0.08–0.06 (m, 4H), 0.23–0.36 (m, 4H), 0.73–0.85 (m, 2H), 2.41 (s, 3H), 2.54 (s, 3H), 2.98–3.12 (m, 4H), 3.71 (s, 3H), 6.75 (s, 1H), 6.95 (s, 2H), 7.94 (d, J=4.6 Hz, 1H), 8.15 (d, J=4.6 Hz, 1H).

Example 216

N-Cyclopropylmethyl-N-isobutyl-N-[2-(methylsulfanyl)-8-(2,4,6-trimethoxyphenyl)imidazo[1,2-a]pyrazin-3-yl]amine Pale Yellow Crystals $^1$H NMR (400 MHz, CDCl$_3$) δ −0.11–0.01 (m, 2H), 0.25–0.35 (m, 2H), 0.73–0.85 (m, 1H), 0.94 (d, J=6.6 Hz, 6H), 1.61 (tqq, J=7.0, 6.6, 6.6 Hz, 1H), 2.54 (s, 3H), 2.89–2.96 (m, 2H), 3.03 (d, J=7.0 Hz, 2H), 3.70 (s, 6H), 3.88 (s, 3H), 6.25 (s, 2H), 7.91 (d, J=4.6 Hz, 1H), 8.04 (d, J=4.6 Hz, 1H).

Example 217

N-Cyclopropylmethyl-N-[8-(2,6-dimethoxy-4-methylphenyl)-2-(methylsulfanyl)imidazo[1,2-a]pyrazin-3-yl]-N-isobutylamine White Crystals $^1$H NMR (400 MHz, CDCl$_3$) δ −0.11–0.02 (m, 2H), 0.25–0.34 (m, 2H), 0.72–0.82 (m, 1H), 0.94 (d, J=6.8 Hz, 6H), 1.61 (tqq, J=7.0, 6.8, 6.8 Hz, 1H), 2.42 (s, 3H), 2.53 (s, 3H), 2.39–2.45 (m, 2H), 3.03 (d, J=7.0 Hz, 2H), 3.70 (s, 6H), 6.50 (s, 2H), 7.92 (d, J=4.6 Hz, 1H), 8.04 (d, J=4.6 Hz, 1H).

Example 218

N-Cyclopropylmethyl-N-isobutyl-N-[8-(2-methoxy-4,6-dimethylphenyl)-2-(methylsulfanyl)imidazo[1,2-a]pyrazin-3-yl]amine White Crystals $^1$H NMR (400 MHz, CDCl$_3$) δ −0.20–0.02 (m, 2H), 0.18–0.35 (m, 2H), 0.73–0.84 (m, 1H), 0.95 (d, J=6.6 Hz, 6H), 1.62 (tqq, J=7.0, 6.6, 6.6 Hz, 1H), 2.03 (s, 3H), 2.38 (s, 3H), 2.53 (s, 3H), 2.86–3.01 (m, 2H), 3.03 (d, J=7.0 Hz, 2H), 3.69 (s, 3H), 6.69 (s, 1H), 6.74 (s, 1H), 7.92 (d, J=4.4 Hz, 1H), 8.07 (d, J=4.4 Hz, 1H).

Example 219

N-[8-(2-Chloro-4-methoxyphenyl)-2-(methylsulfanyl)imidazo[1,2-a]pyrazin-3-yl]-N-cyclopropylmethyl-N-isobutylamine Pale Yellow Oil $^1$H NMR (400 MHz, CDCl$_3$) δ −0.08–0.00 (m, 2H), 0.28–0.36 (m, 2H), 0.72–0.83 (m, 1H), 0.94 (d, J=6.6 Hz, 6H), 1.59 (tqq, J=6.8, 6.6, 6.6 Hz, 1H), 2.60 (s, 3H), 2.91–2.97 (m, 2H), 3.04 (d, J=6.8 Hz, 2H), 3.88 (s, 3H), 6.94 (dd, J=2.6, 8.6 Hz, 1H), 7.08 (d, J=2.6 Hz, 1H), 7.71 (d, J=8.6 Hz, 1H), 7.93 (d, J=4.6 Hz, 1H), 8.09 (d, J=4.6 Hz, 1H).

Example 220

N-Cyclopropylmethyl-N-[8-(4-methoxy-2,6-dimethylphenyl)-2-(methylsulfanyl)imidazo[1,2-a]pyrazin-3-yl]-N-propylamine Pale Yellow Oil $^1$H NMR (400 MHz, CDCl$_3$) δ −0.12–0.06 (m, 2H), 0.21–0.28 (m, 2H), 0.72–0.84 (m, 1H), 0.92 (t, J=7.3 Hz, 3H), 1.42 (ddq, J=7.3, 7.3, 7.3 Hz, 2H), 2.06 (s, 6H), 2.54 (s, 3H), 2.95–3.02 (m, 2H), 3.19 (dd, J=7.3, 7.3 Hz, 2H), 3.84 (s, 3H), 6.68 (s, 2H), 7.91 (d, J=4.6 Hz, 1H), 8.07 (d, J=4.6 Hz, 1H).

Example 221

N-Cyclopropylmethyl-N-[8-(4-methoxy-2-methylphenyl)-2-(methylsulfanyl)imidazo[1,2-a]pyrazin-3-yl]-N-propylamine Pale Yellow Oil $^1$H NMR (400 MHz, CDCl$_3$) δ −0.04–0.02 (m, 2H), 0.26–0.34 (m, 2H), 0.72–0.83 (m, 1H), 0.90 (t, J=7.3 Hz, 3H), 1.40 (ddq, J=7.3, 7.3, 7.3 Hz, 2H), 2.39 (s, 3H), 2.61 (s, 3H), 2.94–3.00 (m, 2H), 3.18 (dd, J=7.3, 7.3 Hz, 2H), 3.86

(s, 3H), 6.86 (d, J=9.2 Hz, 1H), 6.87 (s, 1H), 7.71 (d, J=9.2 Hz, 1H), 7.89 (d, J=4.4 Hz, 1H), 8.03 (d, J=4.4 Hz, 1H).

Example 222

N-Cyclopropylmethyl-N-[8-(2-methoxy-4-methylphenyl)-2-(methylsulfanyl)imidazo[1,2-a]pyrazin-3-yl]-N-propylamine Pale Yellow Oil $^1$H NMR (400 MHz, CDCl$_3$) δ −0.03–0.04 (m, 2H), 0.29–0.37 (m, 2H), 0.71–0.82 (m, 1H), 0.90 (t, J=7.3 Hz, 3H), 1.39 (ddq, J=7.3, 7.3, 7.3 Hz, 2H), 2.43 (s, 3H), 2.59 (s, 3H), 2.93–2.99 (m, 2H), 3.17 (dd, J=7.3, 7.3 Hz, 2H), 3.83 (s, 3H), 6.88 (s, 1H), 6.90 (d, J=7.7 Hz, 1H), 7.59 (d, J=7.7 Hz, 1H), 7.91 (d, J=4.4 Hz, 1H), 8.02 (d, J=4.4 Hz, 1H).

Example 223

N-(8-(4-Chloro-2-methoxyphenyl)-2-(methylsulfanyl)imidazo[1,2-a]pyrazin-3-yl]-N-cyclopropylmethyl-N-propylamine Pale Yellow Oil $^1$H NMR (400 MHz, CDCl$_3$) δ −0.04–0.06 (m, 2H), 0.27–0.38 (m, 2H), 0.71–0.82 (m, 1H), 0.90 (t, J=7.5 Hz, 3H), 1.39 (ddq, J=7.5, 7.5, 7.5 Hz, 2H), 2.59 (s, 3H), 2.93–3.01 (m, 2H), 3.17 (dd, J=7.5, 7.5 Hz, 2H), 3.83 (s, 3H), 7.06 (d, J=1.8 Hz, 1H), 7.08 (dd, J=1.8, 8.1 Hz, 1H), 7.64 (d, J=8.1 Hz, 1H), 7.92 (d, J=4.4 Hz, 1H), 8.05 (d, J=4.4 Hz, 1H).

Example 224

N-Cyclopropylmethyl-N-[8-(2,4-dimethoxy]phenyl)-2-(methylsulfanyl)imidazo[1,2-a]pyrazin-3-yl]-N-propylamine Pale Yellow Oil $^1$H NMR (400 MHz, CDCl$_3$) δ −0.03–0.04 (m, 2H), 0.29–0.36 (m, 2H), 0.71–0.82 (m, 1H), 0.89 (t, J=7.3 Hz, 3H), 1.39 (ddq, J=7.3, 7.3, 7.3 Hz, 2H), 2.60 (s, 3H), 2.93–2.99 (m, 2H), 3.17 (dd, J=7.3, 7.3 Hz, 2H), 3.83 (s, 3H), 3.88 (s, 3H), 6.62 (s, 1H), 6.63 (d, J=8.8 Hz, 1H), 7.71 (d, J=8.8 Hz, 1H), 7.91 (d, J=4.6 Hz, 1H), 8.01 (d, J=4.6 Hz, 1H).

Example 225

4-[3-[(Cyclopropylmethyl)(propyl)amino]-2-(methylsulfanyl)imidazo[1,2-a]pyrazin-8-yl]-3-methylbenzonitrile Pale Yellow Crystals $^1$H NMR (400 MHz, CDCl$_3$) δ −0.05–0.02 (m, 2H), 0.27–0.34 (m, 2H), 0.72–0.83 (m, 1H), 0.91 (t, J=7.3 Hz, 3H), 1.40 (ddq, J=7.3, 7.3, 7.3 Hz, 2H), 2.41 (s, 3H), 2.59 (s, 3H), 2.95–3.00 (m, 2H), 3.18 (dd, J=7.3, 7.3 Hz, 2H), 7.61 (d, J=7.9 Hz, 1H), 7.63 (s, 1H), 7.82 (d, J=7.9 Hz, 1H), 7.94 (d, J=4.6 Hz, 1H), 8.11 (d, J=4.4 Hz, 1H).

Example 226

N-[8-(2-Chloro-4-methoxyphenyl)-2-(methylsulfanyl)imidazo[1,2-a]pyrazin-3-yl]-N-(1-ethylpropyl)amine White Crystals $^1$H NMR (400 MHz, CDCl$_3$) δ 0.99–1.06 (m, 6H), 1.44–1.64 (m, 4H), 2.54 (s, 3H), 3.00–3.10 (m, 1H), 3.13 (br s, 1H), 3.87 (s, 3H), 6.94 (dd, J=2.6, 8.6 Hz, 1H), 7.07 (d, J=2.6 Hz, 1H), 7.67 (d, J=8.6 Hz, 1H), 7.86 (d, J=4.6 Hz, 1H), 7.92 (d, J=4.6 Hz, 1H).

Example 227

N-(1-Ethylpropyl)-N-[8-(2-methoxy-4,6-dimethylphenyl)-2-(methylsulfanyl)imidazo[1,2-a]pyrazin-3-yl]amine Pale Yellow Crystals $^1$H NMR (400 MHz, CDCl$_3$) δ 0.95–1.07 (m, 6H), 1.44–1.63 (m, 4H), 2.03 (s, 3H), 2.37 (s, 3H), 2.47 (s, 3H), 3.00–3.10 (m, 1H), 3.13 (br s, 1H), 3.68 (s, 3H), 6.68 (s, 1H), 6.74 (s, 1H), 7.84 (d, J=4.6 Hz, 1H), 7.91 (d, J=4.6 Hz, 1H).

Example 228

N-Cyclopropylmethyl-N-[8-(4-methyl-1,3-benzodioxol-5-yl)-2-(methylsulfanyl)imidazo[1,2-a]pyrazin-3-yl]-N-propylamine Pale Yellow Oil $^1$H NMR (400 MHz, CDCl$_3$) δ −0.05–0.02 (m, 2H), 0.27–0.34 (m, 2H), 0.72–0.83 (m, 1H), 0.90 (t, J=7.3 Hz, 3H), 1.40 (ddq, J=7.3, 7.3, 7.3 Hz, 2H), 2.24 (s, 3H), 2.62 (s, 3H), 2.95–3.00 (m, 2H), 3.18 (dd, J=7.3, 7.3 Hz, 2H), 6.03 (s, 2H), 6.80 (d, J=8.1 Hz, 1H), 7.32 (d, J=8.1 Hz, 1H), 7.89 (d, J=4.6 Hz, 1H), 8.04 (d, J=4.6 Hz, 1H).

Example 229

N-Cyclopropylmethyl-N-[8-(5-methyl-2,3-dihydro-1,4-benzodioxin-6-yl)-2-(methylsulfanyl)imidazo[1,2-a]pyrazin 3-yl]-N-propylamine Pale Yellow Oil $^1$H NMR (400 MHz, CDCl$_3$) δ −0.05–0.02 (m, 2H), 0.27–0.34 (m, 2H), 0.72–0.83 (m, 1H), 0.90 (t, J=7.5 Hz, 3H), 1.40 (ddq, J=7.5, 7.5, 7.5 Hz, 2H), 2.18 (s, 3H), 2.61 (s, 3H), 2.95–3.00 (m, 2H), 3.17 (dd, J=7.5, 7.5 Hz, 2H), 4.32 (br s, 4H), 6.84 (d, J=8.4 Hz, 1H), 7.21 (d, J=8.4 Hz, 1H), 7.89 (d, J=4.4 Hz, 1H), 8.04 (d, J=4.4 Hz, 1H).

Example 230

N-Cyclopropylmethyl-N-[8-[2-methoxy-4-(trifluoromethyl)phenyl]-2-(methylsulfanyl)imidazo[1,2-a]pyrazin-3-yl]-N-propylamine Yellow Oil $^1$H NMR (400 MHz, CDCl$_3$) δ −0.02–0.02 (m, 2H), 0.30–0.34 (m, 2H), 0.72–0.84 (m, 1H), 0.91 (t, J=7.6 Hz, 3H), 1.34–1.44 (m, 2H), 2.59 (s, 3H), 2.98 (m, 1H), 3.18 (t, J=7.6 Hz, 2H), 3.88 (s, 3H), 7.27 (s, 1H), 7.36 (d, J=8.0 Hz, 1H), 7.79 (d, J=8.0 Hz, 1H), 7.94 (d, J=4.8 Hz, 1H), 8.08 (d, J=4.8 Hz, 1H).

Example 231

N,N-Dicyclopropylmethyl-N-[8-[2-methoxy-4-(trifluoromethyl)phenyl]-2-(methylsulfanyl)imidazo[1,2-a]pyrazin-3-yl]amine Yellow Oil $^1$H NMR (400 MHz, CDCl$_3$) δ −0.00–0.02 (m, 4H), 0.26–0.32 (m, 4H), 0.70–0.80 (m, 2H), 2.57 (s, 3), 3.01 (d, J=7.2 Hz, 4H), 3.84 (s, 3H), 7.24 (s, 1H), 7.33 (d, J=8.0 Hz, 1H), 7.77 (d, J=8.0 Hz, 1H), 7.92 (d, J=4.4 Hz, 1H), 8.13 (d, J=4.4 Hz, 1H).

Example 232

N,N-Dicyclopropylmethyl-N-[8-[4-methoxy-2-(trifluoromethyl)phenyl]-2-(methylsulfanyl)imidazo[1,2-a]pyrazin-3-yl]amine Yellow Oil $^1$H NMR (400 MHz, CDCl$_3$) δ −0.04–0.04 (m, 4H), 0.24–0.34 (m, 4H), 0.74–0.84 (m, 2H), 2.57 (s, 3H), 0.36 (d, J=6.8 Hz, 4H) 3.93 (s, 3H), 7.18 (dd, J=2.4, 8.8 Hz, 1H), 7.33 (d, J=2.4 Hz, 1H), 7.72 (d, J=8.8 Hz, 1H), 7.91 (d, J=4.4 Hz, 1H), 8.16 (d, J=4.8 Hz, 1H).

Example 233

N,N-Dicyclopropylmethyl-N-[8-(2,4-dimethoxyphenyl)-2-(methylsulfanyl)imidazo[1,2-a]pyrazin-3-yl]amine Yellow Oil $^1$H NMR (400 MHz, CDCl$_3$) δ −0.04–0.04 (m, 4H), 0.24–0.34 (m, 4H), 0.68–0.80 (m, 2H), 2.59 (s, 3H), 3.01 (d, J=7.2 Hz, 4H), 3.79 (s, 3H), 3.85 (s, 3H), 6.59 (s, 1H), 6.61 (dd, J=2.0, 8.0 Hz, 1H), 7.71 (dd, J=2.0, 7.6 Hz, 1H), 7.89 (d, J=4.4 Hz, 1H), 8.06 (d, J=4.4 Hz, 1H).

Example 234

N-[8-(4-Chloro-2-methoxyphenyl)-2-(methylsulfanyl)imidazo[1,2-a]pyrazin-3-yl]-N,N-dicyclopropylmethylamine Yellow Oil $^1$H NMR (400 MHz, CDCl$_3$) δ −0.04–0.06 (m, 4H), 0.24–0.36 (m, 4H), 0.68–0.80 (m, 2H), 2.57 (s, 3H), 3.01 (d, J=6.8 Hz, 4H), 3.80 (s, 3H), 7.03 (s, 1H), 7.06 (d, J=8.0 Hz, 1H), 7.63 (d, J=8.0 Hz, 1H), 7.90 (d, J=4.4 Hz, 1H), 8.11 (d, J=4.4 Hz, 1H).

Example 235

N,N-Dicyclopropylmethyl-N-[8-(4-methoxy-2-methylphenyl)-2-(methylsulfanyl)imidazo[1,2-a]pyrazin-3-yl]amine Yellow Oil $^1$H NMR (400 MHz, CDCl$_3$) δ −0.04–0.04 (m, 4H), 0.22–0.32 (m, 4H), 0.70–0.82 (m, 2H), 2.36 (s, 3H), 2.60 (s, 3H), 3.02 (d, J=6.8 Hz, 4H), 3.85 (s, 3H), 6.82–6.86 (m, 2H), 7.71 (d, J=9.2 Hz, 1H), 7.89 (d, J=4.4 Hz, 1H), 8.10 (d, J=4.4 Hz, 1H).

Example 236

N,N-Dicyclopropylmethyl-N-[8-(2-methoxy-4-methylphenyl)-2-(methylsulfanyl)imidazo[1,2-a]pyrazin-3-yl]amine Yellow Oil $^1$H NMR (400 MHz, CDCl$_3$) δ −0.04–0.04 (m, 4H), 0.24–0.32 (m, 4H), 0.68–0.80 (m, 2H), 2.41 (s, 3H), 2.57 (s, 3H), 3.00 (d, J=6.8 Hz, 4H), 3.79 (s, 3H), 6.85 (s, 1H), 6.88 (d, J=7.6 Hz, 1H), 7.58 (d, J=7.6 Hz, 1H), 7.90 (d, J=4.4 Hz, 1H), 8.07 (d, J=4.4 Hz, 1H).

Example 237

N-[8-[2-Chloro-4-(trifluoromethoxy)phenyl]-2-(methylsulfanyl)imidazo[1,2-a]pyrazin-3-yl]-N,N-dicyclopropylmethylamine Yellow Oil $^1$H NMR (400 MHz, CDCl$_3$) δ −0.04–0.04 (m, 4H), 0.22–0.34 (m, 4H), 0.70–0.82 (m, 2H), 2.59 (s, 3H), 3.03 (d, J=6.8 Hz, 4H) 7.27 (d, J=7.6 Hz, 1H), 7.41 (s, 1H), 7.78 (d, J=7.6 Hz, 1H), 7.94 (d, J=4.4 Hz, 1H), 8.18 (d, J=4.4 Hz, 1H).

Example 238

N,N-Dicyclopropylmethyl-N-[8-(2,4-dichlorophenyl)-2-(methylsulfanyl)imidazo[1,2-a]pyrazin-3-yl]amine Yellow Oil $^1$H NMR (400 MHz, CDCl$_3$) δ −0.04–0.04 (m, 4H), 0.24–0.32 (m, 4H), 0.72–0.80 (m, 2H), 2.59 (s, 3H), 3.03 (d, J=6.8 Hz, 4H), 7.38 (dd, J.=2.0, 8.4 Hz, 1H), 7.54 (d, J=2.0 Hz, 1H), 7.69 (d, J=8.4 Hz, 1H), 7.93 (d, J=4.4 Hz, 1H), 8.17 (d, J=4.4 Hz, 1H).

Example 239

N-[8-(2-Bromo-4-methoxyphenyl)-2-(methylsulfanyl)imidazo[1,2-a]pyrazin-3-yl]-N,N-dicyclopropylmethylamine Yellow Oil $^1$H NMR (400 MHz, CDCl$_3$) δ −0.04–0.04 (m, 4H), 0.26–0.30 (m, 4H), 0.70–0.80 (m, 2H), 2.51 (s, 3H), 3.03 (d, J=6.8 Hz, 4H), 3.86 (s, 3H), 6.98 (dd, J=2.4, 8.8 Hz, 1H), 7.25 (d, J=2.4 Hz, 1H), 7.66 (d, J=8.4 Hz, 1H), 7.92 (d, J=4.4 Hz, 1H), 8.15 (d, J=4.8 Hz, 1H).

Example 240

2-[[8-(2-Chloro-4-methoxyphenyl)-2-(methylsulfanyl)imidazo[1,2-a]pyrazin-3-yl](cyclopropylmethyl)amino]-1-ethoanol Yellow Oil $^1$H NMR (400 MHz, CDCl$_3$) δ −0.03–0.05 (m, 2H), 0.33–0.41 (m, 2H), 0.78–0.88 (m, 1H), 2.18 (t, J=5.3 Hz, 1H), 2.62 (s, 3H) 3.03–3.08 (m, 2H), 3.43 (t, J=5.3 Hz, 2H), 3.59 (dt, J=5.3, 5.3 Hz, 2H), 3.88 (s, 3H), 6.95 (dd, J=2.6, 8.6 Hz, 1H), 7.08 (d, J=2.6 Hz, 1H), 7.69 (d, J=8.6 Hz, 1H), 7.96 (d, J=4.6 Hz, 1H), 8.04 (d, J=4.6 Hz, 1H).

Example 241

N-[8-(2-Chloro-4-methoxyphenyl)-2-(methylsulfanyl)imidazo[1,2-a]pyrazin-3-yl]-N-cyclobutylmethyl-N-cyclopropylmethylamine Yellow Oil
$^1$H NMR (400 MHZ, CDCl$_3$) δ −0.04–0.04 (m, 2H), 0.26–0.36 (m, 2H), 0.72–0.82 (m, 1H), 1.64–1.94 (m, 6H), 2.24–2.34 (m, 1H), 2.63 (s, 3H), 2.98 (d, J=7.2 Hz, 2H), 3.24 (d, J=7.0 Hz, 2H), 3.89 (s, 3H), 6.96 (dd, J=2.8, 8.8 Hz, 1H), 7.10 (d, J=2.8 Hz, 1H), 7.72 (d, J=8.4 Hz, 1H), 7.94 (d, J=4.4 Hz, 1H), 8.06 (d, J=4.4 Hz, 1H).

Example 242

N,N-Dicyclopropylmethyl-N-2-ethyl-8-[2-methoxy-4-(trifluoromethyl)phenyl]imidazo[1,2-a]pyrazin-3-ylamine Yellow Oil
$^1$H NMR (400 MHz, CDCl$_3$) δ −0.04–0.02 (m, 4H), 0.28–0.34 (m, 2H), 0.70–0.82 (m, 1H), 1.26 (t, J=7.6 Hz, 3H), 2.76 (q, J=7.6 Hz, 2H), 2.98 (d, J=7.2 Hz, 4H), 3.81 (s, 3H), 7.22 (d, J=2.0 Hz, 1H), 7.32 (dd, J=2.0, 8.4 Hz, 1H), 7.71 (d, J=7.6 Hz, 1H), 7.88 (d, J=4.4 Hz, 1H), 8.12 (d, J=4.4 Hz, 1H).

Example 243

N3,N3-Dicyclopropylmethyl-8-[6-(dimethylamino)-4-methyl-3-pyridyl]-2-(methylsulfanyl)imidazo[1,2-a]pyrazin-3-amine Yellow Oil
$^1$H NMR (400 MHz, CDCl$_3$) δ −0.04–0.04 (m, 4H), 0.24–0.32 (m, 4H), 0.72–0.82 (m, 2H), 2.40 (s, 3H), 2.62 (s, 3H), 3.01 (d, J=7.2 Hz, 4H), 3.13 (s, 6H), 6.43 (s, 1H), 7.86 (d, J=4.4 Hz, 1H), 8.05 (d, J=4.4 Hz, 1H), 8.70 (s, 1H).

Example 244

N-[8-(2-Chloro-4-methoxyphenyl)-2-(methylsulfanyl)imidazo[1,2-a]pyrazin-3-yl]-N-cyclopropylmethyl-N-[3-(methylsulfanyl)propyl]amine Yellow Oil
$^1$H NMR (400 MHz, CDCl$_3$) δ −0.02–0.02 (m, 4H), 0.28–0.36 (m, 2H), 0.76–0.86 (m, 1H), 1.66–2.74 (m, 2H), 2.06 (s, 3H), 2.55 (t, J=7.2 Hz, 2H), 2.63 (s, 3H), 2.99 (d, J=7.2 Hz, 2H), 3.37 (t, J=7.0 Hz, 2H), 3.89 (s, 3H), 6.96 (dd, J=2.4, 8.8 Hz, 1H), 7.09 (d, J=2.4 Hz, 1H), 7.72 (d, J=8.8 Hz, 1H), 7.96 (d, J=4.8 Hz, 1H), 8.06 (d, J=4.4 Hz, 1H).
MS (ESI) m/z 426 MH$^+$

Example 245

N-[8-(2-Chloro-4-methoxyphenyl)-2-(methylsulfanyl)imidazo[1,2-a]pyrazin-3-yl]-N-cyclopropylmethyl-N-tetrahydro-2H-4-pyranylamine Pale Yellow Oil
$^1$H NMR (400 MHz, CDCl$_3$) δ −0.09–0.07 (m, 2H), 0.17–0.33 (m, 2H), 0.60–0.71 (m, 1H), 1.49–1.63 (m, 4H), 2.62 (s, 3H), 3.00–3.09 (m, 2H), 3.32–3.46 (m, 4H), 3.88 (s, 3H), 3.87–4.03 (m, 1H), 6.95 (dd, J=2.6, 8.6 Hz, 1H), 7.08 (d, J=2.6 Hz, 1H), 7.71 (d, J=8.6 Hz, 1H), 7.94 (d, J=4.6 Hz, 1H), 8.08 (d, J=4.6 Hz, 1H).

Example 246

1-[[8-(2-Chloro-4-methoxyphenyl)-2-(methylsulfanyl)imidazo[1,2-a]pyrazin-3-yl](cyclopropylmethyl)amino]-2-propanol Yellow Oil
$^1$H NMR (400 MHz, CDCl$_3$) δ −0.03–0.05 (m, 2H), 0.34–0.42 (m, 2H), 0.78–0.88 (m, 1H), 1.16 (d, J=6.2 Hz, 3H), 2.62 (s, 3H), 2.92 (dd, J=9.7, 13.8 Hz, 1H), 2.97–3.13 (m, 2H), 3.50 (dd, J=3.4, 13.8 Hz, 1H), 3.73 (ddq, J=3.4, 9.7, 6.2 Hz, 1H), 3.88 (s, 3H), 6.95 (dd, J=2.6, 8.6 Hz, 1H), 7.08 (d, J=2.6 Hz, 1H), 7.69 (d, J=8.6 Hz, 1H), 7.96 (d, J=4.6 Hz, 1H), 8.01 (d, J=4.6 Hz, 1H).

Example 247

1-[[8-[2-Chloro-4-(trifluoromethoxy)phenyl]-2-(methylsulfanyl)imidazo[1,2-a]pyrazin-3-yl](cyclopropylmethyl)amino]-2-propanol Yellow Oil
$^1$H NMR (400 MHz, CDCl$_3$) δ −0.05–0.07 (m, 2H), 0.32–0.44 (m, 2H), 0.78–0.90 (m, 1H), 1.17 (d, J=6.2 Hz, 3H), 2.62 (s, 3H), 2.93 (dd, J=9.9, 13.0 Hz, 1H), 2.97–3.04 (m, 1H), 3.06–3.13 (m, 1H), 3.50 (dd, J=3.6, 13.0 Hz, 1H), 3.74 (ddq, J=3.6, 9.9, 6.2 Hz, 1H), 7.28 (dd, J=2.6, 8.4 Hz, 1H), 7.43 (d, J=2.6 Hz, 1H), 7.77 (d, J=8.4 Hz, 1H), 7.98 (d, J=4.6 Hz, 1H), 8.07 (d, J=4.6 Hz, 1H).

Example 248

N-[8-[2-Chloro-4-(trifluoromethoxy)phenyl]-2-(methylsulfanyl)imidazo[1,2-a]pyrazin-3-yl]-N-cyclopropylmethyl-N-tetrahydro-2H-4-pyranylamine Yellow Oil
$^1$H NMR (400 MHz, CDCl$_3$) δ −0.08–0.05 (m, 2H), 0.17–0.32 (m, 2H), 0.61–0.71 (m, 1H), 1.45–1.61 (m, 4H), 2.62 (s, 3H), 3.02–3.08 (m, 2H), 3.33–3.46 (m, 4H), 3.89–4.03 (m, 1H), 7.28 (d, J=8.6 Hz, 1H), 7.43 (s, 1H), 7.80 (d, J=8.6 Hz, 1H), 7.96 (d, J=4.6 Hz, 1H), 8.13 (d, J=4.6 Hz, 1H).

Example 249

N3,N3-Dicyclopropylmethyl-8-[6-(dimethylamino)-2,4-dimethyl-3-pyrizyl]-2-(methylsulfanyl)imidazo[1,2-a]pyrazin-3-amine Pale Yellow Oil
$^1$H NMR (400 MHz, CDCl$_3$) δ −0.06–0.03 (m, 4H), 0.23–0.32 (m, 4H), 0.74–0.86 (m, 2H), 2.05 (s, 3H), 2.18 (s, 3H), 2.55 (s, 3H), 3.02–3.08 (m, 4H), 3.12 (s, 6H), 6.30 (s, 1H), 7.91 (d, J=4.6 Hz, 1H), 8.13 (d, J=4.6 Hz, 1H).

Example 250

2-[[8-[2-Chloro-4-(trifluoromethoxy)phenyl]-2-(methylsulfanyl)imidazo[1,2-a]pyrazin-3-yl](cyclopropylmethyl)amino]acetamide Yellow Oil $^1$H NMR (400 MHz, CDCl$_3$) δ −0.04–0.04 (m, 2H), 0.34–0.46 (m, 2H), 0.80–0.90 (m, 2H), 2.58 (s, 3H), 3.04 (d, J=7.2 Hz, 2H), 3.92 (s, 2H), 5.54 (br s, 1H), 7.00 (br s, 1H), 7.26 (s, 1H), 7.41 (s, 1H), 7.72 (d, J=8.4 Hz, 1H), 7.99 (d, J=4.4 Hz, 1H), 8.03 (d, J=4.4 Hz, 1H).

Example 251

N-[8-[2-Chloro-4-(trifluoromethoxy)phenyl]-2-(methylsulfanyl)imidazo[1,2-a]pyrazin-3-yl]-N-(1-cyclopropylethyl)-N-cyclopropylmethylamine Yellow Oil $^1$H NMR (400 MHz, CDCl$_3$) δ −0.10–0.78 (m, 10H), 1.10–1.25 (m, 3H), 2.52–2.58 (m, 1H), 2.60 (s, 3H), 3.04–3.10 (m, 1H), 3.22–3.28 (m, 1H), 7.28 (dd, J=2.4, 8.4 Hz, 1H), 7.42 (d, J=2.4 Hz, 2H), 7.80 (d, J=8.4 Hz, 1H), 7.94 (d, J=4.4 Hz, 1H), 8.23 (d, J=4.4 Hz, 1H).

MS (ESI) m/z 497 MH$^+$

Example 252

N-[8-(4-Bromo-2-methoxyphenyl)-2-(methylsulfanyl)imidazo[1,2-a]pyrazin-3-yl]-N,N-dicyclopropylmethylamine Pale Yellow Oil $^1$H NMR (400 MHz, CDCl$_3$) δ −0.01–0.08 (m, 4H), 0.27–0.36 (m, 4H), 0.71–0.82 (m, 2H), 2.60 (s, 3H), 2.99–3.07 (m, 4H), 3.83 (s, 3H), 7.21 (d, J=1.8 Hz, 1H), 7.24 (dd, J=1.8, 8.1 Hz, 1H), 7.60 (d, J=8.1 Hz, 1H), 7.93 (d, J=4.4 Hz, 1H), 8.13 (d, J=4.4 Hz, 1H).

Example 253

N2-[8-[2-Chloro-4-(trifluoromethoxy)phenyl]-2-(methylsulfanyl)imidazo[1,2-a]pyrazin-3-yl]-N2-cyclopropylmethyl-2-furamide Yellow Oil $^1$H NMR (400 MHz, CDCl$_3$) δ 0.00–0.52 (m, 4H), 0.96–1.08 (m, 2H), 2.48 (s, 3H), 3.45 (dd, J=7.2, 13.6 Hz, 1H), 4.10 (dd, J=7.2, 13.6 Hz, 1H), 6.25 (s, 1H), 6.33 (s, 1H), 7.14 (s, 1H), 7.29 (d, J=8.8 Hz, 1H), 7.79 (d, J=8.8 Hz, 1H), 7.89 (d, J=4.4 Hz, 1H), 8.01 (d, J=4.4 Hz, 1H).

Example 254

N-[8-[2-Chloro-4-(trifluoromethoxy)phenyl]-2-(methylsulfanyl)imidazo[1,2-a]pyrazin-3-yl]-N-cyclopropylmethyl-N-(2-furylmethyl)amine Yellow Oil $^1$H NMR (400 MHz, CDCl$_3$) δ −0.02–0.04 (m, 2H), 0.26–0.32 (m, 2H), 0.72–0.80 (m, 1H), 2.59 (s, 3H), 3.06 (d, J=7.2 Hz, 2H), 4.30 (s, 2H), 6.07 (s, 1H), 6.20 (s, 2H), 7.20–7.26 (m, 1H), 7.29 (s, 1H), 7.40 (s, 1H), 7.75 (d, J=8.8 Hz, 1H), 7.88 (d, J=4.4 Hz, 1H), 8.03 (d, J=4.4 Hz, 1H).

Example 255

N-(2-Bromoethyl)-N-[8-[2-chloro-4-(trifluoromethoxy)phenyl]-2-(methylsulfanyl)imidazo[1,2-a]pyrazin-3-yl]-N-cyclopropylmethylamine Yellow Oil $^1$H NMR (400 MHz, CDCl$_3$) δ −0.04–0.04 (m, 2H), 0.30–0.36 (m, 2H), 1.78–1.86 (m, 1H), 2.61 (s, 3H), 3.03 (d, J=7.2 Hz, 2H), 3.37 (t, J=6.0 Hz, 2H), 3.64 (t, J=6.0 Hz, 2H), 7.28 (dd, J=2.4, 8.4 Hz, 1H), 7.43 (d, J=2.4 Hz, 1H), 7.78 (d, J=8.4 Hz, 1H), 7.98 (d, J=4.4 Hz, 1H), 8.27 (d, J=4.4 Hz, 1H).

Example 256

N-[8-[2-Chloro-4-(trifluoromethoxy)phenyl]-2-(methylsulfanyl)imidazo[1,2-a]pyrazin-3-yl]-N-cyclopropylmethyl-N-(2-tetrahydro-1H-1-pyrroylethyl)amine Yellow Oil $^1$H NMR (400 MHz, CDCl$_3$) δ −0.02–0.04 (m, 2H), 0.30–0.36 (m, 2H), 1.76–1.82 (m, 1H), 1.66–1.74 (m, 4H), 2.38–2.48 (m, 4H), 2.51 (t, J=7.2 Hz, 2H), 2.61 (s, 3H), 3.03 (q, J=6.8 Hz, 2H), 3.39 (t, J=7.2 Hz, 2H), 7.24–7.30 (m, 1H), 7.43 (s, 1H), 7.79 (d, J=8.4 Hz, 1H), 7.94 (d, J=4.4 Hz, 1H), 8.20 (d, J=4.4 Hz, 1H).

Example 257

N-[8-[2-Chloro-4-(trifluoromethoxy)phenyl]-2-(methylsulfanyl)imidazo[1,2-a]pyrazin-3-yl]-N-cyclopropylmethyl-N-(2-morpholinoethyl)amine Yellow Oil $^1$H NMR (400 MHz, CDCl$_3$) δ −0.04–0.04 (m, 2H), 0.28–0.34 (m, 2H), 0.72–0.82 (m, 1H), 2.28 (br s, 4H), −2.38 (t, J=6.4 Hz, 2H), 2.60 (s, 3H), 3.01 (d, J=7.2 Hz, 2H), 3.36 (br s, 2H), 3.47 (t, J=4.4 Hz, 4H), 7.27 (dd, J=2.4, 8.4 Hz, 1H), 7.43 (d, J=2.4 Hz, 2H), 7.77 (d, J=8.4-Hz, 1H), 7.95 (d, J=4.4 Hz, 1H), 8.19 (d, J=4.4 Hz, 1H).

Example 258

N-[8-[2-Chloro-4-(trifluoromethoxy)phenyl]-2-(methylsulfanyl)imidazo[1,2-a]pyrazin-3-yl]-N-cyclopropylmethyl-N-[2-(1H-1-pyrazoyl)ethyl]amine Yellow Oil $^1$H NMR (400 MHz, CDCl$_3$) δ −0.02–0.04 (m, 2H), 0.32–0.38 (m, 2H), 0.72–0.82 (m, 1H), 2.68 (s, 3H), 3.00 (d, J=6.8 Hz, 2H), 3.82 (t, J=6.0 Hz, 2H), 4.26 (t, J=6.0 Hz, 2H), 6.29 (dd, J=1.6, 1.6 Hz, 1H), 7.30–7.34 (m, 2H), 7.48 (d, J=1.6 Hz, 1H), 7.59 (d, J=1.6 Hz, 1H), 7.65 (d, J=4.4 Hz, 1H), 7.82 (d, J=8.4 Hz, 1H), 7.91 (d, J=4.4 Hz, 1H).

Example 259

N-[8-[2-Chloro-4-(trifluoromethoxy)phenyl]-2-(methylsulfanyl)imidazo[1,2-a]pyrazin-3-yl]-N-cyclopropylmethyl-N-[2-(1H-1-imidazolyl)ethyl]amine Yellow Oil $^1$H NMR (400 MHz, CDCl$_3$) δ −0.04–0.04 (m, 2H), 0.32–0.40 (m, 2H), 0.72–0.82 (m, 1H), 2.67 (s, 3H), 2.99 (d, J=6.8 Hz, 2H), 3.70 (t, J=6.0 Hz, 2H), 4.05 (t, J=6.0 Hz, 2H), 6.88 (s, 1H), 7.11 (s, 1H), 7.30–7.34 (m, 1H), 7.46 (d, J=2.0 Hz, 1H), 7.45 (s, 1H), 7.59 (d, J=4.4 Hz, 1H), 7.80 (d, J=8.4 Hz, 1H), 7.94 (d, J=4.4 Hz, 1H).

Example 260

N3,N3-Dicyclopropylmethyl-8-[4-(dimethylamino)-2-methoxyphenyl]-2-(methylsulfanyl)imidazo[1,2-a]pyrazin-3-amine Yellow Oil $^1$H NMR (400 MHz, CDCl$_3$) δ 0.00–0.07 (m, 4H), 0.28–0.35 (m, 4H), 0.71–0.82 (m, 2H), 2.62 (s, 3H), 2.98–3.05 (m, 4H), 3.05 (s, 6H), 3.86 (s, 3H), 6.36 (d, J=2.4 Hz, 1H), 6.44 (dd, J=2.4, 8.6 Hz, 1H), 7.76 (d, J=8.6 Hz, 1H), 7.89 (d, J=4.6 Hz, 1H), 8.03 (d, J=4.6 Hz, 1H).

Example 261

N-[8-(2-Chloro-4-methoxyphenyl)-2-(methylsulfinyl)imidazo[1,2-a]pyrazin-3-yl]-N-cyclopropylmethyl-N-propylamine m-chloroperbenzoic acid (148 mg) was added to N-[8-(2-chloro-4-methoxyphenyl)-2-(methylsulfanyl)imidazo[1,2-a]pyrazin-3-yl]-N-cyclopropylmethyl-N-propylamine (166 mg) and dichloromethane (2 mL) at room temperature, and the mixture was stirred for 20 minutes. An aqueous sodium thiosulfate solution and an aqueous sodium bicarbonate solution were added thereto, which was extracted with ethyl acetate and evaporated. The resulting residue was separated and purified by silica gel column chromatography (ethyl acetate:n-hexane=1:3) to give the title compound (21 mg) as a pale yellow oil.

$^1$H NMR (400 MHz, CDCl$_3$) δ 0.02–0.07 (m, 2H), 0.31–0.42 (m, 2H), 0.76–0.97 (m, 4H), 1.42–1.54 (m, 2H), 3.02–3.12 (m, 2H), 3.04 (s, 3H), 3.22–3.36 (m, 2H), 3.89 (s, 3H), 6.95 (dd, J=2.6, 8.8 Hz, 1H), 7.09 (d, J=2.6 Hz, 1H), 7.71 (d, J=8.8 Hz, 1H), 8.03 (d, J=4.6 Hz, 1H), 8.16 (d, J=4.6 Hz, 1H).

Example 262

N-[8-(2-Chloro-4-methoxyphenyl)-2-(methylsulfonyl)imidazo[1,2-a]pyrazin-3-yl]-N-cyclopropylmethyl-N-propylamine The mixture produced in the above-mentioned Example 261 was separated and purified by silica gel column chromatography (ethyl acetate:n-hexane=1:3) to give the title compound (130 mg) as a Pale yellow oil.

$^1$H NMR (400 MHz, CDCl$_3$) δ −0.03–0.04 (m, 2H), 0.27–0.34 (m, 2H), 0.72–0.83 (m, 1H), 3.07–3.12 (m, 2H), 3.27 (dd, J=7.3, 7.3 Hz, 2H), 3.30 (s, 3H), 3.89 (s, 3H), 6.96 (dd, J=2.6, 8.6 Hz, 1H), 7.09 (d, J=2.6 Hz, 1H), 7.69 (d, J=8.6 Hz, 1H), 8.08 (d, J=4.6 Hz, 1H), 8.27 (d, J=4.6 Hz, 1H).

Hereinafter, the compound Example 263 was synthesized in the same manner as that of Example 261.

Example 263

N-Cyclopropylmethyl-N-[8-[2-methyl-4-(methylsulfinyl)phenyl]-2-(methylsulfinyl)imidazo[1,2-a]pyrazin-3-yl]-N-propylamine Pale Yellow Crystals $^1$H NMR (400 MHz, CDCl$_3$) δ −0.02–0.09 (m, 2H), 0.31–0.43 (m, 2H), 0.79–0.89 (m, 1H), 0.91–0.97 (m, 3H), 1.41–1.54 (m, 2H), 2.47 (s, 3H), 3.03 (s, 3H), 3.04–3.13 (m, 2H), 3.12 (s, 3H), 3.23–3.37 (m, 2H), 7.87–7.96 (m, 3H), 8.06 (d, J=4.6 Hz, 1H) 8.21 (d, J=4.4 Hz, 1H).

Example 264

4-[3-[Di(cyclopropylmethyl)amino]-2-(methylsulfanyl)imidazo[1,2-a]pyrazin-8-yl]-3-methoxybenzonitrile N-[8-(4-Bromo-2-methoxyphenyl)-2-(methylsulfanyl)imidazo[1,2-a]pyrazin-3-yl]-N,N-dicyclopropylmethylamine (53 mg) was dissolved in N,N-dimethylformamide (0.22 mL), then zinc cyanide (23 mg) and tetrakistriphenylphosphine palladium complex (13 mg) were added thereto. After that, the mixture was heated under stirring at 95° C. for 4 hours and cooled to room temperature, and then ethyl acetate was added thereto. The precipitated insoluble matters were filtered off, and then it was extracted with ethyl acetate. The resulting organic layer was washed with water, dried over magnesium sulfate, and then the solvent was evaporated. The resulting residue was purified by silica gel column chromatography (ethyl acetate:n-hexane=1:5) to give the title compound (26 mg) as yellow crystals.

$^1$H NMR (400 MHz, CDCl$_3$) δ −0.02–0.07 (m, 4H), 0.28–0.37 (m, 4H), 0.71–0.82 (m, 2H), 2.59 (s, 3H), 3.00–3.08 (m, 4H), 3.85 (s, 3H), 7.30 (d, J=1.5 Hz, 1H), 7.41 (dd, J=1.5, 7.9 Hz, 1H), 7.80 (d, J=7.9 Hz, 1H), 7.95 (d, J=4.4 Hz, 1H), 8.17 (d, J=4.4 Hz, 1H).

The compound of Example 265 was synthesized in the same manner as that of Example 264.

Example 265

N,N-Dicyclopropylmethyl-N-[8-(2-methoxy-4-tetrahydro-1H-1-pyrrolylphenyl)-2-(methylsulfanyl)imidazo[1,2-a]pyrazin-3-yl]amine Yellow Oil $^1$H NMR (400 MHz, CDCl$_3$) δ 0.00–0.10 (m, 4H), 0.28–0.38 (m, 4H), 0.71–0.82 (m, 2H), 1.99–2.10 (m, 4H), 2.63 (s, 3H), 2.98–3.07 (m, 4H), 3.33–3.43 (m, 4H), 3.86 (s, 3H), 6.21 (d, J=2.0 Hz, 1H), 6.30 (dd, J=2.0, 8.6 Hz, 1H), 7.77 (d, J=8.6 Hz, 1H), 7.89 (d, J=4.6 Hz, 1H), 8.02 (d, J=4.6 Hz, 1H).

Hereinafter, compounds of Example 266 to Example 269 were synthesized in the same manner as that of Example 110.

Example 266

6-Chloro-3-(1-ethoxybutyl)-2-ethyl-8-(2-methoxy-4,6-dimethylphenyl)imidazo[1,2-a]pyrazine White Crystals $^1$H NMR (400 MHz, CDCl$_3$) δ 0.91–1.00 (m, 3H), 1.17–1.35 (m, 7H), 1.42–1.57 (m, 1H), 1.73–1.85 (m, 1H), 2.01–2.15 (m, 1H), 2.05 (s, 3H), 2.36 (s, 3H), 2–69–2.81 (m, 2H), 3.23–3.45 (m, 2H), 3.68 (s, 3H), 4.70–4.75 (m, 1H), 6.67 (s, 1H), 6.73 (s, 1H), 8.43 (s, 1H).

Example 267

8-(2-Chloro-4-methoxyphenyl)-3-(1-ethoxybutyl)-2-(methylsulfanyl)imidazo[1,2-a]pyrazine White Crystals $^1$H NMR (400 MHz, CDCl$_3$) δ 0.91–0.97 (m, 3H), 1.19 (t, J=7.2 Hz, 3H), 1.21–1.33 (m, 1H), 1.40–1.52 (m, 1H), 1.77–1.89 (m, 1H), 1.99–2.10 (m, 1H), 2.59 (s, 3H), 3.30 (dq, J=7.2, 9.3 Hz, 1H), 3.42 (dq, J=7.2, 9.3 Hz, 1H), 3.88 (s, 3H), 4.84–4.90 (m, 1H), 6.94 (dd, J=2.4, 8.6 Hz, 1H), 7.08 (d, J=2.4 Hz, 1H), 7.69 (d, J=8.6 Hz, 1H), 7.92 (d, J=4.8 Hz, 1H), 8.34 (d, J=4.8 Hz, 1H).

Example 268

3-(1-Ethoxybutyl)-8-(2-methoxy-4,6-dimethylphenyl)-2-(methylsulfanyl)imidazo[1,2-a]pyrazine White Crystals $^1$H NMR (400 MHz, CDCl$_3$) δ 0.90–0.98 (m, 3H), 1.15–1.34 (m, 4H), 1.40–1.53 (m, 1H), 1.77–1.89 (m, 1H), 1.95–2.11 (m, 1H), 2.04 (br s, 3H), 2.38 (s, 3H), 2.52 (s, 3H), 3.23–3.47 (m, 2H), 3.70 (s, 3H), 4.84–4.91 (m, 1H), 6.69 (s, 1H), 6.74 (s, 1H), 7.91 (d, J=4.6 Hz, 1H), 8.31 (d, J=4.6 Hz, 1H).

Example 269

1-[8-(2,4-Dichlorophenyl)-2-(methylsulfanyl)imidazo[1,2-a]pyrazin-3-yl]butyl Ethyl Ether Pale Yellow Oil $^1$H NMR (400 MHz, CDCl$_3$) δ 0.91–0.98 (m, 3H), 1.19 (t, J=7.0 Hz, 3H), 1.21–1.34 (m, 1H), 1.39–1.53 (m, 1H), 1.77–1.88 (m, 1H), 1.99–2.10 (m, 1H), 2.58 (s, 3H), 3.30 (dq, J=9.3, 7.0 Hz, 1H), 3.43 (dq, J=9.3, 7.0 Hz, 1H), 4.83–4.89 (m, 1H), 7.39 (dd, J=2.0, 8.2 Hz, 1H), 7.56 (d, J=2.0 Hz, 1H), 7.68 (d, J=8.2 Hz, 1H), 7.94 (d, J=4.6 Hz, 1H), 8.37 (d, J=4.6 Hz, 1H).

Example 270

1-[8-(2-Chloro-4-methoxyphenyl)-2-ethylimidazo[1,2-a]pyrazin-3-yl]-1-butanone O1-methyloxime 1-[8-(2-Chloro-4-methoxyphenyl)-2-ethylimidazo[1,2-a]pyrazin-3-yl]-1-butanone (60 mg) was dissolved in a mixed solvent of ethanol (0.34 mL) and water (0.28 mL), then O-methylhydroxylamine hydrochloride (71 mg) was added thereto, and the mixture was heated under reflux for 6 hours. The reaction solution was cooled and water was added thereto. It was extracted with ethyl acetate and evaporated. The resulting crude isomer mixture was separated by silica gel column chromatography (ethyl acetate:n-hexane=1:3), to give the isomer 1 (31 mg) having a greater Rf value on TLC and the isomer 2 (13 mg) having a smaller Rf value on TLC were as a colorless oil each.

(a) Isomer 1:

$^1$H NMR (400 MHz, CDCl$_3$) δ 0.93–1.00 (m, 3H), 1.32 (t, J=7.5 Hz, 3H), 1.53–1.65 (m, 2H), 2.77–2.83 (m, 2H), 2.91 (q, J=7.5 Hz, 2H), 3.87 (s, 3H), 4.06 (s, 3H), 6.95 (dd, J=2.4, 8.6 Hz, 1H), 7.08 (d, J=2.4 Hz, 1H), 7.62 (d, J=8.6 Hz, 1H), 8.00 (d, J=4.6 Hz, 1H), 8.68 (d, J=4.6 Hz, 1H).

(b) Isomer 2:

$^1$H NMR (400 MHz, CDCl$_3$) δ 0.94 (t, J=7.3 Hz, 3H), 1.30 (t, J=7.5 Hz, 3H), 1.51 (ddq, J=7.3, 7.3, 7.3 Hz, 2H), 2.66 (dd, J=7.3, 7.3 Hz, 2H), 2.82 (q, J=7.5 Hz, 2H), 3.87 (s, 3H), 3.93 (s, 3H), 6.96 (dd, J=2.6, 8.6 Hz, 1H), 7.09 (d, J=2.6 Hz, 1H), 7.56 (d, J=4.6 Hz, 1H), 7.68 (d, J=8.6 Hz, 1H), 7.98 (d, J=4.6 Hz, 1H).

Hereinafter, compounds of Examples 271 and 272 were synthesized in the same manner as that of Example 270.

Example 271

1-[8-(2-Chloro-4-methoxyphenyl)-2-ethylimidazo[1,2-a]pyrazin-3-yl]-1-butanone Oxime (a) Isomer 1 Having a Greater Rf Value on TLC:

White Crystals $^1$H NMR (400 MHz, CDCl$_3$) δ 0.96–1.02 (m, 3H), 1.33 (t, J=7.5 Hz, 3H), 1.57–1.68 (m, 2H), 2.82–2.89 (m, 2H), 2.92 (q, J=7.5 Hz, 2H), 3.87 (s, 3H), 6.95 (dd, J=2.4, 8.4 Hz, 1H), 7.08 (d, J=2.4 Hz, 1H), 7.63 (d, J=8.4 Hz, 1H), 7.98 (d, J=4.6 Hz, 1H), 8.59 (d, J=4.6 Hz, 1H).

(b) Isomer 2 Having a Smaller Rf Value on TLC:

White Crystals $^1$H NMR (400 MHz, CDCl$_3$) δ 0.95 (t, J=7.3 Hz, 3H), 1.31 (t, J=7.5 Hz, 3H), 1.52 (ddq, J=7.3, 7.3, 7.3 Hz, 2H), 2.67 (dd, J=7.3, 7.3 Hz, 2H), 2.84 (q, J=7.5 Hz, 2H), 3.87 (s, 3H), 6.95 (dd, J=2.4, 8.2 Hz, 1H), 7.09 (d, J=2.4 Hz, 1H), 7.67 (d, J=8.2 Hz, 1H), 7.67 (d, J=4.6 Hz, 1H), 7.99 (d, J=4.6 Hz, 1H).

Example 272

1-[8-(2-Methoxy-4,6-dimethylphenyl)-2-(methylsulfanyl)imidazo[1,2-a]pyrazin-3-yl]-1-butanone O1-methyloxime (a) Isomer 1 Having a Greater Rf Value on TLC:

Colorless Oil $^1$H NMR (400 MHz, CDCl$_3$) δ 0.98–1.04 (m, 3H), 1.61–1.72 (m, 2H), 2.04 (s, 3H), 2.39 (s, 3H), 2.58 (s, 3H), 2.93–2.99 (m, 2H), 3.68 (s, 3H), 4.05 (s, 3H), 6.68 (s, 1H), 6.75 (s, 1H), 8.03 (d, J=4.8 Hz, 1H), 9.08 (d, J=4.8 Hz, 1H).

(b) Isomer 2 Having a Smaller Rf Value on TLC:

Colorless Oil $^1$H NMR (400 MHz, CDCl$_3$) δ 0.93 (t, J=7.3 Hz, 3H), 1.49 (ddq, J=7.3, 7.3, 7.3 Hz, 2H), 2.06 (s, 3H), 2.39 (s, 3H), 2.56 (s, 3H), 2.81 (dd, J=7.3, 7.3 Hz, 2H), 3.70 (s, 3H), 3.95 (s, 3H), 6.70 (s, 1H), 6.76 (s, 1H), 7.52 (d, J=4.6 Hz, 1H), 7.99 (d, J=4.6 Hz, 1H).

Example 273

N-[8-(2-Chloro-4-methoxyphenyl)-2-methoxyimidazo[1,2-a]pyrazin-3-yl]-N-cyclopropylmethyl-N-propylamine A 28% sodium methoxide solution (5 mL) was added to N[8-(2-chloro-4-methoxyphenyl)-2-(methylsulfonyl)imidazo[1,2-a]pyrazin-3-yl]-N-cyclopropylmethyl-N-propylamine (80 mg), and the mixture was stirred for 6 hours by heating under ref lux. After cooled to room temperature, water was added thereto, which was extracted with ethyl acetate, washed with water, dried over anhydrous magnesium sulfate, and then the solvent was evaporated. The resulting residue was purified by silica gel column chromatography (ethyl acetate:n-hexane=1:5) to give the title compound (23 mg) as a pale yellow oil.

$^1$H NMR (400 MHz, CDCl$_3$) δ −0.06–0.03 (m, 2H), 0.26–0.35 (m, 2H), 0.72–0.83 (m, 1H), 0.90 (t, J=7.3 Hz, 3H), 1.39 (ddq, J=7.3, 7.3, 7.3 Hz, 2H), 2.87–2.92 (m, 2H), 3.08 (dd, J=7.3, 7.3 Hz, 2H), 3.88 (s, 3H), 4.03 (s, 3H), 6.95 (dd, J=2.6, 8.6 Hz, 1H), 7.08 (d, J=2.6 Hz, 1H), 7.66 (d, J=8.6 Hz, 1H), 7.96 (d, J=4.4 Hz, 1H), 8.06 (d, J=4.4 Hz, 1H).

The compound of Example 274 was synthesized in the same manner as that of Example 273.

Example 274

N-Cyclopropylmethyl-N-[2-methoxy-8-(2-methoxy-4,6-dimethylphenyl)imidazo[1,2-a]pyrazin-3-yl]-N-propylamine Pale Yellow Oil $^1$H NMR (400 MHz, CDCl$_3$) δ −0.14–0.01 (m, 2H), 0.19–0.24 (m, 2H), 0.72–0.84 (m, 1H), 0.85–0.93 (m, 3H), 1.35–1.47 (m, 2H), 2.02 (s, 3H), 2.39 (s, 3H), 2.80–2.97 (m, 2H), 3.03–3.11 (m, 2H), 3.71 (s, 3H), 3.96 (s, 3H), 6.69 (s, 1H), 6.75 (s, 1H), 7.95 (d, J=4.6 Hz, 1H), 8.03 (d, J=4.6 Hz, 1H).

Hereinafter, compounds of Example 275 to Example 293 were synthesized in the same manner as that of Example 121.

Example 275

N-[2-Ethyl-8-(2-methoxy-4-methylphenyl)imidazo[1,2-b]pyridazin-3-yl]-N,N-dipropylamine Yellow Crystals $^1$H NMR (400 MHz, CDCl$_3$) δ 0.87 (t, J=7.4 Hz, 6H), 1.30 (t, J=7.5 Hz, 3H), 1.32–1.44 (m, 4H), 2.41 (s, 3H), 2.79 (q, J=7.5 Hz, 2H), 3.19 (t, J=7.4 Hz, 4H), 3.83 (s, 3H), 6.86 (s, 1H), 6.93 (dt, J=0.73, 7.9 Hz, 1H), 7.12 (d, J=4.6 Hz, 1H), 7.82 (d, J=7.3 Hz, 1H), 8.24 (d, J=4.8 Hz, 1H).

MS (ESI) m/z 367 MH$^+$

Example 276

N-[2-Ethyl-8-(2-methoxy-4-methylphenyl)imidazo[1,2-b]pyridazin-3-yl]-N-(1-ethylpropyl)amine Orange Oil $^1$H NMR (400 MHz, CDCl$_3$) δ 0.90 (t, J=7.4 Hz, 6H), 1.26 (t, J=7.5 Hz, 3H), 1.36–1.56 (m, 4H), 2.34 (s, 3H), 2.79 (q, J=7.1 Hz, 2H), 3.15–3.28 (m, 1H), 3.58 (s, 1H), 3.75 (s, 3H), 6.79 (s, 1H), 6.85 (dd, J=0.73, 7.9 Hz, 1H), 6.95 (d, J=4.6 Hz, 1H), 7.71 (d, J=6.6 Hz, 1H), 8.15 (d, J=3.8 Hz, 1H).

MS (ESI) m/z 353 MH$^+$

Example 277

N-[8-(2,4-Dichlorophenyl)-2-ethyl-6-methoxyimidazo[1,2-b]pyridazin-3-yl]-N,N-dipropylamine Yellow Crystals $^1$H NMR (400 MHz, CDCl$_3$) δ 0.90 (t, J=7.4 Hz, 6H), 1.24 (t, J=7.5 Hz, 3H), 1.34–1.46 (m, 4H), 2.73 (q, J=7.5 Hz, 2H), 3.18 (t, J=7.4 Hz, 4H), 4.00 (s, 3H), 6.64 (s, 1H), 7.36 (dd, J=2.1, 8.3 Hz, 1H), 7.53 (d, J=2.0 Hz, 1H), 7.64 (d, J=8.4 Hz, 1H).

MS (ESI) m/z 421 MH$^+$

Example 278

N-[2-Ethyl-8-(4-methoxy-2-methylphenyl)imidazo[1,2-b]pyridazin-3-yl]-N-isobutyl-N-propylamine Yellow Crystals $^1$H NMR (400 MHz, CDCl$_3$) δ 0.88 (t, J=7.3 Hz, 3H), 0.92 (d, J=6.6 Hz, 6H), 1.28 (t, J=7.5 Hz, 3H), 1.33–1.46 (m, 2H), 1.53–1.66 (m, 1H), 2.29 (s, 3H), 2.80 (q, J=7.5 Hz, 2H), 3.05 (d, J=7.1 Hz, 2H), 3.17 (t, J=7.4 Hz, 2H), 3.84 (s, 3H), 6.78 (d, J=4.6 Hz, 1H), 6.80–6.92 (m, 2H), 7.40 (d, J=8.4 Hz, 1H), 8.25 (d, J=4.6 Hz, 1H).

Example 279

N-[8-(2,6-Dimethoxy-3-pyridyl)-2-ethylimidazo[1,2-b]pyridazin-3-yl]-N,N-dipropylamine Yellow Crystals $^1$H NMR (400 MHz, CDCl$_3$) δ 0.87 (t, J=7.4 Hz, 6H), 1.32 (t, J=7.5 Hz, 3H), 1.30–1.42 (m, 4H), 2.79 (q, J=7.5 Hz, 2H), 3.18 (t, J=7.5 Hz, 4H), 3.98 (s, 3H), 4.00 (s, 3H), 6.51 (d, J=8.4 Hz, 1H), 7.32 (d, J=4.8 Hz, 1H), 8.24 (d, J=4.8 Hz, 1H), 8.64 (d, J=8.2 Hz, 1H).

Example 280

N-[8-(2,6-Dimethyl-3-pyridyl)-2-ethylimidazo[1,2-b]-pyridazin-3-yl]-N,N-dipropylamine Yellow Crystals $^1$H NMR (400 MHz, CDCl$_3$) δ 0.88 (t, J=7.4 Hz, 6H), 1.27 (t, J=7.6 Hz, 3H), 1.32–1.44 (m, 4H), 2.53 (s, 3H), 2.61 (s, 3H), 2.77 (q, J=7.6 Hz, 2H), 3.20 (t, J=7.4 Hz, 4H), 6.80 (d, J=4.8 Hz, 1H), 7.13 (d, J=7.9 Hz, 1H), 7.74 (d, J=7.7 Hz, 1H), 8.28 (d, J=4.8 Hz, 1H).

MS (ESI) m/z 352 MH$^+$

Example 281

N-[2-Ethyl-8-(6-methoxy-2-methyl-3-pyridyl)imidazo[1,2-b]pyridazin-3-yl]-N,N-dipropylamine Yellow Crystals $^1$H NMR (400 MHz, CDCl$_3$) δ 0.88 (t, J=7.3 Hz, 6H), 1.29 (t, J=7.6 Hz, 3H), 1.33–1.45 (m, 4H), 2.45 (s, 3H), 2.80 (q, J=7.5 Hz, 2H), 3.20 (t, J=7.5 Hz, 4H), 3.97 (s, 3H), 6.69

(d, J=8.4 Hz, 1H), 6.81 (d, J=3.1 Hz, 1H), 7.73 (d, J=8.4 Hz, 1H), 8.28 (d, J=4.4 Hz, 1H).
MS (ESI) m/z 368 MH+

Example 282

N-[2-Ethyl-8-(2-methoxy-4,6-dimethylphenyl)imidazo[1,2-b]pyridazin-3-yl]-N,N-dipropylamine Yellow Crystals
$^1$H NMR (400 MHz, CDCl$_3$) δ 0.88 (t, J=7.3 Hz, 6H), 1.20–1.30 (m, 3H), 1.33–1.46 (m, 4H), 2.05 (s, 3H), 2.37 (s, 3H), 2.66–2.88 (m, 2H), 3.20 (dd, J=6.4, 7.9 Hz, 4H), 3.70 (s, 3H), 6.69 (s, 1H), 6.77 (s, 2H), 8.26 (br s, 1H).
MS (ESI) m/z 381 MH+

Example 283

N-[8-(4-Chlorophenyl)-2-ethylimidazo[1,2-b]pyridazin-3-yl]N,N-dipropylamine

Pale Brown oil
$^1$H NMR (400 MHZ, CDCl$_3$) δ 0.87 (t, J=7.3 Hz, 6H), 1.36 (t, J=7.5 Hz, 3H), 1.32–1.44 (m, 4H), 2.85 (q, J=7.6 Hz, 2H), 3.20 (t, J=7.5 Hz, 4H), 7.04 (d, J=4.8 Hz, 1H), 7.50 (d, J=8.8 Hz, 2H), 8.14 (d, J=8.6 Hz, 2H), 8.31 (d, J=4.8 Hz, 1H).

Example 284

N-[8-(2,4-Dimethoxy-6-methylphenyl)-2-ethylimidazo[1,2-b]pyridazin-3-yl]-N,N-dipropylamine Yellow Crystals
$^1$H NMR (400 MHz, CDCl$_3$) δ 0.88 (t, J=7.4 Hz, 6H), 1.26 (t, J=7.1 Hz, 3H), 1.33–1.46 (m, 4H), 2.08 (s, 3H), 2.68–2.90 (m, 2H), 3.20 (dt, J=0.8, 7.3 Hz, 4H), 3.70 (s, 3H), 3.84 (s, 3H), 6.43 (d, J=1.8 Hz, 1H), 6.47 (d, J=2.2 Hz, 1H), 6.80 (br s, 1H), 8.26 (br s, 1H).

Example 285

N-[8-(2-Chloro-4-methoxyphenyl)-2-ethylimidazo[1,2-b]pyridazin-3-yl]-N,N-dipropylamine Yellow Oil
$^1$H NMR (400 MHz, CDCl$_3$) δ 0.88 (t, J=7.3 Hz, 6H), 1.29 (t, J=7.6 Hz, 3H), 1.34–1.46 (m, 4H), 2.81 (q, J=7.3 Hz, 2H), 3.20 (t, J=7.5 Hz, 4H), 3.86 (s, 3H), 6.95 (dd, J=2.5, 8.7 Hz, 1H), 7.03 (d, J=4.2 Hz, 1H), 7.07 (d, J=2.6 Hz, 1H), 7.70 (d, J=8.6 Hz, 1H), 8.29 (d, J=4.4 Hz, 1H).
MS (ESI) m/z 387 MH+

Example 286

N-[2-Ethyl-8-(4-methoxy-2,6-dimethylphenyl)imidazo[1,2-b]pyridazin-3-yl]-N,N-dipropylamine Yellow Crystals
$^1$H NMR (400 MHz, CDCl$_3$) δ 0.88 (t, J=7.4 Hz, 6H), 1.24 (t, J=7.5 Hz, 3H), 1.33–1.46 (m, 4H), 2.06 (s, 6H), 2.78 (q, J=7.2 Hz, 2H), 3.21 (t, J=7.6 Hz, 4H), 3.82 (s, 3H), 6.70 (s, 2H), 6.74 (br s, 1H), 8.28 (br s, 1H).
MS (ESI) m/z 381 MH+

Example 287

N-(2-Ethyl-8-mesitylimidazo[1,2-b]pyridazin-3-yl)-N,N-dipropylamine

Yellow Crystals
$^1$H NMR (400 MHz, CDCl$_3$) δ 0.88 (t, J=7.4 Hz, 6H), 1.23 (t, J=7.5 Hz, 3H), 1.33–1.46 (m, 4H), 2.03 (s, 6H), 2.33 (s, 3H), 2.76 (q, J=7.5 Hz, 2H), 3.21 (t, J=7.5 Hz, 4H), 6.72 (d, J=4.2 Hz, 1H), 6.97 (s, 2H), 8.27 (d, J=4.4 Hz, 1H).
MS (ESI) m/z 365 MH+

Example 288

N,N-Dicyclopropylmethyl-N-(2-ethyl-8-mesitylimidazo[1,2-b]pyridazin-3-yl)amine

Yellow Crystals
$^1$H NMR (400 MHz, CDCl$_3$) δ −0.18–0.04 (m, 4H), 0.18–0.34 (m, 4H), 0.76–0.92 (m, 2H), 1.26 (t, J=7.5 Hz, 3H), 2.02 (s, 6H), 2.33 (s, 3H), 2.76–2.90 (m, 2H), 3.18 (d, J=6.8 Hz, 4H), 6.72 (br s, 1H), 6.97 (s, 2H), 8.26 (br s, 1H).
MS (ESI) m/z 389 MH+

Example 289

N,N-Dicyclopropylmethyl-N-[2-ethyl-8-(2-methoxy-4,6-dimethylphenyl)imidazo[1,2-b]pyridazin-2-yl]amine Pale Green Crystals
$^1$H NMR (400 MHz, CDCl$_3$) δ −0.18–0.00 (m, 4H), 0.20–0.36 (m, 4H), 0.76–0.92 (m, 2H), 1.20–1.36 (m, 3H), 2.04 (s, 3H), 2.38 (s, 3H), 2.74–2.96 (m, 2H), 3.09–3.26 (m, 4H), 3.70 (s, 3H), 6.69 (s, 1H), 6.77 (s, 1H), 6.80 (br s, 1H), 8.26 (br s, 1H).
MS (ESI) m/z 405 MH+

Example 290

N-Cyclopropylmethyl-N-[2-ethyl-8-(2-methoxy-4,6-dimethylphenyl)imidazo[1,2-b]pyridazin-3-yl]-N-propylamine Yellow Crystals
$^1$H NMR (400 MHz, CDCl$_3$) δ −0.21–0.03 (m, 2H), 0.19–0.35 (m, 2H), 0.75–0.91 (m, 1H), 0.90 (t, J=7.3 Hz, 3H), 1.191.35 (m, 3H), 1.36–1.49 (m, 2H), 2.05 (s, 3H), 2.37 (s, 3H), 2.71–2.99 (m, 2H), 3.10 (d, J=6.8 Hz, 2H), 3.26 (dt, J=1.6, 7.3 Hz, 2H), 3.71 (s, 3H), 6.70 (s, 1H), 6.77 (s, 3H), 6.85 (br s, 1H), 8.29 (br s, 1H).

Example 291

N-[2-Ethyl-8-(2-methoxy-4,6-dimethylphenyl)imidazo[1,2-b]pyridazin-3-yl]-N-isobutyl-N-propylamine Yellow Crystals
$^1$H NMR (400 MHz, CDCl$_3$) δ0.81 (t, J=7.3 Hz, 3H), 0.85 (dd, J=1.8, 6.8 Hz, 6H), 1.18 (t, J=7.3 Hz, 3H), 1.26–1.38 (m, 2H), 1.48–1.62 (m, 1H), 1.99 (s, 3H), 2.31 (s, 3H), 2.63–2.82 (m, 2H), 2.98 (d, J=7.1 Hz, 2H), 3.10 (t, J=7.3 Hz, 2H), 3.64 (s, 3H), 6.62 (s, 1H), 6.70 (s, 1H), 6.75 (br s, 1H), 8.21 (br s, 1H).

Example 292

N-Cyclopropylmethyl-N-[2-ethyl-8-(2-methoxy-4,6-dimethylphenyl)imidazo[1,2-b]pyridazin-3-yl]-N-(3-fluoropropyl)amine Yellow Oil $^1$H NMR (400 MHz, CDCl$_3$) δ −0.21–0.03 (m, 2H), 0.19–0.37 (m, 2H), 0.75–0.91 (m, 1H), 1.26 (t, J=7.5 Hz, 3H), 1.69–1.91 (m, 2H), 2.04 (s, 3H), 2.37 (s, 3H), 2.71–2.89 (m, 2H), 3.12 (d, J=6.8 Hz, 2H), 3.40–3.54 (m, 2H), 3.70 (s, 3H), 4.51 (t, J=5.9 Hz, 1H), 4.62 (t, J=5.9 Hz, 1H), 6.69 (s, 1H), 6.77 (s, 1H), 6.83 (br s, 1H), 8.26 (d, J=4.6 Hz, 1H).

Example 293

N-[2-Ethyl-8-(2-methoxy-4,6-dimethylphenyl)imidazo[1,2-b]pyridazin-3-yl]-N-(3-fluoropropyl)-N-propylamine Yellow Crystals $^1$H NMR (400 MHz, CDCl$_3$) δ 0.89 (t, J=7.3 Hz, 3H), 1.20–1.30 (m, 3H), 1.34–1.48 (m, 2H), 1.66–1.85 (m, 2H), 2.05 (s, 3H), 2.37 (s, 3H), 2.68–2.88 (m, 2H), 3.21 (t, J=7.4 Hz, 2H), 3.41 (t, J=7.1 Hz, 2H), 3.70 (s, 3H), 4.48 (t, J=5.7 Hz, 1H), 4.60 (t, J=5.7 Hz, 1H), 6.69 (s, 1H), 6.77 (s, 1H), 6.84 (br s, 1H), 8.28 (br s, 1H).

Example 294

8-(4-Methoxy-2-methylphenyl)-2-(methylsulfanyl)imidazo[1,2-b]pyridazin-3-amine

A 5N aqueous sodium hydroxide solution (0.88 mL) was added to a solution of ethyl 8-(4-methoxy-2-methylphenyl)-2-(methylsulfanyl)imidazo[1,2-b]pyridazine-3-carboxylate (628 mg) in ethanol (20 mL), and the mixture was heated under reflux for 1 hour. After ice-cooling, 5N hydrochloric acid (0.88 mL) was added thereto, then the solvent was evaporated. The resulting crude 8-(4-methoxy-2-methylphenyl)-2-(methylsulfanyl)imidazo[1,2-b]pyridazine-3-carboxylic acid was used in the next reaction without purification.

The resulting 8-(4-methoxy-2-methylphenyl)-2-(methylsulfanyl)imidazo[1,2-b]pyridazine-3-carboxylic acid was dissolved in toluene (10 mL), then tert-butyl alcohol (10 mL), triethylamine (0.49 mL) and diphenylphosphorylazide (0.38 mL) were added thereto, and the mixture was heated at 100° C. for 4 hours. After completion of the reaction, water was added thereto, which was extracted with ethyl acetate, washed with water, dried over anhydrous magnesium sulfate, and evaporated. The resulting Boc compound was dissolved in ethyl acetate (10 mL) without purification, then a 4N hydrochloric acid-ethyl acetate solution (15 mL) was added thereto, and the mixture was stirred at room temperature for 3 hours. Under ice-cooling, a 5N aqueous sodium hydroxide solution was added thereto, which was neutralized and extracted with ethyl acetate. The material was washed with water, dried over anhydrous magnesium sulfate, and evaporated. The resulting residue was purified by silica gel column chromatography (ethyl acetate:n-hexane=1:2) to give the title compound (73 mg) as a brown oil.

$^1$HNMR (400 MHz, CDCl$_3$) δ 2.29 (s, 3H), 2.55 (s, 3H), 3.85 (s, 3H), 6.80–6.96 (m, 3H), 7.37 (d, J=8.8 Hz, 1H), 8.42 (d, J=4.6 Hz, 1H).

Example 295

N-[8-(4-Methoxy-2-methylphenyl)-2-(methylsulfanyl)imidazo[1,2-b]pyridazin-3-yl]-N,N-dipropylamine 8-(4-Methoxy-2-methylphenyl)-2-(methylsulfanyl)imidazo[1,2-b]pyridazin-3-amine obtained in Example 294 was alkylated at its amino group in the same manner as that of Example 4 to give the title compound as an orange oil.

$^1$H NMR (400 MHz, CDCl$_3$) δ 0.88 (t, J=7.3 Hz, 6H), 1.36–1.48 (m, 4H), 2.31 (s, 3H), 2.56 (s, 3H), 3.23 (t, J=7.6 Hz, 4H), 3.86 (s, 3H), 6.78 (d, J=4.8 Hz, 1H), 6.80–6.92 (m, 2H), 7.43 (d, J=8.4 Hz, 1H), 8.26 (d, J=4.6 Hz, 1H).

Hereinafter, the compound Example 296 was synthesized in the same manner as that of Example 295.

Example 296

N,N-Dicyclopropylmethyl-N-[8-(4-methoxy-2-methylphenyl)-2-(methylsulfanyl)imidazo[1,2-b]pyridazin-3-yl]amine Yellow Oil $^1$H NMR (400 MHz, CDCl$_3$) δ −0.11–0.01 (m, 4H), 0.23–0.34 (m, 4H), 0.85–0.99 (m, 2H), 2.28 (s, 3H), 2.59 (s, 3H), 3.20 (d, J=6.8 Hz, 4H), 3.86 (s, 3H), 6.81 (d, J=4.8 Hz, 1H), 6.83–6.90 (m, 2H), 7.42 (d, J=8.4 Hz, 1H), 8.27 (d, J=4.6 Hz, 1H).

Hereinafter, compounds of Examples 297 to 371 were synthesized in the same manner as that of Example 127.

Example 297

N-[8-(2,4-Dichlorophenyl)-2-(methylsulfanyl)imidazo[1,2-a]pyridin-3-yl]-N,N-dipropylamine Yellow Oil $^1$H NMR (400 MHz, CDCl$_3$) δ 0.88 (t, J=7.6 Hz, 6H), 1.38–1.44 (m, 4H), 2.52 (s, 3H), 3.00–3.20 (m, 4H), 6.82 (dd, J=6.8, 6.8 Hz, 1H), 7.14 (d, J=6.8 Hz, 1H), 7.33 (dd, J=2.0, 8.0 Hz, 1H), 7.52 (d, J=2.0 Hz, 1H9, 7.62 (d, J=8.4 Hz, 1H), 8.11 (d, J=8.4 Hz, 1H).

Example 298

N-[8-(2-Methoxy-4,6-dimethylphenyl)-2-(methylsulfanyl)imidazo[1,2-a]pyridin-3-yl]-N,N-dipropylamine White Crystals $^1$H NMR (400 MHz, CDCl$_3$) δ 0.88 (t, J=7.2 Hz, 6H), 1.38–1.45 (m, 4H), 2.03 (s, 3H), 2.38 (s, 3H), 2.46 (s, 3H), 3.00–3.20 (m, 4H), 3.68 (s, 3H), 6.67 (s, 1H), 6.75 (s, 1H), 6.79 (dd, J=6.8, 6.8 Hz, 1H), 6.95 (dd, J=1.6, 6.8 Hz, 1H), 8.07 (dd, J=1.2, 6.8 Hz, 1H).

Example 299

N-[8-(2-Chloro-4-methoxyphenyl)-2-(methylsulfanyl)imidazo[1,2-a]pyridin-3-yl]-N,N-dipropylamine Yellow Oil $^1$H NMR (400 MHz, CDCl$_3$) δ 0.88 (t, J=6.8 Hz, 6H), 1.38–1.45 (m, 4H), 2.52 (s, 3H), 3.00–3.20 (m, 4H), 3.85 (s, 3H), 6.81 (dd, J=6.8, 6.8 Hz, 1H), 6.90 (dd, J=2.4, 8.4 Hz, 1H), 7.05 (d, J=2.4 Hz, 1H), 7.14 (dd, J=1.2, 6.8 Hz, 1H), 7.60 (d, J=8.0 Hz, 1H), 8.09 (dd, J=1.2, 6.8 Hz, 1H).

Example 300

N-[8-(2,4-Dichlorophenyl)-2-(methylsulfanyl)imidazo[1,2-a]pyridin-3-yl]-N-isobutylamine Yellow Crystals $^1$H NMR (400 MHz, CDCl$_3$) δ 1.06 (d, J=6.8 Hz, 6H), 1.80–1.90 (m, 1H), 2.46 (s, 3H), 2.76–2.96 (m, 2H), 3.30 (br s, 1H), 6.85 (dd, J=7.2, 7.2 Hz, 1H), 7.11 (dd, J=1.2, 2.7 Hz, 1H), 7.33 (dd, J=2.0, 8.0 Hz, 1H), 7.52 (d, J=2.0 Hz, 1H), 7.55 (d, J=8.0 Hz, 1H), 8.00 (dd, J=1.2, 6.4 Hz, 1H).

Example 301

N-[8-(2,4-Dichlorophenyl)-2-(methylsulfanyl)imidazo[1,2-a]pyridin-3-yl]-N-isobutyl-N-propylamine Yellow Crystals $^1$H NMR (400 MHz, CDCl$_3$) δ 0.87 (t, J=7.2 Hz, 3H), 0.92 (d, J=6.8 Hz, 6H), 1.35–1.50 (m, 2H), 1.55–1.63 (m, 1H), 2.52 (s, 3H), 2.90–3.10 (m, 4H), 6.83 (dd, J=7.2, 7.2 Hz, 1H), 7.14 (dd, J=1.2, 6.8 Hz, 1H), 7.33 (dd, J=2.0, 8.4 Hz, 1H), 7.52 (d, J=2.0 Hz, 1H), 7.62 (d, J=8.4 Hz, 1H), 8.14 (dd, J=1.2, 6.8 Hz, 1H).

Example 302

N-Cyclopropylmethyl-N-[8-(2,4-dichlorophenyl)-2-(methylsulfanyl)imidazo[1,2-a]pyridin-3-yl]-N-isobutylamine Yellow Oil $^1$H NMR (400 MHz, CDCl$_3$) δ −0.15–0.10 (m, 2H), 0.15–0.40 (m, 2H), 0.75–0.85 (m, 1H), 0.93 (d, J=6.8 Hz, 6H), 1.53–1.68 (m, 1H), 2.86–3.22 (m, 4H), 6.82 (dd, J=6.8, 6.8 Hz, 1H), 7.13 (dd, J=1.2, 6.8 Hz, 1H), 7.33 (dd, J=2.0, 8.4 Hz, 1H), 7.52 (d, J=2.4 Hz, 1H), 7.61 (d, J=8.4 Hz, 1H), 8.23 (dd, J=1.2, 6.8 Hz, 1H).

Example 303

N-Butyl-N-[8-(2,4-dichlorophenyl)-2-(methylsulfanyl)imidazo[1,2-a]pyridin-3-yl]-N-isobutylamine Yellow Crystals $^1$H NMR (400 MHz, CDCl$_3$) δ 0.86 (t, J=7.2 Hz, 3H), 0.92 (d, J=6.4 Hz, 6H), 1.24–1.41 (m, 4H), 1.50–1.65 (m, 1H), 2.52 (s, 3H), 2.80–3.10 (m, 4H), 6.83 (dd, J=6.8, 6.8 Hz, 1H), 7.14 (dd, J=1.2, 6.8 Hz, 1H), 7.33 (dd, J=2.0, 8.4 Hz, 1H), 7.52 (d, J=2.0 Hz, 1H), 7.63 (d, J=8.4 Hz, 1H), 8.13 (dd, J=1.2, 7.2 Hz, 1H).

Example 304

N-[8-(2,4-Dichlorophenyl)-2-(methylsulfanyl)imidazo[1,2-a]pyridin-3-yl]-N-isobutyl-N-(2-methoxyethyl)amine Greenish Brown Oil $^1$H NMR (400 MHz, CDCl$_3$) δ 0.92 (d, J=6.8 Hz, 6H), 1.50–1.65 (m, 1H), 2.52 (s, 3H) 2.80–3.45 (m, 6H), 6.83 (dd, J=7.2, 6.8 Hz, 1H), 7.14 (dd, J=1.2, 7.2 Hz, 1H), 7.33 (dd, J=2.0, 8.4 Hz, 1H), 7.52 (d, J=2.0 Hz, 1H), 7.61 (d, J=8.4 Hz, 1H), 8.24 (dd, J=1.2, 6.8 Hz, 1H).

Example 305

N-[8-(2,6-Dimethoxy-3-pyridyl)-2-(methylsulfanyl)imidazo[1,2-a]pyridin-3-yl]-N,N-dipropylamine Yellow Crystals $^1$H NMR (400 MHz, CDCl$_3$) δ 0.87 (t, J=7.2 Hz, 6H), 1.35–1.43 (m, 4H), 2.56 (s, 3H), 3.00–3.20 (m, 4H), 3.96 (s, 3H), 3.97 (s, 3H), 6.45 (d, J=8.0 Hz, 1H), 6.80 (dd, J=6.8, 7.2 Hz, 1H), 7.39 (dd, J=1.2, 7.2 Hz, 1H), 8.03 (dd, J=1.2, 6.4 Hz, 1H), 8.31 (d, J=8.4 Hz, 1H).

Example 306

N-[8-(2,6-Dimethoxy-4-methylphenyl)-2-(methylsulfanyl)imidazo[1,2-a]pyridin-3-yl]-N,N-dipropylamine White Crystals $^1$H NMR (400 MHz, CDCl$_3$) δ 0.88 (t, J=7.2 Hz, 6H), 1.39–1.46 (m, 4H), 2.41 (s, 3H), 2.47 (s, 3H), 3.00–3.20 (m, 4H), 3.71 (s, 6H), 6.51 (s, 2H), 6.78 (dd, J=6.8, 6.8 Hz, 1H), 7.02 (dd, J=1.2, 6.8 Hz, 1H), 8.04 (dd, J=1.6, 6.8 Hz, 1H).

Example 307

N-[8-(2,4-Dichlorophenyl)-2-(methylsulfanyl)imidazo[1,2-a]pyridin-3-yl]-N-(3-fluoropropyl)-N-isobutylamine Yellow Oil $^1$H NMR (400 MHz, CDCl$_3$) δ 0.94 (d, J=6.8 Hz, 6H), 1.50–1.65 (m, 1H), 1.70–1.90 (m, 2H), 2.53 (s, 3H), 2.82–3.38 (m, 4H), 4.43 (t, J=6.0 Hz, 1H), 4.54 (t, J=5.5 Hz, 1H), 6.85 (dd, J=6.8, 6.8 Hz, 1H), 7.15 (dd, J=1.2, 6.8 Hz, 1H), 7.35 (dd, J=2.8, 8.0 Hz, 1H), 7.53 (d, J=2.0 Hz, 1H), 7.61 (d, J=8.0 Hz, 1H), 8.10 (dd, J=1.2, 6.8 Hz, 1H).

Example 308

N-[8-(2,4-Dichlorophenyl)-2-(methylsulfanyl)imidazo[1,2-a]pyridin-3-yl]-N-(4-fluorobutyl)-N-isobutylamine Green Oil $^1$H NMR (400 MHz, CDCl$_3$) δ 0.93 (d, J=6.8 Hz, 6H), 1.40–1.80 (m, 5H), 2.82–3.22 (m, 4H), 4.34 (t, J=5.6 Hz, 1H), 4.46 (t, J=6.0 Hz, 1H), 6.84 (dd, J=6.8, 6.8 Hz, 1H), 7.15 (dd, J=1.2, 6.8 Hz, 1H), 7.34 (dd, J=2.0, 8.4 Hz, 1H), 7.53 (d, J=2.4 Hz, 1H), 7.62 (d, J=8.4 Hz, 1H), 8.11 (dd, J=1.2, 6.8 Hz, 1H).

Example 309

N-[8-(2,4-Dimethoxyphenyl)-2-(methylsulfanyl)imidazo[1,2-a]pyridin-3-yl]-N,N-dipropylamine White Crystals $^1$H NMR (400 MHz, CDCl$_3$) δ 0.87 (t, J=7.2 Hz, 6H), 1.37–1.44 (m, 4H), 2.54 (s, 3H), 3.00–3.20 (m, 4H), 3.80 (s, 3H), 3.87 (s, 3H), 6.60–6.63 (m, 2H), 6.79 (dd, J=7.2, 7.2 Hz, 1H), 7.75 (br d, J=8.0 Hz, 1H), 8.03 (br d, J=6.4 Hz, 1H).

Example 310

N-[8-(2,6-Dimethyl-3-pyridyl)-2-(methylsulfanyl)imidazo[1,2-a]pyridin-3-yl]-N,N-dipropylamine Yellow Oil $^1$H NMR (400 MHz, CDCl$_3$) δ 0.87 (t, J=7.2 Hz, 6H), 1.30–1.50 (m, 4H), 2.47 (s, 3H), 2.52 (s, 3H), 2.60 (s, 3H), 6.81 (dd, J=6.8, 6.8 Hz, 1H), 6.97 (dd, J=1.6, 6.8 Hz, 1H), 7.07 (d, J=8.0 Hz, 1H), 7.64 (d, J=7.6 Hz, 1H), 8.11 (dd, J=1.6, 6.8 Hz, 1H).

Example 311

N-Cyclopropylmethyl-N-[8-(2,4-dichlorophenyl)-2-(methylsulfanyl)imidazo[1,2-a]pyridin-3-yl]-N-propylamine Yellow Oil $^1$H NMR (400 MHz, CDCl$_3$) δ −0.10–0.10 (m, 2H), 0.24–0.38 (m, 2H), 0.72–0.83 (m, 1H), 0.89 (t, J=7.6 Hz, 3H), 1.35–1.43 (m, 2H), 2.52 (s, 3H), 2.98 (br d, J=6.8 Hz, 2H), 3.05–3.30 (m, 2H), 6.82 (dd, J=7.2, 7.2 Hz, 1H), 7.13 (br d, J=6.8 Hz, 1H), 7.33 (dd, J=2.0, 8.4 Hz, 1H), 7.52 (d, J=2.0 Hz, 1H), 7.62 (d, J=8.4 Hz, 1H), 8.21 (dd, J=1.2, 6.8 Hz, 1H).

Example 312

N-[8-(2,4-Dichlorophenyl)-2-(methylsulfanyl)imidazo[1,2-a]pyridin-3-yl]-N-(3-fluoropropyl)-N-propylamine Yellow Oil $^1$H NMR (400 MHz, CDCl$_3$) δ 0.89 (t, J=7.2 Hz, 3H), 1.36–1.50 (m, 2H), 1.70–1.90 (m, 2H), 2.53 (s, 3H), 3.04–3.18 (m, 2H), 3.20–3.42 (m, 2H), 4.44 (t, J=6.0 Hz, 1H), 4.56 (t, J=6.0 Hz, 1H), 6.84 (dd, J=6.8 Hz, 1H), 7.15 (dd, J=1.2, 7.2 Hz, 1H), 7.33 (dd, J=1.6, 8.4 Hz, 1H), 7.52 (d, J=2.4 Hz, 1H), 7.61 (d, J=8.4 Hz, 1H), 8.08 (dd, J=1.6, 6.8 Hz, 1H).

Example 313

N-Cyclobutylmethyl-N-[8-(2,4-dichlorophenyl)-2-(methylsulfanyl)imidazo[1,2-a]pyridin-3-yl]-N-propylamine Yellow Oil $^1$H NMR (400 MHz, CDCl$_3$) δ 0.88 (t, J=7.2 Hz, 3H), 1.30–1.43 (m, 2H), 1.50–1.63 (m, 2H), 1.70–1.90 (m, 4H), 2.22–2.36 (m, 1H), 2.52 (s, 3H), 2.90–3.35 (m, 4H), 6.81 (dd, J=6.8 Hz, 1H) 7.12 (dd, J=1.2, 6.8 Hz, 1H), 7.33 (dd, J=2.4, 8.4 Hz, 1H), 7.52 (d, J=2.0 Hz, 1H), 7.61 (d, J=8.4 Hz, 1H), 8.09 (dd, J=1.2, 6.8 Hz, 1H).

Example 314

N-[8-(6-Methoxy-2-methyl-3-pyridyl)-2-(methylsulfanyl)imidazo[1,2-a]pyridin-3-yl]-N,N-dipropylamine Yellow Oil $^1$H NMR (400 MHz, CDCl$_3$) δ 0.88 (t, J=7.2 Hz, 6H), 1.30–1.50 (m, 4H), 2.41 (s, 3H), 2.53 (s, 3H), 3.00–3.20 (m, 4H), 3.98 (s, 3H), 6.65 (d, J=8.4 Hz, 1H), 6.80 (dd, J=8.0, 8.0 Hz, 1H), 6.96 (dd, J=2.0, 6.8 Hz, 1H), 7.66 (d, J=8.0 Hz, 1H), 8.09 (dd, J=2.0, 6.8 Hz, 1H).

Example 315

N-[8-(2,4-Dichlorophenyl)-2-(methylsulfanyl)imidazo[1,2-a]pyridin-3-yl]-N-(4-fluorobutyl)-N-propylamine Yellow Oil $^1$H NMR (400 MHz, CDCl$_3$) δ 0.88 (t, J=7.6 Hz, 3H), 1.35–1.80 (m, 6H), 2.53 (s, 3H), 3.02–3.25 (m, 4H), 4.35 (t, J=6.0 Hz, 1H), 4.47 (t, J=6.4 Hz, 1H), 6.84 (dd, J=6.8 Hz, 1H), 7.15 (dd, J=1.2, 6.8 Hz, 1H), 7.33 (dd, J=2.0, 8.0 Hz, 1H), 7.53 (d, J=2.4 Hz, 1H), 7.62 (d, J=8.4 Hz, 1H), 8.09 (dd, J=1.6, 6.8 Hz, 1H).

Example 316

N-Cyclopropylmethyl-N-[8-(2,6-dimethoxy-4-methylphenyl)-2-(methylsulfanyl)imidazo[1,2-a]pyridin-3-yl]-N-(3-fluoropropyl)amine Pale Green Crystals $^1$H NMR (400 MHz, CDCl$_3$) δ −0.10–0.10 (m, 2H), 0.20–0.40 (m, 2H), 0.75–0.90 (m, 1H), 1.70–1.90 (m, 2H), 2.41 (s, 3H), 2.48 (s, 3H), 2.98 (br d, J=6.8 Hz, 2H), 3.20–3.60 (m, 2H), 3.70 (s, 3H), 4.45 (t, J=5.2 Hz, 1H), 4.57 (t, J=5.6 Hz, 1H), 6.51 (s, 2H), 6.80 (dd, J=6.8, 6.8 Hz, 1H), 7.02 (dd, J=1.2, 7.2 Hz, 1H), 8.07 (dd, J=1.2, 6.8 Hz, 1H).

Example 317

N-[8-(2,6-Dimethoxy-4-methylphenyl)-2-(methylsulfanyl)imidazo[1,2-a]pyridin-3-yl]-N-(3-fluoropropyl)-N-propylamine Pale Gray Crystals $^1$H NMR (400 MHz, CDCl$_3$) δ 0.88 (t, J=6.8 Hz, 3H), 1.30–1.50 (m, 2H), 1.70–1.83 (m, 2H), 2.42 (s, 3H), 2.47 (s, 3H), 3.05–3.12 (m, 2H), 3.22–3.60 (m, 2H), 3.71 (s, 6H), 4.44 (t, J=5.6 Hz, 1H), 4.56 (t, J=6.0 Hz, 1H), 6.51 (s, 2H), 6.80 (dd, J=6.8, 6.8 Hz, 1H), 7.03 (br d, J=6.8 Hz, 1H), 7.99 (br d, J=6.8 Hz, 1H).

Example 318

N-Cyclopropylmethyl-N-[8-(2,4-dichlorophenyl)-2-(methylsulfanyl)imidazo[1,2-a]pyridin-3-yl]-N-(3-fluoropropyl)amine Yellow Oil $^1$H NMR (400 MHz, CDCl$_3$) δ −0.10–1.00 (m, 2H), 0.25–0.40 (m, 2H), 0.75–0.85 (m, 1H), 1.72–1.82 (m, 2H), 2.53 (s, 3H), 2.99 (br d, J=7.2 Hz, 2H), 3.20–3.60 (m, 2H), 4.45 (t, J=6.6 Hz, 1H), 4.57 (t, J=5.6 Hz, 1H), 6.84 (dd, J=6.8, 6.8 Hz, 1H), 7.15 (dd, J=1.2, 6.8 Hz, 1H), 7.34 (dd, J=2.0, 8.4 Hz, 1H), 7.52 (d, J=2.0 Hz, 1H), 7.60 (d, J=8.4 Hz, 1H), 8.16 (dd, J=1.6, 6.8 Hz, 1H).

Example 319

N-[8-(2,4-Dichlorophenyl)-2-(methylsulfanyl)imidazo[1,2-a]pyridin-3-yl]-N-propyl-N-tetrahydro-2-franylmethylamine Yellow Oil $^1$H NMR (400 MHz, CDCl$_3$) δ 0.87 (t, J=7.2 Hz, 3H), 1.30–1.60 (m,4H), 1.70–1.90 (m, 2H), 3.10–3.30 (m,4H), 3.60–3.90 (m, 3H), 6.83 (dd, J=7.2, 7.2 Hz, 1H), 7.15 (dd, J=2.0, 7.2 Hz, 1H), 7.33 (dd, J=2.0, 8.4 Hz, 1H), 7.61 (d, J=8.0 Hz, 1H), 8.25 (dd, J=1.2, 6.8 Hz, 1H).

Example 320

N-[8-(2,6-Dimethoxy-4-methylphenyl)-2-(methylsulfanyl)imidazo[1,2-a]pyridin-3-yl]-N-(3-fluoropropyl)-N-isobutylamine Yellow Oil $^1$H NMR (400 MHz, CDCl$_3$) δ 0.94 (d, J=6.4 Hz, 1H), 1.50–1.60 (m, 1H), 1.70–1.85 (m, 2H), 2.42 (s, 3H), 2.48 (s, 3H), 2.90–3.08 (m, 2H), 3.10–3.40 (m, 2H), 3.71 (s, 6H), 4.43 (t, J=6.0 Hz, 1H), 4.55 (t, J=6.0 Hz, 1H), 6.51 (s, 2H), 6.81 (dd, J=6.8, 6.8 Hz, 1H), 7.03 (d, J=6.0 Hz, 1H), 8.03 (br d, J=6.4 Hz, 1H).

Example 321

N-[8-(2,4-Dimethoxy-6-methylphenyl)-2-(methylsulfanyl)imidazo[1,2-a]pyridin-3-yl]-N,N-dipropylamine Yellow Oil $^1$H NMR (400 MHz, CDCl$_3$) δ 0.88 (t, J=7.2 Hz, 6H), 1.35–1.45 (m, 4H), 2.06 (s, 3H), 2.47 (s, 3H), 3.00–3.20 (m, 4H), 3,67 (s, 3H), 3.85 (s, 3H), 6.43 (d, J=2.4 Hz, 1H), 6.47 (d, J=2.0 Hz, 1H), 6.79 (dd, J=6.8, 6.8 Hz, 1H), 6.94 (dd, J=1.2, 6.4 Hz, 1H), 8.07 (dd, J=1.2, 8.0 Hz, 1H).

Example 322

N-[8-(2-Ethoxy-6-methoxy-4-methylphenyl)-2-(methylsulfanyl)imidazo[1,2-a]pyridin-3-yl]-N,N-dipropylamine Yellow Crystals $^1$H NMR (400 MHz, CDCl$_3$) δ 0.86 (t, J=7.6 Hz, 6H), 1.05 (t, J=6.8 Hz, 3H), 1.35–1.43 (m, 4H), 2.40 (s, 3H), 2.47 (s, 3H), 3.00–3.20 (m, 4H), 3.72 (s, 3H), 3.91–4.05 (m, 2H), 6.50 (br s, 2H), 6.78 (dd, J=6.8, 6.8 Hz, 1H), 7.03 (dd, J=1.2, 6.8 Hz, 1H), 8.04 (dd, J=1.2, 6.8 Hz, 1H).

Example 323

N-[8-(2,6-Dimethoxy-4-methylphenyl)-2-(methylsulfanyl)imidazo[1,2-a]pyridin-3-yl]-N,N-di(3-fluoropropyl)amine Pale Green Crystals $^1$H NMR (400 MHz, CDCl$_3$) δ 1.70–1.89 (m, 4H), 2.42 (s, 3H), 2.49 (s, 3H), 3.20–3.40 (m, 4H), 3.71 (s, 6H), 4.44 (t, J=5.6 Hz, 1H), 4.56 (t, J=5.6 Hz, 1H), 6.51 (s, 2H), 6.83 (dd, J=6.8, 6.8 Hz, 1H), 7.05 (dd, J=1.2, 5.6 Hz, 1H), 7.97 (dd, J=1.6, 6.8 Hz, 1H).

Example 324

N-[8-(2-Chloro-6-methoxy-4-methylphenyl)-2-(methylsulfanyl)imidazo[1,2-a]pyridin-3-yl]-N,N-dipropylamine Yellow Crystals $^1$H NMR (400 MHz, CDCl$_3$) δ 0.88 (t, J=7.2 Hz, 6H), 1.35–1.45 (m, 4H), 2.39 (s, 3H), 2.46 (s, 3H), 3.05–3.20 (m, 4H), 3.70 (s, 3H), 6.73 (s, 3H), 6.80 (dd, J=7.2, 7.2 Hz, 1H), 6.95 (br s, 1H), 6.99 (dd, J=1.2, 5.6 Hz, 1H), 8.09 (br d, J=6.8 Hz, 1H).

Example 325

N-[8-Mesityl-2-(methylsulfanyl)imidazo[1,2-a]pyridin-3-yl]-N,N-dipropylamine

Yellow Oil $^1$H NMR (400 MHz, CDCl$_3$) δ 0.88 (t, J=7.2 Hz, 6H), 1.35–1.42 (m, 4H), 2.02 (s, 6H), 2.34 (s, 3H), 2.45 (s, 3H), 3.05–3.20 (m, 4H), 6.78 (dd, J=6.8, 6.8 Hz, 1H), 6.88 (dd, J=1.2, 6.8 Hz, 1H), 6.96 (s, 2H), 8.09 (dd, J=1.2, 6.4 Hz, 1H).

Example 326

N-[8-(2-Methoxy-4-methylphenyl)-2-(methylsulfanyl)imidazo[1,2-a]pyridin-3-yl]-N,N-dipropylamine Yellow Oil $^1$H NMR (400 MHz, CDCl$_3$) δ 0.87 (t, J=7.2 Hz, 6H), 1.35–1.45 (m, 4H), 2.42 (s, 3H), 2.53 (s, 3H), 3.00–3.20 (m, 4H), 3.80 (s, 3H), 6.76–6.90 (m, 3H), 7.22 (dd, J=1.6, 7.2 Hz, 1H), 7.64 (d, J=8.0 Hz, 1H), 8.04 (dd, J=1.6, 6.8 Hz, 1H).

Example 327

N-[8-(4-Ethyl-2,6-dimethoxyphenyl)-2-(methylsulfanyl)imidazo[1,2-a]pyridin-3-yl]-N,N-dipropylamine Pale Yellow Crystals $^1$H NMR (400 MHz, CDCl$_3$) δ 0.88 (t, J=7.2 Hz, 6H), 1.31 (t, J=7.6 Hz, 3H), 1.30–1.50 (m, 4H), 2.47 (s, 3H), 2.70 (q, J=7.6 Hz, 2H), 3.02–3.18 (m, 4H), 3.72 (s, 6H), 6.53 (s, 2H), 6.79 (dd, J=6.8, 6.8 Hz, 1H), 7.03 (br d, J=6.8 Hz, 1H).

Example 328

N-Cyclopropylmethyl-N-[8-(2,6-dimethoxy-4-methylphenyl)-2-(methylsulfanyl)imidazo[1,2-a]pyridin-3-yl]-N-propylamine Yellow Oil $^1$H NMR (400 MHz, CDCl$_3$) δ −0.10–0.06 (m, 2H), 0.22–0.40 (m, 2H), 0.75–0.86 (m, 1H), 0.89 (t, J=7.2 Hz, 1H), 1.32–1.50 (m, 2H), 2.41 (s, 3H), 2.47 (s, 3H), 2.97 (br d, J=6.8 Hz, 2H), 3.10–3.30 (m, 2H), 3.70 (s, 6H), 6.51 (s, 2H), 6.78 (dd, J=6.8, 6.8 Hz, 1H), 7.02 (br d, J=6.4 Hz, 1H), 8.12 (dd, J=1.6, 6.8 Hz, 1H).

Example 329

N,N-Dicyclopropylmethyl-N-[8-(2,6-dimethoxy-4-methylphenyl)-2-(methylsulfanyl)imidazo[1,2-a]pyridin-3-yl]amine Yellow Oil $^1$H NMR (400 MHz, CDCl$_3$) δ −0.10–0.15 (m, 4H), 0.20–0.40 (m, 4H), 0.75–0.85 (m, 2H), 2.41 (s, 3H), 2.48 (s, 3H), 3.00–3.10 (m, 4H), 3.70 (s, 6H), 6.51 (s, 2H), 6.79 (dd, J=6.8, 6.8 Hz, 1H), 7.02 (dd, J=1.2, 6.4 Hz, 1H), 8.20 (dd, J=1.2, 6.8 Hz, 1H).

Example 330

N,N-Dicyclopropylmethyl-N-[8-(2-methoxy-4,6-dimethylphenyl)-2-(methylsulfanyl)-imidazo[1,2-a]pyridin-3-yl]amine Yellow Oil $^1$H NMR (400 MHz, CDCl$_3$) δ −0.10–0.10 (m, 4H), 0.20–0.30 (m, 4H), 0.75–0.85 (m, 2H), 2.02 (s, 3H), 2.38 (s, 3H), 2.46 (s, 3H), 3.00–3.10 (m, 4H), 3.68 (s, 3H), 6.68 (br s, 1H), 6.75–6.81 (m, 2H), 6.95 (dd, J=1.2, 6.4 Hz, 1H), 8.23 (dd, J=1.2, 6.8 Hz, 1H).

Example 331

N-[8-(2-Fluoro-4,6-dimethoxyphenyl)-2-(methylsulfanyl)imidazo[1,2-a]pyridin-3-yl]-N,N-dipropylamine Pale Yellow Crystals $^1$H NMR (400 MHz, CDCl$_3$) δ 0.87 (t, J=7.2 Hz, 6H), 1.30–1.50 (m, 4H), 2.49 (s, 3H), 3.00–3.20 (m, 4H), 3.74 (s, 3H), 3.84 (s, 3H), 6.36–6.40 (m, 2H), 6.79 (dd, J=7.2, 7.2 Hz, 1H), 7.04 (br d, J=6.8 Hz, 1H), 8.07 (dd, J=1.2, 6.8 Hz, 1H).

Example 332

N-[8-(4-Chloro-2-methoxyphenyl)-2-(methylsulfanyl)imidazo[1,2-a]pyridin-3-yl]-N,N-dipropylamine Pale Yellow Crystals $^1$H NMR (400 MHz, CDCl$_3$) δ 0.87 (t, J=7.2 Hz, 6H), 1.35–1.43 (m, 4H), 2.53 (s, 3H), 3.00–3.17 (m, 4H), 3.81 (s, 3H), 6.80 (dd, J=6.8, 6.8 Hz, 1H), 7.01 (d, J=2.4 Hz, 1H), 7.05 (dd, J=1.6, 8.0 Hz, 1H), 7.72 (dd, J=1.2, 8.4 Hz, 1H), 8.06 (dd, J=1.2, 6.8 Hz, 1H).

Example 333

N-[2-(Methylsulfanyl)-8-(2,4,6-trimethoxyphenyl)imidazo[1,2-a]pyridin-3-yl]-N,N-dipropylamine Yellow Oil $^1$H NMR (400 MHz, CDCl$_3$) δ 0.88 (t, J=7.6 Hz, 6H), 1.35–1.45 (m, 4H), 2.47 (s, 3H), 3.03–3.16 (m, 4H), 3.71 (s, 6H), 3.87 (s, 3H), 6.26 (s, 2H), 6.78 (dd, J=6.8, 6.8 Hz, 1H), 7.01 (dd, J=1.6, 6.8 Hz, 1H), 8.04 (dd, 1.6, 6.8 Hz, 1H).

Example 334

N-[8-(2,4-Dichlorophenyl)-2-(methylsulfanyl)imidazo[1,2-a]pyridin-3-yl]-N-propyl-N-(2-propinyl)amine Yellow Oil $^1$H NMR (400 MHz, CDCl$_3$) δ 0.91 (t, J=7.6 Hz, 3H), 1.41–1.50 (m, 2H), 2.17 (t, J=2.4 Hz, 1H), 2.52 (s, 3H), 3.20–3.30 (m, 2H), 3.92 (d, J=2.8 Hz, 2H), 6.84 (dd, 7.2, 7.2 Hz, 1H), 7.16 (dd, J=1.2, 6.8 Hz, 1H), 7.33 (dd, J=2.0, 8.4 Hz, 1H), 7.53 (d, J=2.0 Hz, 1H), 7.60 (d, J=8.0 Hz, 1H), 8.17 (dd, J=1.2, 6.8 Hz, 1H).

Example 335

N-[8-(4-Methoxyphenyl)-2-(methylsulfanyl)-imidazo[1,2-a]pyridin-3-yl]-N,N-dipropylamine Yellow Oil $^1$H NMR (400 MHz, CDCl$_3$) δ 0.87 (t, J=7.6 Hz, 6H), 1.35–1.43 (m, 4H), 2.62 (s, 3H), 3.00–3.18 (m, 4H), 3.87 (s, 3H), 6.81 (dd, J=6.8, 6.8 Hz, 1H), 7.00–7.02 (m, 2H), 7.20 (dd, J=1.6, 7.2 Hz, 1H), 8.03–8.08 (m, 3H).

Example 336

N-[8-(2,6-Dimethoxy-4-methylphenyl)-2-(methylsulfanyl)imidazo[1,2-a]pyridin-3-yl]-N-propyl-N-(3-thienyl)amine Yellow Crystals $^1$H NMR (400 MHz, CDCl$_3$) δ 0.94 (t, J=7.6 Hz, 3H), 1.63–1.72 (m, 2H), 2.43 (br s, 6H), 3.55–3.63 (m, 1H), 3.73 (s, 6H), 6.02–6.03 (m, 1H), 6.29–6.31 (m, 1H), 6.53 (s, 2H), 6.79 (dd, J=6.8, 6.8 Hz, 1H), 7.08–7.13 (m, 2H), 7.71 (dd, J=1.6, 6.8 Hz, 1H).

Example 337

N-(2-Butynyl)-N-[8-(2,4-dichlorophenyl)-2-(methylsulfanyl)imidazo[1,2-a]pyridin-3-yl]-N-propylamine Yellow Oil $^1$H NMR (400 MHz, CDCl$_3$) δ 0.90 (t, J=7.2 Hz, 3H), 1.35–1.46 (m, 2H), 1.72 (t, J=2.4 Hz, 3H), 3.20–3.30 (m, 2H), 3.81 (q, J=2.4 Hz, 2H), 6.83 (dd, J=6.8, 6.8 Hz, 1H), 7.14 (dd, J=1.2, 6.8 Hz, 1H), 7.33 (dd, J=2.0, 8.4 Hz, 1H), 7.52 (d, J=2.0 Hz, 1H), 7.61 (d, J=8.4 Hz, 1H), 8,17 (dd, J=1.2, 6.8 Hz, 1H).

Example 338

N-[8-(2,4-Dichloro-6-methoxyphenyl)-2-(methylsulfanyl)imidazo[1,2-a]pyridin-3-yl]-N,N-dipropylamine Yellow Oil $^1$H NMR (400 MHz, CDCl$_3$) δ0.88 (t, J=7.2 Hz, 6H), 1.35–1.45 (m, 4H), 2.47 (s, 3H), 3.03–3.20 (m, 4H), 3.71 (s, 3H), 6.81 (dd, J=6.8, 6.8 Hz, 1H), 6.90 (d, J=1.6 Hz, 1H), 6.97 (dd, J=1.2, 6.8 Hz, 1H), 7.14 (d, J=1.6 Hz, 1H), 8.11 (dd, J=1.6, 6.8 Hz, 1H).

Example 339

N-[8-(2,4-Dichlorophenyl)-2-(methylsulfanyl)imidazo[1,2-a]pyridin-3-yl]-N-ethyl-N-propylamine Green Oil $^1$H NMR (400 MHz, CDCl$_3$) δ 0.88 (t, J=7.6 Hz, 3H), 0.99 (t, J=7.2 Hz, 3H), 1.32–1.48 (m, 2H), 2.52 (s, 3H), 3.10–3.25 (m, 4H), 6.82 (dd, J=6.8, 6.8 Hz, 1H), 7.14 (dd, J=1.2, 6.8 Hz, 1H), 7.33 (dd, J=2.0, 8.4 Hz, 1H), 7.52 (d, J=2.0 Hz, 1H), 7.62 (d, J=8.4 Hz, 1H), 8.12 (dd, J=1.6, 6.8 Hz, 1H).

Example 340

N-[8-(4-Methoxy-2-methylphenyl)-2-(methylsulfanyl)imidazo[1,2-a]pyridin-3-yl]-N,N-dipropylamine Yellow Oil $^1$H NMR (400 MHz, CDCl$_3$) δ 0.88 (t, J=7.6 Hz, 6H), 1.35–1.44 (m, 4H), 2.24 (s, 3H), 2.52 (s, 3H), 3.05–3.18 (m, 4H), 3.85 (s, 3H), 6.77–6.86 (m, 3H), 6.95 (dd, J=1.6, 7.2 Hz, 1H), 7.32 (d, J=8.4 Hz, 1H), 8.08 (dd, J=1.6, 6.8 Hz, 1H).

Example 341

N-Cyclobutylmethyl-N-[8-(2,6-dimethoxy-4-methylphenyl)-2-(methylsulfanyl)imidazo[1,2-a]pyridin-3-yl]-N-propylamine Yellow Oil $^1$H NMR (400 MHz, CDCl$_3$) δ 0.87 (t, J=7.2 Hz, 3H), 1.30–1.45 (m, 2H), 1.50–1.60 (m, 2H), 1.60–1.90 (m, 4H), 2.22–2.80 (m, 1H), 2.41 (s, 3H), 2.47 (s, 3H), 3.00–3.25 (m, 4H), 3.70 (s, 3H), 6.51 (s, 2H), 6.77 (dd, J=6.8, 6.8 Hz, 1H), 7.01 (dd, J=1.2, 6.8 Hz, 1H), 8.02 (dd, J=1.2, 6.8 Hz, 1H).

Example 342

N-[8-(2,6-Dimethoxy-4-methylphenyl)-2-(methylsulfanyl)imidazo[1,2-a]pyridin-3-yl]-N-propyl-N-(2-propynyl)amine Tan Oil $^1$H NMR (400 MHz, CDCl$_3$) δ 0.90 (t, J=7.2 Hz, 3H), 1.40–1.50 (m, 2H), 2.19 (t, J=1.6 Hz, 1H), 2.42 (s, 3H), 2.47 (s, 3H), 2.20–2.31 (m, 2H), 3.70 (s, 6H), 3.91 (d, J=1.6 Hz, 2H), 6.51 (s, 2H), 6.81 (dd, J=6.8, 6.8 Hz, 1H), 7.04 (br d, J=7.2 Hz, 1H), 8.08 (dd, J=1.2, 6.8 Hz, 1H).

Example 343

N-[8-[4-Chloro-2-(trifluoromethyl)phenyl]-2-(methylsulfanyl)imidazo[1,2-a]pyridin-3-yl]-N,N-dipropylamine Yellow Oil $^1$H NMR (400 MHz, CDCl$_3$) δ 0.88 (t, J=7.2 Hz, 6H), 1.35–1.45 (m, 4H), 2.46 (s, 3H), 3.02–3.18 (m, 4H), 6.79 (dd, J=7.2, 7.2 Hz, 1H), 6.99 (d, J=7.2 Hz, 1H), 7.50–7.60 (m, 2H), 7.77 (br s, 1H), 8.12 (dd, J=1.2, 6.8 Hz, 1H).

Example 344

N-[8-(4-Chloro-2,6-dimethoxyphenyl)-2-(methylsulfanyl)imidazo[1,2-a]pyridin-3-yl]-N,N-dipropylamine Pale Green Crystals $^1$H NMR (400 MHz, CDCl$_3$) δ 0.88 (t, J=7.6 Hz, 6H), 1.35–1.47 (m, 4H), 2.47 (s, 3H), 3.04–3.16 (m, 4H), 3.71 (s, 6H), 6.68 (s, 2H), 6.79 (dd, J=6.8, 6.8 Hz, 1H), 6.99 (dd, J=1.2, 6.8 Hz, 1H), 8.06 (dd, J=0.8, 6.8 Hz, 1H).

Example 345

N-[8-(4-Chloro-2,6-dimethoxyphenyl)-2-(methylsulfanyl)imidazo[1,2-a]pyridin-3-yl]-N-cyclobutylmethyl-N-propylamine Yellow Crystals $^1$H NMR (400 MHz, CDCl$_3$) δ 0.87 (t, J=7.6 Hz, 3H), 1.35–1.45 (m, 2H), 1.50–1.90 (m, 6H), 2.22–2.40 (m, 1H), 2.47 (s, 3H), 3.00–3.20 (m, 4H), 3.70 (s, 6H), 6.68 (s, 2H), 6.78 (dd, J=6.8, 6.8 Hz, 1H), 6.99 (br d, J=6.8 Hz, 1H), 8.03 (d, J=6.8 Hz, 1H).

Example 346

N-[8-[4-Methoxy-2-(trifluoromethyl)phenyl]-2-(methylsulfanyl)imidazo[1,2-a]pyridin-3-yl]-N,N-dipropylamine Yellow Oil $^1$H NMR (400 MHz, CDCl$_3$) δ 0.88 (t, J=7.2 Hz, 6H), 1.25–1.45 (m, 4H), 2.46 (s, 3H), 3.04–3.20 (m, 4H), 3.90 (s, 3H), 6.78 (dd, J=6.8, 6.8 Hz, 1H), 6.99 (d, J=7.2 Hz, 1H), 7.12 (dd, J=2.4, 6.8 Hz, 1H), 7.25–7.29 (m, 1H), 7.50 (d, J=8.8 Hz, 1H), 8.10 (dd, J=1.2, 6.8 Hz, 1H).

Example 347

N-[8-(4-Methyl-1,3-benzodioxol-5-yl)-2-(methylsulfanyl)imidazo[1,2-a]pyridin-3-yl]-N,N-dipropylamine Yellow Oil $^1$H NMR (400 MHz, CDCl$_3$) δ 0.88 (t, J=7.2 Hz, 6H), 1.35–1.43 (m, 4H), 2.10 (s, 3H), 2.52 (s, 3H), 3.02–3.18 (m, 4H), 6.01 (br s, 2H), 6.73–6.80 (m, 2H), 6.88–6.97 (m, 2H), 8.08 (dd, J=2.0, 6.8 Hz, 1H).

Example 348

N-Butyl-N-cyclobutylmethyl-N-[8-(2,6-dimethoxy-4-methylphenyl)-2-(methylsulfanyl)imidazo[1,2-a]pyridin-3-yl]amine Yellow Crystals $^1$H NMR (400 MHz, CDCl$_3$) δ 0.86 (t, J=7.2 Hz, 3H), 1.25–1.37 (m, 4H), 1.60–1.90 (m, 4H), 2.22–2.38 (m, 1H), 2.41 (s, 3H); 2.47 (s, 3H), 3.00–3.25 (m, 4H), 3.70 (s, 6H), 6.50 (s, 2H), 6.75–6.80 (m, 1H), 7.01 (br d, J=6.8 Hz, 1H), 8.01 (dd, J=2.0, 8.4 Hz, 1H).

Example 349

N-Cyclobutylmethyl-N-[8-(2,6-dimethoxy-4-methylphenyl)-2-(methylsulfanyl)imidazo[1,2-a]pyridin-3-yl]-N-ethylamine Yellow Oil $^1$H NMR (400 MHz, CDCl$_3$) δ 0.98 (t, J=6.8 Hz, 3H), 1.50–1.90 (m, 6H), 2.22–2.40 (m, 1H), 2.41 (s, 3H), 2.47 (s, 3H), 3.08–3.24 (m, 4H), 3.70 (s, 6H), 6.51 (s, 2H), 6.78 (dd, J=6.8, 6.8 Hz, 1H), 7.01 (br d, J=6.8 Hz, 1H), 8.02 (br d, J=6.8 Hz, 1H).

Example 350

N-[8-[2-Chloro-4-(trifluoromethoxy)phenyl]-2-(methylsulfanyl)imidazo[1,2-a]pyridin-3-yl]-N,N-dipropylamine Yellow Oil $^1$H NMR (400 MHz, CDCl$_3$) δ 0.88 (t, J=7.6 Hz, 6H), 1.35–1.45 (m, 4H), 2.52 (s, 3H), 3.03–3.18 (m, 4H), 2.52 (s, 3H), 3.03–3.18 (m, 4H), 6.83 (dd, 7.2, 7.2 Hz, 1H), 7.15 (dd, J=1.2, 6.8 Hz, 1H), 7.22 (br d, J=7.2 Hz, 1H), 7.39 (s, 1H), 7.71 (d, J=8.4 Hz, 1H), 8.13 (dd, J=1.2, 7.2 Hz, 1H).

Example 351

N-Cyclobutylmethyl-N-cyclopropylmethyl-N-[8-(2,6-dimethoxy-4-methylphenyl)-2-(methylsulfanyl)imidazo[1,2-a]pyridin-3-yl]amine Yellow Oil $^1$H NMR (400 MHz, CDCl$_3$) δ −0.18–0.12 (m, 2H), 0.20–0.40 (m, 2H), 0.70–0.85 (m, 1H), 1.50–1.85 (m, 6H), 2.22–2.38 (m, 1H), 2.41 (s, 3H), 2.47 (s, 3H), 2.90–3.00 (m, 2H), 3.10–3.35 (m, 2H), 3.70 (s, 6H), 6.51 (s, 2H), 6.77 (dd, J=6.8, 6.8 Hz, 1H), 7.01 (dd, J=1.2, 6.8 Hz, 1H), 8.09 (dd, J=1.2, 7.2 Hz, 1H).

Example 352

N-[8-(5-Methyl-2,3-dihydro-1,4-benzodioxin-6-yl-2-(methylsulfanyl)imidazo[1,2-a]pyridin-3-yl]-N,N-dipropylamine Yellow Oil $^1$H NMR (400 MHz, CDCl$_3$) δ 0.88 (t, J=7.2 Hz, 6H), 1.38–1.45 (m, 4H), 2.06 (s, 3H), 2.52 (s, 3H), 3.02–3.20 (m, 4H), 4.25–4.36 (m, 4H), 6.76–6.80 (m, 2H), 6.89–6.96 (m, 2H), 8.08 (dd, J=1.2, 6.8 Hz, 1H).

Example 353

N-Cyclobutylmethyl-N-[8-(2,6-dimethoxy-4-methylphenyl)-2-(methylsulfanyl)imidazo[1,2-a]pyridin-3-yl]-N-(3-fluoropropyl)amine Yellow Crystals $^1$H NMR (400 MHz, CDCl$_3$) δ 1.50–1.85 (m, 8H), 2.30–2.40 (m, 1H), 2.41 (s, 3H), 2.48 (s, 3H), 3.00–3.40 (m, 4H), 3.70 (s, 6H), 4.43 (t, J=6.0 Hz, 1H), 4.55 (t, J=6.0 Hz, 1H), 6.51 (s, 2H), 6.80 (dd, J=6.8, 6.8 Hz, 1H), 7.03 (dd, J=1.2, 6.8 Hz, 1H), 7.97 (dd, J=1.2, 6.8 Hz, 1H).

Example 354

N3,N3-Dipropyl-8-[6-(dimethylamino)-4-methyl-3-pyridyl]-2-(methylsulfanyl)imidazo[1,2-a]pyridin-3-amine Orange Crystals $^1$H NMR (400 MHz, CDCl$_3$) δ 0.88 (t, J=7.2 Hz, 6H), 1.35–1.45 (m, 4H), 2.24 (s, 3H), 2.53 (s, 3H), 3.00–3.20 (m, 4H), 3.12 (s, 6H), 6.45 (s, 1H), 6.78 (dd, J=6.8, 6.8 Hz, 1H), 6.95 (dd, J=1.2, 6.0 Hz, 1H), 8.07 (d, J=6.8 Hz, 1H), 8.15 (s, 1H).

Example 355

N-[8-(2,6-Dimethoxy-4-methylphenyl)-2-(methylsulfanyl)imidazo[1,2-a]pyridin-3-yl]-N-propyl-N-tetrahydro-2H-4-pyranylamine Yellow Crystals $^1$H NMR (400 MHz, CDCl$_3$) δ 0.84 (t, J=7.2 Hz, 3H), 1.22–1.40 (m, 4H), 1.50–1.70 (m, 2H), 2.42 (s, 3H), 2.48 (s, 3H), 2.95–3.05 (m, 1H), 3.22–3.42 (m, 4H), 3.71 (s, 6H), 3.89–4.05 (m, 2H), 6.51 (s, 2H), 6.79 (dd. J=6.8, 6.8 Hz, 1H), 7.03 (br d, J=6.8 Hz, 1H), 8.03 (dd, 1.2, 6.4 Hz, 1H).

Example 356

N3-Cyclobutylmethyl-N-3-propyl-8-[6-(dimethylamino)-4-methyl-3-pyridyl]-2-(methylsulfanyl)imidazo[1,2-a]pyridin-3-amine Brown Oil $^1$H NMR (400 MHz, CDCl$_3$) δ 0.88 (t, J=7.2 Hz, 3H), 1.32–1.43 (m, 2H), 1.50–1.90 (m, 6H), 2.23 (s, 3H), 2.21–2.36 (m, 1H), 2.53 (s, 3H), 2.95–3.30 (m, 4H), 3.13 (s, 6H), 6.45 (s, 1H), 6.78 (dd, J=6.8, 6.8 Hz, 1H), 6.95 (dd, J=1.2, 6.8 Hz, 1H), 8.05 (dd, J=1.2, 6.8 Hz, 1H), 8.15 (s, 1H).

Example 357

N3-Cyclobutylmethyl-N-3-(3-fluoropropyl)-8-[6-(dimethylamino)-4-methyl-3-pyridyl]-2-(methylsulfanyl)imidazo[1,2-a]pyridin-3-amine Brown Oil $^1$H NMR (400 MHz, CDCl$_3$) δ 1.50–1.85 (m, 8H), 2.23 (s, 3H), 2.25–2.38 (m, 1H), 2.54 (s, 3H), 3.00–3.40 (m, 4H), 3.13 (s, 6H), 4.44 (t, J=6.0 Hz, 1H), 4.55 (t, J=6.0 Hz, 1H), 6.45 (s, 1H), 6.80 (dd, J=6.8, 6.8 Hz, 1H), 6.97 (dd, J=1.2, 7.2 Hz, 1H), 8.00 (dd, J=1.2, 6.8 Hz, 1H), 8.15 (s, 1H).

Example 358

N3,N3-Dicyclopropylmethyl-8-[6-(dimethylamino)-4-methyl-3-pyridyl]-2-(methylsulfanyl)imidazo[1,2-a]pyridin-3-amine Brown Oil $^1$H NMR (400 MHz, CDCl$_3$) δ −0.15–0.12 (m, 4H), 0.18–0.40 (m, 4H), 0.75–0.85 (m, 2H), 2.22 (s, 3H), 2.52 (s, 3H), 2.95–3.20 (m, 4H), 3.12 (s, 6H), 6.46 (s, 1H), 6.79 (dd, J=6.8, 6.8 Hz, 1H), 6.96 (dd, J=1.2, 6.8 Hz, 1H), 8.16 (s, 1H), 8.24 (dd, J=1.2, 6.8 Hz, 1H).

Example 359

N3,N3-Dipropyl-8-[6-(dimethylamino)-2,4-dimethyl-3-pyridyl]-2-(methylsulfanyl)imidazo[1,2-a]pyridin-3-amine Yellow Oil $^1$H NMR (400 MHz, CDCl$_3$) δ 0.89 (t, J=7.2 Hz, 6H), 1.35–1.45 (m, 4H), 2.00 (s, 3H), 2.18 (s, 3H), 2.47 (s, 3H), 3.00–3.20 (m, 4H), 3.11 (s, 6H), 6.31 (s, 1H), 6.78 (dd, J=6.8, 6.8 Hz, 1H), 6.88 (dd, J=1.2, 6.8 Hz, 1H), 8.08 (dd, J=1.2, 6.8 Hz, 1H).

Example 360

N3-Butyl-N-3-ethyl-8-[6-(dimethylamino)-4-methyl-3-pyridyl]2-(methylsulfanyl)imidazo[1,2-a]pyridin-3-amine Yellow Oil $^1$H NMR (400 MHz, CDCl$_3$) δ 0.86 (t, J=7.2 Hz, 3H), 0.98 (t, J=7.2 Hz, 3H), 1.23–1.40 (m, 4H), 2.24 (s, 3H), 2.53 (s, 3H), 3.12 (s, 6H), 3.13–3.25 (m, 4H), 6.46 (s, 1H), 6.79 (dd, J=6.8, 6.8 Hz, 1H), 6.95 (dd, J=1.2, 6.8 Hz, 1H), 8.07 (dd, J=1.6, 6.8 Hz, 1H), 8.16 (s, 1H).

Example 361

N3-Propyl-N-3-tetrahydro-2H-4-pyranyl-8-[6-(dimethylamino)$_4$-methyl-3-pyridyl]-2-(methylsulfanyl)imidazo[1,2-a]pyridin-3-amine Brown Oil $^1$H NMR (400 MHz, CDCl$_3$) δ 0.85 (t, J=7.4 Hz, 3H), 1.23–1.40 (m, 2H), 1.45–1.70 (m, 4H), 2.24 (s, 3H), 2.54 (s, 3H), 2.95–3.07 (m, 1H), 3.13 (s, 6H), 3.25–3.42 (m, 4H), 3.87–4.03 (m, 2H), 6.46 (s, 1H), 6.79 (dd, J=6.8, 6.8 Hz, 1H), 6.96 (dd, J=1.6, 6.4 Hz, 1H), 8.07 (dd, J=1.6, 6.8 Hz, 1H), 8.16 (s, 1H).

Example 362

N3,N3-Dipropyl-8-[6-(dimethylamino)-2-methyl-3-pyridyl]-2-(methylsulfanyl)imidazo[1,2-a]pyiridin-3-amine Yellow Oil $^1$H NMR (400 MHz, CDCl$_3$) δ 0.88 (t, J=7.2 Hz, 6H), 1.38–1.44 (m, 4H), 2.39 (s, 3H), 2.54 (s, 3H), 3.02–3.18 (m, 4H), 3.12 (s, 6H), 6.44 (d, J=8.4 Hz, 1H), 6.77 (dd, J=7.2, 7.2 Hz, 1H), 6.94 (dd, J=1.2, 6.8 Hz, 1H), 7.59 (d, J=8.8 Hz, 1H), 8.05 (dd, J=1.2, 6.8 Hz, 1H).

Example 363

N-[8-(2,4-Dichlorophenyl)-2-(methylsulfanyl)imidazo[1,2-a]pyridin-3-yl]-N-propyl-N-tetrahydro-2H-4-pyranylamine Yellow Oil $^1$H NMR (400 MHz, CDCl$_3$) δ 0.85 (t, J=7.4 Hz, 3H), 1.20–1.40 (m, 2H), 1.40–1.80 (m, 4H), 2.53 (s, 3H), 2.95–3.05 (m, 1H), 3.25–3.43 (m, 4H), 3.84–4.05 (m, 2H), 6.83 (dd, J=7.2, 7.2 Hz, 1H), 7.15 (dd, J=1.2, 7.2 Hz, 1H), 7.34 (dd, J=2.4, 8.4 Hz, 1H), 7.53 (d, J=2.4 Hz, 1H), 7.62 (d, J=8.4 Hz, 1H), 8.11 (dd, J=1.2, 6.8 Hz, 1H).

Example 364

N-[8-(2,6-Dimethoxy-4-methylphenyl)-2-(methylsulfanyl)imidazo[1,2-a]pyridin-3-yl]-N-cyclobutylmethyl-N-tetrahydro-2H-4-pyranylamine Yellow Oil $^1$H NMR (400 MHz, CDCl$_3$) δ 1.25–2.02 (m, 10H), 2.10–2.20 (m, 1H), 2.41 (s, 3H), 2.49 (s, 3H), 3.05–3.10 (m, 1H), 3.20–3.40 (m, 2H), 3.69 (s, 3H), 3.71 (s, 3H), 3.90–4.00 (m, 2H), 6.51 (s, 2H), 6.78 (dd, J=6.8, 6.8 Hz, 1H), 7.03 (br d, J=6.8 Hz, 1H), 7.99 (dd, J=1.2, 6.8 Hz, 1H).

Example 365

N-Cyclopropylmethyl-N-[8-(2,6-dimethoxy-4-methylphenyl)-2-(methylsulfanyl)imidazo[1,2-a]pyridin-3-yl]-N-tetrahydro-2H-4-pyranylamine Yellow Amorphous $^1$H NMR (400 MHz, CDCl$_3$) δ −0.20–0.10 (m, 1H), −0.50–0.08 (m, 1H), 0.12–0.20 (m, 1H), 0.25–0.35 (m, 1H), 1.40–1.70 (m, 4H), 2.41 (s, 3H), 2.49 (s, 3H), 2.97–3.10 (m, 2H), 3.30–3.45 (m, 3H), 3.69 (s, 3H), 3.72 (s, 3H), 3.85–3.92 (m, 1H), 3.95–4.02 (m, 1H), 6.51 (s, 2H), 6.79 (dd, J=6.8, 6.8 Hz, 1H), 7.03 (dd, J=1.2, 6.8 Hz, 1H), 8.13 (dd, J=1.2, 6.8 Hz, 1H).

Example 366

N-[8-(2,4-Dimethoxy-6-methylphenyl)-2-(methylsulfanyl)imidazo[1,2-a]pyridin-3-yl]-N-propyl-N-tetrahyrdo-2H-4-pyranylamine Yellow Oil $^1$H NMR (400 MHz, CDCl$_3$) δ 0.85 (t, J=7.2 Hz, 3H), 1.20–1.40 (m, 2H), 1.40–1.75 (m, 4H), 2.05 (s, 3H), 2.49 (s, 3H), 2.95–3.10 (m, 1H), 3.22–3.45 (m 3H), 3.68 (s, 3H), 3.85 (s, 3H), 3.85–4.05 (m, 2H), 6.43 (d, J=2.4 Hz, 1H), 6.47 (d, J=2.4 Hz, 1H), 6.79 (dd, J=6.8, 6.8 Hz, 1H), 6.96 (dd, J=1.6, 7.2 Hz, 1H), 8.06 (dd, J=1.6, 6.8 Hz, 1H).

Example 367

N-Cyclopropylmethyl-N-[8-(2,4-dimethoxy-6-methylpheyl)-2-(methylsulfanyl)imidazo[1,2-a]pyridin-3-yl]-N-tetrahydro-2H-4-pyranylamine Yellow Oil $^1$H NMR (400 MHz, CDCl$_3$) δ −0.30–0.08 (m, 1H), −0.02–0.10 (m, 1H), 0.15–0.40 (m, 2H), 0.60–0.75 (m, 1H), 1.40–1.70 (m, 4H), 2.03–2.08 (m, 3H), 2.49 (s, 3H), 2.95–3.12 (m, 2H), 3.30–3.45 (m, 3H), 3.66–3.69 (m, 3H), 3.85 (s, 3H), 3.80–3.92 (m, 1H), 3.95–4.02 (m, 1H), 6.44 (br s, 1H), 6.47 (br s, 1H), 6.79 (dd, J=6.8, 6.8 Hz, 1H), 6.96 (br d, J=6.8 Hz, 1H), 8.16 (br d, J=6.8 Hz, 1H).

Example 368

N-[8-(2,6-Dimethoxy-4-methylphenyl)-2-(methylsulfanyl)imidazo[1,2-a]pyridin-3-yl]-N-propyl-N-tetrahydro-2-furanylmethylamine Brown Crystals $^1$H NMR (400 MHz, CDCl$_3$) δ 0.87 (t, J=7.6 Hz, 3H), 1.35–1.57 (m, 3H), 1.70–1.95 (m, 3H), 2.41 (s, 3H), 2.47 (s, 3H), 3.00–3.35 (m, 5H), 3.50–3.90 (m, 8H), 6.51 (br s, 2H), 6.79 (dd, J=6.8, 6.8 Hz, 1H), 7.02 (dd, J=1.2, 6.8 Hz, 1H), 8.14 (dd, J=1.2, 6.8 Hz, 1H).

Example 369

N-[8-(2,6-Dimethoxy-4-methylphenyl)-2-(methylsulfanyl)imidazo[1,2-a]pyridin-3-yl]-N-propyl-N-tetrahydro-3-furanylmethylamine Brown Crystals $^1$H NMR (400 MHz, CDCl$_3$) δ 0.88 (t, J=8.0 Hz, 3H), 1.35–1.50 (m, 2H), 1.60–1.95 (m, 2H), 2.10–2.30 (m, 1H), 2.42 (s, 3H), 2.48 (s, 3H), 2.90–3.10 (m, 4H), 3.60–3.84 (m, 10H), 6.51 (br s, 2H), 6.80 (dd, J=6.8, 6.8 Hz, 1H), 7.03 (br d, J=6.8 Hz, 1H), 7.93–8.02 (m, 1H).

Example 370

N-Butyl-N-cyclobutylmethyl-N-[8-(2,4-dimethoxy-6-methylphenyl)-2-(methylsulfanyl)imidazo[1,2-a]pyridin-3-yl]amine Yellow Oil
$^1$H NMR (400 MHz, CDCl$_3$) δ 0.86 (t, J=6.8 Hz, 3H), 1.22–1.42 (m, 1H), 1.65–1.90 (m, 4H), 2.05 (s, 3H), 2.24–2.36 (m, 1H), 2.48 (s, 3H), 2.94–3.32 (m, 4H), 3.67 (s, 3H), 3.85 (s, 3H), 6.43 (d, J=2.0 Hz, 1H), 6.47 (d, J=2.4 Hz, 1H), 6.78 (dd, J=6.8, 6.8 Hz, 1H), 6.93 (br d, J=6.8 Hz, 1H), 8.03 (br d, J=6.8 Hz, 1H).

Example 371

N-Butyl-N-cyclobutylmethyl-N-[8-(2,4-dimethyl-6-methoxyphenyl)-2-(methylsulfanyl)imidazo[1,2-a]pyridin-3-yl]amine
Yellow Oil
$^1$H NMR (400 MHZ, CDCl$_3$) δ 0.86 (t, J=7.2 Hz, 3H), 1.20–1.45 (m, 4H), 1.65–1.90 (m, 4H), 2.02 (s, 3H), 2.20–2.35 (s, 1H), 2.38 (s, 3H), 2.47 (s, 3H), 2.95–3.35 (m, 4H), 3.68 (s, 3H), 6.67 (br s, 1H), 6.75–6.80 (m, 2H), 6.95 (dd, J=1.2, 6.8 Hz, 1H), 8.04 (dd, J=1.2, 6.4 Hz, 1H).

Example 372

8-(2,4-Dichlorophenyl)-3-methyl-2-(methylsulfanyl)imidazo[1,2-a]pyridine

Ethyl bromo-2-(methylsulfanyl)imidazo[1,2-a]pyridine-3-carboxylate (840 mg) was dissolved in tetrahydrofuran (30 mL), then a 1M solution of diisobutyl aluminum hydride in toluene (10 mL) was added dropwise at −70° C., and the temperature was raised to room temperature. An aqueous ammonium chloride solution was added to the reaction mixture at 0° C. After the temeperature was raised to room temperature, it was extracted with ethyl acetate. The resulting [8-bromo-2-(methylsulfanyl) imidazo[1,2-a]pyridin-3-yl]methanol was used in the next reaction without purification.
The resulting [8-bromo-2-(methylsulfanyl)imidazo[1,2-a]pyridin-3-yl]methanol (640 mg) was dissolved in acetone (50 mL), then activated manganese (IV) oxide (4 g) was added thereto, and the mixture was stirred overnight. Manganese (IV) oxide was filtered off through Celite, and the filtrate was evaporated. The resulting residue was purified by column chromatography using silica gel (ethyl acetate:n-hexane=1:10), to give 8-bromo-3-methyl-2-(methylsulfanyl)imidazo[1,2-a]pyridine (120 mg) as a brown oil.
The resulting 8-bromo-3-methyl-2-(methylsulfanyl)imidazo[1,2-a]pyridine was reacted in the same manner as that of Example 4 to give the title compound as white crystals.
$^1$H NMR (400 MHz, CDCl$_3$) δ2.50 (s, 3H), 2.52 (s, 3H), 6.91 (dd, J=7.2 Hz, 1H), 7.17 (dd, J=1.2, 6.8 Hz, 1H), 7.34 (dd, J=2.0, 8.4 Hz, 1H), 7.52–7.57 (m, 2H), 7.83 (d, J=6.8 Hz, 1H).
The compound of Example 373 was synthesized in the same manner as that of Example 1.

Example 373

1-[8-(2,4-Dichlorophenyl)-2-ethylimidazo[1,2-c]pyrimidin-3-yl]butyl Ethyl Ether

White Crystals
$^1$H NMR (400 MHz, CDCl$_3$) δ 0.95 (t, J=7.2 Hz, 3H), 1.21 (t, J=7.6 Hz, 3H), 1.22–1.35 (m, 1H), 1.29 (t, J=7.2 Hz, 3H), 1.42–1.52 (m, 1H), 1.77–1.85 (m, 1H), 2.05–2.15 (m, 1H), 2.73–2.84 (m, 2H), 3.30–3.48 (m, 2H), 4.77 (t, J=7.2 Hz, 1H), 7.39 (dd, J=8.4, 2.0 Hz, 1H), 7.56 (d, J=8.4 Hz, 1H), 7.57 (d, J=2.0 Hz, 1H), 7.97 (br s, 1H), 9.39 (br s, 1H).
Hereinafter, compounds of Examples 374 to 376 were synthesized in the same manner as that of Example 373.

Example 374

3-(1-Ethoxybutyl)-2-ethyl-8-(2-methoxy-4,6-dimethylphenyl)imidazo[1,2-c]pyrimidine (a) Isomer 1 having a greater Rf value on TLC White Crystals
$^1$H NMR (400 MHz, CDCl$_3$) δ 0.95 (t, J=7.2 Hz, 3H), 1.14–1.36 (m, 1H), 1.19 (t, J=7.2 Hz, 3H), 1.25 (t, J=7.2 Hz, 3H), 1.41–1.54 (m, 1H), 1.77–1.88 (m, 1H), 2.06–2.16 (m, 1H), 2.07 (s, 3H), 2.37 (s, 3H), 2.68–2.80 (m, 2H), 3.27–3.44 (m, 2H), 3.70 (s, 3H), 4.75 (t, J=7.2 Hz, 1H), 6.69 (s, 1H), 6.77 (s, 1H), 7.78 (br s, 1H), 9.32 (br s, 1H).
(b) Isomer 2 having a smaller Rf value on TLC
White Crystals
$^1$H NMR (400 MHz, CDCl$_3$) δ 0.94 (t, J=7.2 Hz, 3H), 1.14–1.34 (m, 1H), 1.20 (t, J=7.2 Hz, 3H), 1.25 (t, J=7.2 Hz, 3H), 1.41–1.54 (m, 1H), 1.78–1.88 (m, 1H), 2.06–2.16 (m, 1H), 2.07 (s, 3H), 2.38 (s, 3H), 2.68–2.84 (m, 2H), 3.30–3.44 (m, 2H), 3.71 (s, 3H), 4.75 (t, J=7.2 Hz, 1H), 6.69 (s, 1H), 6.77 (s, 1H), 7.78 (br s, 1H), 9.34 (br s, 1H).

Examples 375

8-(2-Chloro-4-methoxyphenyl)-3-(1-ethoxybutyl)-2-ethylimidazo[1,2-c]pyrimidine

White Crystals
$^1$H NMR (400 MHz, CDCl$_3$) δ 0.94 (t, J=7.2 Hz, 3H), 1.19 (t, J=7.2 Hz, 3H), 1.22–1.35 (m, 1H), 1.28 (t, J=7.2 Hz, 3H), 1.42–1.52 (m, 1H), 1.78–1.88 (m, 1H), 2.05–2.15 (m, 1H), 2.71–2.82 (m, 2H), 3.29–3.45 (m, 2H), 3.86 (s, 3H), 4.76 (t, J=7.2 Hz, 1H), 6.94 (dd, J=8.4, 2.8 Hz, 1H), 7.08 (d, J=2.8 Hz, 1H), 7.53 (d, J=8.4 Hz, 1H), 7.93 (s, 1H), 9.34 (s, 1H).

Example 376

3-(1-Ethoxybutyl)-2-ethyl-8-(6-methoxy-2-methyl-3-pyridyl)imidazo[1,2-c]pyrimidine White Crystals
$^1$H NMR (400 MHz, CDCl$_3$) δ 0.94 (t, J=7.2 Hz, 3H), 1.19 (t, J=7.2 Hz, 3H), 1.26–1.38 (m, 1H), 1.28 (t, J=7.2 Hz, 3H), 1.42–1.52 (m, 1H), 1.78–1.88 (m, 1H), 2.05–2.15 (m, 1H), 2.42 (s, 3H), 2.70–2.81 (m, 2H), 3.29–3.46 (m, 2H), 3.97 (s, 3H), 4.77 (t, J=7.2 Hz, 1H), 6.69 (d, J=8.4 Hz, 1H), 7.64 (d, J=8.4 Hz, 1H), 7.79 (s, 1H), 9.34 (s, 1H).
Among the above-mentioned Examples, particularly preferable compounds are N-(2-ethyhl-8-mesitylimidazo[1,2-a]pyrazin-3-yl)-N,N-dipropylamine hydrochloride, N-(2-ethyl-8-mesitylimidazo[1,2-a]pyrazin-3-yl)-N-(1- ethylpropyl)amine, N-[8-(2-chloro-4-methoxyphenyl)-2-ethylimdazo[1,2-a]pyrazin-3-yl]-N,N-dipropylamine hydrochloride, N-cyclopropylmethyl-N-[8-(2,4-dichloropheyl)-2-ethylimidazo[1,2-a]pyrazin-3-yl]-N-isobutylamine, N-[8-(2,4-dichlorophenyl)-2-ethylimidazo[1,2-a]pyrazin-3-yl]-N-propyl-N-tetrahydro-3-thiophenylamine, N3,N3-dipropyl-2-isopropyl-8-(2-methoxy-4,6-dimethylphenyl)imidazo[1,2-a]pyrazin-3-amine, N-[2-ethyl-8-(6-methyl-1,3-benzodioxol-5-yl)imidazo[1,2-a]pyrazin-3-yl]-N,N-dipropylamine, N-[2-ethyl-8-(4-methoxy-2,5-dimethylphenyl)imidazo[1,2-a]pyrazin-3-yl]-N,N-dipropylamine, N-cyclopropylmethyl-N-[8-(2,4-dichlorophenyl)-2-ethylimidazo[1,2-a]pyrazin-3-yl]-N-(2-methoxyethyl)amine hydrochloride, N-[8-(2-chloro-4-methoxyphenyl)-2-ethylimidazo[1,2-a]pyrazin-3-yl]-N,N-dicyclopropylmethylamine, N-8-[5-chloro-4-(2,5-dimethyl-1H-1-pyrroyl)-2-methoxyphenyl]-2-ethylimidazo[1,2-a]pyrazin-3-yl-N,N-dicyclopropylmethylamine, N-[8-(2,4-dichlorophenyl)-2-ethyl-6-methylimidazo[1,2-a]pyrazin-3-yl]-N,N-dipropylamine hydrochloride, N3,N3-dipropyl-5-bromo-8-(2,4-dichlorophenyl)-2-ethylimidazo[1,2-a]pyrazin-3-amine, 8-(2,4-dichlorophenyl)-3-(dipropylamino)-2-ethylimidazo[1,2-a]pyrazin-6-yl cyanide, N-[8-(2,4-dichlorophenyl)-2-ethyl-6-methoxyimidazo[1,2-a]pyrazin-3-yl]-N,N-dipropylamine, N-[6-chloro-2-ethyl-8-(2-methoxy-4,6-dimethylphenyl)imidazo[1,2-a]pyrazin-3-yl]-N,N-dipropylamine, N3,N3-dipropyl-8-(2,4-dichlorophenyl)-2-(methylsulfanyl)imidazo[1,2-a]pyrazin-3-amine, N,N-dicyclopropylmethyl-N-[8-(2-methoxy-4,6-dimethylphenyl)-2-(methylsulfanyl)imidazo[1,2-a]pyrazin-3-yl]amine, N-[8-(2-chloro-4-methoxyphenyl)-2-(methylsulfanyl)imidazo[1,2-a]pyrazin-3-yl]-N-cyclopropylmethyl-N-propylamine, N-[8-(2-bromo-4-methoxyphenyl)-2-(methylsulfanyl)imidazo[1,2-a]pyrazin-3-yl]-N-cyclopropylmethyl-N-(3-fluoropropyl)amine, N-[8-(2-chloro-6-methoxy-4-methylphenyl)-2-(methylsulfanyl)imidazo[1,2-a]pyrazin-3-yl]-N,N-dicyclopropylmethylamine, N-[8-(2-chloro-4-methoxyphenyl)-2-(methylsulfanyl)imidazo[1,2-a]pyrazin-3-yl]-N-cyclopropylmethyl-N-isobutylamine, N-cyclopropylmethyl-N-[8-[2-methyl-4-(methylsulfinyl)phenyl]-2-(methylsulfinyl)imidazo[1,2-a]pyrazin-3-yl]-N-propylamine, N-[8-(2-chloro-4-methoxyphenyl)-2-(methylsulfonyl)imidazo[1,2-a]pyrazin-3-yl]-N-cyclopropylmethyl-N-propylamine, N-[8-[2-chloro-4-(trifluoromethoxy)phenyl]-2-(methylsulfanyl)imidazo[1,2-a]pyrazin-3-yl]-N,N-dicyclopropylmethylamine, 1-[[8-[2-chloro-4-(trifluoromethoxy)phenyl]-2-(methylsulfanyl)imidazo[1,2-a]pyrazin-3-yl](cyclopropylmethyl)amino]-2-propanol, 2-[[8-[2-chloro-4-(trifluoromethoxy)phenyl]-2-(methylsulfanyl)imidazo[1,2-a]pyrazin-3-yl](cyclopropylmethyl)amino]acetamide, 4-[3-[di(cyclopropylmethyl)amino]-2-(methylsulfanyl)imidazo[1,2-a]pyrazin-8-yl]-3-methoxybenzonitrile, N,N-dicyclopropylmethyl-N-[8-(2-methoxy-4-tetrahydro-1H-1-pyrrolylphenyl)-2-(methylsulfanyl)imidazo[1,2-a]pyrazin-3-yl]amine, N2-[8-[2-chloro-4-(trifluoromethoxy)phenyl]-2-(methylsulfanyl)imidazo[1,2-a]pyrazin-3-yl]-N2-cyclopropylmethyl-2-furamide, N-[8-[2-chloro-4-(trifluoromethoxy)phenyl]-2-(methylsulfanyl)imidazo[1,2-a]pyrazin-3-yl]-N-cyclopropylmethyl-N-(2-furylmethyl)amine, N-[8-[2-chloro-4-(trifluoromethoxy)phenyl]-2-(methylsulfanyl)imidazo[1,2-a]pyrazin-3-yl]-N-cyclopropylmethyl-N-(2-morpholinoethyl)amine, N-[8-[2-chloro-4-(trifluoromethoxy)phenyl]-2-(methylsulfanyl)imidazo[1,2-a]pyrazin-3-yl]-N-cyclopropylmethyl-N-[2-(1H-1-pyrazoyl)ethyl]amine, N-[8-[2-chloro-4-(trifluoromethoxy)phenyl]-2-(methylsulfanyl)imidazo[1,2-a]pyrazin-3-yl]-N-cyclopropylmethyl-N-[2-(1H-1-imidazoyl)ethyl]amine, 2-[2-ethyl-3-(1-ethylpropyl)imidazo[1,2-a]pyrazin-8-yl]-3,5-dimethylphenyl methyl ether, 3-(1-ethoxybutyl)-2-ethyl-8-(2-methoxy-4,6-dimethylphenyl)imidazo[1,2-a]pyrazine, 1-[8-(2-chloro-4-methoxyphenyl)-2-ethylimidazo[1,2-a]pyrazin-3-yl]-1-butanone O1-methyloxime, 3-(1-ethoxybutyl)-8-(2-methoxy-4,6-dimethylphenyl)-2-(methylsulfanyl)imidazo[1,2-a]pyrazine, N-[8-(2-chloro-4-methoxyphenyl)-2-methoxyimidazo[1,2-a]pyrazin-3-yl]-N-cyclopropylmethyl-N-propylamine, N-[2-ethyl-8-(4-methoxy-2-methylphenyl)imidazo[1,2-b]pyridazin-3-yl]-N,N-dipropylamine, N-[2-ethyl-8-(2-methoxy-4,6-dimethylphenyl)imidazo[1,2-b]pridazin-3-yl]-N,N-dipropylamine, N,N-dicyclopropylmethyl-N-[2-ethyl-8-(2-methoxy-4,6-dimethylphenyl)imidazo[1,2-b]pyridazin-3-yl]amine, N-[8-(4-methoxy-2-methylphenyl)-2(methylsulfanyl)imidazo[1,2-b]pyridazin-3-yl]-N,N-dipropylamine, N-[8-(2,4-dichlorophenyl)-2-(methylsulfanyl)imidazo[1,2-a]pyridin-3-yl]-N,N-dipropylamine, N-[8-(2-methoxy-4,6-dimethylphenyl)-2-(methylsulfanyl)imidazo[1,2-a]pyridin-3-yl]-N,N-dipropylamine, N-[8-(2,6-dimethoxy-4-methylphenyl)-2-(methylsulfanyl)imidazo[1,2-a]pyridin-3-yl]-N,N-dipropylamine, N-[8-(2,4-dimethoxy-6-methylphenyl)-2-(methylsulfanyl)imidazo[1,2-a]pyridin-3-yl]-N,N-dipropylamine, N-[8-(2-chloro-6-methoxy-4-methylphenyl)-2-(methylsulfanyl)imidazo[1,2-a]pyridin-3-yl]-N,N-dipropylamine, N-[8-(2,4-dichlorophenyl)-2-(methylsulfanyl)imidazo[1,2-a]pyridin-3-yl]-N-propyl-N-(2-propynyl)amine, N-[8-(4-chloro-2-methoxyphenyl)-2-(methylsulfanyl)imidazo[1,2-a]pyridin-3-yl]-N,N-dipropylamine, N-[8-(2,6-dimethoxy-4-methylphenyl)-2-(methylsulfanyl)imidazo[1,2-a]pyridin-3-yl-N-propyl-N-(3-thienyl)amine, N-[8-(4-methoxy-2-methylphenyl)-2-(methylsulfanyl)imidazo[1,2-a]pyridin-3-yl]-N,N-dipropylamine, N-cyclobutylmethyl-N-[8-(2,6-dimethoxy-4-methylphenyl)-2-(methylsulfanyl)imidazo[1,2-a]pyridin-3-yl]-N-propylamine, N-[8-(4-chloro-2,6-dimethoxyphenyl)-2-(methylsulfanyl)imidazo[1,2-a]pyridin-3-yl]-N,N-dipropylamine, N-[8-(4-chloro-2,6-dimethoxyphenyl)-2-(methylsulfanyl)imidazo[1,2-a]pyridin-3-yl]-N-cyclobutylmethyl-N-propylamine, N-butyl-N-cyclobutylmethyl-N-[8-(2,6-dimethoxy-4-methylphenyl)-2-(methylsulfanyl)imidazo[1,2-a]pyridin-3-yl]amine, N-cyclobutylmethyl-N-cyclopropylmethyl-N-[8-(2,6-dimethoxy-4-methylphenyl)-2-(methylsulfanyl)imidazo[1,2-a]pyridin-3-yl]amine, N3,N3-dipropyl-8-[6-(dimethylamino)-4-methyl-3-pyridyl]-2-(methylsulfanyl)imidazo[1,2-a]pyridin-3-amine, N-[8-(2,6-dimethoxy-4-methylphenyl)-2-(methylsulfanyl)imidazo[1,2-a]pyridin-3-yl]-N-propyl-N-tetrahydro-2H-4-pyranylamine, N3-cyclobutylmethyl-N3-propyl-8-[6-(dimethylamino)-4-methyl-3-pyridyl]-2-(methylsulfanyl)imidazo[1,2-a]pyridin-3-amine, N3-cyclobutylmethyl-N-3-(3-fluoropropyl)-8-[6-(dimethylamino)-4-methyl-3-pyridyl]-2-(methylsulfanyl)imidazo[1,2-a]pyridin-3-amine, N3,N3-dicyclopropylmethyl-8-[6-(dimethylamino)-4-methyl-3-pyridyl]-2-(methylsulfanyl)imidazo[1,2-a]pyridin-3-amine, N3-propyl-N3-tetrahydro-2H-4-pyranyl-8-[6-(dimethylamino)-4-methyl-3-pyridyl]-2-(methylsulfanyl)imidazo[1,2-a]pyridin-3-amine, N-[8-(2,6-dimethoxy-4-methylphenyl)-2-(methylsulfanyl)imidazo[1,2-a]pyridin-3-yl]-N-cyclobutylmethyl-N-tetrahydro-2H-4-pyranylamine, N-cyclopropylmethyl-N-[8-(2,6-dimethoxy-4-methylphenyl)-2-(methylsulfanyl)imidazo[1,2-a]pyridin-3-yl]-N-tetrahydro-2H-4-pyranylamine etc., and free compounds, salts, solvates (preferably hydrate) thereof.

TEST EXAMPLES

The present compounds were evaluated for the ability to bind to a corticotrophin releasing hormone receptor (CRFR) and the adenylate cyclase activity inhibitory ability. Each test procedures and the results-are as follows:

Test Example 1

CRFR Binding Experiment (1) Preparation of CRFR expressing cell: As an experiment material for the CRFR binding experiment, a membrane fraction of a cell which expressed highly human CRFR 1. CRFR expressing cell was prepared as follows. The full length gene of CRFR[1] was obtained by a PCT method using human brain (QuickClone™ Clontech) as cDNA library. The resulting DNA fragment was inserted into a cloning vector to confirm the base sequence. A cDNA having the correct base sequence was ligated to an expression vector (pcDNA$_{3.1}$™, Invitrogen). A gene was inserted into Hek 283 cell and grown in a cell culturing solution containing G418 (1 mg/ml) to obtain a resistance cell, into which a CRFR 1 expression vector was cloned by a limitation diluting method. A clone having the high binding ability of membrane and sauvigine per unit protein was finally selected from cloned cells by a binding experiment shown by the method shown below, which was used for an experiment.

(2) Preparation of a membrane fraction: G418 resistant cells into which a gene for CRFR 1 was introduced were collected, and cell rupture was performed by an ultrasound generator with a sonicate buffer (D-PBS-10 mM MgCl$_2$, 2 mM EGTA). A suspension after ultrasound rupture was centrifuged (46,000×g, 10 minutes), the sediment thereof was further resuspended with a sonicate buffer, and the same procedures were related. Finally, the sediment was suspended inabinding buffer (D-PBS-10 mMMgCl$_2$, 2 mM EGTA, 1.5% BSA, 0.15 mM bacitracin, 1× protease inhibitor cocktail (COMPLETE™, Boehringer), to adjust the protein concentration at 1.6 mg/ml, which was used as a membrane fraction. (3) Binding experiment: Binding experiment with sauvigine was performed using a 96-well plate and SPA™ (Amersham pharmacia). An experiment was according to the specification of SPA beads. 40 mg of a membrane fraction protein, 0.5 mg of beads and 40 pM [$^{125}$I]-sauvigine (Amersham pharmacia) were allowed to stand at room temperature for two hours in the presence a test compound, centrifuged (1,000×g, 5 minutes), and then the radioactivity of each well was measured with Top-Count™ (Packard).

(4) Calculation of the binding ability: The radioactivity as the non-specific binding when 1,000-fold excessive amount of non-radioactive sauvigine was added was substacted from each value, the radioactivity where no test material is added is regarded as 100% (control), and each value is shown by % (% of control). The concentration showing 50% in % (% of control) was obtained from a graph where the concentration test material is plotted on an abscissa axis and %(% of control) is plotted on a coordinate axis and IC$_{50}$ value was calculated.

Test Example 2

Experiment for Measuring Adenyrate Cyclase the Activity Using AtT-20cell (1) Test procedures: AtT-20 cell is a cell strain derived from mouse pytuitari gland tumor, it is known that the intracellular adenyrate cyclase system is activated in response to corticotrophin release hormone (CRF), to produce cyclic AMP (cAMP), releasing adrenocortical hormone (ACTH) (Biochem. Piophys. Res. Com. 106. 1364–1371, 1982). In this experiment, the cell (1×10$^5$) suspended in D-MEM medium (0.1% FPS), seeded on a 96-well plate, a phosphodiesterase inhibitor (IBMX, Calbiochem) was added to the final concentration of 1 mM, which was cultured at 37° C. for 30 minutes. A diluted test compound solution and CRF (30 nM) were added, which was further cultured at 37° C. for 10 minutes, cells were collected by centrifugation (500×g, 5 minutes), cells were lysed with a lysis buffer (Amersham Pharmacia), and an amount of intracellular cAMP produced was quantitated using the ELISA method. For ELISA, cAMP EIA system (BIOTRAK™ Amersham Pharmacia) was used. (2) Calculation of adenyrate cyclase activity inhibitory ability: Treatment of the resulting data was carried out as follows. An amount of cAMP produced by a cell to which 30 nM CRF was added is regarded as 100% (control) and a value of each sample is expressed as % (% of control). The concentration showing 50% in % (% of control) was obtained from a graph where the concentration of a test material is plotted on an abscissa axis and % (% of control) is plotted on a coordinate and IC$_{50}$ value was calculated.

In Test Example 1, the compounds of the present invention exhibited an excellent binding ability to CRFR, and IC$_{50}$ values thereof were 10 to 5000 nM. Further, in Test Example 2, the compounds of the present invention exhibited an excellent inhibitory activity to the adenylate cyclase by CRF.

What is claimed is:
1. A compound represented by the formula:

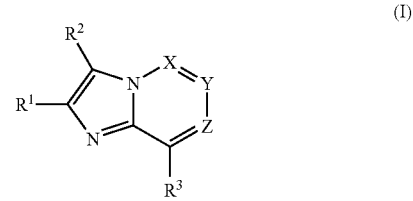

(I)

(wherein R$^1$ denotes a C$_{1-6}$ alkyl group, a C$_{2-8}$ alkenyl group, a C$_{2-8}$ alkynyl group, a C$_{1-6}$ alkoxy group, a C$_{1-6}$ alkylsulfinyl group, a C$_{1-6}$ alkylsulfonyl group or a C$_{1-6}$ alkylthio group;

R$^2$ denotes:
a halogen atom, a cyano group, a nitro group, a C$_{1-10}$ alkyl group, a C$_{2-10}$ alkenyl group, a C$_{2-10}$ alkynyl group, a C$_{3-8}$ cycloalkyl group, a C$_{3-8}$ cycloalkenyl group, a C$_{3-8}$ cycloalkyl C$_{1-6}$ alkyl group, a C$_{3-8}$ cycloalkyl C$_{2-6}$ alkenyl group, a C$_{1-10}$ alkoxy group, a C$_{2-6}$ alkenyloxy group, a C$_{1-10}$ alkoxy C$_{1-10}$ alkyl group, a C$_{1-6}$ alkoxy C$_{2-8}$ alkenyl group, a C$_{2-6}$ alkenyloxy C$_{1-6}$ alkyl group, a $C_{2-6}$ alkenyloxy $C_{2-6}$ alkenyl group, a group represented by —$NR^{2a}R^{2b}$ ($R^{2a}$ and $R^{2b}$ are independent of each other and each denotes a hydrogen atom, a $C_{1-8}$ alkyl group, a $C_{2-8}$ alkenyl group, a $C_{2-6}$ alkynyl group, a $C_{1-6}$ hydroxyalkyl group, a $C_{1-6}$ alkyl group substituted with a 5- to 14-membered non-aromatic heterocyclic group, a $C_{1-6}$ alkylthio group, a $C_{1-6}$ alkylsulfinyl group, a $C_{1-6}$ alkylsulfonyl group, a $C_{1-6}$ alkoxy $C_{1-6}$ alkyl group, a $C_{1-6}$ alkylthio $C_{1-6}$ alkyl group, an aminocarbonyl $C_{1-6}$ alkyl group, a heteroarylcarbonyl group, a $C_{3-8}$ cycloalkyl group, a $C_{3-8}$ cycloalkyl $C_{1-6}$ alkyl group, a heteroaryl $C_{1-6}$ alkyl group, an aryl $C_{1-6}$ alkyl group, an aryl group, a 5- to 14-membered heterocyclic group, a $C_{1-6}$ alkoxycarbonyl group or a $C_{2-6}$ alkenyloxycarbonyl group), —CO—$NR^{2a}R^{2b}$ ($R^{2a}$ and $R^{2b}$ have the same meanings as defined above, respectively), —CO-$A^3$ ($A^3$ denotes a hydrogen atom, a hydroxyl group, a $C_{1-6}$ alkyl group, a $C_{2-8}$ alkenyl group, a $C_{2-8}$ alkynyl group, a $C_{1-6}$ alkoxy group, a $C_{2-8}$ alkenyloxy group, an aryl group or a heteroaryl group), —O—C(O)-$A^4$ ($A^4$ denotes a $C_{1-6}$ alkyl group, a $C_{2-8}$ alkenyl group or a $C_{2-8}$ alkynyl group) or -$G^2$-$A^5$ ($G^2$ denotes S, SO or $SO_2$; and $A^5$ denotes a $C_{1-6}$ alkyl group or a $C_{2-6}$ alkenyl group), or a 5- to 14-membered non-aromatic heterocyclic group, and further, $R^2$ may be substituted with at least one group selected from a halogen atom, a hydroxyl group, a cyano group, a $C_{1-6}$ alkyl group, a $C_{2-6}$ alkenyl group, a $C_{2-6}$ alkynyl group, a $C_{3-8}$ cycloalkyl group, a $C_{3-8}$ cycloalkenyl group, a $C_{1-6}$ alkoxy group, a $C_{2-6}$ alkenyloxy group, a $C_{1-6}$ alkylthio group, a $C_{2-6}$ alkenylthio group, —$NR^{2a}R^{2b}$ ($R^{2a}$ and $R^{2b}$ have the same meanings as defined above, respectively), an aryl group and a heteroaryl group;

$R^3$ denotes a $C_{6-14}$ aromatic hydrocarbon cyclic group or a 5- to 14-membered aromatic heterocyclic group, each of which may be substituted by one to three substituents selected from the group consisting of a halogen atom, a hydroxyl group, a nitro group, a cyano group, a carboxyl group, a $C_{1-6}$ alkyloxycarbonyl group, —$S(O)_rR^{13}$ (wherein r denotes an integer of 0, 1 or 2; and $R^{13}$ denotes (a) a hydrogen atom, (b) a $C_{1-6}$ alkyl group, (c) the formula —$NR^{14}R^{15}$ (wherein $R^{14}$ and $R^{15}$ are the same as or different from each other and each denotes a hydrogen atom, a $C_{1-6}$ alkyl group, a $C_{1-6}$ alkyl group substituted with an aryl group, a $C_{1-4}$ alkylacyl group, an aryl $C_{1-4}$ alkyl group, a heteroaryl $C_{1-4}$ alkyl group, an aryl group or a heteroaryl group), (d) an aryl $C_{1-4}$ alkyl group, (e) an aryl group, (f) a heteroaryl $C_{1-4}$ alkyl group or (g) a heteroaryl group), —$NR^{16}R^{17}$ (wherein $R^{16}$ and $R^{17}$ are the same as or different from each other and each denotes a hydrogen atom, a $C_{1-6}$ alkyl group or a $C_{1-4}$ alkylacyl group), a $C_{1-6}$ alkyl group, a $C_{1-6}$ alkoxy group, a $C_{1-6}$ alkylthio group, a $C_{1-4}$ alkoxy $C_{1-6}$ alkyl group, a halogeno-$C_{1-6}$ alkyl group and a halogeno-$C_{1-6}$ alkoxy group; and X is N (nitrogen), Y is CH and Z denotes $CR^4$ (wherein $R^4$ (aa) denotes a hydrogen atom, a halogen atom, a cyano group, a nitro group, an optionally halogenated $C_{1-6}$ alkyl group, a $C_{2-6}$ alkenyl group, a $C_{2-6}$ alkynyl group, a $C_{3-8}$ cycloalkyl group, a $C_{3-8}$ cycloalkenyl group, a $C_{1-6}$ alkoxy group, a $C_{2-6}$ alkenyloxy group, —$NR^{4a}R^{4b}$ (wherein $R^{4a}$ and $R^{4b}$ are independent of each other and each denotes a hydrogen atom, a $C_{1-8}$ alkyl group, a $C_{2-8}$ alkenyl group, a $C_{2-6}$ alkynyl group, a $C_{1-6}$ alkylthio group, a $C_{1-6}$ alkylsulfinyl group, a $C_{1-6}$ alkylsulfonyl group, a $C_{1-6}$ alkoxy $C_{1-6}$ alkyl group, a $C_{3-8}$ cycloalkyl group, a $C_{3-8}$ cycloalkyl $C_{1-6}$ alkyl group, a heteroaryl $C_{1-6}$ alkyl group, an aryl $C_{1-6}$ alkyl group, an aryl group, a 5- to 14-membered heterocyclic group, a $C_{1-6}$ alkoxycarbonyl group or a $C_{2-6}$ alkenyloxycarbonyl group) or -$G^3$-$A^6$ (wherein $G^3$ denotes S, SO or $SO_2$; $A^6$ denotes a $C_{1-6}$ alkyl group or a $C_{2-6}$ alkenyl group), or (bb) $R^4$s, or $R^2$ and $R^4$ may be bound together to form a ring); or a pharmacologically salt thereof.

2. The compound according to claim 1 or a pharmacologically acceptable salt thereof, wherein $R^1$ is a methyl group, an ethyl group, a n-propyl group, an iso-propyl group, a methoxy group, an ethoxy group, a n-propyloxy group, an iso-propyloxy group, a methylthio group, an ethylthio group, a n-propylthio group, an iso-propylthio group, a methylsulfinyl group, an ethylsulfinyl group, a methylsulfonyl group or an ethylsulfonyl group.

3. The compound according to claim 1 or a pharmacologically acceptable salt thereof, wherein $R^1$ is -$G^4$-$CH_3$ (wherein $G^4$ denotes a single bond, $CH_2$, O or S).

4. The compound according to claim 1 or a pharmacologically acceptable salt thereof, wherein $R^2$ denotes a $C_{1-6}$ alkyl group, $C_{1-6}$ alkoxy $C_{1-6}$ alkyl group, a $C_{1-6}$ alkylsulfonyl group, a $C_{2-6}$ alkenylsulfonyl group or —$NR^{2a}R^{2b}$ ($R^{2a}$ and $R^{2b}$ have the same meanings as defined in claim 1), each of which may be substituted.

5. The compound according to claim 1 or a pharmacologically acceptable salt thereof, wherein $R^2$ is —$NR^{2aa}R^{2bb}$ (wherein $R^{2aa}$ and $R^{2bb}$ are independent of each other and each denotes a hydrogen atom, a $C_{1-8}$ alkyl group, a $C_{2-8}$ s alkenyl group, a $C_{2-6}$ alkynyl group, a $C_{1-6}$ alkyl group substituted with a 5- to 14-membered non-aromatic heterocyclic group, a $C_{1-8}$ alkoxy group, a $C_{1-8}$ alkoxy $C_{1-8}$ alkyl group, a $C_{1-6}$ alkylsulfinyl group, a $C_{1-6}$ alkylsulfonyl group, a $C_{3-8}$ cycloalkyl group, a $C_{3-8}$ cycloalkyl $C_{1-6}$ alkyl group or a 5- to 14-membered heterocyclic group, and further, the $R^{2aa}$ and $R^{2bb}$ are independent of each other and each may be substituted with a halogen atom).

6. The compound according to claim 1 or a pharmacologically acceptable salt thereof, wherein $R^2$ is a di($C_{1-6}$ alkyl)amino group.

7. The compound according to claim 1 or a pharmacologically acceptable salt thereof, wherein $R^3$ is a phenyl group or a pyridyl group, each of which may be substituted with 1 to 4 group(s) selected from a halogen atom, a $C_{1-6}$ alkyl group, a halogeno-$C_{1-6}$ alkyl group, a $C_{1-6}$ alkoxy group, a halogeno-$C_{1-6}$ alkoxy group, a $C_{1-6}$ alkylthio group and a 5- to 8-membered aromatic heterocyclic group.

8. The compound according to claim 1 or a pharmacologically acceptable salt thereof, wherein $R^3$ is a phenyl group or a pyridyl group, each of which may be substituted with 1 to 3 group(s) selected from a fluorine atom, a chlorine atom, a bromine atom, a methyl group, an ethyl group, a trifluoromethyl group, a methoxy group, a trifluoromethoxy group, a methylthio group and a pyrrolyl group.

9. The compound according to claim 1 or a pharmacologically acceptable salt thereof, wherein $R^4$ is a hydrogen atom, a halogen atom, a methyl group, an ethyl group, a methoxy group or an ethoxy group.

10. The compound according to claim 1 or a pharmacologically acceptable salt thereof, wherein $R^4$ is a hydrogen atom.

11. The compound according to claim 1 which is represented by the following formula or a pharmacologically acceptable salt thereof

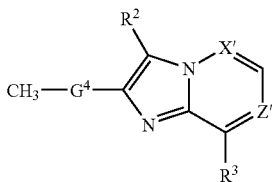
(II)

wherein X' is a nitrogen atom and Z' is CH; $R^2$ and $R^3$ are as defined in claim 1, and $G^4$ denotes a single bond, $CH_2$, O or S.

12. The compound according to claim 11 or a pharmacologically acceptable salt thereof, wherein $R^2$ is —$NR^{2aa}R^{2bb}$ (wherein $R^{2aa}$ and $R^{2bb}$ are independent of each other and each denotes a hydrogen atom, a $C_{1-8}$ alkyl group, a $C_{2-8}$ alkenyl group, a $C_{2-6}$ alkynyl group, a $C_{1-6}$ alkyl group which may be substituted with a 5- to 14-membered non-aromatic heterocyclic group, a $C_{1-8}$ alkoxy group, a $C_{1-8}$ alkoxy $C_{1-8}$ alkyl group, a $C_{1-6}$ alkylsulfinyl group, a $C_{1-6}$ alkylsulfonyl group, a $C_{3-8}$ cycloalkyl group, a $C_{3-8}$ s cycloalkyl $C_{1-6}$ alkyl group or a 5- to 14-membered heterocyclic group, and further, the $R^{2aa}$ and $R^{2bb}$ are independent of each other and each may be substituted with a halogen atom).

13. The compound according to claim 11 or a pharmacologically acceptable salt thereof, wherein $R^2$ is a di($C_{1-6}$ alkyl)amino group.

14. The compound according to claim 11 or a pharmacologically acceptable salt thereof, wherein $R^3$ is a phenyl group or a pyridyl group, each of which may be substituted with 1 to 4 group(s) selected from a halogen group, a $C_{1-6}$ alkyl group, a halogeno-$C_{1-6}$ alkyl group, a halogeno-$C_{1-6}$ alkoxy group, a $C_{1-6}$ alkoxy group, a $C_{1-6}$ alkylthio group and a 5- to 8-membered aromatic heterocyclic group.

15. A pharmaceutical composition comprising the compound according to claim 1 or a pharmacologically acceptable salt thereof, and a pharmacologically acceptable carrier.

16. A method of treating a disease selected from depression, recurrent depression, anxiety, generalized anxiety disorder, panic disorder, compulsive disorder, posttraumatic stress disorder, bipolar disorder, drug abstinence symptoms and alcohol abstinence symptoms, by administering a pharmacologically effective amount of the compound of claim 1 or a pharmacologically acceptable pharmacologically acceptable salt thereof to a subject.

* * * * *